United States Patent
Stevanin et al.

(10) Patent No.: US 9,522,933 B2
(45) Date of Patent: Dec. 20, 2016

(54) DIAGNOSIS OF HEREDITARY SPASTIC PARAPLEGIAS (HSP) BY IDENTIFICATION OF A MUTATION IN THE ZFYVE26 GENE OR PROTEIN

(71) Applicant: Institut National de la Sante et de la Recherche Medical (INSERM), Parix (FR)

(72) Inventors: Giovanni Stevanin, Paris (FR); Sylvain Hanein, Paris (FR); Amir Boukhris, Paris (FR); Cyril Goizet, Paris (FR); Elodie Martin, Paris (FR); Alexis Brice, Paris (FR)

(73) Assignee: INSTITUT NATIONAL DE LA SANTÉ ET DE LA RECHERCHE MÉDICALE (INSERM), Paris (FR)

( * ) Notice: Subject to any disclaimer, the term of this patent is extended or adjusted under 35 U.S.C. 154(b) by 0 days.

(21) Appl. No.: 13/664,868

(22) Filed: Oct. 31, 2012

(65) Prior Publication Data
US 2013/0137096 A1 May 30, 2013

Related U.S. Application Data

(63) Continuation of application No. 12/934,841, filed as application No. PCT/EP2009/053838 on Mar. 31, 2009, now abandoned.

(30) Foreign Application Priority Data

Apr. 2, 2008 (EP) .................... 08305079

(51) Int. Cl.
| | |
|---|---|
| *C07H 21/04* | (2006.01) |
| *C12Q 1/68* | (2006.01) |
| *C07K 14/47* | (2006.01) |
| *G01N 33/68* | (2006.01) |

(52) U.S. Cl.
CPC .............. *C07H 21/04* (2013.01); *C07K 14/47* (2013.01); *C12Q 1/6883* (2013.01); *G01N 33/6893* (2013.01); *C12Q 2600/156* (2013.01); *G01N 2800/385* (2013.01)

(58) Field of Classification Search
None
See application file for complete search history.

(56) References Cited

PUBLICATIONS

NCBI dbSNP database, Accession rs35358017, Jul. 17, 2005.*
DbSNP Database rs35358017, Jul. 17, 2005 (see ss40466420).*

Den Dunnen J T et al: "Nomenclature for the description of human sequence variations." Human Genetics Jul. 2001 vol. 109, No. 1, Jul. 2001 (Jul. 2001)pp. 121-124, XP002488023 ISSN: 0340-6717 cited in the application the whole document.*
ABI (Batch ID xplore_hum_chrom14_2, Jul. 17, 2005).*
Venter et al. (Science, vol. 291, No. 5507, pp. 1304-1351, 2001).*
Database EMBL (online) Aug. 13, 2003 (Aug. 13, 2003). "Preparation and use of superior vaccines." XP002488024 retrieved from EBI accession No. EMBL:BD240616 Database accession No. BD240616 the whole document.
Neft, Re., et al., "Toxicologically relevant human PCR Primer #1152. Toxicologically relevant gene; toxicological response; PCR primer;ss." XP-002488025. May 14, 2003.
Database UniProt (Online) Jan. 15, 2008 (Jan. 15, 2008), "Zinc finger FYVE domain-containing protein 26." XP002488026 retrieved from EBI accession No. UNIPROT:Q68DK2 Database accession No. Q68DK2 the whole document.
Nizar Elleunch et al:"Refinement of the SPG15 candidate interval and phenotypic heterogeneityin three large Arab families" Neurogenetics, Springer-Verlag, BE, vol. 8, No. 4, Jul. 28, 2007 (Jul. 28, 2007)pp. 307-315, XP019545430ISSN: 1364-6753 cited in the application the whole document.
Mannan Ashraf U et al: "ZFYVE27 (SPG33), a novel spastin-binding protein, is mutated in hereditary spastic paraplegia." American Journal of Human Genetics Aug. 2006. vol. 79, No. 2, Aug. 2006 (Aug. 2006), pp. 351-357, XP002488022 ISSN: 0002-9297 cited in the application the whole document.
Hanein Sylvain et al: "Identfication of SPG15 gene, encoding spastizin, as a frequent cause of complicated autosomal-recessive spastic paraplegia, including Kjellin syndrome" American Journal of Human Genetics, vol. 82, No. 4, Apr. 11, 2008 (Apr. 11, 2008), pp. 992-1002, XP009102077 ISSN: 1537-6605 the whole document.
Denora P S et al., Spastic paraplegia with thinning of the corpus callosum and white matter abnormalities: Further mutations and relative frequency in ZFYVE26/SPG15 in the Italian population Journal of Neurological Sciences, Elsevier Scientific Publishing Co., Amsterdam, NL, vol. 277, No. 1-2 Feb. 15, 2009 (2009-22-15), pp. 22-25, XP025885514 ISSN: 0022-510X (retrieved on Dec. 13, 2008) the whole document.
Yu, Li-Rong, et al., "Improved Titanium Dioxide Enrichment of Phosphopeptides from HeLa Cells and High Confident Phosphopeptide Identification by Cross-Validation of MS/MS and MS/MS/MS Spectra." Journal of Proteome, 2007, pp. 4150-4162.

* cited by examiner

Primary Examiner — Jeanine A Goldberg
(74) Attorney, Agent, or Firm — Whitham, Curtis & Cook, P.C.

(57) ABSTRACT

The Invention relates to an ex vivo method of diagnosing or predicting a hereditary spastic paraplegias (HSP), in a subject, which method comprises detecting a mutation in the ZFYVE26 gene or protein (spastizin), wherein said mutation is indicative of a hereditary spastic paraplegias (HSP).

4 Claims, 24 Drawing Sheets

Figure 1:
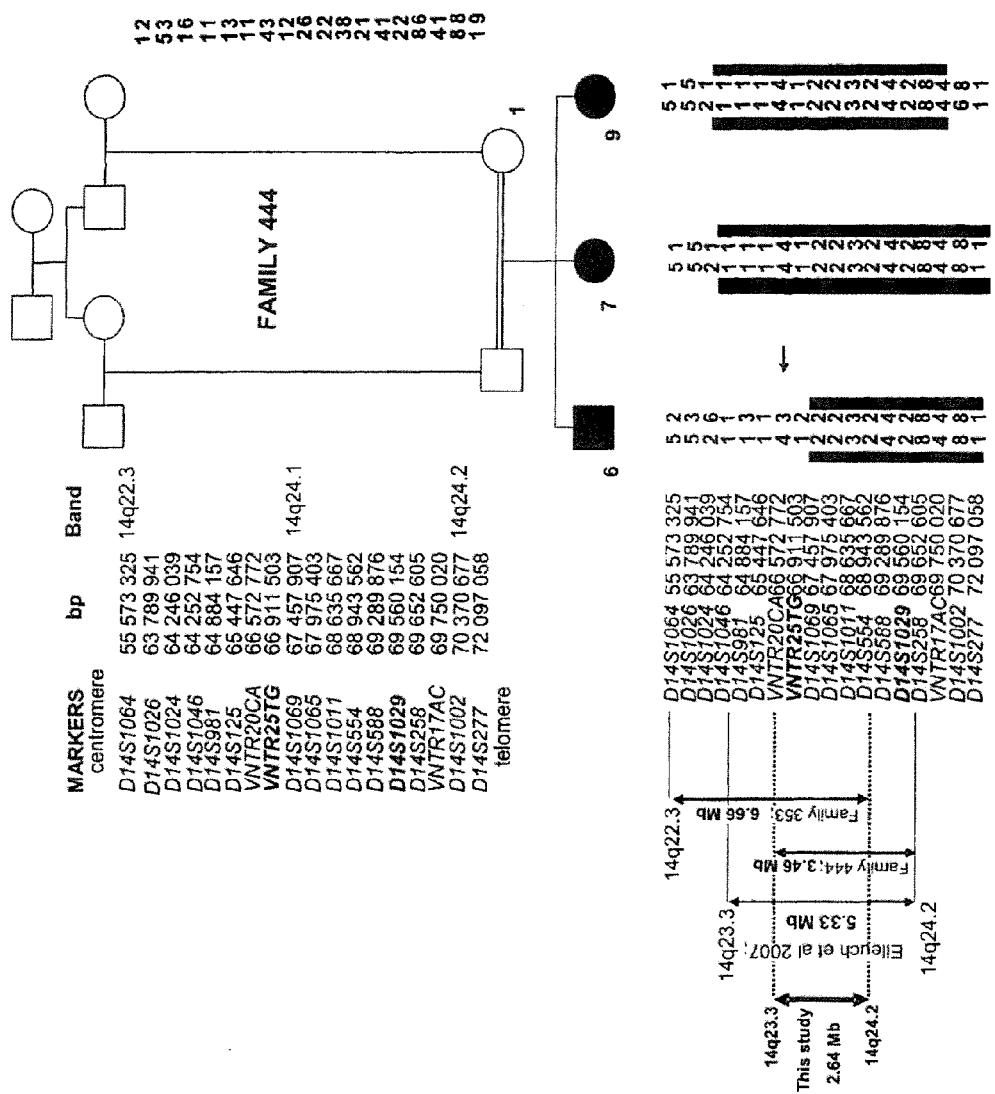

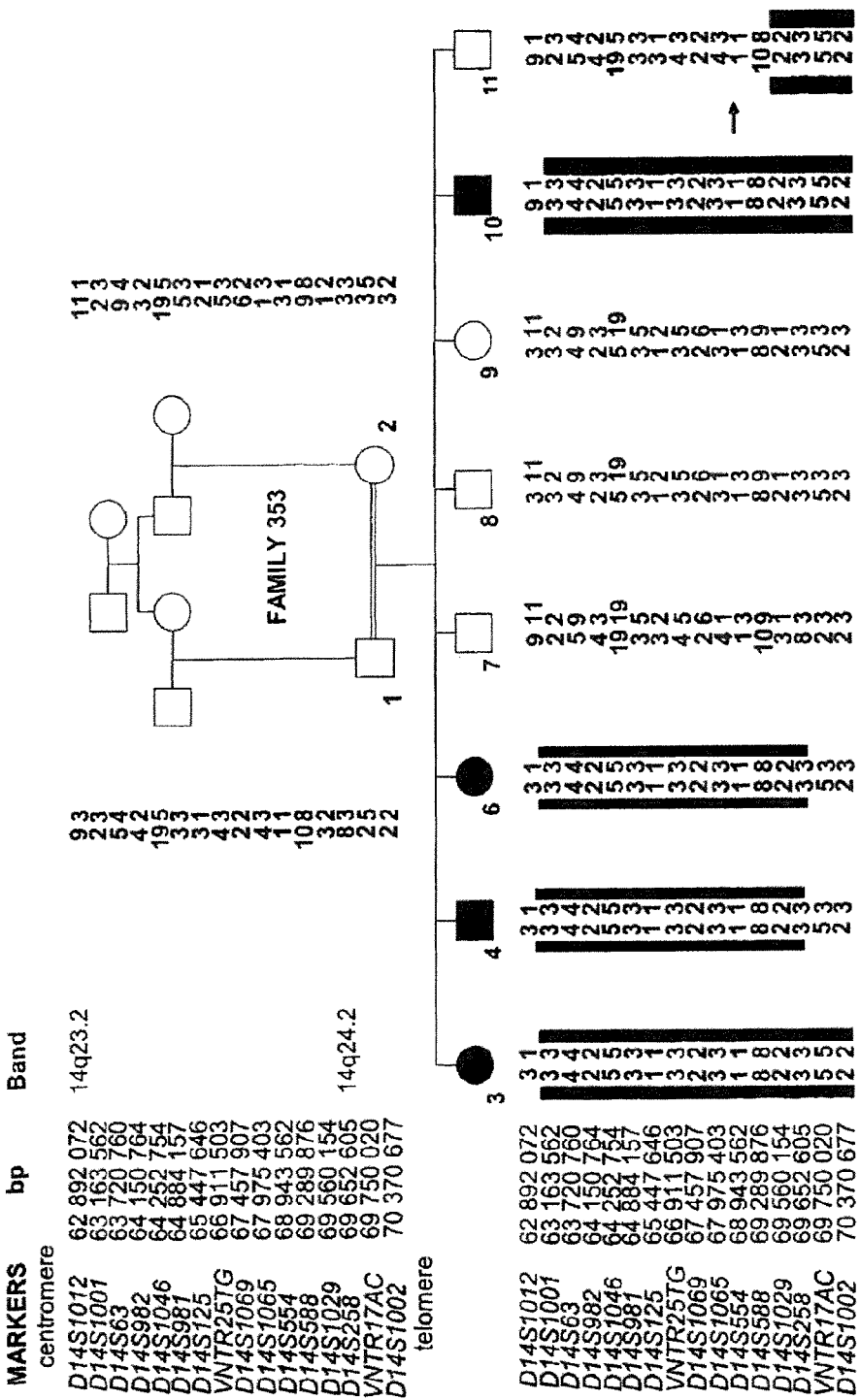
Figure 1 (continuation)

Figure 3:
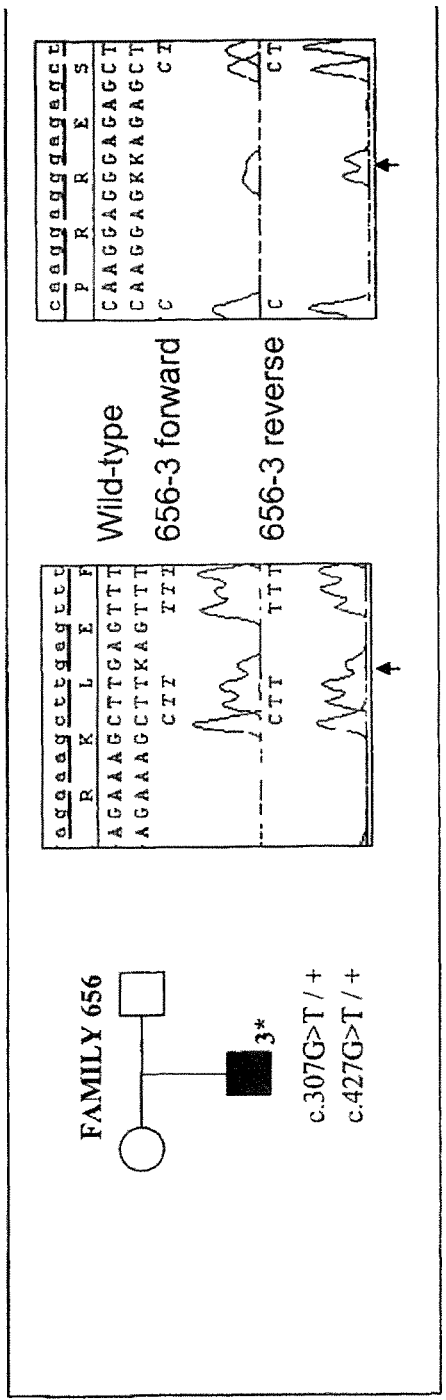

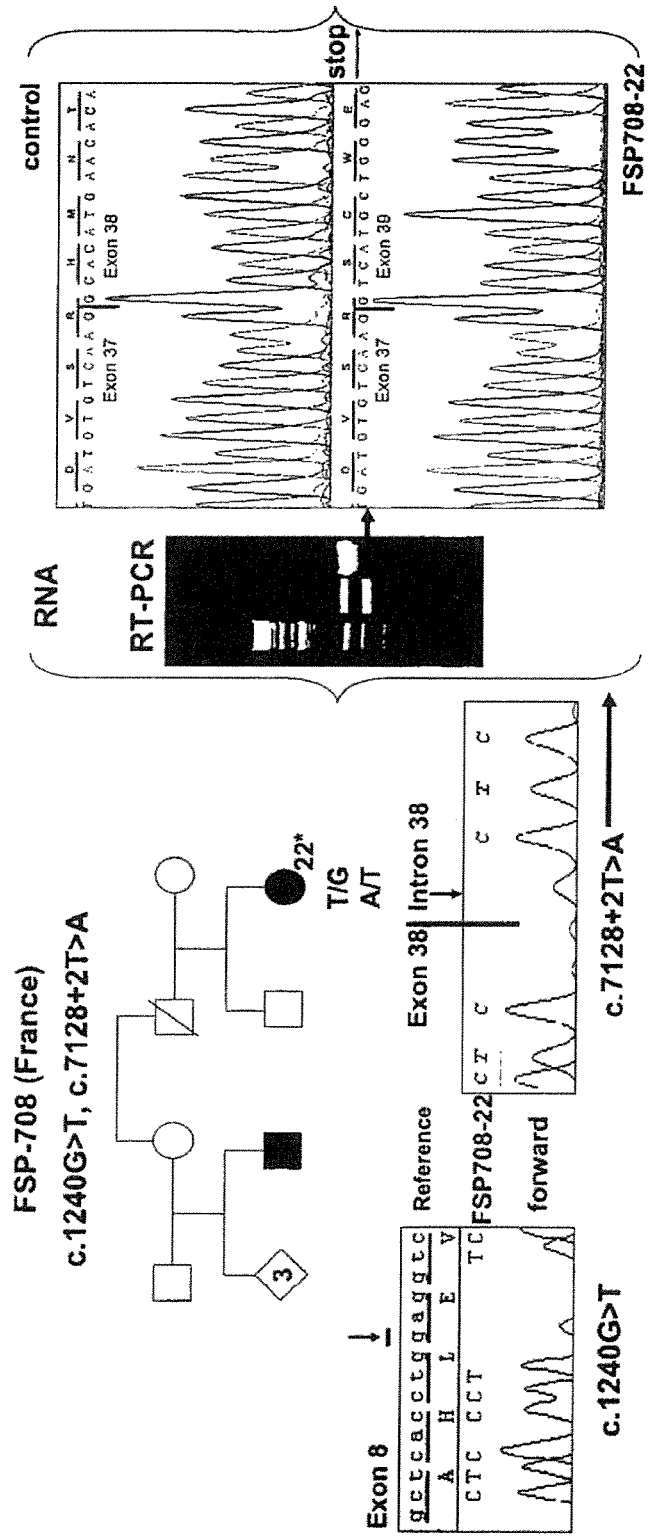
Figure 3 (continuation)

Figure 4:
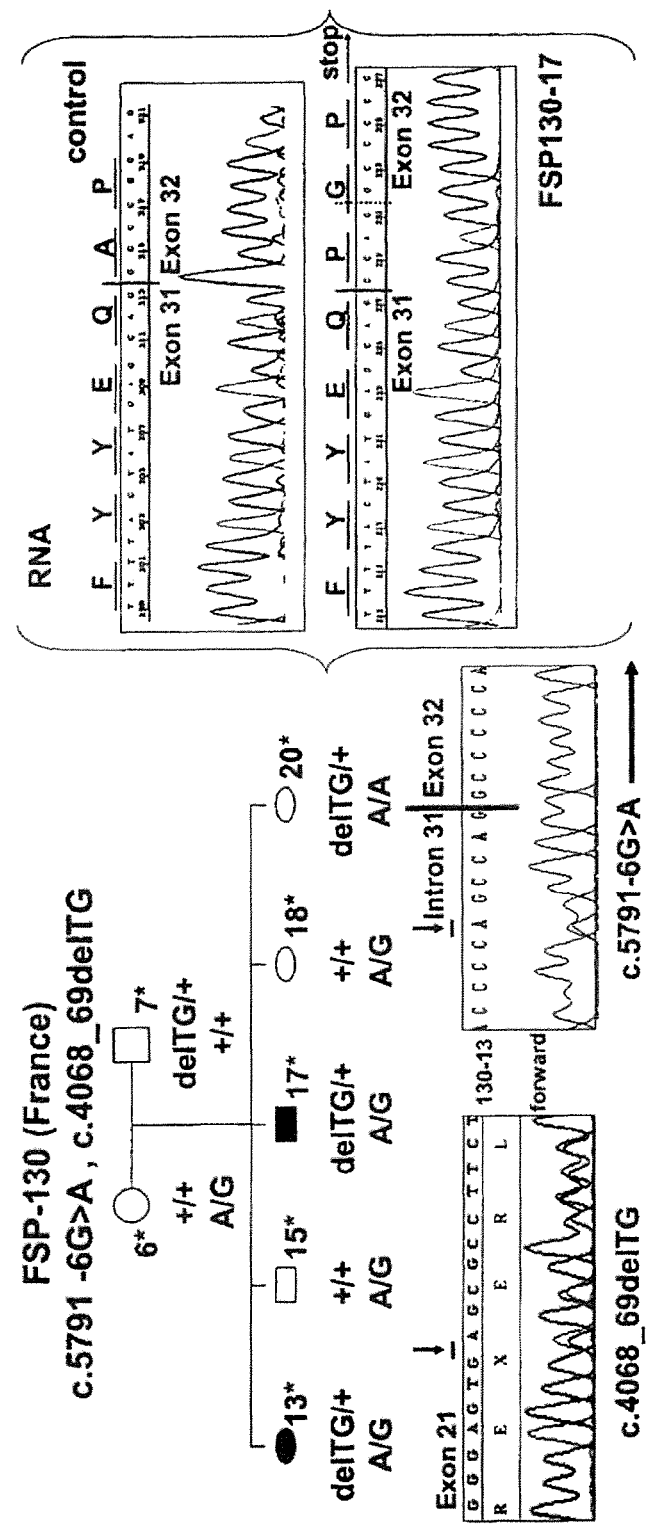

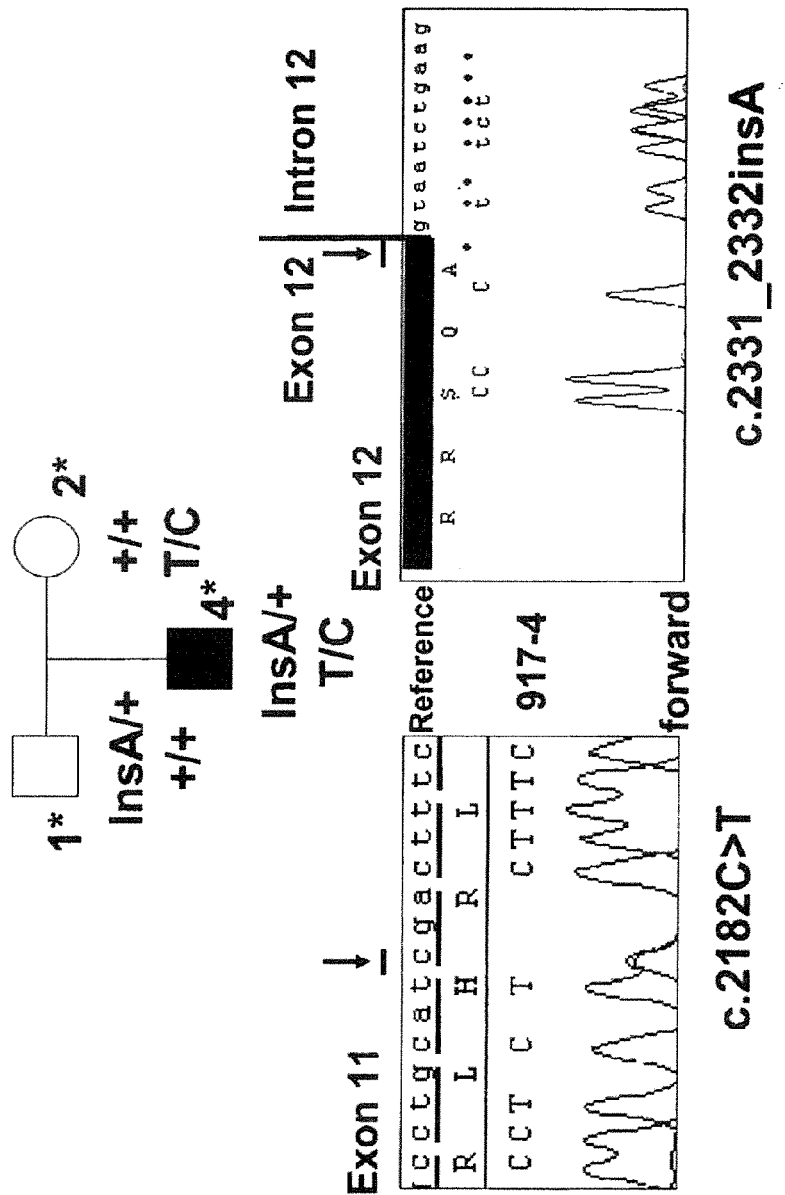
Figure 4 (continuation)

Figure 5:
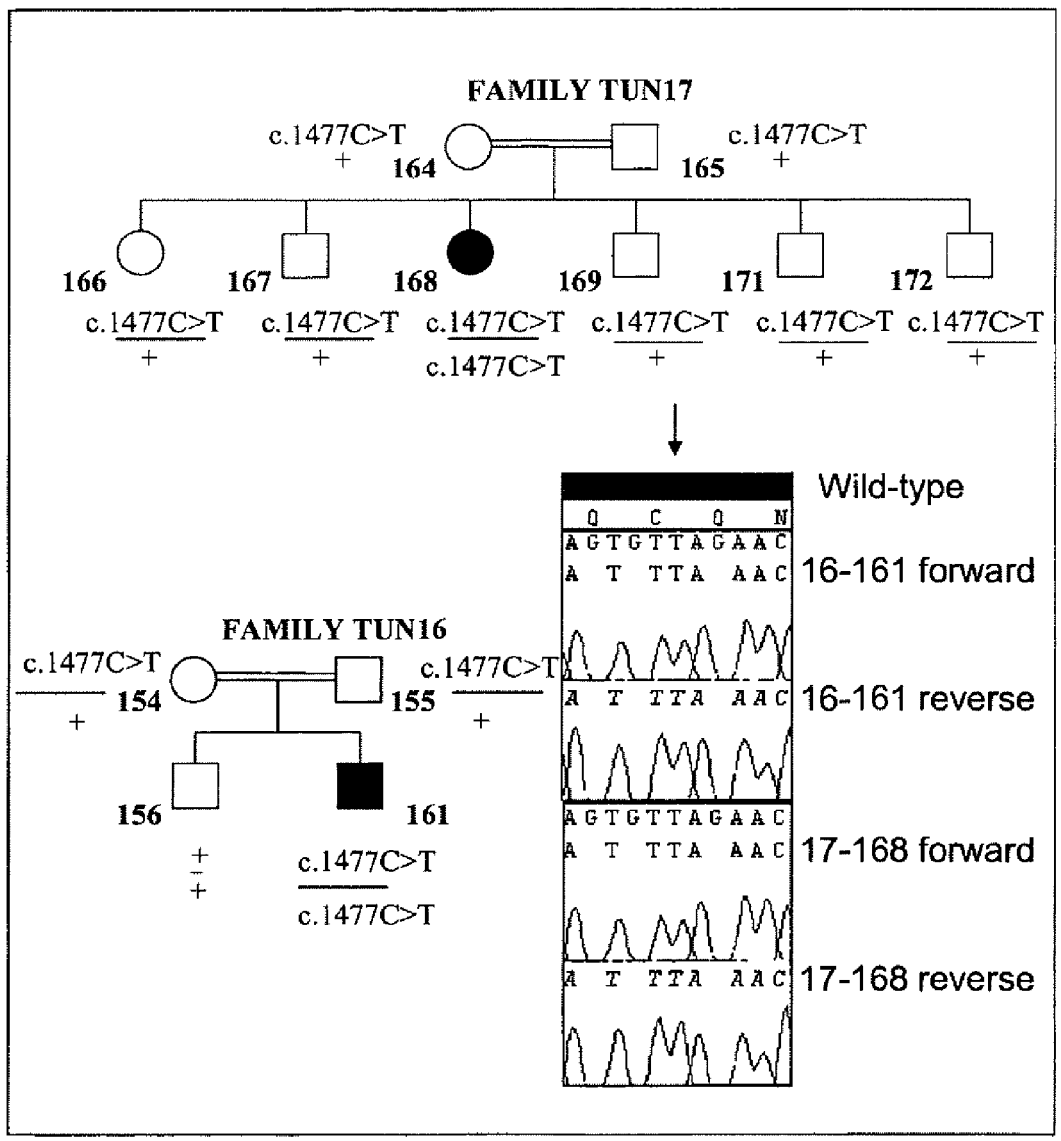

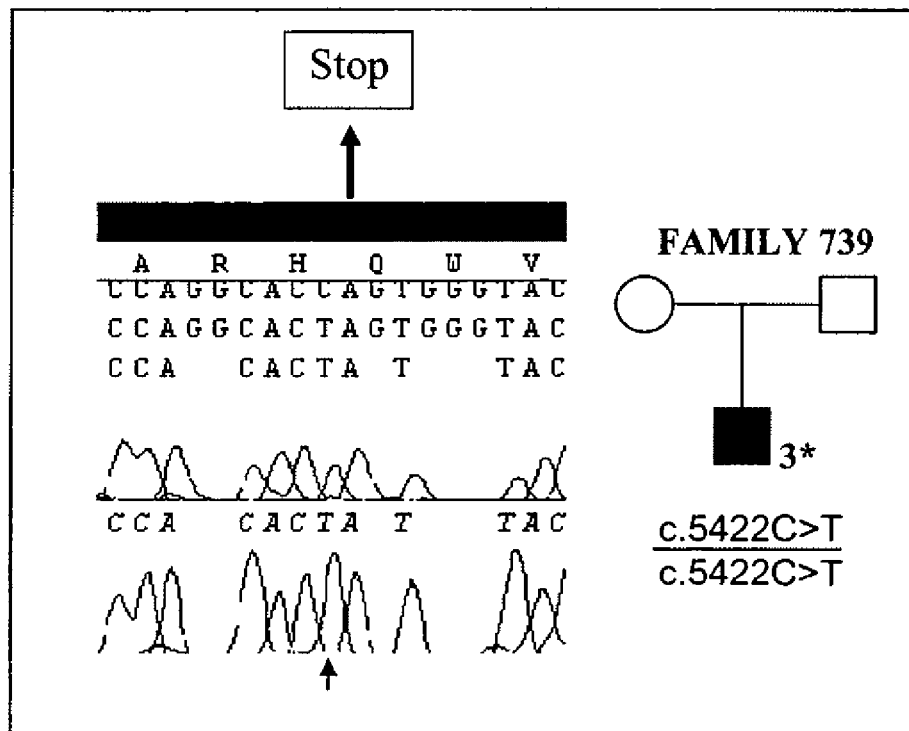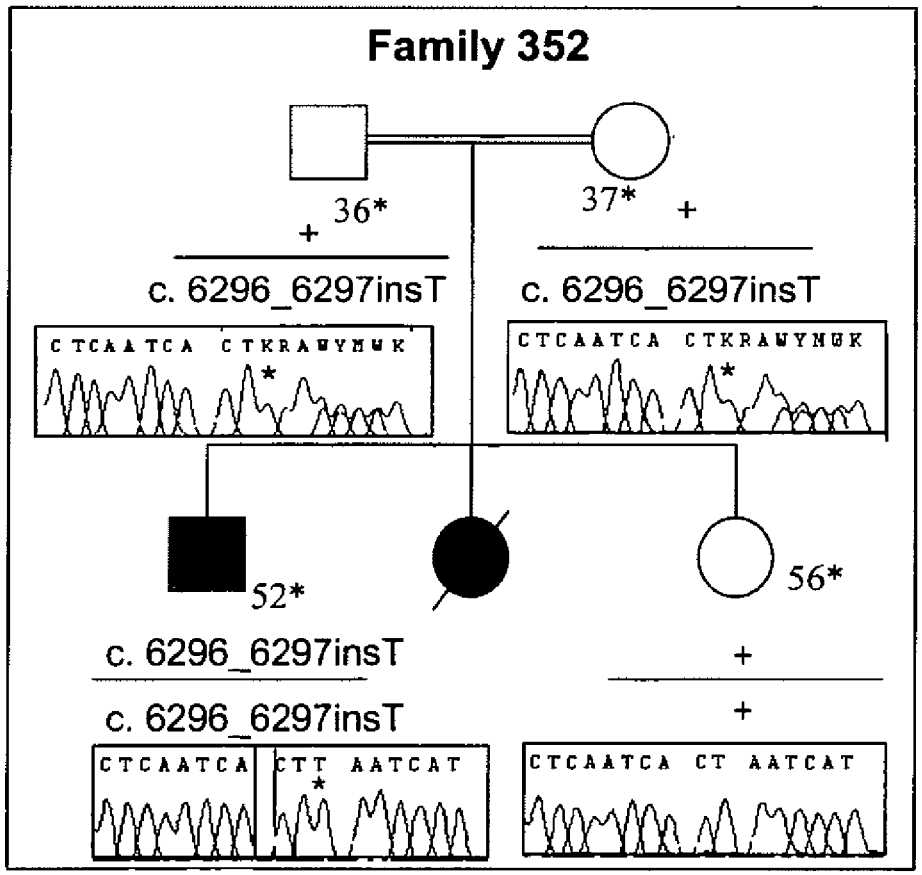
Figure 5 (continuation)

Figure 6:
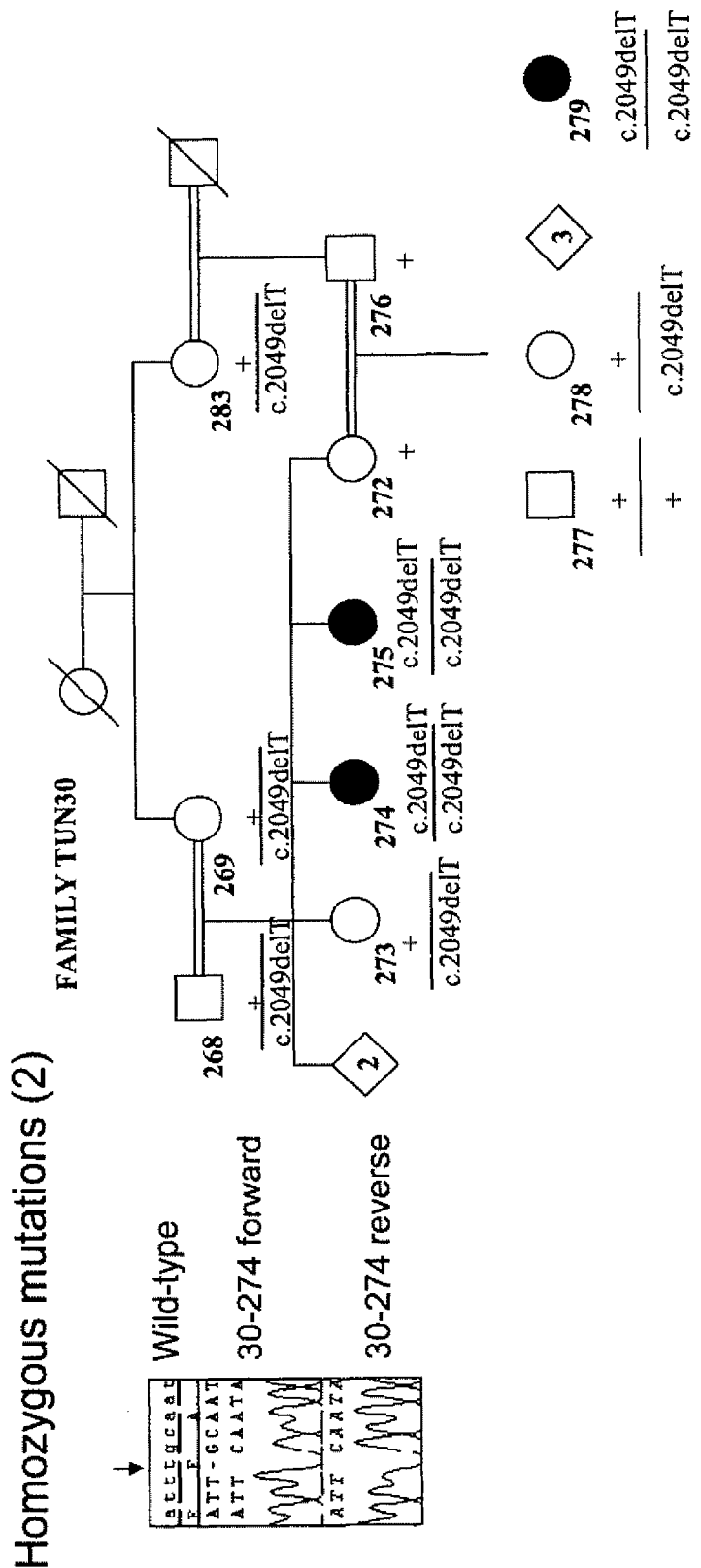

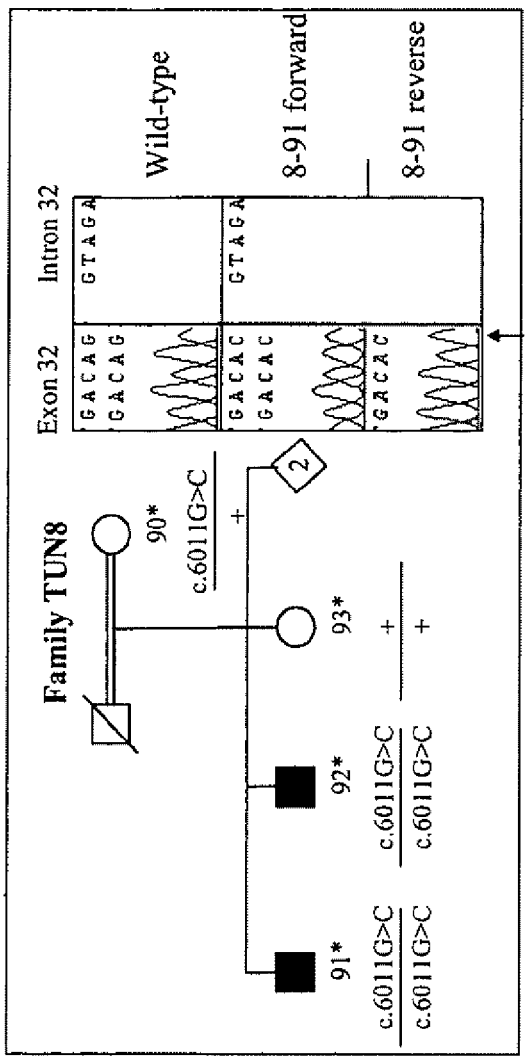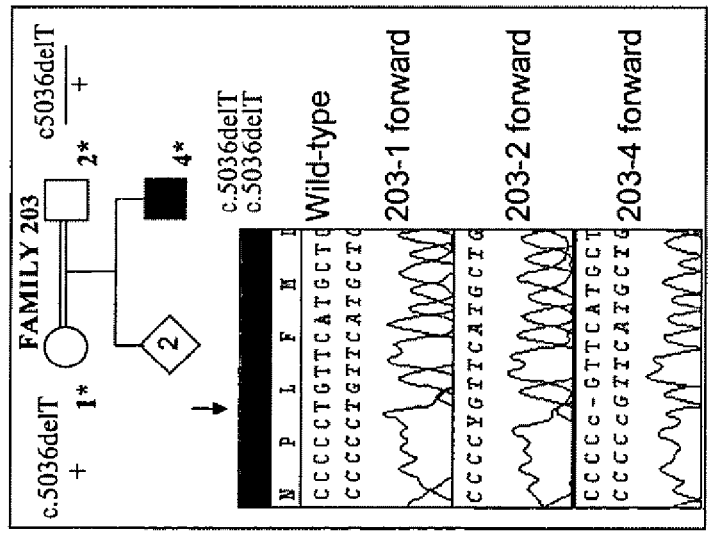
Figure 6 (continuation)

Figure 7-2

Figure 9:
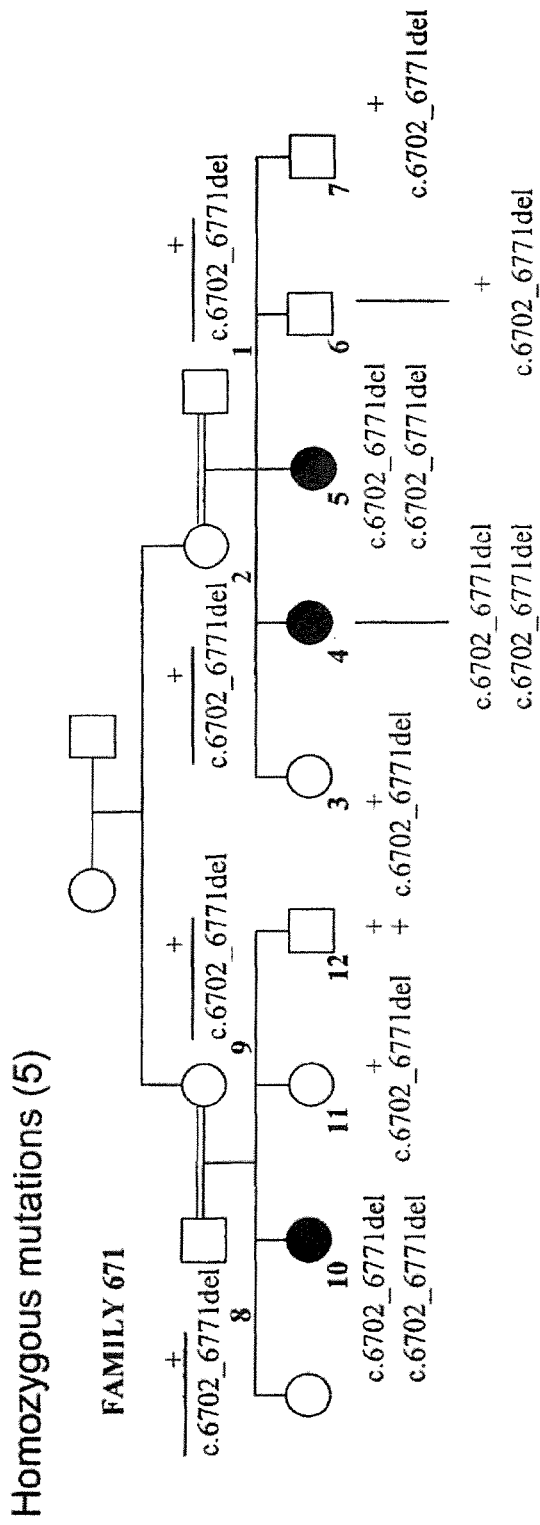

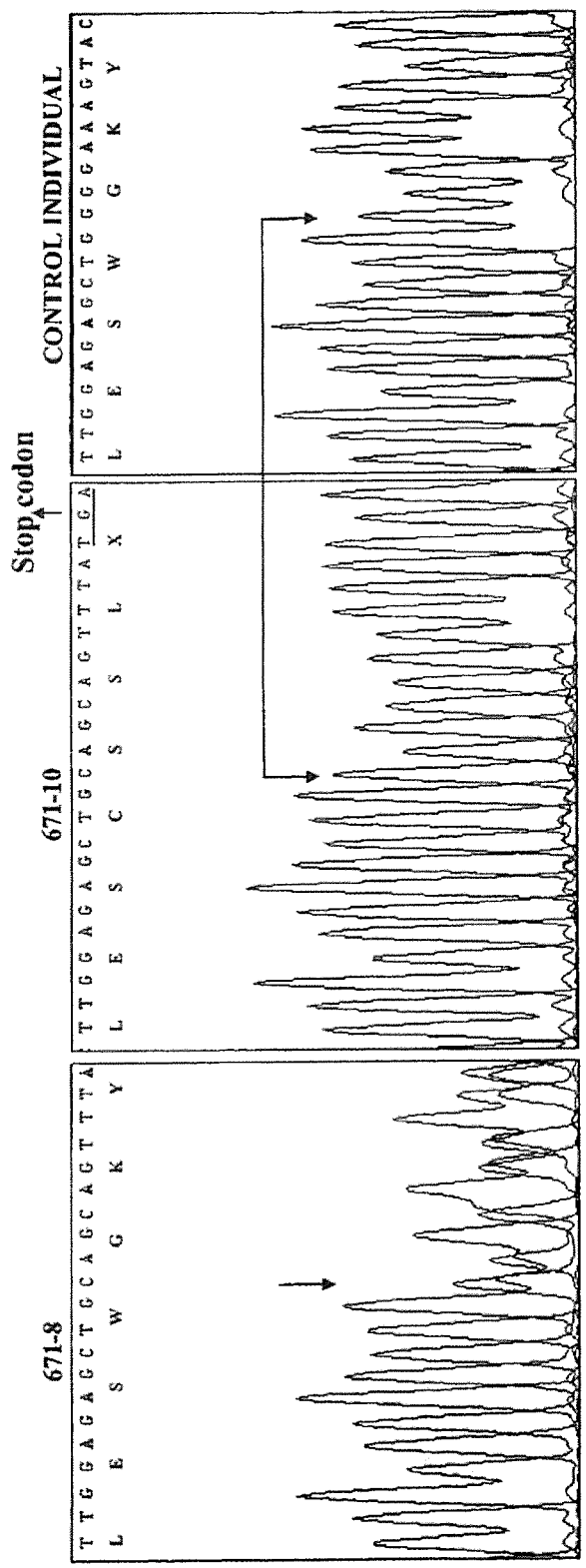
Figure 9 (continuation)

Figure 10:
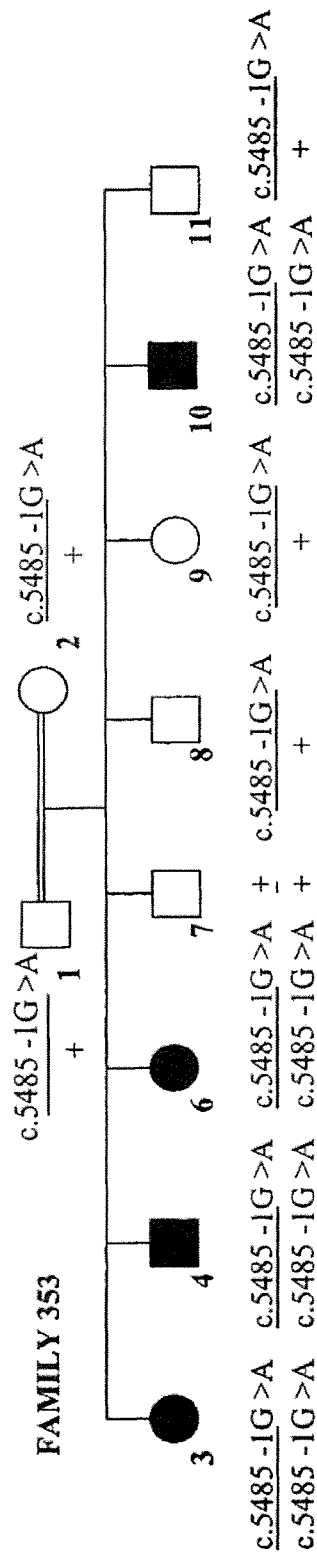

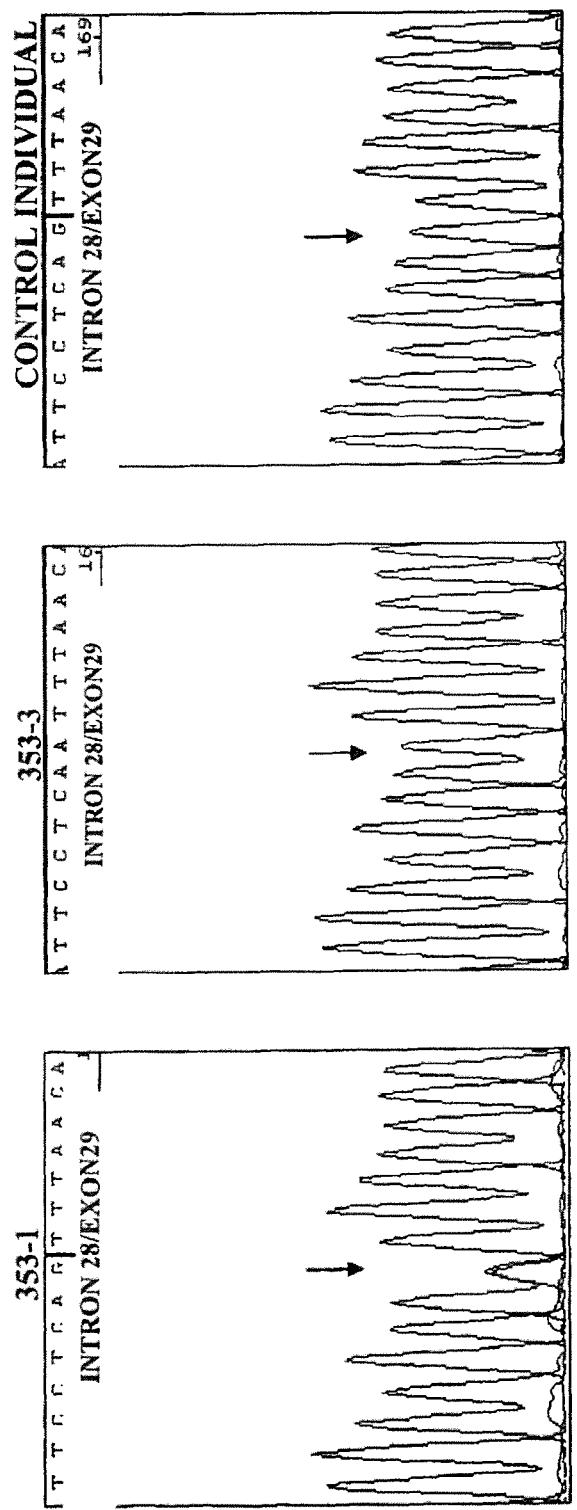
Figure 10 (continuation)

SEQUENCE LISTING

```
<160> NUMBER OF SEQ ID NOS: 131

<210> SEQ ID NO 1
<211> LENGTH: 9688
<212> TYPE: DNA
<213> ORGANISM: Homo sapiens

<400> SEQUENCE: 1
ggctcaaaca tggctgcgct gagagctcta ttgctttggg cgccgggagc aggaggtact      60
ccgcgaatga gaacattgag aatgtgttcg gcataactca tttctttgta tctccctgca     120
ctctgtgctg ggaaaatgaa tcatccattt ggaaaagagg aagctgcttc gcagaagcag     180 cttttttggat ttttctgcga atgcctgcgg aggggagaat gggagctggc acaggcatgt    240
gtacctcagc tacaggaggg acaagggat atcccaaaga gggtagaaga catacttcag      300
gcattggtgg tgtgtccaaa tctgctgaga tgtgggcagg acatcaaccc tcaaagagta     360
gcctgggtct ggcttcttgt actggagaaa tggttggccc gggaaaagaa gttactccca     420
gttgttttcc ggagaaagct tgagtttctt ttattgtcag aagacctcca aggtgacatt     480
ccagagaaca tcctcgagga gctgtatgag accttaacac agggtgcagt aggccacgtg     540
cctgacggaa atccaaggag ggagagctgg actcctcgtc tcagctccga agctgtctct     600
gtgctctggg atctcctgag gcagtctccc cagccagcac aggccctgct ggagctcctg     660
cttgaggagg atgacggtac tggcctctgt cactggcctc tgcagaatgc actggtggac     720
ctcattcgaa aggcattgcg ggctttgcag ggccctgatt cggtgccccc tggggtagtc     780
gatgccatct atggagccct gcggactctg cgttgccccg cagaaccact tggggttgag     840
ttgcatctcc tgtgtgagga actactagag gcctgcagga ccgagggag tcccctgcgg      900 gaggagcggc tgctcagctg cctgctgcac aaggccagcc ggggcctgct gtccctgtat     960
ggccatacct atgcagagaa ggtcacagaa aagccaccga gggctacagc ctcgggaaaa    1020
gtctcaccgg atcatctaga tcctgagcgg gcaatgctag ccctgttctc caatcccaac    1080
ccagccgagg cttggaaagt ggcctatttc tactgcctga gcaacaacaa acacttcctc    1140
gagcagattc tggtaacagc actaacattg ttgaaagaag aagacttccc aaatcttggc    1200
tgcctacttg atagagaatt caggcccctc agttgcctgc ttgtactcct gggctggaca    1260
cactgccaga gcctagagtc agccaagagg ctgctccaga ccctgcacag gacccagggc    1320
ccaggctgtg atgagctcct cagggatgcc tgtgatgggt tgtgggctca cctggaggtc    1380
ctggagtggt gcatacagca gagcagcaac cccataccaa agagagatct gttgtatcat    1440
ttacacggtg gagacagcca ctcagtgctc tacactctcc atcaccttac aaaccttcca    1500
gccctcaggg aggaagatgt tctcaagctc ttacagaaag tgccagccaa ggaccccag     1560 caagagcctg atgcagttga tgctccagtc cctgagcacc tgagccagtg tcagaacctg    1620
acactctacc agggcttctg tgccatgaag tatgccatct atgccctctg tgtaaactca    1680
```

```
caccagcact cccagtgcca ggactgcaaa gacagcctct ctgaggacct ggcctcagct    1740
acagagccag cgaatgactc tctctcctcc ccaggtgctg caaatctctt ctcaacttac    1800
ctggccaggt gtcaacagta tctgtgcagt attcctgact ctctgtgcct ggagcttctg    1860
gaaaacatct tctcattgct tctcatcacc tctgctgatc ttcacccaga gcctcacttg    1920
cctgaggact atgctgagga tgatgacatt gaggggaaga gcccctcagg tttgaggtcc    1980
ccatcagaga gccctcagca catagcacat cctgaaagga agtcagaacg gggttccctg    2040
ggagtcccaa agaccctttgc ttatacaatg ccaagccatg tgaaggcaga gccaaaagac    2100
agttacccag ggcctcatag gcacagcttt ttggacttaa aacactttac tagtggtatc    2160
agtggatttc tggctgatga atttgcaata ggggccttcc tcaggcttct ccaagagcaa    2220
ctggatgaga tcagtagccg cagccccct gagaagccaa agcaagaaag tcagagctgc    2280
tcaggaagca gagatggact gcagagccgc ctgcatcgac tttccaaggt tgtctctgag    2340
gcccagtgga gacacaaggt ggtgacaagc aaccatcgtt cagaggagca accttcccga    2400
agataccagc ctgccacacg tcaccccagt ctccgccggg gtcgtcggac aagaaggagc    2460
caggcagatg gccgagacag aggttcaaac ccatccctgg aaagtacaag tagtgagctg    2520
agcacaagta cgtcagaggg aagtctgagt gccatgtctg gccggaatga gctgcacagt    2580
agattgcacc cccatcctca aagttcactc atccccatga tgttctcccc acctgagtca    2640
ctgctggcat cctgcatcct tcgcgggaac ttcgcagaag cccatcaggt gctgttcacg    2700
ttcaacctga agtcctcacc cagttcaggg gaactgatgt tcatggagcg ctaccaggaa    2760
gtgatccaag aactggccca agtagagcac aagattgaaa accagaactc agatgcgggt    2820
agcagcacca ttcggagaac tggcagtggc cgctcaactc tacaggccat tggcagcgct    2880
gcagcagcag gaatggtgtt ttactctatc tctgacgtga ctgacaagct gctcaacacc    2940
tctggagacc ccatccccat gctccaggag acttttgga taagcacggc tctagtggag    3000
cccactgctc ccctgagaga ggttctggaa gacctcagtc cccctgccat ggctgcattt    3060
gacctagctt gctctcagtg ccagctctgg aaaacctgca agcagctttt ggagacagcc    3120
gaacggcgtt tgaatagtag ccttgaaagg cggggtcgac ggatagacca cgtactccta    3180
aatgctgatg gcattcgagg ttttccagtt gttcttcagc aaatcagtaa gagtctcaat    3240
tatctgctta tgtcagccag tcaaaccaaa tcagagagtg tggaagaaaa gggaggaggc    3300
cctccacggt gcagcatcac tgaactgctt cagatgtgct ggcccagcct aagcgaggac    3360
tgtgttgcca gccacaccac cctctcccag cagctagatc aggtccttca gtcactgaga    3420
gaggcactag agctgccaga gcccaggact cctccactgt cttccctggt ggagcaggca    3480
gcccagaaag ctccagaggc agaggcccac cctgtgcaga tccagactca gctcctccag    3540
aagaacctgg gcaaacagac cccatcaggc agcaggcaga tggactactt gggcaccttc    3600
ttcagttact gcagcaccct tgctgcagtt ctccttcaaa gtttgagctc tgagcctgat    3660
catgtggagg tcaaggtagg aaatcccttt gttctgctgc aacagagctc ttcccaactg    3720
gtgtcacatc tcctgtttga gagacaagtt cccccagaga gactggcagc ccttctggcc    3780
caagagaatc tcagcctaag tgtgccacag gtcatcgtca gctgctgctg tgagcccctt    3840
gctctttgct catcccggca aagccagcag acctcctccc tcctgactcg tctgggtact    3900
ctggcccagc tacacgcctc tcactgcctg gatgacctcc cactttctac accgagctcc    3960
ccgaggacaa ctgagaaccc tacattggaa agaaagccct actcctcccc aagggactca    4020
tcactcccag ccctcacctc ctctgccttg gcctttctta agtcacgctc aaagctccta    4080
```

```
gctacggtgg cctgcctggg ggcttccccg aggttaaagg tcagcaaacc cagcttgtca   4140
tggaaggaac ttcgtggccg cagggaggtg cctctggctg cagagcaggt agcccgggag   4200
tgtgagcgcc ttctggaaca attccctctg tttgaggcct tcctcctggc tgcctgggag   4260
cccctgcgag ggtctttgca gcaggggcag agtctggcag tgaatctctg tggttgggcc   4320
agtctttcta ccgttctcct gggcctacat tctcccattg ccctagatgt actgagtgag   4380
gcttttgagg aatccttggt ggccagagat tggtcccggg cccttcagct cactgaagtg   4440
tacgggcgag atgtggacga tttgagcagc ataaaggatg cagtcctgag ctgtgctgtg   4500
gcatgtgaca aagaaggttg gcaatacctg tttcccgtga aggatgcatc tctgagaagt   4560
cggctggccc tacagtttgt ggacaggtgg cccctggagt catgcctgga gattctggcc   4620
tactgcattt cagacacggc tgtccaagaa ggactaaagt gtgagctaca gaggaagctg   4680
gcggagctgc aggtgtatca gaagattctg ggtttgcagt ctcccccagt gtggtgtgac   4740
tggcagacct tgaggagctg ttgtgttgag gacccatcaa ctgtcatgaa catgattcta   4800
gaagcacagg agtatgaact gtgtgaagag tggggctgcc tgtaccccat tccaagagaa   4860
catttaatca gccttcatca aaagcatctt ctccaccttc tagaaagaag agatcatgac   4920
aaggctctgc aactcctgcg aagaatccct gaccccacca tgtgccttga agtgacagag   4980
caatccctcg accagcacac tagcttggcc acttctcact tcttggccaa ctacctcacc   5040
acccacttct atggacaact gactgctgtc cgacaccgtg aaatccaggc gctgtatgtg   5100
ggatccaaga ttctgctgac cctgcctgag cagcaccggg ccagctattc ccacttgtcc   5160 tctaacccc tgttcatgct ggagcagctg cttatgaaca tgaaggtgga ttgggccact   5220
gtggctgtgc agactctcca gcagctgctg gttggacagg agattggctt cactatggac   5280
gaggtggact cactgctttc cagatacgca gagaaagccc tggactttcc ataccctcag   5340
agggagaaac gatcagattc tgtgattcac ctccaagaaa ttgtccacca ggctgcagat   5400
cccgagaccc tccctagatc accatcagca gagttctctc ctgctgctcc tcctggtatc   5460
tccagtatac attcccctag tctaagggaa aggagtttcc caccaaccca gccctcacag   5520
gaatttgtgc ccccagcgac acccctgcc aggcaccagt gggtaccgga tgagactgag   5580
agtatctgca tggtctgctg cagggagcac ttcaccatgt ttaacaggcg tcatcattgt   5640
cgccgctgtg gccggctagt gtgcagctcc tgctccacta agaaaatggt ggttgaaggc   5700
tgcagagaga accctgctcg tgtgtgtgat cagtgctata gttactgcaa caaagatgta   5760
ccagaggagc cttcagaaaa accagaagct ctagacagct ccaagaatga aagccctcca   5820
tactcgtttg tggtgagagt ccccaaagca gatgaggtgg aatggatttt ggatctcaaa   5880
gaggaggaaa atgagctggt gcggagtgaa ttttactatg agcaggcccc cagcgcctcc   5940
ttgtgcattg ccatcctgaa tctgcaccgg acagcattg cctgtggtca ccagctgatt   6000
gagcactgct gcaggctctc caagggcctc accaacccag aggtgatgc cgggctgctc   6060 acggacatca tgaagcagct gctgttcagc gccaagatga tgttcgtcaa agccggccag   6120
agccaagact ggctcttttg tgacagctac atcagcaagg tagatgtgct gaatatttta   6180
gttgctgctg cctatcgcca cgtgccatct ttggatcaga tcttgcagcc agctgcagta   6240
accaggctaa ggaaccagct tttggaagcc gagtactacc aactgggcgt tgaggtctcc   6300
acaaagactg gcttgatac caccggggcg tggcatgctt ggggcatggc ctgcctcaaa   6360
gccgggaacc tcactgctgc acgggagaag ttcagtcgct gtctgaagcc cccatttgac   6420
```

```
ctcaatcagc tgaatcatgg ctcaaggctg gtgcaggatg tggttgagta cctagagtcc    6480
acagtgaggc cctttgtatc cttgcaagat gacgattact ttgccaccct gagggaactg    6540
gaagctaccc ttcggacgca gagcctttct ctggcagtga ttcctgaagg gaaaatcatg    6600
aacaacacct actaccagga atgcctcttc tacctgcaca actatagcac caacctggcc    6660
atcatcagct tctacgtgag gcacagctgc ctgcgggaag ctcttctgca ccttctcaac    6720
aaggagagtc ctccagaagt ttttatagaa ggcattttcc aaccaagcta taaaagtggg    6780
aagctacaca ctttggagaa cttgctagaa tccattgatc caaccttgga gagctgggga    6840
aagtacttga ttgctgcctg ccaacattta cagaagaaga actactacca cattctgtat    6900
gagctgcagc agtttatgaa ggaccaagtt cgggccgcca tgacctgtat tcggttcttc    6960
agtcacaaag caaagtcata tacagaactg ggagagaagc tctcatggct acttaaggcc    7020
aaggaccacc tgaagatcta cctccaagaa acatcccgca gctctggaag gaagaaaacc    7080
acattcttca gaaagaagat gactgcagct gatgtgtcaa ggcacatgaa cacacttcag    7140
ctgcagatgg aagtgaccag gttcttgcat cggtgcgaaa gtgctgggac ctctcaaatc    7200
accactttgc ctctgccaac cctgtttgga aataaccaca tgaaaatgga tgttgcctgc    7260
aaggtcatgc tgggagggaa aaatgtagaa gatggttttg gaattgcttt ccgtgttctg    7320
caggacttcc agctggatgc tgccatgacc tactgcagag ctgcccgcca gttggtggag    7380
aaagagaagt acagtgagat ccagcaactg ctcaaatgtg tcagtgagtc aggcatggca    7440
gccaaaagtg acggggacac catcctcctc aactgcctgg aagcgttcaa gagaattccg    7500
ccccaggagc tggagggcct gatccaggca atacacaatg atgacaacaa ggttcgggcc    7560
tacctgatat gttgcaaact gcgttctgcc tacttgattg ctgtgaagca agaacactca    7620
cgggccacag cccttgtcca gcaggtgcag caggccgcca agagcagcgg ggatgcagta    7680
gtgcaagaca tctgtgccca gtggcttctg acaagccacc cccggggtgc ccatggccca    7740
ggctccagga agtgaccttg gcagtgggg ccaggaacac gtggcctgag agctgggcaa    7800
cagcagtgat ggcgatgccc tccacctctt tcctccagtg gagtgggact tctctggctc    7860
tgccctaggt tggaaagagt tggattggac cctacttgcc ttcccgggca aggataggac    7920 cttttcacgca agtgccatgt ttctctaaaa ttgtggaatc tatgtgtgtt tgtctggaga    7980
tggccagttc tttctacctc agagtgagtg agtgagtatg tgtgcacaca cgtgtgcatg    8040
ttcctgtgcg ctgatgttta cgcccaagca tttctgaaca aatgaaactc ttctccattt    8100
aaaagaggca ctttactta gacttgccac tctgaaaacc ttccctgcgt tttggttctt    8160
gacccgggtt gtcctgtttg tatagtcccc cctctgtgga cgtgctttag tagctcctct    8220
tacctagagg gcttttacag agaattagag caacaccaaa aggattgcct cttttccttc    8280
cttcccattc caaaattcag agatggcttt ggggcaagtg ctacctgtgg aataaacctg    8340
ttttccaggt gtctcttctc ccaagcacaa gaagtcctgg agtctttgga aggtagtctg    8400
aatagaaggg ttttcaggtg caggcatctg aaagctgtgg gtatgtgtat aaatgatcag    8460
gtctgtgagg ctaacacggg caagagggaa agaaaggcta accatccaaa cagggataca    8520
ggggaggcgg tgggggtgg tgggggagc gggtgctcac aagcacagag ctgcctgttg    8580
tgaatgtccc tgctgcaaag ttggtgggtg agagaatggg acttcctctt tgagagtctg    8640
gggagagaaa aggtggccag gatcctagga ctgaatgact cgattttacc tatttgagct    8700
gcagtcctgt ttgcgctcct tgaattggtt aggaagctgc ttccttttcc ctcctgcttc    8760
ccttcagtct cttcaggacc acaggatgga tatgcagaca tgtgggtca ttgggaaggg    8820
```

```
agtgcgcttc ttttctctgt cttagaaaag ggagtcaagg gttggctttg gaattgggcc    8880
tctggacaga gtcagaatga gggaataatg aataggtcac atctggttgg tggaaaacta    8940
ggtgaagtgc ttctttaata tgcactgtct tgtcttccca cgcaagatgt gacaatgttt    9000
gagaaaaggt gtgtcatact cagtgacttc aatttgcaaa tgtggggcct aaagaaagct    9060
ctgcagctct gaacctctca ctggccagag ctcagcctat tggtcccatc catgatgctg    9120
agacaaacag aaactggaag ctgaagtcag tgtctctggt gcttagaaac cctgtggatt    9180
tccctctgaa ccaagatttt tagtagtaaa ataaacaact catggacatc tgtcagatga    9240
gaagttttgg tcctgttaga gaggagaaag actgtaatga aactactaga cccatttggg    9300
ctaaagtttg cttttccctt ccttgagtca tagaacatat ccatctccca ggaaatgtcc    9360
ttctctggcg tctgcttgcc cttctgagtc tgcctttttt gcactgaaca taagcacttt    9420
atactaatgg gtcacaaatc ttgcagccct taatttggga taagaccaga ttttcctgac    9480
attttcctct aactcattga actatcaaat tataggcaac cactgactag actgatatga    9540
gatgaggcta aaagcctttg aacaccacgc tgtagtctcc aacagaaaaa caccaccaaa    9600
acagataccc atgttgaggg gttgaatgtt ttactacaaa caagccacaa taaagtgtct    9660
atcaacatga aaaaaaaaaa aaaaaaaa                                        9688
```

<210> SEQ ID NO 2
<211> LENGTH: 2539
<212> TYPE: PRT
<213> ORGANISM: Homo sapiens

<400> SEQUENCE: 2

```
Met Asn His Pro Phe Gly Lys Glu Glu Ala Ala Ser Gln Lys Gln Leu
1               5                   10                  15

Phe Gly Phe Phe Cys Glu Cys Leu Arg Arg Gly Glu Trp Glu Leu Ala
                20                  25                  30

Gln Ala Cys Val Pro Gln Leu Gln Glu Gly Gln Gly Asp Ile Pro Lys
            35                  40                  45

Arg Val Glu Asp Ile Leu Gln Ala Leu Val Val Cys Pro Asn Leu Leu
        50                  55                  60

Arg Cys Gly Gln Asp Ile Asn Pro Gln Arg Val Ala Trp Val Trp Leu
65                  70                  75                  80

Leu Val Leu Glu Lys Trp Leu Ala Arg Glu Lys Lys Leu Leu Pro Val
                85                  90                  95

Val Phe Arg Arg Lys Leu Glu Phe Leu Leu Ser Glu Asp Leu Gln
                100                 105                 110

Gly Asp Ile Pro Glu Asn Ile Leu Glu Glu Leu Tyr Glu Thr Leu Thr
            115                 120                 125

Gln Gly Ala Val Gly His Val Pro Asp Gly Asn Pro Arg Arg Glu Ser
        130                 135                 140

Trp Thr Pro Arg Leu Ser Ser Glu Ala Val Ser Val Leu Trp Asp Leu
145                 150                 155                 160

Leu Arg Gln Ser Pro Gln Pro Ala Gln Ala Leu Leu Glu Leu Leu
                165                 170                 175

Glu Glu Asp Asp Gly Thr Gly Leu Cys His Trp Pro Leu Gln Asn Ala
            180                 185                 190

Leu Val Asp Leu Ile Arg Lys Ala Leu Arg Ala Leu Gln Gly Pro Asp
        195                 200                 205

Ser Val Pro Pro Gly Val Val Asp Ala Ile Tyr Gly Ala Leu Arg Thr
```

-continued

```
            210                 215                 220
Leu Arg Cys Pro Ala Glu Pro Leu Gly Val Glu Leu His Leu Leu Cys
225                 230                 235                 240

Glu Glu Leu Leu Glu Ala Cys Arg Thr Glu Gly Ser Pro Leu Arg Glu
                245                 250                 255

Glu Arg Leu Leu Ser Cys Leu Leu His Lys Ala Ser Arg Gly Leu Leu
                260                 265                 270

Ser Leu Tyr Gly His Thr Tyr Ala Glu Lys Val Thr Glu Lys Pro Pro
            275                 280                 285

Arg Ala Thr Ala Ser Gly Lys Val Ser Pro Asp His Leu Asp Pro Glu
290                 295                 300

Arg Ala Met Leu Ala Leu Phe Ser Asn Pro Asn Pro Ala Glu Ala Trp
305                 310                 315                 320

Lys Val Ala Tyr Phe Tyr Cys Leu Ser Asn Asn Lys His Phe Leu Glu
                325                 330                 335

Gln Ile Leu Val Thr Ala Leu Thr Leu Leu Lys Glu Glu Asp Phe Pro
                340                 345                 350

Asn Leu Gly Cys Leu Leu Asp Arg Glu Phe Arg Pro Leu Ser Cys Leu
                355                 360                 365

Leu Val Leu Leu Gly Trp Thr His Cys Gln Ser Leu Glu Ser Ala Lys
            370                 375                 380

Arg Leu Leu Gln Thr Leu His Arg Thr Gln Gly Pro Gly Cys Asp Glu
385                 390                 395                 400

Leu Leu Arg Asp Ala Cys Asp Gly Leu Trp Ala His Leu Glu Val Leu
                405                 410                 415

Glu Trp Cys Ile Gln Gln Ser Ser Asn Pro Ile Pro Lys Arg Asp Leu
            420                 425                 430

Leu Tyr His Leu His Gly Gly Asp Ser His Ser Val Leu Tyr Thr Leu
                435                 440                 445

His His Leu Thr Asn Leu Pro Ala Leu Arg Glu Glu Asp Val Leu Lys
450                 455                 460

Leu Leu Gln Lys Val Pro Ala Lys Asp Pro Gln Gln Glu Pro Asp Ala
465                 470                 475                 480

Val Asp Ala Pro Val Pro Glu His Leu Ser Gln Cys Gln Asn Leu Thr
                485                 490                 495

Leu Tyr Gln Gly Phe Cys Ala Met Lys Tyr Ala Ile Tyr Ala Leu Cys
            500                 505                 510

Val Asn Ser His Gln His Ser Gln Cys Gln Asp Cys Lys Asp Ser Leu
                515                 520                 525

Ser Glu Asp Leu Ala Ser Ala Thr Glu Pro Ala Asn Asp Ser Leu Ser
530                 535                 540

Ser Pro Gly Ala Ala Asn Leu Phe Ser Thr Tyr Leu Ala Arg Cys Gln
545                 550                 555                 560

Gln Tyr Leu Cys Ser Ile Pro Asp Ser Leu Cys Leu Glu Leu Leu Glu
                565                 570                 575

Asn Ile Phe Ser Leu Leu Ile Thr Ser Ala Asp Leu His Pro Glu
                580                 585                 590

Pro His Leu Pro Glu Asp Tyr Ala Glu Asp Asp Ile Glu Gly Lys
            595                 600                 605

Ser Pro Ser Gly Leu Arg Ser Pro Ser Glu Ser Pro Gln His Ile Ala
            610                 615                 620

His Pro Glu Arg Lys Ser Glu Arg Gly Ser Leu Gly Val Pro Lys Thr
625                 630                 635                 640
```

```
Leu Ala Tyr Thr Met Pro Ser His Val Lys Ala Glu Pro Lys Asp Ser
                645                 650                 655

Tyr Pro Gly Pro His Arg His Ser Phe Leu Asp Leu Lys His Phe Thr
            660                 665                 670

Ser Gly Ile Ser Gly Phe Leu Ala Asp Glu Phe Ala Ile Gly Ala Phe
        675                 680                 685

Leu Arg Leu Leu Gln Glu Gln Leu Asp Glu Ile Ser Ser Arg Ser Pro
    690                 695                 700

Pro Glu Lys Pro Lys Gln Glu Ser Gln Ser Cys Ser Gly Ser Arg Asp
705                 710                 715                 720

Gly Leu Gln Ser Arg Leu His Arg Leu Ser Lys Val Val Ser Glu Ala
                725                 730                 735

Gln Trp Arg His Lys Val Val Thr Ser Asn His Arg Ser Glu Glu Gln
            740                 745                 750

Pro Ser Arg Arg Tyr Gln Pro Ala Thr Arg His Pro Ser Leu Arg Arg
        755                 760                 765

Gly Arg Arg Thr Arg Arg Ser Gln Ala Asp Gly Arg Asp Arg Gly Ser
    770                 775                 780

Asn Pro Ser Leu Glu Ser Thr Ser Ser Glu Leu Ser Thr Ser Thr Ser
785                 790                 795                 800

Glu Gly Ser Leu Ser Ala Met Ser Gly Arg Asn Glu Leu His Ser Arg
                805                 810                 815

Leu His Pro His Pro Gln Ser Ser Leu Ile Pro Met Met Phe Ser Pro
            820                 825                 830

Pro Glu Ser Leu Leu Ala Ser Cys Ile Leu Arg Gly Asn Phe Ala Glu
        835                 840                 845

Ala His Gln Val Leu Phe Thr Phe Asn Leu Lys Ser Ser Pro Ser Ser
    850                 855                 860

Gly Glu Leu Met Phe Met Glu Arg Tyr Gln Glu Val Ile Gln Glu Leu
865                 870                 875                 880

Ala Gln Val Glu His Lys Ile Glu Asn Gln Asn Ser Asp Ala Gly Ser
                885                 890                 895

Ser Thr Ile Arg Arg Thr Gly Ser Gly Arg Ser Thr Leu Gln Ala Ile
            900                 905                 910

Gly Ser Ala Ala Ala Gly Met Val Phe Tyr Ser Ile Ser Asp Val
        915                 920                 925

Thr Asp Lys Leu Leu Asn Thr Ser Gly Asp Pro Ile Pro Met Leu Gln
    930                 935                 940

Glu Asp Phe Trp Ile Ser Thr Ala Leu Val Glu Pro Thr Ala Pro Leu
945                 950                 955                 960

Arg Glu Val Leu Glu Asp Leu Ser Pro Pro Ala Met Ala Ala Phe Asp
                965                 970                 975

Leu Ala Cys Ser Gln Cys Gln Leu Trp Lys Thr Cys Lys Gln Leu Leu
            980                 985                 990

Glu Thr Ala Glu Arg Arg Leu Asn  Ser Ser Leu Glu Arg  Arg Gly Arg
        995                 1000                  1005

Arg Ile  Asp His Val Leu Leu  Asn Ala Asp Gly Ile  Arg Gly Phe
    1010                  1015                  1020

Pro Val  Val Leu Gln Gln Ile  Ser Lys Ser Leu Asn  Tyr Leu Leu
    1025                  1030                  1035

Met Ser  Ala Ser Gln Thr Lys  Ser Glu Ser Val Glu  Glu Lys Gly
    1040                  1045                  1050
```

-continued

```
Gly Gly Pro Pro Arg Cys Ser Ile Thr Glu Leu Leu Gln Met Cys
    1055             1060                 1065

Trp Pro Ser Leu Ser Glu Asp Cys Val Ala Ser His Thr Thr Leu
    1070             1075                 1080

Ser Gln Gln Leu Asp Gln Val Leu Gln Ser Leu Arg Glu Ala Leu
    1085             1090                 1095

Glu Leu Pro Glu Pro Arg Thr Pro Pro Leu Ser Ser Leu Val Glu
    1100             1105                 1110

Gln Ala Ala Gln Lys Ala Pro Glu Ala Glu Ala His Pro Val Gln
    1115             1120                 1125

Ile Gln Thr Gln Leu Leu Gln Lys Asn Leu Gly Lys Gln Thr Pro
    1130             1135                 1140

Ser Gly Ser Arg Gln Met Asp Tyr Leu Gly Thr Phe Phe Ser Tyr
    1145             1150                 1155

Cys Ser Thr Leu Ala Ala Val Leu Leu Gln Ser Leu Ser Ser Glu
    1160             1165                 1170

Pro Asp His Val Glu Val Lys Val Gly Asn Pro Phe Val Leu Leu
    1175             1180                 1185

Gln Gln Ser Ser Ser Gln Leu Val Ser His Leu Leu Phe Glu Arg
    1190             1195                 1200

Gln Val Pro Pro Glu Arg Leu Ala Ala Leu Leu Ala Gln Glu Asn
    1205             1210                 1215

Leu Ser Leu Ser Val Pro Gln Val Ile Val Ser Cys Cys Cys Glu
    1220             1225                 1230

Pro Leu Ala Leu Cys Ser Ser Arg Gln Ser Gln Gln Thr Ser Ser
    1235             1240                 1245

Leu Leu Thr Arg Leu Gly Thr Leu Ala Gln Leu His Ala Ser His
    1250             1255                 1260

Cys Leu Asp Asp Leu Pro Leu Ser Thr Pro Ser Ser Pro Arg Thr
    1265             1270                 1275

Thr Glu Asn Pro Thr Leu Glu Arg Lys Pro Tyr Ser Ser Pro Arg
    1280             1285                 1290

Asp Ser Ser Leu Pro Ala Leu Thr Ser Ser Ala Leu Ala Phe Leu
    1295             1300                 1305

Lys Ser Arg Ser Lys Leu Leu Ala Thr Val Ala Cys Leu Gly Ala
    1310             1315                 1320

Ser Pro Arg Leu Lys Val Ser Lys Pro Ser Leu Ser Trp Lys Glu
    1325             1330                 1335

Leu Arg Gly Arg Arg Glu Val Pro Leu Ala Ala Glu Gln Val Ala
    1340             1345                 1350

Arg Glu Cys Glu Arg Leu Leu Glu Gln Phe Pro Leu Phe Glu Ala
    1355             1360                 1365

Phe Leu Leu Ala Ala Trp Glu Pro Leu Arg Gly Ser Leu Gln Gln
    1370             1375                 1380

Gly Gln Ser Leu Ala Val Asn Leu Cys Gly Trp Ala Ser Leu Ser
    1385             1390                 1395

Thr Val Leu Leu Gly Leu His Ser Pro Ile Ala Leu Asp Val Leu
    1400             1405                 1410

Ser Glu Ala Phe Glu Glu Ser Leu Val Ala Arg Asp Trp Ser Arg
    1415             1420                 1425

Ala Leu Gln Leu Thr Glu Val Tyr Gly Arg Asp Val Asp Asp Leu
    1430             1435                 1440

Ser Ser Ile Lys Asp Ala Val Leu Ser Cys Ala Val Ala Cys Asp
```

-continued

```
            1445                1450                1455
Lys Glu Gly Trp Gln Tyr Leu Phe Pro Val Lys Asp Ala Ser Leu
            1460                1465                1470
Arg Ser Arg Leu Ala Leu Gln Phe Val Asp Arg Trp Pro Leu Glu
            1475                1480                1485
Ser Cys Leu Glu Ile Leu Ala Tyr Cys Ile Ser Asp Thr Ala Val
            1490                1495                1500
Gln Glu Gly Leu Lys Cys Glu Leu Gln Arg Lys Leu Ala Glu Leu
            1505                1510                1515
Gln Val Tyr Gln Lys Ile Leu Gly Leu Gln Ser Pro Pro Val Trp
            1520                1525                1530
Cys Asp Trp Gln Thr Leu Arg Ser Cys Cys Val Glu Asp Pro Ser
            1535                1540                1545
Thr Val Met Asn Met Ile Leu Glu Ala Gln Glu Tyr Glu Leu Cys
            1550                1555                1560
Glu Glu Trp Gly Cys Leu Tyr Pro Ile Pro Arg Glu His Leu Ile
            1565                1570                1575
Ser Leu His Gln Lys His Leu Leu His Leu Leu Glu Arg Arg Asp
            1580                1585                1590
His Asp Lys Ala Leu Gln Leu Leu Arg Arg Ile Pro Asp Pro Thr
            1595                1600                1605
Met Cys Leu Glu Val Thr Glu Gln Ser Leu Asp Gln His Thr Ser
            1610                1615                1620
Leu Ala Thr Ser His Phe Leu Ala Asn Tyr Leu Thr Thr His Phe
            1625                1630                1635
Tyr Gly Gln Leu Thr Ala Val Arg His Arg Glu Ile Gln Ala Leu
            1640                1645                1650
Tyr Val Gly Ser Lys Ile Leu Leu Thr Leu Pro Glu Gln His Arg
            1655                1660                1665
Ala Ser Tyr Ser His Leu Ser Ser Asn Pro Leu Phe Met Leu Glu
            1670                1675                1680
Gln Leu Leu Met Asn Met Lys Val Asp Trp Ala Thr Val Ala Val
            1685                1690                1695
Gln Thr Leu Gln Gln Leu Leu Val Gly Gln Glu Ile Gly Phe Thr
            1700                1705                1710
Met Asp Glu Val Asp Ser Leu Leu Ser Arg Tyr Ala Glu Lys Ala
            1715                1720                1725
Leu Asp Phe Pro Tyr Pro Gln Arg Glu Lys Arg Ser Asp Ser Val
            1730                1735                1740
Ile His Leu Gln Glu Ile Val His Gln Ala Ala Asp Pro Glu Thr
            1745                1750                1755
Leu Pro Arg Ser Pro Ser Ala Glu Phe Ser Pro Ala Ala Pro Pro
            1760                1765                1770
Gly Ile Ser Ser Ile His Ser Pro Ser Leu Arg Glu Arg Ser Phe
            1775                1780                1785
Pro Pro Thr Gln Pro Ser Gln Glu Phe Val Pro Ala Thr Pro
            1790                1795                1800
Pro Ala Arg His Gln Trp Val Pro Asp Glu Thr Glu Ser Ile Cys
            1805                1810                1815
Met Val Cys Cys Arg Glu His Phe Thr Met Phe Asn Arg Arg His
            1820                1825                1830
His Cys Arg Arg Cys Gly Arg Leu Val Cys Ser Ser Cys Ser Thr
            1835                1840                1845
```

-continued

Lys Lys Met Val Val Glu Gly Cys Arg Glu Asn Pro Ala Arg Val
1850            1855                1860

Cys Asp Gln Cys Tyr Ser Tyr Cys Asn Lys Asp Val Pro Glu Glu
1865            1870                1875

Pro Ser Glu Lys Pro Glu Ala Leu Asp Ser Ser Lys Asn Glu Ser
1880            1885                1890

Pro Pro Tyr Ser Phe Val Val Arg Val Pro Lys Ala Asp Glu Val
1895            1900                1905

Glu Trp Ile Leu Asp Leu Lys Glu Glu Glu Asn Glu Leu Val Arg
1910            1915                1920

Ser Glu Phe Tyr Tyr Glu Gln Ala Pro Ser Ala Ser Leu Cys Ile
1925            1930                1935

Ala Ile Leu Asn Leu His Arg Asp Ser Ile Ala Cys Gly His Gln
1940            1945                1950

Leu Ile Glu His Cys Cys Arg Leu Ser Lys Gly Leu Thr Asn Pro
1955            1960                1965

Glu Val Asp Ala Gly Leu Leu Thr Asp Ile Met Lys Gln Leu Leu
1970            1975                1980

Phe Ser Ala Lys Met Met Phe Val Lys Ala Gly Gln Ser Gln Asp
1985            1990                1995

Leu Ala Leu Cys Asp Ser Tyr Ile Ser Lys Val Asp Val Leu Asn
2000            2005                2010

Ile Leu Val Ala Ala Ala Tyr Arg His Val Pro Ser Leu Asp Gln
2015            2020                2025

Ile Leu Gln Pro Ala Ala Val Thr Arg Leu Arg Asn Gln Leu Leu
2030            2035                2040

Glu Ala Glu Tyr Tyr Gln Leu Gly Val Glu Val Ser Thr Lys Thr
2045            2050                2055

Gly Leu Asp Thr Thr Gly Ala Trp His Ala Trp Gly Met Ala Cys
2060            2065                2070

Leu Lys Ala Gly Asn Leu Thr Ala Ala Arg Glu Lys Phe Ser Arg
2075            2080                2085

Cys Leu Lys Pro Pro Phe Asp Leu Asn Gln Leu Asn His Gly Ser
2090            2095                2100

Arg Leu Val Gln Asp Val Val Glu Tyr Leu Glu Ser Thr Val Arg
2105            2110                2115

Pro Phe Val Ser Leu Gln Asp Asp Asp Tyr Phe Ala Thr Leu Arg
2120            2125                2130

Glu Leu Glu Ala Thr Leu Arg Thr Gln Ser Leu Ser Leu Ala Val
2135            2140                2145

Ile Pro Glu Gly Lys Ile Met Asn Asn Thr Tyr Tyr Gln Glu Cys
2150            2155                2160

Leu Phe Tyr Leu His Asn Tyr Ser Thr Asn Leu Ala Ile Ile Ser
2165            2170                2175

Phe Tyr Val Arg His Ser Cys Leu Arg Glu Ala Leu Leu His Leu
2180            2185                2190

Leu Asn Lys Glu Ser Pro Pro Glu Val Phe Ile Glu Gly Ile Phe
2195            2200                2205

Gln Pro Ser Tyr Lys Ser Gly Lys Leu His Thr Leu Glu Asn Leu
2210            2215                2220

Leu Glu Ser Ile Asp Pro Thr Leu Glu Ser Trp Gly Lys Tyr Leu
2225            2230                2235

-continued

```
Ile Ala Ala Cys Gln His Leu Gln Lys Lys Asn Tyr Tyr His Ile
    2240            2245                2250
Leu Tyr Glu Leu Gln Gln Phe Met Lys Asp Gln Val Arg Ala Ala
    2255            2260                2265
Met Thr Cys Ile Arg Phe Phe Ser His Lys Ala Lys Ser Tyr Thr
    2270            2275                2280
Glu Leu Gly Glu Lys Leu Ser Trp Leu Leu Lys Ala Lys Asp His
    2285            2290                2295
Leu Lys Ile Tyr Leu Gln Glu Thr Ser Arg Ser Ser Gly Arg Lys
    2300            2305                2310
Lys Thr Thr Phe Phe Arg Lys Lys Met Thr Ala Ala Asp Val Ser
    2315            2320                2325
Arg His Met Asn Thr Leu Gln Leu Gln Met Glu Val Thr Arg Phe
    2330            2335                2340
Leu His Arg Cys Glu Ser Ala Gly Thr Ser Gln Ile Thr Thr Leu
    2345            2350                2355
Pro Leu Pro Thr Leu Phe Gly Asn Asn His Met Lys Met Asp Val
    2360            2365                2370
Ala Cys Lys Val Met Leu Gly Gly Lys Asn Val Glu Asp Gly Phe
    2375            2380                2385
Gly Ile Ala Phe Arg Val Leu Gln Asp Phe Gln Leu Asp Ala Ala
    2390            2395                2400
Met Thr Tyr Cys Arg Ala Ala Arg Gln Leu Val Glu Lys Glu Lys
    2405            2410                2415
Tyr Ser Glu Ile Gln Gln Leu Leu Lys Cys Val Ser Glu Ser Gly
    2420            2425                2430
Met Ala Ala Lys Ser Asp Gly Asp Thr Ile Leu Leu Asn Cys Leu
    2435            2440                2445
Glu Ala Phe Lys Arg Ile Pro Pro Gln Leu Glu Gly Leu Ile
    2450            2455                2460
Gln Ala Ile His Asn Asp Asp Asn Lys Val Arg Ala Tyr Leu Ile
    2465            2470                2475
Cys Cys Lys Leu Arg Ser Ala Tyr Leu Ile Ala Val Lys Gln Glu
    2480            2485                2490
His Ser Arg Ala Thr Ala Leu Val Gln Val Gln Gln Ala Ala
    2495            2500                2505
Lys Ser Ser Gly Asp Ala Val Val Gln Asp Ile Cys Ala Gln Trp
    2510            2515                2520
Leu Leu Thr Ser His Pro Arg Gly Ala His Gly Pro Gly Ser Arg
    2525            2530                2535
Lys
```

<210> SEQ ID NO 3
<211> LENGTH: 26
<212> TYPE: DNA
<213> ORGANISM: Artificial
<220> FEATURE:
<223> OTHER INFORMATION: primer

<400> SEQUENCE: 3
tgcttcatct tagagaaata gcagaa                                          26

<210> SEQ ID NO 4
<211> LENGTH: 20
<212> TYPE: DNA
<213> ORGANISM: Artificial

```
<220> FEATURE:
<223> OTHER INFORMATION: primer

<400> SEQUENCE: 4
atgggcaaca tcttggagac                                              20

<210> SEQ ID NO 5
<211> LENGTH: 20
<212> TYPE: DNA
<213> ORGANISM: Artificial
<220> FEATURE:
<223> OTHER INFORMATION: primer

<400> SEQUENCE: 5
gaaagcatga aggcacacaa                                              20

<210> SEQ ID NO 6
<211> LENGTH: 20
<212> TYPE: DNA
<213> ORGANISM: Artificial
<220> FEATURE:
<223> OTHER INFORMATION: primer

<400> SEQUENCE: 6
ggctgggcat actggaatta                                              20

<210> SEQ ID NO 7
<211> LENGTH: 20
<212> TYPE: DNA
<213> ORGANISM: Artificial
<220> FEATURE:
<223> OTHER INFORMATION: primer

<400> SEQUENCE: 7
cttaggctga atgcagagcc                                              20

<210> SEQ ID NO 8
<211> LENGTH: 20
<212> TYPE: DNA
<213> ORGANISM: Artificial
<220> FEATURE:
<223> OTHER INFORMATION: primer

<400> SEQUENCE: 8
ggtcaacatt gccaactcaa                                              20

<210> SEQ ID NO 9
<211> LENGTH: 20
<212> TYPE: DNA
<213> ORGANISM: Artificial
<220> FEATURE:
<223> OTHER INFORMATION: primer

<400> SEQUENCE: 9
aggaagtgca gggaactgaa                                              20

<210> SEQ ID NO 10
<211> LENGTH: 20
<212> TYPE: DNA
<213> ORGANISM: Artificial
<220> FEATURE:
<223> OTHER INFORMATION: primer

<400> SEQUENCE: 10
ccctgggtga aataaaacca                                              20
```

```
<210> SEQ ID NO 11
<211> LENGTH: 23
<212> TYPE: DNA
<213> ORGANISM: Artificial
<220> FEATURE:
<223> OTHER INFORMATION: primer

<400> SEQUENCE: 11
taaatgagct aaagttgcga gaa                                          23

<210> SEQ ID NO 12
<211> LENGTH: 19
<212> TYPE: DNA
<213> ORGANISM: Artificial
<220> FEATURE:
<223> OTHER INFORMATION: primer

<400> SEQUENCE: 12
cctgaggaag gccctatt                                                19

<210> SEQ ID NO 13
<211> LENGTH: 19
<212> TYPE: DNA
<213> ORGANISM: Artificial
<220> FEATURE:
<223> OTHER INFORMATION: primer

<400> SEQUENCE: 13
gaagtcagaa cggggttcc                                               19

<210> SEQ ID NO 14
<211> LENGTH: 20
<212> TYPE: DNA
<213> ORGANISM: Artificial
<220> FEATURE:
<223> OTHER INFORMATION: primer

<400> SEQUENCE: 14
ggtgacgata tgccctgagt                                              20

<210> SEQ ID NO 15
<211> LENGTH: 27
<212> TYPE: DNA
<213> ORGANISM: Artificial
<220> FEATURE:
<223> OTHER INFORMATION: primer

<400> SEQUENCE: 15
caattaggaa cttttattta catttgc                                      27

<210> SEQ ID NO 16
<211> LENGTH: 19
<212> TYPE: DNA
<213> ORGANISM: Artificial
<220> FEATURE:
<223> OTHER INFORMATION: primer

<400> SEQUENCE: 16
ccgcctcggc cagaatgtg                                               19

<210> SEQ ID NO 17
<211> LENGTH: 18
<212> TYPE: DNA
<213> ORGANISM: Artificial
<220> FEATURE:
<223> OTHER INFORMATION: primer
```

```
<400> SEQUENCE: 17
actcccgggc tacctgct                                                  18

<210> SEQ ID NO 18
<211> LENGTH: 20
<212> TYPE: DNA
<213> ORGANISM: Artificial
<220> FEATURE:
<223> OTHER INFORMATION: primer

<400> SEQUENCE: 18
ctctgccttg gcctttctta                                                20

<210> SEQ ID NO 19
<211> LENGTH: 22
<212> TYPE: DNA
<213> ORGANISM: Artificial
<220> FEATURE:
<223> OTHER INFORMATION: primer

<400> SEQUENCE: 19
gggcttctct ctagagttac cg                                             22

<210> SEQ ID NO 20
<211> LENGTH: 20
<212> TYPE: DNA
<213> ORGANISM: Artificial
<220> FEATURE:
<223> OTHER INFORMATION: primer

<400> SEQUENCE: 20
cccctcatct ggtgaaggta                                                20

<210> SEQ ID NO 21
<211> LENGTH: 22
<212> TYPE: DNA
<213> ORGANISM: Artificial
<220> FEATURE:
<223> OTHER INFORMATION: primer

<400> SEQUENCE: 21
tcctccaaga ccaagatctc tc                                             22

<210> SEQ ID NO 22
<211> LENGTH: 20
<212> TYPE: DNA
<213> ORGANISM: Artificial
<220> FEATURE:
<223> OTHER INFORMATION: primer

<400> SEQUENCE: 22
tcaggaggca cacaatgttc                                                20

<210> SEQ ID NO 23
<211> LENGTH: 20
<212> TYPE: DNA
<213> ORGANISM: Artificial
<220> FEATURE:
<223> OTHER INFORMATION: primer

<400> SEQUENCE: 23
atggctgttt gagggtgtct                                                20

<210> SEQ ID NO 24
```

```
<211> LENGTH: 21
<212> TYPE: DNA
<213> ORGANISM: Artificial
<220> FEATURE:
<223> OTHER INFORMATION: primer

<400> SEQUENCE: 24
gcccatcagc tgacagatat t                                          21

<210> SEQ ID NO 25
<211> LENGTH: 21
<212> TYPE: DNA
<213> ORGANISM: Artificial
<220> FEATURE:
<223> OTHER INFORMATION: primer

<400> SEQUENCE: 25
tggcatttca gtgtgaatgt t                                          21

<210> SEQ ID NO 26
<211> LENGTH: 23
<212> TYPE: DNA
<213> ORGANISM: Artificial
<220> FEATURE:
<223> OTHER INFORMATION: primer

<400> SEQUENCE: 26
gctttcttgt agaatctggt tcc                                        23

<210> SEQ ID NO 27
<211> LENGTH: 21
<212> TYPE: DNA
<213> ORGANISM: Artificial
<220> FEATURE:
<223> OTHER INFORMATION: primer

<400> SEQUENCE: 27
ggaagaacac ttgagatctg g                                          21

<210> SEQ ID NO 28
<211> LENGTH: 20
<212> TYPE: DNA
<213> ORGANISM: Artificial
<220> FEATURE:
<223> OTHER INFORMATION: primer

<400> SEQUENCE: 28
ggcagatagt gggaatgagg                                            20

<210> SEQ ID NO 29
<211> LENGTH: 20
<212> TYPE: DNA
<213> ORGANISM: Artificial
<220> FEATURE:
<223> OTHER INFORMATION: primer

<400> SEQUENCE: 29
cttgatgctg agccaggact                                            20

<210> SEQ ID NO 30
<211> LENGTH: 21
<212> TYPE: DNA
<213> ORGANISM: Artificial
<220> FEATURE:
<223> OTHER INFORMATION: primer

<400> SEQUENCE: 30
```
aggagagaag tgaagcagtc g                                            21

<210> SEQ ID NO 31
<211> LENGTH: 20
<212> TYPE: DNA
<213> ORGANISM: Artificial
<220> FEATURE:
<223> OTHER INFORMATION: primer

<400> SEQUENCE: 31
gctctagggt cagccaaaca                                              20

<210> SEQ ID NO 32
<211> LENGTH: 21
<212> TYPE: DNA
<213> ORGANISM: Artificial
<220> FEATURE:
<223> OTHER INFORMATION: primer

<400> SEQUENCE: 32
tggcacatag gtgctcaata a                                            21

<210> SEQ ID NO 33
<211> LENGTH: 20
<212> TYPE: DNA
<213> ORGANISM: Artificial
<220> FEATURE:
<223> OTHER INFORMATION: primer

<400> SEQUENCE: 33
gaggcagcca tcaaacaaac                                              20

<210> SEQ ID NO 34
<211> LENGTH: 20
<212> TYPE: DNA
<213> ORGANISM: Artificial
<220> FEATURE:
<223> OTHER INFORMATION: primer

<400> SEQUENCE: 34
cagccaggta gctgatttcc                                              20

<210> SEQ ID NO 35
<211> LENGTH: 21
<212> TYPE: DNA
<213> ORGANISM: Artificial
<220> FEATURE:
<223> OTHER INFORMATION: primer

<400> SEQUENCE: 35
aattcagcag gaacctccct a                                            21

<210> SEQ ID NO 36
<211> LENGTH: 20
<212> TYPE: DNA
<213> ORGANISM: Artificial
<220> FEATURE:
<223> OTHER INFORMATION: primer

<400> SEQUENCE: 36
ataggaatcc gcgtgaagag                                              20

<210> SEQ ID NO 37
<211> LENGTH: 20
<212> TYPE: DNA

```
<213> ORGANISM: Artificial
<220> FEATURE:
<223> OTHER INFORMATION: primer

<400> SEQUENCE: 37
gcagccaggc ttacattcag                                               20

<210> SEQ ID NO 38
<211> LENGTH: 20
<212> TYPE: DNA
<213> ORGANISM: Artificial
<220> FEATURE:
<223> OTHER INFORMATION: primer

<400> SEQUENCE: 38
caccgcactt ggctaatttt                                               20

<210> SEQ ID NO 39
<211> LENGTH: 20
<212> TYPE: DNA
<213> ORGANISM: Artificial
<220> FEATURE:
<223> OTHER INFORMATION: primer

<400> SEQUENCE: 39
ggcacaagac tcatggtggt                                               20

<210> SEQ ID NO 40
<211> LENGTH: 20
<212> TYPE: DNA
<213> ORGANISM: Artificial
<220> FEATURE:
<223> OTHER INFORMATION: primer

<400> SEQUENCE: 40
tgaagctccc aagggaagta                                               20

<210> SEQ ID NO 41
<211> LENGTH: 22
<212> TYPE: DNA
<213> ORGANISM: Artificial
<220> FEATURE:
<223> OTHER INFORMATION: primer

<400> SEQUENCE: 41
cgatgtaaaa tgactgcaac tg                                            22

<210> SEQ ID NO 42
<211> LENGTH: 20
<212> TYPE: DNA
<213> ORGANISM: Artificial
<220> FEATURE:
<223> OTHER INFORMATION: primer

<400> SEQUENCE: 42
ctcccaaagt gctgggatta                                               20

<210> SEQ ID NO 43
<211> LENGTH: 20
<212> TYPE: DNA
<213> ORGANISM: Artificial
<220> FEATURE:
<223> OTHER INFORMATION: primer

<400> SEQUENCE: 43
ctctgcattc agcctaagcc                                               20
```

```
<210> SEQ ID NO 44
<211> LENGTH: 20
<212> TYPE: DNA
<213> ORGANISM: Artificial
<220> FEATURE:
<223> OTHER INFORMATION: primer

<400> SEQUENCE: 44
ggccctttct aggacctttc                                               20

<210> SEQ ID NO 45
<211> LENGTH: 20
<212> TYPE: DNA
<213> ORGANISM: Artificial
<220> FEATURE:
<223> OTHER INFORMATION: primer

<400> SEQUENCE: 45
agacctcctc accaccctct                                               20

<210> SEQ ID NO 46
<211> LENGTH: 21
<212> TYPE: DNA
<213> ORGANISM: Artificial
<220> FEATURE:
<223> OTHER INFORMATION: primer

<400> SEQUENCE: 46
tcagaacact ggggtatgct c                                             21

<210> SEQ ID NO 47
<211> LENGTH: 21
<212> TYPE: DNA
<213> ORGANISM: Artificial
<220> FEATURE:
<223> OTHER INFORMATION: primer

<400> SEQUENCE: 47
gcatggaaaa tttctgaaag g                                             21

<210> SEQ ID NO 48
<211> LENGTH: 20
<212> TYPE: DNA
<213> ORGANISM: Artificial
<220> FEATURE:
<223> OTHER INFORMATION: primer

<400> SEQUENCE: 48
acccaggtga actctgttgc                                               20

<210> SEQ ID NO 49
<211> LENGTH: 20
<212> TYPE: DNA
<213> ORGANISM: Artificial
<220> FEATURE:
<223> OTHER INFORMATION: primer

<400> SEQUENCE: 49
gctaaaatct ggccatctgc                                               20

<210> SEQ ID NO 50
<211> LENGTH: 20
<212> TYPE: DNA
<213> ORGANISM: Artificial
<220> FEATURE:
```

```
<223> OTHER INFORMATION: primer

<400> SEQUENCE: 50
gtttgccctt catttgagga                                           20

<210> SEQ ID NO 51
<211> LENGTH: 20
<212> TYPE: DNA
<213> ORGANISM: Artificial
<220> FEATURE:
<223> OTHER INFORMATION: primer

<400> SEQUENCE: 51
cttgatgtgg acccctgagt                                           20

<210> SEQ ID NO 52
<211> LENGTH: 20
<212> TYPE: DNA
<213> ORGANISM: Artificial
<220> FEATURE:
<223> OTHER INFORMATION: primer

<400> SEQUENCE: 52
tgaggctttg gtggttttct                                           20

<210> SEQ ID NO 53
<211> LENGTH: 20
<212> TYPE: DNA
<213> ORGANISM: Artificial
<220> FEATURE:
<223> OTHER INFORMATION: primer

<400> SEQUENCE: 53
tggacgtatc aggtttgctg                                           20

<210> SEQ ID NO 54
<211> LENGTH: 20
<212> TYPE: DNA
<213> ORGANISM: Artificial
<220> FEATURE:
<223> OTHER INFORMATION: primer

<400> SEQUENCE: 54
gaaaaagccc tccctcatct                                           20

<210> SEQ ID NO 55
<211> LENGTH: 20
<212> TYPE: DNA
<213> ORGANISM: Artificial
<220> FEATURE:
<223> OTHER INFORMATION: primer

<400> SEQUENCE: 55
ccatctgcct cctccaataa                                           20

<210> SEQ ID NO 56
<211> LENGTH: 20
<212> TYPE: DNA
<213> ORGANISM: Artificial
<220> FEATURE:
<223> OTHER INFORMATION: primer

<400> SEQUENCE: 56
tttgcattcc ctcttccttc                                           20
```

```
<210> SEQ ID NO 57
<211> LENGTH: 21
<212> TYPE: DNA
<213> ORGANISM: Artificial
<220> FEATURE:
<223> OTHER INFORMATION: primer

<400> SEQUENCE: 57
tgttgctgac ctaatgttcc a                                              21

<210> SEQ ID NO 58
<211> LENGTH: 20
<212> TYPE: DNA
<213> ORGANISM: Artificial
<220> FEATURE:
<223> OTHER INFORMATION: primer

<400> SEQUENCE: 58
tgtcagccag tcaaaccaaa                                                20

<210> SEQ ID NO 59
<211> LENGTH: 20
<212> TYPE: DNA
<213> ORGANISM: Artificial
<220> FEATURE:
<223> OTHER INFORMATION: primer

<400> SEQUENCE: 59
cctctgctcc aaagtgcttc                                                20

<210> SEQ ID NO 60
<211> LENGTH: 20
<212> TYPE: DNA
<213> ORGANISM: Artificial
<220> FEATURE:
<223> OTHER INFORMATION: primer

<400> SEQUENCE: 60
ctggctggga atcacttgtc                                                20

<210> SEQ ID NO 61
<211> LENGTH: 22
<212> TYPE: DNA
<213> ORGANISM: Artificial
<220> FEATURE:
<223> OTHER INFORMATION: primer

<400> SEQUENCE: 61
gccagagatg aataagagag ga                                             22

<210> SEQ ID NO 62
<211> LENGTH: 20
<212> TYPE: DNA
<213> ORGANISM: Artificial
<220> FEATURE:
<223> OTHER INFORMATION: primer

<400> SEQUENCE: 62
gagagcagga gttggctgtc                                                20

<210> SEQ ID NO 63
<211> LENGTH: 20
<212> TYPE: DNA
<213> ORGANISM: Artificial
<220> FEATURE:
<223> OTHER INFORMATION: primer
```

```
<400> SEQUENCE: 63
agtgcagagt cacccactga                                               20

<210> SEQ ID NO 64
<211> LENGTH: 23
<212> TYPE: DNA
<213> ORGANISM: Artificial
<220> FEATURE:
<223> OTHER INFORMATION: primer

<400> SEQUENCE: 64
tcttccttct gaaagtctca tgg                                           23

<210> SEQ ID NO 65
<211> LENGTH: 20
<212> TYPE: DNA
<213> ORGANISM: Artificial
<220> FEATURE:
<223> OTHER INFORMATION: primer

<400> SEQUENCE: 65
atgcaaagca aaacccagac                                               20

<210> SEQ ID NO 66
<211> LENGTH: 21
<212> TYPE: DNA
<213> ORGANISM: Artificial
<220> FEATURE:
<223> OTHER INFORMATION: primer

<400> SEQUENCE: 66
tcctggatag gttcactctg c                                             21

<210> SEQ ID NO 67
<211> LENGTH: 21
<212> TYPE: DNA
<213> ORGANISM: Artificial
<220> FEATURE:
<223> OTHER INFORMATION: primer

<400> SEQUENCE: 67
tgaacagtaa gcctgcttca a                                             21

<210> SEQ ID NO 68
<211> LENGTH: 20
<212> TYPE: DNA
<213> ORGANISM: Artificial
<220> FEATURE:
<223> OTHER INFORMATION: primer

<400> SEQUENCE: 68
agctgagatt gcatgggatt                                               20

<210> SEQ ID NO 69
<211> LENGTH: 23
<212> TYPE: DNA
<213> ORGANISM: Artificial
<220> FEATURE:
<223> OTHER INFORMATION: primer

<400> SEQUENCE: 69
gagaaagggt tagtccaaaa tga                                           23

<210> SEQ ID NO 70
<211> LENGTH: 20
```

```
<212> TYPE: DNA
<213> ORGANISM: Artificial
<220> FEATURE:
<223> OTHER INFORMATION: primer

<400> SEQUENCE: 70
ggcaaaagag ccattgaaaa                                            20

<210> SEQ ID NO 71
<211> LENGTH: 20
<212> TYPE: DNA
<213> ORGANISM: Artificial
<220> FEATURE:
<223> OTHER INFORMATION: primer

<400> SEQUENCE: 71
gtttgttttt cgaggcgttt                                            20

<210> SEQ ID NO 72
<211> LENGTH: 25
<212> TYPE: DNA
<213> ORGANISM: Artificial
<220> FEATURE:
<223> OTHER INFORMATION: primer

<400> SEQUENCE: 72
ttctgaagga tagaataagg caaga                                      25

<210> SEQ ID NO 73
<211> LENGTH: 20
<212> TYPE: DNA
<213> ORGANISM: Artificial
<220> FEATURE:
<223> OTHER INFORMATION: primer

<400> SEQUENCE: 73
cgcataggaa ggaagacaca                                            20

<210> SEQ ID NO 74
<211> LENGTH: 21
<212> TYPE: DNA
<213> ORGANISM: Artificial
<220> FEATURE:
<223> OTHER INFORMATION: primer

<400> SEQUENCE: 74
ggctgataca aatgccaaga a                                          21

<210> SEQ ID NO 75
<211> LENGTH: 22
<212> TYPE: DNA
<213> ORGANISM: Artificial
<220> FEATURE:
<223> OTHER INFORMATION: primer

<400> SEQUENCE: 75
aagcaaacaa aaggaaccaa gg                                         22

<210> SEQ ID NO 76
<211> LENGTH: 23
<212> TYPE: DNA
<213> ORGANISM: Artificial
<220> FEATURE:
<223> OTHER INFORMATION: primer

<400> SEQUENCE: 76
```
ccaagatgtt cattattttc tgc                                                23

<210> SEQ ID NO 77
<211> LENGTH: 20
<212> TYPE: DNA
<213> ORGANISM: Artificial
<220> FEATURE:
<223> OTHER INFORMATION: primer

<400> SEQUENCE: 77
gaatcgtttg aacccaggag                                                    20

<210> SEQ ID NO 78
<211> LENGTH: 20
<212> TYPE: DNA
<213> ORGANISM: Artificial
<220> FEATURE:
<223> OTHER INFORMATION: primer

<400> SEQUENCE: 78
gtcatgtccc cgattctacc                                                    20

<210> SEQ ID NO 79
<211> LENGTH: 21
<212> TYPE: DNA
<213> ORGANISM: Artificial
<220> FEATURE:
<223> OTHER INFORMATION: primer

<400> SEQUENCE: 79
cacaacgtgc aggtttgtta c                                                  21

<210> SEQ ID NO 80
<211> LENGTH: 20
<212> TYPE: DNA
<213> ORGANISM: Artificial
<220> FEATURE:
<223> OTHER INFORMATION: primer

<400> SEQUENCE: 80
gttgtgcaga gtcccctgtt                                                    20

<210> SEQ ID NO 81
<211> LENGTH: 20
<212> TYPE: DNA
<213> ORGANISM: Artificial
<220> FEATURE:
<223> OTHER INFORMATION: primer

<400> SEQUENCE: 81
ccagtcagtg cacttcagga                                                    20

<210> SEQ ID NO 82
<211> LENGTH: 21
<212> TYPE: DNA
<213> ORGANISM: Artificial
<220> FEATURE:
<223> OTHER INFORMATION: primer

<400> SEQUENCE: 82
caggattcaa ggaatggaca a                                                  21

<210> SEQ ID NO 83
<211> LENGTH: 20
<212> TYPE: DNA
<213> ORGANISM: Artificial

```
<220> FEATURE:
<223> OTHER INFORMATION: primer

<400> SEQUENCE: 83
tggtgatcag gtccattttg                                              20

<210> SEQ ID NO 84
<211> LENGTH: 23
<212> TYPE: DNA
<213> ORGANISM: Artificial
<220> FEATURE:
<223> OTHER INFORMATION: primer

<400> SEQUENCE: 84
tcttgaattt gacccagttc tgt                                          23

<210> SEQ ID NO 85
<211> LENGTH: 21
<212> TYPE: DNA
<213> ORGANISM: Artificial
<220> FEATURE:
<223> OTHER INFORMATION: primer

<400> SEQUENCE: 85
tgtggatgct tcctaaaggt c                                            21

<210> SEQ ID NO 86
<211> LENGTH: 20
<212> TYPE: DNA
<213> ORGANISM: Artificial
<220> FEATURE:
<223> OTHER INFORMATION: primer

<400> SEQUENCE: 86
ccattattgc agagggttc                                               20

<210> SEQ ID NO 87
<211> LENGTH: 22
<212> TYPE: DNA
<213> ORGANISM: Artificial
<220> FEATURE:
<223> OTHER INFORMATION: primer

<400> SEQUENCE: 87
caggcagaca ttttcattct ga                                           22

<210> SEQ ID NO 88
<211> LENGTH: 20
<212> TYPE: DNA
<213> ORGANISM: Artificial
<220> FEATURE:
<223> OTHER INFORMATION: primer

<400> SEQUENCE: 88
gtccatgttc acctgctcct                                              20

<210> SEQ ID NO 89
<211> LENGTH: 24
<212> TYPE: DNA
<213> ORGANISM: Artificial
<220> FEATURE:
<223> OTHER INFORMATION: primer

<400> SEQUENCE: 89
gcatatgtcc agaatattga aaga                                         24
```

<210> SEQ ID NO 90
<211> LENGTH: 20
<212> TYPE: DNA
<213> ORGANISM: Artificial
<220> FEATURE:
<223> OTHER INFORMATION: primer

<400> SEQUENCE: 90
tgcgtgaaag gtcctatcct                                              20

<210> SEQ ID NO 91
<211> LENGTH: 19
<212> TYPE: DNA
<213> ORGANISM: Artificial
<220> FEATURE:
<223> OTHER INFORMATION: primer

<400> SEQUENCE: 91
tctaatcaaa gcgctaggc                                               19

<210> SEQ ID NO 92
<211> LENGTH: 20
<212> TYPE: DNA
<213> ORGANISM: Artificial
<220> FEATURE:
<223> OTHER INFORMATION: primer

<400> SEQUENCE: 92
tgttgacttt gtacccctgc                                              20

<210> SEQ ID NO 93
<211> LENGTH: 21
<212> TYPE: DNA
<213> ORGANISM: Artificial
<220> FEATURE:
<223> OTHER INFORMATION: primer

<400> SEQUENCE: 93
gcagcagcaa agcaaagata g                                            21

<210> SEQ ID NO 94
<211> LENGTH: 20
<212> TYPE: DNA
<213> ORGANISM: Artificial
<220> FEATURE:
<223> OTHER INFORMATION: primer

<400> SEQUENCE: 94
cctgtaatct caaacattcc                                              20

<210> SEQ ID NO 95
<211> LENGTH: 20
<212> TYPE: DNA
<213> ORGANISM: Artificial
<220> FEATURE:
<223> OTHER INFORMATION: primer

<400> SEQUENCE: 95
caaggaccta atgaattcct                                              20

<210> SEQ ID NO 96
<211> LENGTH: 20
<212> TYPE: DNA
<213> ORGANISM: Artificial
<220> FEATURE:
<223> OTHER INFORMATION: primer -continued

<400> SEQUENCE: 96 ggaatttca ttctctgggc                           20

<210> SEQ ID NO 97
<211> LENGTH: 20
<212> TYPE: DNA
<213> ORGANISM: Artificial
<220> FEATURE:
<223> OTHER INFORMATION: primer

<400> SEQUENCE: 97
gtgtgtagct gtcagtcaga                          20

<210> SEQ ID NO 98
<211> LENGTH: 21
<212> TYPE: DNA
<213> ORGANISM: Artificial
<220> FEATURE:
<223> OTHER INFORMATION: primer

<400> SEQUENCE: 98
ttgaagacag ctccccttat c                        21

<210> SEQ ID NO 99
<211> LENGTH: 20
<212> TYPE: DNA
<213> ORGANISM: Artificial
<220> FEATURE:
<223> OTHER INFORMATION: primer

<400> SEQUENCE: 99
aggggatatc ccaaagaggg                          20

<210> SEQ ID NO 100
<211> LENGTH: 20
<212> TYPE: DNA
<213> ORGANISM: Artificial
<220> FEATURE:
<223> OTHER INFORMATION: primer

<400> SEQUENCE: 100
cctttcgaat gaggtccacc                          20

<210> SEQ ID NO 101
<211> LENGTH: 20
<212> TYPE: DNA
<213> ORGANISM: Artificial
<220> FEATURE:
<223> OTHER INFORMATION: primer

<400> SEQUENCE: 101
tcaccacttt gcctctgcca                          20

<210> SEQ ID NO 102
<211> LENGTH: 20
<212> TYPE: DNA
<213> ORGANISM: Artificial
<220> FEATURE:
<223> OTHER INFORMATION: primer

<400> SEQUENCE: 102
gccactgggc acagatgtct                          20

<210> SEQ ID NO 103

-continued

```
<211> LENGTH: 20
<212> TYPE: DNA
<213> ORGANISM: Artificial
<220> FEATURE:
<223> OTHER INFORMATION: primer

<400> SEQUENCE: 103
accagctaac caacgacaaa                                                   20

<210> SEQ ID NO 104
<211> LENGTH: 20
<212> TYPE: DNA
<213> ORGANISM: Artificial
<220> FEATURE:
<223> OTHER INFORMATION: primer

<400> SEQUENCE: 104
tgctgttcct gaatctgagc                                                   20

<210> SEQ ID NO 105
<211> LENGTH: 102
<212> TYPE: PRT
<213> ORGANISM: Homo sapiens

<400> SEQUENCE: 105

Met Asn His Pro Phe Gly Lys Glu Glu Ala Ser Gln Lys Gln Leu
1               5                   10                  15

Phe Gly Phe Phe Cys Glu Cys Leu Arg Arg Gly Glu Trp Glu Leu Ala
                20                  25                  30

Gln Ala Cys Val Pro Gln Leu Gln Glu Gly Gln Gly Asp Ile Pro Lys
            35                  40                  45

Arg Val Glu Asp Ile Leu Gln Ala Leu Val Val Cys Pro Asn Leu Leu
        50                  55                  60

Arg Cys Gly Gln Asp Ile Asn Pro Gln Arg Val Ala Trp Val Trp Leu
65                  70                  75                  80

Leu Val Leu Glu Lys Trp Leu Ala Arg Glu Lys Lys Leu Leu Pro Val
                85                  90                  95

Val Phe Arg Arg Lys Leu
            100

<210> SEQ ID NO 106
<211> LENGTH: 142
<212> TYPE: PRT
<213> ORGANISM: Homo sapiens

<400> SEQUENCE: 106

Met Asn His Pro Phe Gly Lys Glu Glu Ala Ser Gln Lys Gln Leu
1               5                   10                  15

Phe Gly Phe Phe Cys Glu Cys Leu Arg Arg Gly Glu Trp Glu Leu Ala
                20                  25                  30

Gln Ala Cys Val Pro Gln Leu Gln Glu Gly Gln Gly Asp Ile Pro Lys
            35                  40                  45

Arg Val Glu Asp Ile Leu Gln Ala Leu Val Val Cys Pro Asn Leu Leu
        50                  55                  60

Arg Cys Gly Gln Asp Ile Asn Pro Gln Arg Val Ala Trp Val Trp Leu
65                  70                  75                  80

Leu Val Leu Glu Lys Trp Leu Ala Arg Glu Lys Lys Leu Leu Pro Val
                85                  90                  95

Val Phe Arg Arg Lys Leu Glu Phe Leu Leu Ser Glu Asp Leu Gln
            100                 105                 110
```

```
Gly Asp Ile Pro Glu Asn Ile Leu Glu Glu Leu Tyr Glu Thr Leu Thr
        115                 120                 125

Gln Gly Ala Val Gly His Val Pro Asp Gly Asn Pro Arg Arg
    130                 135                 140

<210> SEQ ID NO 107
<211> LENGTH: 413
<212> TYPE: PRT
<213> ORGANISM: Homo sapiens

<400> SEQUENCE: 107

Met Asn His Pro Phe Gly Lys Glu Glu Ala Ala Ser Gln Lys Gln Leu
1               5                   10                  15

Phe Gly Phe Phe Cys Glu Cys Leu Arg Arg Gly Glu Trp Glu Leu Ala
            20                  25                  30

Gln Ala Cys Val Pro Gln Leu Gln Glu Gly Gln Gly Asp Ile Pro Lys
        35                  40                  45

Arg Val Glu Asp Ile Leu Gln Ala Leu Val Val Cys Pro Asn Leu Leu
    50                  55                  60

Arg Cys Gly Gln Asp Ile Asn Pro Gln Arg Val Ala Trp Val Trp Leu
65                  70                  75                  80

Leu Val Leu Glu Lys Trp Leu Ala Arg Glu Lys Lys Leu Leu Pro Val
                85                  90                  95

Val Phe Arg Arg Lys Leu Glu Phe Leu Leu Leu Ser Glu Asp Leu Gln
            100                 105                 110

Gly Asp Ile Pro Glu Asn Ile Leu Glu Glu Leu Tyr Glu Thr Leu Thr
        115                 120                 125

Gln Gly Ala Val Gly His Val Pro Asp Gly Asn Pro Arg Arg Glu Ser
    130                 135                 140

Trp Thr Pro Arg Leu Ser Ser Glu Ala Val Ser Val Leu Trp Asp Leu
145                 150                 155                 160

Leu Arg Gln Ser Pro Gln Pro Ala Gln Ala Leu Leu Glu Leu Leu Leu
                165                 170                 175

Glu Glu Asp Asp Gly Thr Gly Leu Cys His Trp Pro Leu Gln Asn Ala
            180                 185                 190

Leu Val Asp Leu Ile Arg Lys Ala Leu Arg Ala Leu Gln Gly Pro Asp
        195                 200                 205

Ser Val Pro Pro Gly Val Val Asp Ala Ile Tyr Gly Ala Leu Arg Thr
    210                 215                 220

Leu Arg Cys Pro Ala Glu Pro Leu Gly Val Glu Leu His Leu Leu Cys
225                 230                 235                 240

Glu Glu Leu Leu Glu Ala Cys Arg Thr Glu Gly Ser Pro Leu Arg Glu
                245                 250                 255

Glu Arg Leu Leu Ser Cys Leu Leu His Lys Ala Ser Arg Gly Leu Leu
            260                 265                 270

Ser Leu Tyr Gly His Thr Tyr Ala Glu Lys Val Thr Glu Lys Pro Pro
        275                 280                 285

Arg Ala Thr Ala Ser Gly Lys Val Ser Pro Asp His Leu Asp Pro Glu
    290                 295                 300

Arg Ala Met Leu Ala Leu Phe Ser Asn Pro Pro Ala Glu Ala Trp
305                 310                 315                 320

Lys Val Ala Tyr Phe Tyr Cys Leu Ser Asn Asn Lys His Phe Leu Glu
                325                 330                 335

Gln Ile Leu Val Thr Ala Leu Thr Leu Leu Lys Glu Glu Asp Phe Pro
```

```
                    340                 345                 350
Asn Leu Gly Cys Leu Leu Asp Arg Glu Phe Arg Pro Leu Ser Cys Leu
                355                 360                 365

Leu Val Leu Leu Gly Trp Thr His Cys Gln Ser Leu Glu Ser Ala Lys
        370                 375                 380

Arg Leu Leu Gln Thr Leu His Arg Thr Gln Gly Pro Gly Cys Asp Glu
385                 390                 395                 400

Leu Leu Arg Asp Ala Cys Asp Gly Leu Trp Ala His Leu
                405                 410

<210> SEQ ID NO 108
<211> LENGTH: 492
<212> TYPE: PRT
<213> ORGANISM: Homo sapiens

<400> SEQUENCE: 108

Met Asn His Pro Phe Gly Lys Glu Glu Ala Ala Ser Gln Lys Gln Leu
1               5                   10                  15

Phe Gly Phe Phe Cys Glu Cys Leu Arg Arg Gly Glu Trp Glu Leu Ala
            20                  25                  30

Gln Ala Cys Val Pro Gln Leu Gln Glu Gly Gln Gly Asp Ile Pro Lys
        35                  40                  45

Arg Val Glu Asp Ile Leu Gln Ala Leu Val Val Cys Pro Asn Leu Leu
    50                  55                  60

Arg Cys Gly Gln Asp Ile Asn Pro Gln Arg Val Ala Trp Val Trp Leu
65                  70                  75                  80

Leu Val Leu Glu Lys Trp Leu Ala Arg Glu Lys Lys Leu Leu Pro Val
                85                  90                  95

Val Phe Arg Arg Lys Leu Glu Phe Leu Leu Ser Glu Asp Leu Gln
            100                 105                 110

Gly Asp Ile Pro Glu Asn Ile Leu Glu Glu Leu Tyr Glu Thr Leu Thr
        115                 120                 125

Gln Gly Ala Val Gly His Val Pro Asp Gly Asn Pro Arg Arg Glu Ser
    130                 135                 140

Trp Thr Pro Arg Leu Ser Ser Glu Ala Val Ser Val Leu Trp Asp Leu
145                 150                 155                 160

Leu Arg Gln Ser Pro Gln Pro Ala Gln Ala Leu Leu Glu Leu Leu Leu
                165                 170                 175

Glu Glu Asp Asp Gly Thr Gly Leu Cys His Trp Pro Leu Gln Asn Ala
            180                 185                 190

Leu Val Asp Leu Ile Arg Lys Ala Leu Arg Ala Leu Gln Gly Pro Asp
        195                 200                 205

Ser Val Pro Pro Gly Val Val Asp Ala Ile Tyr Gly Ala Leu Arg Thr
    210                 215                 220

Leu Arg Cys Pro Ala Glu Pro Leu Gly Val Glu Leu His Leu Leu Cys
225                 230                 235                 240

Glu Glu Leu Leu Glu Ala Cys Arg Thr Glu Gly Ser Pro Leu Arg Glu
                245                 250                 255

Glu Arg Leu Leu Ser Cys Leu Leu His Lys Ala Ser Arg Gly Leu Leu
            260                 265                 270

Ser Leu Tyr Gly His Thr Tyr Ala Glu Lys Val Thr Glu Lys Pro Pro
        275                 280                 285

Arg Ala Thr Ala Ser Gly Lys Val Ser Pro Asp His Leu Asp Pro Glu
    290                 295                 300
```

Arg Ala Met Leu Ala Leu Phe Ser Asn Pro Asn Pro Ala Glu Ala Trp
305                 310                 315                 320

Lys Val Ala Tyr Phe Tyr Cys Leu Ser Asn Asn Lys His Phe Leu Glu
            325                 330                 335

Gln Ile Leu Val Thr Ala Leu Thr Leu Leu Lys Glu Glu Asp Phe Pro
        340                 345                 350

Asn Leu Gly Cys Leu Leu Asp Arg Glu Phe Arg Pro Leu Ser Cys Leu
            355                 360                 365

Leu Val Leu Leu Gly Trp Thr His Cys Gln Ser Leu Glu Ser Ala Lys
        370                 375                 380

Arg Leu Leu Gln Thr Leu His Arg Thr Gln Gly Pro Gly Cys Asp Glu
385                 390                 395                 400

Leu Leu Arg Asp Ala Cys Asp Gly Leu Trp Ala His Leu Glu Val Leu
            405                 410                 415

Glu Trp Cys Ile Gln Gln Ser Ser Asn Pro Ile Pro Lys Arg Asp Leu
        420                 425                 430

Leu Tyr His Leu His Gly Gly Asp Ser His Ser Val Leu Tyr Thr Leu
        435                 440                 445

His His Leu Thr Asn Leu Pro Ala Leu Arg Glu Glu Asp Val Leu Lys
450                 455                 460

Leu Leu Gln Lys Val Pro Ala Lys Asp Pro Gln Gln Glu Pro Asp Ala
465                 470                 475                 480

Val Asp Ala Pro Val Pro Glu His Leu Ser Gln Cys
            485                 490

<210> SEQ ID NO 109
<211> LENGTH: 684
<212> TYPE: PRT
<213> ORGANISM: Homo sapiens

<400> SEQUENCE: 109

Met Asn His Pro Phe Gly Lys Glu Glu Ala Ser Gln Lys Gln Leu
1               5                   10                  15

Phe Gly Phe Phe Cys Glu Cys Leu Arg Arg Gly Glu Trp Glu Leu Ala
            20                  25                  30

Gln Ala Cys Val Pro Gln Leu Gln Glu Gly Gln Gly Asp Ile Pro Lys
        35                  40                  45

Arg Val Glu Asp Ile Leu Gln Ala Leu Val Val Cys Pro Asn Leu Leu
50                  55                  60

Arg Cys Gly Gln Asp Ile Asn Pro Gln Arg Val Ala Trp Val Trp Leu
65                  70                  75                  80

Leu Val Leu Glu Lys Trp Leu Ala Arg Glu Lys Lys Leu Leu Pro Val
            85                  90                  95

Val Phe Arg Arg Lys Leu Glu Phe Leu Leu Ser Glu Asp Leu Gln
        100                 105                 110

Gly Asp Ile Pro Glu Asn Ile Leu Glu Glu Leu Tyr Glu Thr Leu Thr
        115                 120                 125

Gln Gly Ala Val Gly His Val Pro Asp Gly Asn Pro Arg Arg Glu Ser
    130                 135                 140

Trp Thr Pro Arg Leu Ser Ser Glu Ala Val Ser Val Leu Trp Asp Leu
145                 150                 155                 160

Leu Arg Gln Ser Pro Gln Pro Ala Gln Ala Leu Leu Glu Leu Leu Leu
            165                 170                 175

Glu Glu Asp Asp Gly Thr Gly Leu Cys His Trp Pro Leu Gln Asn Ala
        180                 185                 190

-continued

```
Leu Val Asp Leu Ile Arg Lys Ala Leu Arg Ala Leu Gln Gly Pro Asp
        195                 200                 205

Ser Val Pro Pro Gly Val Val Asp Ala Ile Tyr Gly Ala Leu Arg Thr
    210                 215                 220

Leu Arg Cys Pro Ala Glu Pro Leu Gly Val Glu Leu His Leu Leu Cys
225                 230                 235                 240

Glu Glu Leu Leu Glu Ala Cys Arg Thr Glu Gly Ser Pro Leu Arg Glu
                245                 250                 255

Glu Arg Leu Leu Ser Cys Leu His Lys Ala Ser Arg Gly Leu Leu
            260                 265                 270

Ser Leu Tyr Gly His Thr Tyr Ala Glu Lys Val Thr Glu Lys Pro Pro
        275                 280                 285

Arg Ala Thr Ala Ser Gly Lys Val Ser Pro Asp His Leu Asp Pro Glu
    290                 295                 300

Arg Ala Met Leu Ala Leu Phe Ser Asn Pro Asn Pro Ala Glu Ala Trp
305                 310                 315                 320

Lys Val Ala Tyr Phe Tyr Cys Leu Ser Asn Asn Lys His Phe Leu Glu
                325                 330                 335

Gln Ile Leu Val Thr Ala Leu Thr Leu Leu Lys Glu Glu Asp Phe Pro
            340                 345                 350

Asn Leu Gly Cys Leu Leu Asp Arg Glu Phe Arg Pro Leu Ser Cys Leu
        355                 360                 365

Leu Val Leu Leu Gly Trp Thr His Cys Gln Ser Leu Glu Ser Ala Lys
    370                 375                 380

Arg Leu Leu Gln Thr Leu His Arg Thr Gln Gly Pro Gly Cys Asp Glu
385                 390                 395                 400

Leu Leu Arg Asp Ala Cys Asp Gly Leu Trp Ala His Leu Glu Val Leu
                405                 410                 415

Glu Trp Cys Ile Gln Gln Ser Ser Asn Pro Ile Pro Lys Arg Asp Leu
            420                 425                 430

Leu Tyr His Leu His Gly Gly Asp Ser His Ser Val Leu Tyr Thr Leu
        435                 440                 445

His His Leu Thr Asn Leu Pro Ala Leu Arg Glu Glu Asp Val Leu Lys
    450                 455                 460

Leu Leu Gln Lys Val Pro Ala Lys Asp Pro Gln Gln Glu Pro Asp Ala
465                 470                 475                 480

Val Asp Ala Pro Val Pro Glu His Leu Ser Gln Cys Gln Asn Leu Thr
                485                 490                 495

Leu Tyr Gln Gly Phe Cys Ala Met Lys Tyr Ala Ile Tyr Ala Leu Cys
            500                 505                 510

Val Asn Ser His Gln His Ser Gln Cys Gln Asp Cys Lys Asp Ser Leu
        515                 520                 525

Ser Glu Asp Leu Ala Ser Ala Thr Glu Pro Ala Asn Asp Ser Leu Ser
    530                 535                 540

Ser Pro Gly Ala Ala Asn Leu Phe Ser Thr Tyr Leu Ala Arg Cys Gln
545                 550                 555                 560

Gln Tyr Leu Cys Ser Ile Pro Asp Ser Leu Cys Leu Glu Leu Glu
                565                 570                 575

Asn Ile Phe Ser Leu Leu Ile Thr Ser Ala Asp Leu His Pro Glu
            580                 585                 590

Pro His Leu Pro Glu Asp Tyr Ala Glu Asp Asp Ile Glu Gly Lys
        595                 600                 605
```

-continued

```
Ser Pro Ser Gly Leu Arg Ser Pro Ser Glu Ser Pro Gln His Ile Ala
610                 615                 620
His Pro Glu Arg Lys Ser Glu Arg Gly Ser Leu Gly Val Pro Lys Thr
625                 630                 635                 640
Leu Ala Tyr Thr Met Pro Ser His Val Lys Ala Glu Pro Lys Asp Ser
                645                 650                 655
Tyr Pro Gly Pro His Arg His Ser Phe Leu Asp Leu Lys His Phe Thr
                660                 665                 670
Ser Gly Ile Ser Gly Phe Leu Ala Asp Glu Leu Gln
                675                 680

<210> SEQ ID NO 110
<211> LENGTH: 1219
<212> TYPE: PRT
<213> ORGANISM: Homo sapiens

<400> SEQUENCE: 110

Met Asn His Pro Phe Gly Lys Glu Ala Ala Ser Gln Lys Gln Leu
1               5                   10                  15
Phe Gly Phe Phe Cys Glu Cys Leu Arg Arg Gly Glu Trp Glu Leu Ala
                20                  25                  30
Gln Ala Cys Val Pro Gln Leu Gln Glu Gly Gln Gly Asp Ile Pro Lys
            35                  40                  45
Arg Val Glu Asp Ile Leu Gln Ala Leu Val Val Cys Pro Asn Leu Leu
        50                  55                  60
Arg Cys Gly Gln Asp Ile Asn Pro Gln Arg Val Ala Trp Val Trp Leu
65                  70                  75                  80
Leu Val Leu Glu Lys Trp Leu Ala Arg Glu Lys Lys Leu Leu Pro Val
                85                  90                  95
Val Phe Arg Lys Leu Glu Phe Leu Leu Ser Glu Asp Leu Gln
                100                 105                 110
Gly Asp Ile Pro Glu Asn Ile Leu Glu Glu Leu Tyr Glu Thr Leu Thr
            115                 120                 125
Gln Gly Ala Val Gly His Val Pro Asp Gly Asn Pro Arg Arg Glu Ser
        130                 135                 140
Trp Thr Pro Arg Leu Ser Ser Glu Ala Val Ser Val Leu Trp Asp Leu
145                 150                 155                 160
Leu Arg Gln Ser Pro Gln Pro Ala Gln Ala Leu Leu Glu Leu Leu
                165                 170                 175
Glu Glu Asp Asp Gly Thr Gly Leu Cys His Trp Pro Leu Gln Asn Ala
            180                 185                 190
Leu Val Asp Leu Ile Arg Lys Ala Leu Arg Ala Leu Gln Gly Pro Asp
        195                 200                 205
Ser Val Pro Pro Gly Val Val Asp Ala Ile Tyr Gly Ala Leu Arg Thr
    210                 215                 220
Leu Arg Cys Pro Ala Glu Pro Leu Gly Val Glu Leu His Leu Leu Cys
225                 230                 235                 240
Glu Glu Leu Leu Glu Ala Cys Arg Thr Glu Gly Ser Pro Leu Arg Glu
                245                 250                 255
Glu Arg Leu Leu Ser Cys Leu Leu His Lys Ala Ser Arg Gly Leu Leu
            260                 265                 270
Ser Leu Tyr Gly His Thr Tyr Ala Glu Lys Val Thr Glu Lys Pro Pro
        275                 280                 285
Arg Ala Thr Ala Ser Gly Lys Val Ser Pro Asp His Leu Asp Pro Glu
    290                 295                 300
```

```
Arg Ala Met Leu Ala Leu Phe Ser Asn Pro Asn Pro Ala Glu Ala Trp
305                 310                 315                 320

Lys Val Ala Tyr Phe Tyr Cys Leu Ser Asn Asn Lys His Phe Leu Glu
            325                 330                 335

Gln Ile Leu Val Thr Ala Leu Thr Leu Leu Lys Glu Glu Asp Phe Pro
        340                 345                 350

Asn Leu Gly Cys Leu Leu Asp Arg Glu Phe Arg Pro Leu Ser Cys Leu
            355                 360                 365

Leu Val Leu Leu Gly Trp Thr His Cys Gln Ser Leu Glu Ser Ala Lys
        370                 375                 380

Arg Leu Leu Gln Thr Leu His Arg Thr Gln Gly Pro Gly Cys Asp Glu
385                 390                 395                 400

Leu Leu Arg Asp Ala Cys Asp Gly Leu Trp Ala His Leu Glu Val Leu
                405                 410                 415

Glu Trp Cys Ile Gln Gln Ser Ser Asn Pro Ile Pro Lys Arg Asp Leu
            420                 425                 430

Leu Tyr His Leu His Gly Gly Asp Ser His Ser Val Leu Tyr Thr Leu
            435                 440                 445

His His Leu Thr Asn Leu Pro Ala Leu Arg Glu Glu Asp Val Leu Lys
450                 455                 460

Leu Leu Gln Lys Val Pro Ala Lys Asp Pro Gln Gln Glu Pro Asp Ala
465                 470                 475                 480

Val Asp Ala Pro Val Pro Glu His Leu Ser Gln Cys Gln Asn Leu Thr
                485                 490                 495

Leu Tyr Gln Gly Phe Cys Ala Met Lys Tyr Ala Ile Tyr Ala Leu Cys
            500                 505                 510

Val Asn Ser His Gln His Ser Gln Cys Gln Asp Cys Lys Asp Ser Leu
            515                 520                 525

Ser Glu Asp Leu Ala Ser Ala Thr Glu Pro Ala Asn Asp Ser Leu Ser
    530                 535                 540

Ser Pro Gly Ala Ala Asn Leu Phe Ser Thr Tyr Leu Ala Arg Cys Gln
545                 550                 555                 560

Gln Tyr Leu Cys Ser Ile Pro Asp Ser Leu Cys Leu Glu Leu Leu Glu
                565                 570                 575

Asn Ile Phe Ser Leu Leu Leu Ile Thr Ser Ala Asp Leu His Pro Glu
            580                 585                 590

Pro His Leu Pro Glu Asp Tyr Ala Glu Asp Asp Ile Glu Gly Lys
    595                 600                 605

Ser Pro Ser Gly Leu Arg Ser Pro Glu Ser Pro Gln His Ile Ala
    610                 615                 620

His Pro Glu Arg Lys Ser Glu Arg Gly Ser Leu Gly Val Pro Lys Thr
625                 630                 635                 640

Leu Ala Tyr Thr Met Pro Ser His Val Lys Ala Glu Pro Lys Asp Ser
            645                 650                 655

Tyr Pro Gly Pro His Arg His Ser Phe Leu Asp Leu Lys His Phe Thr
            660                 665                 670

Ser Gly Ile Ser Gly Phe Leu Ala Asp Glu Phe Ala Ile Gly Ala Phe
            675                 680                 685

Leu Arg Leu Leu Gln Glu Gln Leu Asp Glu Ile Ser Ser Arg Ser Pro
            690                 695                 700

Pro Glu Lys Pro Lys Gln Glu Ser Gln Ser Cys Ser Gly Ser Arg Asp
705                 710                 715                 720
```

```
Gly Leu Gln Ser Arg Leu His Arg Leu Ser Lys Val Val Ser Glu Ala
            725                 730                 735

Gln Trp Arg His Lys Val Val Thr Ser Asn His Arg Ser Glu Glu Gln
            740                 745                 750

Pro Ser Arg Arg Tyr Gln Pro Ala Thr Arg His Pro Ser Leu Arg Arg
            755                 760                 765

Gly Arg Arg Thr Arg Arg Ser Gln Ala Asp Gly Arg Asp Arg Gly Ser
            770                 775                 780

Asn Pro Ser Leu Glu Ser Thr Ser Ser Glu Leu Ser Thr Ser Thr Ser
785                 790                 795                 800

Glu Gly Ser Leu Ser Ala Met Ser Gly Arg Asn Glu Leu His Ser Arg
                805                 810                 815

Leu His Pro His Pro Gln Ser Ser Leu Ile Pro Met Met Phe Ser Pro
                820                 825                 830

Pro Glu Ser Leu Leu Ala Ser Cys Ile Leu Arg Gly Asn Phe Ala Glu
                835                 840                 845

Ala His Gln Val Leu Phe Thr Phe Asn Leu Lys Ser Ser Pro Ser Ser
                850                 855                 860

Gly Glu Leu Met Phe Met Glu Arg Tyr Gln Glu Val Ile Gln Glu Leu
865                 870                 875                 880

Ala Gln Val Glu His Lys Ile Glu Asn Gln Asn Ser Asp Ala Gly Ser
                885                 890                 895

Ser Thr Ile Arg Arg Thr Gly Ser Gly Arg Ser Thr Leu Gln Ala Ile
                900                 905                 910

Gly Ser Ala Ala Ala Ala Gly Met Val Phe Tyr Ser Ile Ser Asp Val
                915                 920                 925

Thr Asp Lys Leu Leu Asn Thr Ser Gly Asp Pro Ile Pro Met Leu Gln
            930                 935                 940

Glu Asp Phe Trp Ile Ser Thr Ala Leu Val Glu Pro Thr Ala Pro Leu
945                 950                 955                 960

Arg Glu Val Leu Glu Asp Leu Ser Pro Pro Ala Met Ala Ala Phe Asp
                965                 970                 975

Leu Ala Cys Ser Gln Cys Gln Leu Trp Lys Thr Cys Lys Gln Leu Leu
                980                 985                 990

Glu Thr Ala Glu Arg Arg Leu Asn Ser Ser Leu Glu Arg Arg Gly Arg
            995                 1000                1005

Arg Ile Asp His Val Leu Leu Asn Ala Asp Gly Ile Arg Gly Phe
            1010                1015                1020

Pro Val Val Leu Gln Gln Ile Ser Lys Ser Leu Asn Tyr Leu Leu
            1025                1030                1035

Met Ser Ala Ser Gln Thr Lys Ser Glu Ser Val Glu Glu Lys Gly
            1040                1045                1050

Gly Gly Pro Pro Arg Cys Ser Ile Thr Glu Leu Leu Gln Met Cys
            1055                1060                1065

Trp Pro Ser Leu Ser Glu Asp Cys Val Ala Ser His Thr Thr Leu
            1070                1075                1080

Ser Gln Gln Leu Asp Gln Val Leu Gln Ser Leu Arg Glu Ala Leu
            1085                1090                1095

Glu Leu Pro Glu Pro Arg Thr Pro Pro Leu Ser Ser Leu Val Glu
            1100                1105                1110

Gln Ala Ala Gln Lys Ala Pro Glu Ala Glu Ala His Pro Val Gln
            1115                1120                1125

Ile Gln Thr Gln Leu Leu Gln Lys Asn Leu Gly Lys Gln Thr Pro
```

-continued

```
                 1130                1135                1140

Ser Gly Ser Arg Gln Met Asp Tyr Leu Gly Thr Phe Phe Ser Tyr
             1145                1150                1155

Cys Ser Thr Leu Ala Ala Val Leu Leu Gln Ser Leu Ser Ser Glu
             1160                1165                1170

Pro Asp His Val Glu Val Lys Val Gly Asn Pro Phe Val Leu Leu
             1175                1180                1185

Gln Gln Ser Ser Ser Gln Leu Val Ser His Leu Leu Phe Glu Arg
             1190                1195                1200

Gln Val Pro Pro Glu Arg Lys Gly Leu Ile Gln Pro Ala Lys Gly
             1205                1210                1215

Leu

<210> SEQ ID NO 111
<211> LENGTH: 1355
<212> TYPE: PRT
<213> ORGANISM: Homo sapiens

<400> SEQUENCE: 111

Met Asn His Pro Phe Gly Lys Glu Glu Ala Ser Gln Lys Gln Leu
1               5                   10                  15

Phe Gly Phe Phe Cys Glu Cys Leu Arg Arg Gly Glu Trp Glu Leu Ala
                20                  25                  30

Gln Ala Cys Val Pro Gln Leu Gln Glu Gly Gln Gly Asp Ile Pro Lys
                35                  40                  45

Arg Val Glu Asp Ile Leu Gln Ala Leu Val Val Cys Pro Asn Leu Leu
50                  55                  60

Arg Cys Gly Gln Asp Ile Asn Pro Gln Arg Val Ala Trp Val Trp Leu
65                  70                  75                  80

Leu Val Leu Glu Lys Trp Leu Ala Arg Glu Lys Lys Leu Leu Pro Val
                85                  90                  95

Val Phe Arg Arg Lys Leu Glu Phe Leu Leu Leu Ser Glu Asp Leu Gln
                100                 105                 110

Gly Asp Ile Pro Glu Asn Ile Leu Glu Glu Leu Tyr Glu Thr Leu Thr
                115                 120                 125

Gln Gly Ala Val Gly His Val Pro Asp Gly Asn Pro Arg Arg Glu Ser
                130                 135                 140

Trp Thr Pro Arg Leu Ser Ser Glu Ala Val Ser Val Leu Trp Asp Leu
145                 150                 155                 160

Leu Arg Gln Ser Pro Gln Pro Ala Gln Ala Leu Leu Glu Leu Leu
                165                 170                 175

Glu Glu Asp Asp Gly Thr Gly Leu Cys His Trp Pro Leu Gln Asn Ala
                180                 185                 190

Leu Val Asp Leu Ile Arg Lys Ala Leu Arg Ala Leu Gln Gly Pro Asp
                195                 200                 205

Ser Val Pro Pro Gly Val Val Asp Ala Ile Tyr Gly Ala Leu Arg Thr
                210                 215                 220

Leu Arg Cys Pro Ala Glu Pro Leu Gly Val Glu Leu His Leu Leu Cys
225                 230                 235                 240

Glu Glu Leu Leu Glu Ala Cys Arg Thr Glu Gly Ser Pro Leu Arg Glu
                245                 250                 255

Glu Arg Leu Leu Ser Cys Leu His Lys Ala Ser Arg Gly Leu Leu
                260                 265                 270

Ser Leu Tyr Gly His Thr Tyr Ala Glu Lys Val Thr Glu Lys Pro Pro
```

-continued

```
                275                 280                 285
Arg Ala Thr Ala Ser Gly Lys Val Ser Pro Asp His Leu Asp Pro Glu
290                 295                 300
Arg Ala Met Leu Ala Leu Phe Ser Asn Pro Asn Pro Ala Glu Ala Trp
305                 310                 315                 320
Lys Val Ala Tyr Phe Tyr Cys Leu Ser Asn Asn Lys His Phe Leu Glu
                325                 330                 335
Gln Ile Leu Val Thr Ala Leu Thr Leu Leu Lys Glu Glu Asp Phe Pro
            340                 345                 350
Asn Leu Gly Cys Leu Leu Asp Arg Glu Phe Arg Pro Leu Ser Cys Leu
                355                 360                 365
Leu Val Leu Leu Gly Trp Thr His Cys Gln Ser Leu Glu Ser Ala Lys
            370                 375                 380
Arg Leu Leu Gln Thr Leu His Arg Thr Gln Gly Pro Gly Cys Asp Glu
385                 390                 395                 400
Leu Leu Arg Asp Ala Cys Asp Gly Leu Trp Ala His Leu Glu Val Leu
                405                 410                 415
Glu Trp Cys Ile Gln Gln Ser Ser Asn Pro Ile Pro Lys Arg Asp Leu
            420                 425                 430
Leu Tyr His Leu His Gly Gly Asp Ser His Ser Val Leu Tyr Thr Leu
                435                 440                 445
His His Leu Thr Asn Leu Pro Ala Leu Arg Glu Glu Asp Val Leu Lys
450                 455                 460
Leu Leu Gln Lys Val Pro Ala Lys Asp Pro Gln Gln Glu Pro Asp Ala
465                 470                 475                 480
Val Asp Ala Pro Val Pro Glu His Leu Ser Gln Cys Gln Asn Leu Thr
                485                 490                 495
Leu Tyr Gln Gly Phe Cys Ala Met Lys Tyr Ala Ile Tyr Ala Leu Cys
            500                 505                 510
Val Asn Ser His Gln His Ser Gln Cys Gln Asp Cys Lys Asp Ser Leu
                515                 520                 525
Ser Glu Asp Leu Ala Ser Ala Thr Glu Pro Ala Asn Asp Ser Leu Ser
530                 535                 540
Ser Pro Gly Ala Ala Asn Leu Phe Ser Thr Tyr Leu Ala Arg Cys Gln
545                 550                 555                 560
Gln Tyr Leu Cys Ser Ile Pro Asp Ser Leu Cys Leu Glu Leu Leu Glu
                565                 570                 575
Asn Ile Phe Ser Leu Leu Leu Ile Thr Ser Ala Asp Leu His Pro Glu
            580                 585                 590
Pro His Leu Pro Glu Asp Tyr Ala Glu Asp Asp Ile Glu Gly Lys
                595                 600                 605
Ser Pro Ser Gly Leu Arg Pro Ser Glu Ser Pro Gln His Ile Ala
610                 615                 620
His Pro Glu Arg Lys Ser Glu Arg Gly Ser Leu Gly Val Pro Lys Thr
625                 630                 635                 640
Leu Ala Tyr Thr Met Pro Ser His Val Lys Ala Glu Pro Lys Asp Ser
                645                 650                 655
Tyr Pro Gly Pro His Arg His Ser Phe Leu Asp Leu Lys His Phe Thr
            660                 665                 670
Ser Gly Ile Ser Gly Phe Leu Ala Asp Glu Phe Ala Ile Gly Ala Phe
                675                 680                 685
Leu Arg Leu Leu Gln Glu Gln Leu Asp Glu Ile Ser Ser Arg Ser Pro
            690                 695                 700
```

-continued

```
Pro Glu Lys Pro Lys Gln Glu Ser Gln Ser Cys Ser Gly Ser Arg Asp
705                 710                 715                 720

Gly Leu Gln Ser Arg Leu His Arg Leu Ser Lys Val Val Ser Glu Ala
            725                 730                 735

Gln Trp Arg His Lys Val Val Thr Ser Asn His Arg Ser Glu Glu Gln
        740                 745                 750

Pro Ser Arg Arg Tyr Gln Pro Ala Thr Arg His Pro Ser Leu Arg Arg
            755                 760                 765

Gly Arg Arg Thr Arg Arg Ser Gln Ala Asp Gly Arg Asp Arg Gly Ser
770                 775                 780

Asn Pro Ser Leu Glu Ser Thr Ser Ser Glu Leu Ser Thr Ser Thr Ser
785                 790                 795                 800

Glu Gly Ser Leu Ser Ala Met Ser Gly Arg Asn Glu Leu His Ser Arg
            805                 810                 815

Leu His Pro His Pro Gln Ser Ser Leu Ile Pro Met Met Phe Ser Pro
            820                 825                 830

Pro Glu Ser Leu Leu Ala Ser Cys Ile Leu Arg Gly Asn Phe Ala Glu
            835                 840                 845

Ala His Gln Val Leu Phe Thr Phe Asn Leu Lys Ser Ser Pro Ser Ser
850                 855                 860

Gly Glu Leu Met Phe Met Glu Arg Tyr Gln Glu Val Ile Gln Glu Leu
865                 870                 875                 880

Ala Gln Val Glu His Lys Ile Glu Asn Gln Asn Ser Asp Ala Gly Ser
                885                 890                 895

Ser Thr Ile Arg Arg Thr Gly Ser Gly Arg Ser Thr Leu Gln Ala Ile
            900                 905                 910

Gly Ser Ala Ala Ala Ala Gly Met Val Phe Tyr Ser Ile Ser Asp Val
            915                 920                 925

Thr Asp Lys Leu Leu Asn Thr Ser Gly Asp Pro Ile Pro Met Leu Gln
        930                 935                 940

Glu Asp Phe Trp Ile Ser Thr Ala Leu Val Glu Pro Thr Ala Pro Leu
945                 950                 955                 960

Arg Glu Val Leu Glu Asp Leu Ser Pro Pro Ala Met Ala Ala Phe Asp
                965                 970                 975

Leu Ala Cys Ser Gln Cys Gln Leu Trp Lys Thr Cys Lys Gln Leu Leu
            980                 985                 990

Glu Thr Ala Glu Arg Arg Leu Asn  Ser Ser Leu Glu Arg Arg Gly Arg
            995                 1000                1005

Arg Ile Asp His Val Leu Leu  Asn Ala Asp Gly Ile  Arg Gly Phe
    1010                1015                 1020

Pro Val Val Leu Gln Gln Ile  Ser Lys Ser Leu Asn  Tyr Leu Leu
    1025                1030                 1035

Met Ser Ala Ser Gln Thr Lys  Ser Glu Ser Val Glu  Glu Lys Gly
    1040                1045                 1050

Gly Gly Pro Pro Arg Cys Ser  Ile Thr Glu Leu Leu  Gln Met Cys
    1055                1060                 1065

Trp Pro Ser Leu Ser Glu Asp  Cys Val Ala Ser His  Thr Thr Leu
    1070                1075                 1080

Ser Gln Gln Leu Asp Gln Val  Leu Gln Ser Leu Arg  Glu Ala Leu
    1085                1090                 1095

Glu Leu Pro Glu Pro Arg Thr  Pro Pro Leu Ser Ser  Leu Val Glu
    1100                1105                 1110
```

```
Gln Ala Ala Gln Lys Ala Pro Glu Ala Glu Ala His Pro Val Gln
    1115                1120                1125

Ile Gln Thr Gln Leu Leu Gln Lys Asn Leu Gly Lys Gln Thr Pro
    1130                1135                1140

Ser Gly Ser Arg Gln Met Asp Tyr Leu Gly Thr Phe Phe Ser Tyr
    1145                1150                1155

Cys Ser Thr Leu Ala Ala Val Leu Leu Gln Ser Leu Ser Ser Glu
    1160                1165                1170

Pro Asp His Val Glu Val Lys Val Gly Asn Pro Phe Val Leu Leu
    1175                1180                1185

Gln Gln Ser Ser Ser Gln Leu Val Ser His Leu Leu Phe Glu Arg
    1190                1195                1200

Gln Val Pro Pro Glu Arg Leu Ala Ala Leu Leu Ala Gln Glu Asn
    1205                1210                1215

Leu Ser Leu Ser Val Pro Gln Val Ile Val Ser Cys Cys Cys Glu
    1220                1225                1230

Pro Leu Ala Leu Cys Ser Ser Arg Gln Ser Gln Gln Thr Ser Ser
    1235                1240                1245

Leu Leu Thr Arg Leu Gly Thr Leu Ala Gln Leu His Ala Ser His
    1250                1255                1260

Cys Leu Asp Asp Leu Pro Leu Ser Thr Pro Ser Ser Pro Arg Thr
    1265                1270                1275

Thr Glu Asn Pro Thr Leu Glu Arg Lys Pro Tyr Ser Ser Pro Arg
    1280                1285                1290

Asp Ser Ser Leu Pro Ala Leu Thr Ser Ser Ala Leu Ala Phe Leu
    1295                1300                1305

Lys Ser Arg Ser Lys Leu Leu Ala Thr Val Ala Cys Leu Gly Ala
    1310                1315                1320

Ser Pro Arg Leu Lys Val Ser Lys Pro Ser Leu Ser Trp Lys Glu
    1325                1330                1335

Leu Arg Gly Arg Arg Glu Val Pro Leu Ala Ala Glu Gln Val Ala
    1340                1345                1350

Arg Glu
    1355

<210> SEQ ID NO 112
<211> LENGTH: 1437
<212> TYPE: PRT
<213> ORGANISM: Homo sapiens

<400> SEQUENCE: 112

Met Asn His Pro Phe Gly Lys Glu Glu Ala Ser Gln Lys Gln Leu
1                   5                   10                  15

Phe Gly Phe Phe Cys Glu Cys Leu Arg Arg Gly Glu Trp Glu Leu Ala
                    20                  25                  30

Gln Ala Cys Val Pro Gln Leu Gln Glu Gly Gln Gly Asp Ile Pro Lys
            35                  40                  45

Arg Val Glu Asp Ile Leu Gln Ala Leu Val Val Cys Pro Asn Leu Leu
        50                  55                  60

Arg Cys Gly Gln Asp Ile Asn Pro Gln Arg Val Ala Trp Val Trp Leu
65                  70                  75                  80

Leu Val Leu Glu Lys Trp Leu Ala Arg Glu Lys Lys Leu Leu Pro Val
                    85                  90                  95

Val Phe Arg Arg Lys Leu Glu Phe Leu Leu Leu Ser Glu Asp Leu Gln
                    100                 105                 110
```

```
Gly Asp Ile Pro Glu Asn Ile Leu Glu Glu Leu Tyr Glu Thr Leu Thr
            115                 120                 125

Gln Gly Ala Val Gly His Val Pro Asp Gly Asn Pro Arg Arg Glu Ser
    130                 135                 140

Trp Thr Pro Arg Leu Ser Ser Glu Ala Val Ser Val Leu Trp Asp Leu
145                 150                 155                 160

Leu Arg Gln Ser Pro Gln Pro Ala Gln Ala Leu Leu Glu Leu Leu Leu
                165                 170                 175

Glu Glu Asp Asp Gly Thr Gly Leu Cys His Trp Pro Leu Gln Asn Ala
            180                 185                 190

Leu Val Asp Leu Ile Arg Lys Ala Leu Arg Ala Leu Gln Gly Pro Asp
            195                 200                 205

Ser Val Pro Pro Gly Val Val Asp Ala Ile Tyr Gly Ala Leu Arg Thr
    210                 215                 220

Leu Arg Cys Pro Ala Glu Pro Leu Gly Val Glu Leu His Leu Leu Cys
225                 230                 235                 240

Glu Glu Leu Leu Glu Ala Cys Arg Thr Glu Gly Ser Pro Leu Arg Glu
                245                 250                 255

Glu Arg Leu Leu Ser Cys Leu Leu His Lys Ala Ser Arg Gly Leu Leu
            260                 265                 270

Ser Leu Tyr Gly His Thr Tyr Ala Glu Lys Val Thr Glu Lys Pro Pro
    275                 280                 285

Arg Ala Thr Ala Ser Gly Lys Val Ser Pro Asp His Leu Asp Pro Glu
290                 295                 300

Arg Ala Met Leu Ala Leu Phe Ser Asn Pro Asn Pro Ala Glu Ala Trp
305                 310                 315                 320

Lys Val Ala Tyr Phe Tyr Cys Leu Ser Asn Asn Lys His Phe Leu Glu
                325                 330                 335

Gln Ile Leu Val Thr Ala Leu Thr Leu Leu Lys Glu Glu Asp Phe Pro
            340                 345                 350

Asn Leu Gly Cys Leu Leu Asp Arg Glu Phe Arg Pro Leu Ser Cys Leu
            355                 360                 365

Leu Val Leu Leu Gly Trp Thr His Cys Gln Ser Leu Glu Ser Ala Lys
    370                 375                 380

Arg Leu Leu Gln Thr Leu His Arg Thr Gln Gly Pro Gly Cys Asp Glu
385                 390                 395                 400

Leu Leu Arg Asp Ala Cys Asp Gly Leu Trp Ala His Leu Glu Val Leu
                405                 410                 415

Glu Trp Cys Ile Gln Ser Ser Asn Pro Ile Pro Lys Arg Asp Leu
            420                 425                 430

Leu Tyr His Leu His Gly Gly Asp Ser His Ser Val Leu Tyr Thr Leu
            435                 440                 445

His His Leu Thr Asn Leu Pro Ala Leu Arg Glu Glu Asp Val Leu Lys
450                 455                 460

Leu Leu Gln Lys Val Pro Ala Lys Asp Pro Gln Glu Pro Asp Ala
465                 470                 475                 480

Val Asp Ala Pro Val Pro Glu His Leu Ser Gln Cys Gln Asn Leu Thr
                485                 490                 495

Leu Tyr Gln Gly Phe Cys Ala Met Lys Tyr Ala Ile Tyr Ala Leu Cys
            500                 505                 510

Val Asn Ser His Gln His Ser Gln Cys Gln Asp Cys Lys Asp Ser Leu
            515                 520                 525
```

```
Ser Glu Asp Leu Ala Ser Ala Thr Glu Pro Ala Asn Asp Ser Leu Ser
    530                 535                 540

Ser Pro Gly Ala Ala Asn Leu Phe Ser Thr Tyr Leu Ala Arg Cys Gln
545                 550                 555                 560

Gln Tyr Leu Cys Ser Ile Pro Asp Ser Leu Cys Leu Glu Leu Leu Glu
                565                 570                 575

Asn Ile Phe Ser Leu Leu Ile Thr Ser Ala Asp Leu His Pro Glu
            580                 585                 590

Pro His Leu Pro Glu Asp Tyr Ala Glu Asp Asp Ile Glu Gly Lys
        595                 600                 605

Ser Pro Ser Gly Leu Arg Ser Pro Ser Glu Ser Pro Gln His Ile Ala
    610                 615                 620

His Pro Glu Arg Lys Ser Glu Arg Gly Ser Leu Gly Val Pro Lys Thr
625                 630                 635                 640

Leu Ala Tyr Thr Met Pro Ser His Val Lys Ala Glu Pro Lys Asp Ser
                645                 650                 655

Tyr Pro Gly Pro His Arg His Ser Phe Leu Asp Leu Lys His Phe Thr
                660                 665                 670

Ser Gly Ile Ser Gly Phe Leu Ala Asp Glu Phe Ala Ile Gly Ala Phe
            675                 680                 685

Leu Arg Leu Leu Gln Glu Gln Leu Asp Glu Ile Ser Ser Arg Ser Pro
690                 695                 700

Pro Glu Lys Pro Lys Gln Glu Ser Gln Ser Cys Ser Gly Ser Arg Asp
705                 710                 715                 720

Gly Leu Gln Ser Arg Leu His Arg Leu Ser Lys Val Val Ser Glu Ala
                725                 730                 735

Gln Trp Arg His Lys Val Val Thr Ser Asn His Arg Ser Glu Glu Gln
                740                 745                 750

Pro Ser Arg Arg Tyr Gln Pro Ala Thr Arg His Pro Ser Leu Arg Arg
                755                 760                 765

Gly Arg Arg Thr Arg Arg Ser Gln Ala Asp Gly Arg Asp Arg Gly Ser
770                 775                 780

Asn Pro Ser Leu Glu Ser Thr Ser Ser Glu Leu Ser Thr Ser Thr Ser
785                 790                 795                 800

Glu Gly Ser Leu Ser Ala Met Ser Gly Arg Asn Glu Leu His Ser Arg
                805                 810                 815

Leu His Pro His Pro Gln Ser Ser Leu Ile Pro Met Met Phe Ser Pro
            820                 825                 830

Pro Glu Ser Leu Leu Ala Ser Cys Ile Leu Arg Gly Asn Phe Ala Glu
        835                 840                 845

Ala His Gln Val Leu Phe Thr Phe Asn Leu Lys Ser Ser Pro Ser Ser
850                 855                 860

Gly Glu Leu Met Phe Met Glu Arg Tyr Gln Glu Val Ile Gln Glu Leu
865                 870                 875                 880

Ala Gln Val Glu His Lys Ile Glu Asn Gln Asn Ser Asp Ala Gly Ser
                885                 890                 895

Ser Thr Ile Arg Arg Thr Gly Ser Gly Arg Ser Thr Leu Gln Ala Ile
                900                 905                 910

Gly Ser Ala Ala Ala Gly Met Val Phe Tyr Ser Ile Ser Asp Val
            915                 920                 925

Thr Asp Lys Leu Leu Asn Thr Ser Gly Asp Pro Ile Pro Met Leu Gln
    930                 935                 940

Glu Asp Phe Trp Ile Ser Thr Ala Leu Val Glu Pro Thr Ala Pro Leu
```

```
945                 950                 955                 960
Arg Glu Val Leu Glu Asp Leu Ser Pro Pro Ala Met Ala Ala Phe Asp
                965                 970                 975
Leu Ala Cys Ser Gln Cys Gln Leu Trp Lys Thr Cys Lys Gln Leu Leu
                980                 985                 990
Glu Thr Ala Glu Arg Arg Leu Asn Ser Ser Leu Glu Arg Arg Gly Arg
                995                 1000                1005
Arg Ile Asp His Val Leu Leu Asn Ala Asp Gly Ile Arg Gly Phe
    1010                1015                1020
Pro Val Val Leu Gln Gln Ile Ser Lys Ser Leu Asn Tyr Leu Leu
    1025                1030                1035
Met Ser Ala Ser Gln Thr Lys Ser Glu Ser Val Glu Glu Lys Gly
    1040                1045                1050
Gly Gly Pro Pro Arg Cys Ser Ile Thr Glu Leu Leu Gln Met Cys
    1055                1060                1065
Trp Pro Ser Leu Ser Glu Asp Cys Val Ala Ser His Thr Thr Leu
    1070                1075                1080
Ser Gln Gln Leu Asp Gln Val Leu Gln Ser Leu Arg Glu Ala Leu
    1085                1090                1095
Glu Leu Pro Glu Pro Arg Thr Pro Pro Leu Ser Ser Leu Val Glu
    1100                1105                1110
Gln Ala Ala Gln Lys Ala Pro Glu Ala Glu Ala His Pro Val Gln
    1115                1120                1125
Ile Gln Thr Gln Leu Leu Gln Lys Asn Leu Gly Lys Gln Thr Pro
    1130                1135                1140
Ser Gly Ser Arg Gln Met Asp Tyr Leu Gly Thr Phe Phe Ser Tyr
    1145                1150                1155
Cys Ser Thr Leu Ala Ala Val Leu Leu Gln Ser Leu Ser Ser Glu
    1160                1165                1170
Pro Asp His Val Glu Val Lys Val Gly Asn Pro Phe Val Leu Leu
    1175                1180                1185
Gln Gln Ser Ser Ser Gln Leu Val Ser His Leu Leu Phe Glu Arg
    1190                1195                1200
Gln Val Pro Pro Glu Arg Leu Ala Ala Leu Leu Ala Gln Glu Asn
    1205                1210                1215
Leu Ser Leu Ser Val Pro Gln Val Ile Val Ser Cys Cys Cys Glu
    1220                1225                1230
Pro Leu Ala Leu Cys Ser Ser Arg Gln Ser Gln Gln Thr Ser Ser
    1235                1240                1245
Leu Leu Thr Arg Leu Gly Thr Leu Ala Gln Leu His Ala Ser His
    1250                1255                1260
Cys Leu Asp Asp Leu Pro Leu Ser Thr Pro Ser Ser Pro Arg Thr
    1265                1270                1275
Thr Glu Asn Pro Thr Leu Glu Arg Lys Pro Tyr Ser Ser Pro Arg
    1280                1285                1290
Asp Ser Ser Leu Pro Ala Leu Thr Ser Ser Ala Leu Ala Phe Leu
    1295                1300                1305
Lys Ser Arg Ser Lys Leu Leu Ala Thr Val Ala Cys Leu Gly Ala
    1310                1315                1320
Ser Pro Arg Leu Lys Val Ser Lys Pro Ser Leu Ser Trp Lys Glu
    1325                1330                1335
Leu Arg Gly Arg Arg Glu Val Pro Leu Ala Ala Glu Gln Val Ala
    1340                1345                1350
```

```
Arg Glu Cys Glu Arg Leu Leu Glu Gln Phe Pro Leu Phe Glu Ala
    1355                1360                1365

Phe Leu Leu Ala Ala Trp Glu Pro Leu Arg Gly Ser Leu Gln Gln
    1370                1375                1380

Gly Gln Ser Leu Ala Val Asn Leu Cys Gly Trp Ala Ser Leu Ser
    1385                1390                1395

Thr Val Leu Leu Gly Leu His Ser Pro Ile Ala Leu Asp Val Leu
    1400                1405                1410

Ser Glu Ala Phe Glu Ser Leu Val Ala Arg Asp Trp Ser Arg
    1415                1420                1425

Ala Leu Gln Leu Thr Glu Val Tyr Gly
    1430                1435

<210> SEQ ID NO 113
<211> LENGTH: 1686
<212> TYPE: PRT
<213> ORGANISM: Homo sapiens

<400> SEQUENCE: 113

Met Asn His Pro Phe Gly Lys Glu Ala Ala Ser Gln Lys Gln Leu
1               5                   10                  15

Phe Gly Phe Phe Cys Glu Cys Leu Arg Arg Gly Glu Trp Glu Leu Ala
                20                  25                  30

Gln Ala Cys Val Pro Gln Leu Gln Glu Gly Gln Gly Asp Ile Pro Lys
            35                  40                  45

Arg Val Glu Asp Ile Leu Gln Ala Leu Val Val Cys Pro Asn Leu Leu
    50                  55                  60

Arg Cys Gly Gln Asp Ile Asn Pro Gln Arg Val Ala Trp Val Trp Leu
65                  70                  75                  80

Leu Val Leu Glu Lys Trp Leu Ala Arg Glu Lys Lys Leu Leu Pro Val
                85                  90                  95

Val Phe Arg Arg Lys Leu Glu Phe Leu Leu Leu Ser Glu Asp Leu Gln
            100                 105                 110

Gly Asp Ile Pro Glu Asn Ile Leu Glu Glu Leu Tyr Glu Thr Leu Thr
        115                 120                 125

Gln Gly Ala Val Gly His Val Pro Asp Gly Asn Pro Arg Arg Glu Ser
    130                 135                 140

Trp Thr Pro Arg Leu Ser Ser Glu Ala Val Ser Val Leu Trp Asp Leu
145                 150                 155                 160

Leu Arg Gln Ser Pro Gln Pro Ala Gln Ala Leu Leu Glu Leu Leu
                165                 170                 175

Glu Glu Asp Asp Gly Thr Gly Leu Cys His Trp Pro Leu Gln Asn Ala
            180                 185                 190

Leu Val Asp Leu Ile Arg Lys Ala Leu Arg Ala Leu Gln Gly Pro Asp
        195                 200                 205

Ser Val Pro Pro Gly Val Val Asp Ala Ile Tyr Gly Ala Leu Arg Thr
    210                 215                 220

Leu Arg Cys Pro Ala Glu Pro Leu Gly Val Glu Leu His Leu Cys
225                 230                 235                 240

Glu Glu Leu Leu Glu Ala Cys Arg Thr Glu Gly Ser Pro Leu Arg Glu
                245                 250                 255

Glu Arg Leu Leu Ser Cys Leu Leu His Lys Ala Ser Arg Gly Leu Leu
            260                 265                 270

Ser Leu Tyr Gly His Thr Tyr Ala Glu Lys Val Thr Glu Lys Pro Pro
```

```
            275                 280                 285
Arg Ala Thr Ala Ser Gly Lys Val Ser Pro Asp His Leu Asp Pro Glu
290                 295                 300

Arg Ala Met Leu Ala Leu Phe Ser Asn Pro Asn Pro Ala Glu Ala Trp
305                 310                 315                 320

Lys Val Ala Tyr Phe Tyr Cys Leu Ser Asn Asn Lys His Phe Leu Glu
                325                 330                 335

Gln Ile Leu Val Thr Ala Leu Thr Leu Leu Lys Glu Glu Asp Phe Pro
            340                 345                 350

Asn Leu Gly Cys Leu Leu Asp Arg Glu Phe Arg Pro Leu Ser Cys Leu
                355                 360                 365

Leu Val Leu Leu Gly Trp Thr His Cys Gln Ser Leu Glu Ser Ala Lys
            370                 375                 380

Arg Leu Leu Gln Thr Leu His Arg Thr Gln Gly Pro Gly Cys Asp Glu
385                 390                 395                 400

Leu Leu Arg Asp Ala Cys Asp Gly Leu Trp Ala His Leu Glu Val Leu
                405                 410                 415

Glu Trp Cys Ile Gln Gln Ser Ser Asn Pro Ile Pro Lys Arg Asp Leu
            420                 425                 430

Leu Tyr His Leu His Gly Gly Asp Ser His Ser Val Leu Tyr Thr Leu
                435                 440                 445

His His Leu Thr Asn Leu Pro Ala Leu Arg Glu Glu Asp Val Leu Lys
450                 455                 460

Leu Leu Gln Lys Val Pro Ala Lys Asp Pro Gln Gln Glu Pro Asp Ala
465                 470                 475                 480

Val Asp Ala Pro Val Pro Glu His Leu Ser Gln Cys Gln Asn Leu Thr
                485                 490                 495

Leu Tyr Gln Gly Phe Cys Ala Met Lys Tyr Ala Ile Tyr Ala Leu Cys
            500                 505                 510

Val Asn Ser His Gln His Ser Gln Cys Gln Asp Cys Lys Asp Ser Leu
                515                 520                 525

Ser Glu Asp Leu Ala Ser Ala Thr Glu Pro Ala Asn Asp Ser Leu Ser
530                 535                 540

Ser Pro Gly Ala Ala Asn Leu Phe Ser Thr Tyr Leu Ala Arg Cys Gln
545                 550                 555                 560

Gln Tyr Leu Cys Ser Ile Pro Asp Ser Leu Cys Leu Glu Leu Leu Glu
                565                 570                 575

Asn Ile Phe Ser Leu Leu Leu Ile Thr Ser Ala Asp Leu His Pro Glu
            580                 585                 590

Pro His Leu Pro Glu Asp Tyr Ala Glu Asp Asp Ile Glu Gly Lys
                595                 600                 605

Ser Pro Ser Gly Leu Arg Ser Pro Glu Ser Pro Gln His Ile Ala
            610                 615                 620

His Pro Glu Arg Lys Ser Glu Arg Gly Ser Leu Gly Val Pro Lys Thr
625                 630                 635                 640

Leu Ala Tyr Thr Met Pro Ser His Val Lys Ala Glu Pro Lys Asp Ser
                645                 650                 655

Tyr Pro Gly Pro His Arg His Ser Phe Leu Asp Leu Lys His Phe Thr
                660                 665                 670

Ser Gly Ile Ser Gly Phe Leu Ala Asp Glu Phe Ala Ile Gly Ala Phe
            675                 680                 685

Leu Arg Leu Leu Gln Glu Gln Leu Asp Glu Ile Ser Ser Arg Ser Pro
            690                 695                 700
```

-continued

Pro Glu Lys Pro Lys Gln Glu Ser Gln Ser Cys Ser Gly Ser Arg Asp
705                 710                 715                 720

Gly Leu Gln Ser Arg Leu His Arg Leu Ser Lys Val Val Ser Glu Ala
            725                 730                 735

Gln Trp Arg His Lys Val Val Thr Ser Asn His Arg Ser Glu Glu Gln
            740                 745                 750

Pro Ser Arg Arg Tyr Gln Pro Ala Thr Arg His Pro Ser Leu Arg Arg
            755                 760                 765

Gly Arg Arg Thr Arg Arg Ser Gln Ala Asp Gly Arg Asp Arg Gly Ser
770                 775                 780

Asn Pro Ser Leu Glu Ser Thr Ser Ser Glu Leu Ser Thr Ser Thr Ser
785                 790                 795                 800

Glu Gly Ser Leu Ser Ala Met Ser Gly Arg Asn Glu Leu His Ser Arg
                805                 810                 815

Leu His Pro His Pro Gln Ser Ser Leu Ile Pro Met Met Phe Ser Pro
                820                 825                 830

Pro Glu Ser Leu Leu Ala Ser Cys Ile Leu Arg Gly Asn Phe Ala Glu
            835                 840                 845

Ala His Gln Val Leu Phe Thr Phe Asn Leu Lys Ser Ser Pro Ser Ser
850                 855                 860

Gly Glu Leu Met Phe Met Glu Arg Tyr Gln Glu Val Ile Gln Glu Leu
865                 870                 875                 880

Ala Gln Val Glu His Lys Ile Glu Asn Gln Asn Ser Asp Ala Gly Ser
                885                 890                 895

Ser Thr Ile Arg Arg Thr Gly Ser Gly Arg Ser Thr Leu Gln Ala Ile
            900                 905                 910

Gly Ser Ala Ala Ala Gly Met Val Phe Tyr Ser Ile Ser Asp Val
            915                 920                 925

Thr Asp Lys Leu Leu Asn Thr Ser Gly Asp Pro Ile Pro Met Leu Gln
    930                 935                 940

Glu Asp Phe Trp Ile Ser Thr Ala Leu Val Glu Pro Thr Ala Pro Leu
945                 950                 955                 960

Arg Glu Val Leu Glu Asp Leu Ser Pro Pro Ala Met Ala Ala Phe Asp
                965                 970                 975

Leu Ala Cys Ser Gln Cys Gln Leu Trp Lys Thr Cys Lys Gln Leu Leu
            980                 985                 990

Glu Thr Ala Glu Arg Arg Leu Asn Ser Ser Leu Glu Arg Arg Gly Arg
        995                 1000                1005

Arg Ile Asp His Val Leu Leu Asn Ala Asp Gly Ile Arg Gly Phe
    1010                1015                1020

Pro Val Val Leu Gln Gln Ile Ser Lys Ser Leu Asn Tyr Leu Leu
    1025                1030                1035

Met Ser Ala Ser Gln Thr Lys Ser Glu Ser Val Glu Glu Lys Gly
    1040                1045                1050

Gly Gly Pro Pro Arg Cys Ser Ile Thr Glu Leu Leu Gln Met Cys
    1055                1060                1065

Trp Pro Ser Leu Ser Glu Asp Cys Val Ala Ser His Thr Thr Leu
    1070                1075                1080

Ser Gln Gln Leu Asp Gln Val Leu Gln Ser Leu Arg Glu Ala Leu
    1085                1090                1095

Glu Leu Pro Glu Pro Arg Thr Pro Pro Leu Ser Ser Leu Val Glu
    1100                1105                1110

-continued

```
Gln Ala  Ala Gln Lys Ala  Pro Glu Ala Glu  Ala His  Pro Val Gln
    1115              1120             1125

Ile Gln  Thr Gln Leu Leu  Gln Lys Asn Leu  Gly Lys  Gln Thr Pro
    1130              1135             1140

Ser Gly  Ser Arg Gln Met  Asp Tyr Leu Gly  Thr Phe  Phe Ser Tyr
    1145              1150             1155

Cys Ser  Thr Leu Ala Ala  Val Leu Leu Gln  Ser Leu  Ser Ser Glu
    1160              1165             1170

Pro Asp  His Val Glu Val  Lys Val Gly Asn  Pro Phe  Val Leu Leu
    1175              1180             1185

Gln Gln  Ser Ser Ser Gln  Leu Val Ser His  Leu Leu  Phe Glu Arg
    1190              1195             1200

Gln Val  Pro Pro Glu Arg  Leu Ala Ala Leu  Leu Ala  Gln Glu Asn
    1205              1210             1215

Leu Ser  Leu Ser Val Pro  Gln Val Ile Val  Ser Cys  Cys Cys Glu
    1220              1225             1230

Pro Leu  Ala Leu Cys Ser  Ser Arg Gln Ser  Gln Gln  Thr Ser Ser
    1235              1240             1245

Leu Leu  Thr Arg Leu Gly  Thr Leu Ala Gln  Leu His  Ala Ser His
    1250              1255             1260

Cys Leu  Asp Asp Leu Pro  Leu Ser Thr Pro  Ser Ser  Pro Arg Thr
    1265              1270             1275

Thr Glu  Asn Pro Thr Leu  Glu Arg Lys Pro  Tyr Ser  Ser Pro Arg
    1280              1285             1290

Asp Ser  Ser Leu Pro Ala  Leu Thr Ser Ser  Ala Leu  Ala Phe Leu
    1295              1300             1305

Lys Ser  Arg Ser Lys Leu  Leu Ala Thr Val  Ala Cys  Leu Gly Ala
    1310              1315             1320

Ser Pro  Arg Leu Lys Val  Ser Lys Pro Ser  Leu Ser  Trp Lys Glu
    1325              1330             1335

Leu Arg  Gly Arg Arg Glu  Val Pro Leu Ala  Ala Glu  Gln Val Ala
    1340              1345             1350

Arg Glu  Cys Glu Arg Leu  Leu Glu Gln Phe  Pro Leu  Phe Glu Ala
    1355              1360             1365

Phe Leu  Leu Ala Ala Trp  Glu Pro Leu Arg  Gly Ser  Leu Gln Gln
    1370              1375             1380

Gly Gln  Ser Leu Ala Val  Asn Leu Cys Gly  Trp Ala  Ser Leu Ser
    1385              1390             1395

Thr Val  Leu Leu Gly Leu  His Ser Pro Ile  Ala Leu  Asp Val Leu
    1400              1405             1410

Ser Glu  Ala Phe Glu Glu  Ser Leu Val Ala  Arg Asp  Trp Ser Arg
    1415              1420             1425

Ala Leu  Gln Leu Thr Glu  Val Tyr Gly Arg  Asp Val  Asp Asp Leu
    1430              1435             1440

Ser Ser  Ile Lys Asp Ala  Val Leu Ser Cys  Ala Val  Ala Cys Asp
    1445              1450             1455

Lys Glu  Gly Trp Gln Tyr  Leu Phe Pro Val  Lys Asp  Ala Ser Leu
    1460              1465             1470

Arg Ser  Arg Leu Ala Leu  Gln Phe Val Asp  Arg Trp  Pro Leu Glu
    1475              1480             1485

Ser Cys  Leu Glu Ile Leu  Ala Tyr Cys Ile  Ser Asp  Thr Ala Val
    1490              1495             1500

Gln Glu  Gly Leu Lys Cys  Glu Leu Gln Arg  Lys Leu  Ala Glu Leu
```

```
                    1505                1510                1515

Gln Val Tyr Gln Lys Ile Leu Gly Leu Gln Ser Pro Pro Val Trp
            1520                1525                1530

Cys Asp Trp Gln Thr Leu Arg Ser Cys Cys Val Glu Asp Pro Ser
        1535                1540                1545

Thr Val Met Asn Met Ile Leu Glu Ala Gln Glu Tyr Glu Leu Cys
    1550                1555                1560

Glu Glu Trp Gly Cys Leu Tyr Pro Ile Pro Arg Glu His Leu Ile
1565                1570                1575

Ser Leu His Gln Lys His Leu Leu His Leu Leu Glu Arg Arg Asp
        1580                1585                1590

His Asp Lys Ala Leu Gln Leu Leu Arg Arg Ile Pro Asp Pro Thr
    1595                1600                1605

Met Cys Leu Glu Val Thr Glu Gln Ser Leu Asp Gln His Thr Ser
1610                1615                1620

Leu Ala Thr Ser His Phe Leu Ala Asn Tyr Leu Thr Thr His Phe
        1625                1630                1635

Tyr Gly Gln Leu Thr Ala Val Arg His Arg Glu Ile Gln Ala Leu
    1640                1645                1650

Tyr Val Gly Ser Lys Ile Leu Leu Thr Leu Pro Glu Gln His Arg
1655                1660                1665

Ala Ser Tyr Ser His Leu Ser Ser Asn Pro Arg Ser Cys Trp Ser
        1670                1675                1680

Ser Cys Leu
    1685

<210> SEQ ID NO 114
<211> LENGTH: 1807
<212> TYPE: PRT
<213> ORGANISM: Homo sapiens

<400> SEQUENCE: 114

Met Asn His Pro Phe Gly Lys Glu Glu Ala Ala Ser Gln Lys Gln Leu
1               5                   10                  15

Phe Gly Phe Phe Cys Glu Cys Leu Arg Arg Gly Glu Trp Glu Leu Ala
                20                  25                  30

Gln Ala Cys Val Pro Gln Leu Gln Glu Gly Gln Gly Asp Ile Pro Lys
            35                  40                  45

Arg Val Glu Asp Ile Leu Gln Ala Leu Val Val Cys Pro Asn Leu Leu
        50                  55                  60

Arg Cys Gly Gln Asp Ile Asn Pro Gln Arg Val Ala Trp Val Trp Leu
65                  70                  75                  80

Leu Val Leu Glu Lys Trp Leu Ala Arg Glu Lys Lys Leu Leu Pro Val
                85                  90                  95

Val Phe Arg Arg Lys Leu Glu Phe Leu Leu Leu Ser Glu Asp Leu Gln
                100                 105                 110

Gly Asp Ile Pro Glu Asn Ile Leu Glu Glu Leu Tyr Glu Thr Leu Thr
            115                 120                 125

Gln Gly Ala Val Gly His Val Pro Asp Gly Asn Pro Arg Arg Glu Ser
        130                 135                 140

Trp Thr Pro Arg Leu Ser Ser Glu Ala Val Ser Val Leu Trp Asp Leu
145                 150                 155                 160

Leu Arg Gln Ser Pro Gln Pro Ala Gln Ala Leu Leu Glu Leu Leu Leu
                165                 170                 175
```

-continued

Glu Glu Asp Asp Gly Thr Gly Leu Cys His Trp Pro Leu Gln Asn Ala
            180                 185                 190

Leu Val Asp Leu Ile Arg Lys Ala Leu Arg Ala Leu Gln Gly Pro Asp
        195                 200                 205

Ser Val Pro Pro Gly Val Val Asp Ala Ile Tyr Gly Ala Leu Arg Thr
    210                 215                 220

Leu Arg Cys Pro Ala Glu Pro Leu Gly Val Glu Leu His Leu Leu Cys
225                 230                 235                 240

Glu Glu Leu Leu Glu Ala Cys Arg Thr Glu Gly Ser Pro Leu Arg Glu
                245                 250                 255

Glu Arg Leu Leu Ser Cys Leu Leu His Lys Ala Ser Arg Gly Leu Leu
            260                 265                 270

Ser Leu Tyr Gly His Thr Tyr Ala Glu Lys Val Thr Glu Lys Pro Pro
        275                 280                 285

Arg Ala Thr Ala Ser Gly Lys Val Ser Pro Asp His Leu Asp Pro Glu
    290                 295                 300

Arg Ala Met Leu Ala Leu Phe Ser Asn Pro Asn Pro Ala Glu Ala Trp
305                 310                 315                 320

Lys Val Ala Tyr Phe Tyr Cys Leu Ser Asn Asn Lys His Phe Leu Glu
                325                 330                 335

Gln Ile Leu Val Thr Ala Leu Thr Leu Leu Lys Glu Glu Asp Phe Pro
            340                 345                 350

Asn Leu Gly Cys Leu Leu Asp Arg Glu Phe Arg Pro Leu Ser Cys Leu
        355                 360                 365

Leu Val Leu Leu Gly Trp Thr His Cys Gln Ser Leu Glu Ser Ala Lys
    370                 375                 380

Arg Leu Leu Gln Thr Leu His Arg Thr Gln Gly Pro Gly Cys Asp Glu
385                 390                 395                 400

Leu Leu Arg Asp Ala Cys Asp Gly Leu Trp Ala His Leu Glu Val Leu
                405                 410                 415

Glu Trp Cys Ile Gln Gln Ser Ser Asn Pro Ile Pro Lys Arg Asp Leu
            420                 425                 430

Leu Tyr His Leu His Gly Gly Asp Ser His Ser Val Leu Tyr Thr Leu
        435                 440                 445

His His Leu Thr Asn Leu Pro Ala Leu Arg Glu Glu Asp Val Leu Lys
    450                 455                 460

Leu Leu Gln Lys Val Pro Ala Lys Asp Pro Gln Gln Glu Pro Asp Ala
465                 470                 475                 480

Val Asp Ala Pro Val Pro Glu His Leu Ser Gln Cys Gln Asn Leu Thr
                485                 490                 495

Leu Tyr Gln Gly Phe Cys Ala Met Lys Tyr Ala Ile Tyr Ala Leu Cys
            500                 505                 510

Val Asn Ser His Gln His Ser Gln Cys Gln Asp Cys Lys Asp Ser Leu
        515                 520                 525

Ser Glu Asp Leu Ala Ser Ala Thr Glu Pro Ala Asn Asp Ser Leu Ser
    530                 535                 540

Ser Pro Gly Ala Ala Asn Leu Phe Ser Thr Tyr Leu Ala Arg Cys Gln
545                 550                 555                 560

Gln Tyr Leu Cys Ser Ile Pro Asp Ser Leu Cys Leu Glu Leu Leu Glu
                565                 570                 575

Asn Ile Phe Ser Leu Leu Leu Ile Thr Ser Ala Asp Leu His Pro Glu
            580                 585                 590

Pro His Leu Pro Glu Asp Tyr Ala Glu Asp Asp Asp Ile Glu Gly Lys

```
                595                 600                 605
Ser Pro Ser Gly Leu Arg Ser Pro Ser Glu Ser Pro Gln His Ile Ala
610                 615                 620

His Pro Glu Arg Lys Ser Arg Gly Ser Leu Gly Val Pro Lys Thr
625                 630                 635                 640

Leu Ala Tyr Thr Met Pro Ser His Val Lys Ala Glu Pro Lys Asp Ser
                    645                 650                 655

Tyr Pro Gly Pro His Arg His Ser Phe Leu Asp Leu Lys His Phe Thr
                660                 665                 670

Ser Gly Ile Ser Gly Phe Leu Ala Asp Glu Phe Ala Ile Gly Ala Phe
            675                 680                 685

Leu Arg Leu Leu Gln Glu Gln Leu Asp Glu Ile Ser Ser Arg Ser Pro
690                 695                 700

Pro Glu Lys Pro Lys Gln Glu Ser Gln Ser Cys Ser Gly Ser Arg Asp
705                 710                 715                 720

Gly Leu Gln Ser Arg Leu His Arg Leu Ser Lys Val Val Ser Glu Ala
                725                 730                 735

Gln Trp Arg His Lys Val Val Thr Ser Asn His Arg Ser Glu Glu Gln
            740                 745                 750

Pro Ser Arg Arg Tyr Gln Pro Ala Thr Arg His Pro Ser Leu Arg Arg
            755                 760                 765

Gly Arg Arg Thr Arg Arg Ser Gln Ala Asp Gly Arg Asp Arg Gly Ser
770                 775                 780

Asn Pro Ser Leu Glu Ser Thr Ser Ser Glu Leu Ser Thr Ser Thr Ser
785                 790                 795                 800

Glu Gly Ser Leu Ser Ala Met Ser Gly Arg Asn Glu Leu His Ser Arg
                805                 810                 815

Leu His Pro His Pro Gln Ser Ser Leu Ile Pro Met Met Phe Ser Pro
            820                 825                 830

Pro Glu Ser Leu Leu Ala Ser Cys Ile Leu Arg Gly Asn Phe Ala Glu
            835                 840                 845

Ala His Gln Val Leu Phe Thr Phe Asn Leu Lys Ser Ser Pro Ser Ser
850                 855                 860

Gly Glu Leu Met Phe Met Glu Arg Tyr Gln Glu Val Ile Gln Glu Leu
865                 870                 875                 880

Ala Gln Val Glu His Lys Ile Glu Asn Gln Asn Ser Asp Ala Gly Ser
                885                 890                 895

Ser Thr Ile Arg Arg Thr Gly Ser Gly Arg Ser Thr Leu Gln Ala Ile
                900                 905                 910

Gly Ser Ala Ala Ala Gly Met Val Phe Tyr Ser Ile Ser Asp Val
            915                 920                 925

Thr Asp Lys Leu Leu Asn Thr Ser Gly Asp Pro Ile Pro Met Leu Gln
            930                 935                 940

Glu Asp Phe Trp Ile Ser Thr Ala Leu Val Glu Pro Thr Ala Pro Leu
945                 950                 955                 960

Arg Glu Val Leu Glu Asp Leu Ser Pro Pro Ala Met Ala Ala Phe Asp
                965                 970                 975

Leu Ala Cys Ser Gln Cys Gln Leu Trp Lys Thr Cys Lys Gln Leu Leu
                980                 985                 990

Glu Thr Ala Glu Arg Arg Leu Asn  Ser Ser Leu Glu Arg  Arg Gly Arg
            995                 1000                 1005

Arg Ile  Asp His Val Leu Leu  Asn Ala Asp Gly Ile  Arg Gly Phe
    1010                 1015                 1020
```

-continued

```
Pro Val Val Leu Gln Gln Ile Ser Lys Ser Leu Asn Tyr Leu Leu
    1025                1030                1035

Met Ser Ala Ser Gln Thr Lys Ser Glu Ser Val Glu Glu Lys Gly
    1040                1045                1050

Gly Gly Pro Pro Arg Cys Ser Ile Thr Glu Leu Leu Gln Met Cys
    1055                1060                1065

Trp Pro Ser Leu Ser Glu Asp Cys Val Ala Ser His Thr Thr Leu
    1070                1075                1080

Ser Gln Gln Leu Asp Gln Val Leu Gln Ser Leu Arg Glu Ala Leu
    1085                1090                1095

Glu Leu Pro Glu Pro Arg Thr Pro Pro Leu Ser Ser Leu Val Glu
    1100                1105                1110

Gln Ala Ala Gln Lys Ala Pro Glu Ala Glu Ala His Pro Val Gln
    1115                1120                1125

Ile Gln Thr Gln Leu Leu Gln Lys Asn Leu Gly Lys Gln Thr Pro
    1130                1135                1140

Ser Gly Ser Arg Gln Met Asp Tyr Leu Gly Thr Phe Phe Ser Tyr
    1145                1150                1155

Cys Ser Thr Leu Ala Ala Val Leu Leu Gln Ser Leu Ser Ser Glu
    1160                1165                1170

Pro Asp His Val Glu Val Lys Val Gly Asn Pro Phe Val Leu Leu
    1175                1180                1185

Gln Gln Ser Ser Ser Gln Leu Val Ser His Leu Leu Phe Glu Arg
    1190                1195                1200

Gln Val Pro Pro Glu Arg Leu Ala Ala Leu Leu Ala Gln Glu Asn
    1205                1210                1215

Leu Ser Leu Ser Val Pro Gln Val Ile Val Ser Cys Cys Cys Glu
    1220                1225                1230

Pro Leu Ala Leu Cys Ser Ser Arg Gln Ser Gln Gln Thr Ser Ser
    1235                1240                1245

Leu Leu Thr Arg Leu Gly Thr Leu Ala Gln Leu His Ala Ser His
    1250                1255                1260

Cys Leu Asp Asp Leu Pro Leu Ser Thr Pro Ser Ser Pro Arg Thr
    1265                1270                1275

Thr Glu Asn Pro Thr Leu Glu Arg Lys Pro Tyr Ser Ser Pro Arg
    1280                1285                1290

Asp Ser Ser Leu Pro Ala Leu Thr Ser Ser Ala Leu Ala Phe Leu
    1295                1300                1305

Lys Ser Arg Ser Lys Leu Leu Ala Thr Val Ala Cys Leu Gly Ala
    1310                1315                1320

Ser Pro Arg Leu Lys Val Ser Lys Pro Ser Leu Ser Trp Lys Glu
    1325                1330                1335

Leu Arg Gly Arg Arg Glu Val Pro Leu Ala Ala Glu Gln Val Ala
    1340                1345                1350

Arg Glu Cys Glu Arg Leu Leu Glu Gln Phe Pro Leu Phe Glu Ala
    1355                1360                1365

Phe Leu Leu Ala Ala Trp Glu Pro Leu Arg Gly Ser Leu Gln Gln
    1370                1375                1380

Gly Gln Ser Leu Ala Val Asn Leu Cys Gly Trp Ala Ser Leu Ser
    1385                1390                1395

Thr Val Leu Leu Gly Leu His Ser Pro Ile Ala Leu Asp Val Leu
    1400                1405                1410
```

-continued

```
Ser Glu Ala Phe Glu Glu Ser Leu Val Ala Arg Asp Trp Ser Arg
1415                1420                1425

Ala Leu Gln Leu Thr Glu Val Tyr Gly Arg Asp Val Asp Asp Leu
    1430                1435                1440

Ser Ser Ile Lys Asp Ala Val Leu Ser Cys Ala Val Ala Cys Asp
1445                1450                1455

Lys Glu Gly Trp Gln Tyr Leu Phe Pro Val Lys Asp Ala Ser Leu
1460                1465                1470

Arg Ser Arg Leu Ala Leu Gln Phe Val Asp Arg Trp Pro Leu Glu
1475                1480                1485

Ser Cys Leu Glu Ile Leu Ala Tyr Cys Ile Ser Asp Thr Ala Val
1490                1495                1500

Gln Glu Gly Leu Lys Cys Glu Leu Gln Arg Lys Leu Ala Glu Leu
1505                1510                1515

Gln Val Tyr Gln Lys Ile Leu Gly Leu Gln Ser Pro Pro Val Trp
1520                1525                1530

Cys Asp Trp Gln Thr Leu Arg Ser Cys Cys Val Glu Asp Pro Ser
1535                1540                1545

Thr Val Met Asn Met Ile Leu Glu Ala Gln Glu Tyr Glu Leu Cys
1550                1555                1560

Glu Glu Trp Gly Cys Leu Tyr Pro Ile Pro Arg Glu His Leu Ile
1565                1570                1575

Ser Leu His Gln Lys His Leu Leu His Leu Leu Glu Arg Arg Asp
1580                1585                1590

His Asp Lys Ala Leu Gln Leu Leu Arg Arg Ile Pro Asp Pro Thr
1595                1600                1605

Met Cys Leu Glu Val Thr Glu Gln Ser Leu Asp Gln His Thr Ser
1610                1615                1620

Leu Ala Thr Ser His Phe Leu Ala Asn Tyr Leu Thr Thr His Phe
1625                1630                1635

Tyr Gly Gln Leu Thr Ala Val Arg His Arg Glu Ile Gln Ala Leu
1640                1645                1650

Tyr Val Gly Ser Lys Ile Leu Leu Thr Leu Pro Glu Gln His Arg
1655                1660                1665

Ala Ser Tyr Ser His Leu Ser Asn Pro Leu Phe Met Leu Glu
1670                1675                1680

Gln Leu Leu Met Asn Met Lys Val Asp Trp Ala Thr Val Ala Val
1685                1690                1695

Gln Thr Leu Gln Gln Leu Leu Val Gly Gln Glu Ile Gly Phe Thr
1700                1705                1710

Met Asp Glu Val Asp Ser Leu Leu Ser Arg Tyr Ala Glu Lys Ala
1715                1720                1725

Leu Asp Phe Pro Tyr Pro Gln Arg Glu Lys Arg Ser Asp Ser Val
1730                1735                1740

Ile His Leu Gln Glu Ile Val His Gln Ala Ala Asp Pro Glu Thr
1745                1750                1755

Leu Pro Arg Ser Pro Ser Ala Glu Phe Ser Pro Ala Ala Pro Pro
1760                1765                1770

Gly Ile Ser Ser Ile His Ser Pro Ser Leu Arg Glu Arg Ser Phe
1775                1780                1785

Pro Pro Thr Gln Pro Ser Gln Glu Phe Val Pro Pro Ala Thr Pro
1790                1795                1800

Pro Ala Arg His
```

-continued

1805

<210> SEQ ID NO 115
<211> LENGTH: 2539
<212> TYPE: PRT
<213> ORGANISM: Homo sapiens

<400> SEQUENCE: 115

Met Asn His Pro Phe Gly Lys Glu Glu Ala Ser Gln Lys Gln Leu
1               5                   10                  15

Phe Gly Phe Phe Cys Glu Cys Leu Arg Arg Gly Glu Trp Glu Leu Ala
            20                  25                  30

Gln Ala Cys Val Pro Gln Leu Gln Glu Gly Gln Gly Asp Ile Pro Lys
        35                  40                  45

Arg Val Glu Asp Ile Leu Gln Ala Leu Val Val Cys Pro Asn Leu Leu
    50                  55                  60

Arg Cys Gly Gln Asp Ile Asn Pro Gln Arg Val Ala Trp Val Trp Leu
65                  70                  75                  80

Leu Val Leu Glu Lys Trp Leu Ala Arg Glu Lys Lys Leu Leu Pro Val
                85                  90                  95

Val Phe Arg Arg Lys Leu Glu Phe Leu Leu Ser Glu Asp Leu Gln
            100                 105                 110

Gly Asp Ile Pro Glu Asn Ile Leu Glu Glu Leu Tyr Glu Thr Leu Thr
        115                 120                 125

Gln Gly Ala Val Gly His Val Pro Asp Gly Asn Pro Arg Arg Glu Ser
    130                 135                 140

Trp Thr Pro Arg Leu Ser Ser Glu Ala Val Ser Val Leu Trp Asp Leu
145                 150                 155                 160

Leu Arg Gln Ser Pro Gln Pro Ala Gln Ala Leu Leu Glu Leu Leu Leu
                165                 170                 175

Glu Glu Asp Asp Gly Thr Gly Leu Cys His Trp Pro Leu Gln Asn Ala
            180                 185                 190

Leu Val Asp Leu Ile Arg Lys Ala Leu Arg Ala Leu Gln Gly Pro Asp
        195                 200                 205

Ser Val Pro Pro Gly Val Val Asp Ala Ile Tyr Gly Ala Leu Arg Thr
    210                 215                 220

Leu Arg Cys Pro Ala Glu Pro Leu Gly Val Glu Leu His Leu Leu Cys
225                 230                 235                 240

Glu Glu Leu Leu Glu Ala Cys Arg Thr Glu Gly Ser Pro Leu Arg Glu
                245                 250                 255

Glu Arg Leu Leu Ser Cys Leu Leu His Lys Ala Ser Arg Gly Leu Leu
            260                 265                 270

Ser Leu Tyr Gly His Thr Tyr Ala Glu Lys Val Thr Glu Lys Pro Pro
        275                 280                 285

Arg Ala Thr Ala Ser Gly Lys Val Ser Pro Asp His Leu Asp Pro Glu
    290                 295                 300

Arg Ala Met Leu Ala Leu Phe Ser Asn Pro Asn Pro Ala Glu Ala Trp
305                 310                 315                 320

Lys Val Ala Tyr Phe Tyr Cys Leu Ser Asn Asn Lys His Phe Leu Glu
                325                 330                 335

Gln Ile Leu Val Thr Ala Leu Thr Leu Leu Lys Glu Glu Asp Phe Pro
            340                 345                 350

Asn Leu Gly Cys Leu Leu Asp Arg Glu Phe Arg Pro Leu Ser Cys Leu
        355                 360                 365

```
Leu Val Leu Leu Gly Trp Thr His Cys Gln Ser Leu Glu Ser Ala Lys
            370             375             380
Arg Leu Leu Gln Thr Leu His Arg Thr Gln Gly Pro Gly Cys Asp Glu
385                 390                 395                 400
Leu Leu Arg Asp Ala Cys Asp Gly Leu Trp Ala His Leu Glu Val Leu
                405                 410                 415
Glu Trp Cys Ile Gln Gln Ser Ser Asn Pro Ile Pro Lys Arg Asp Leu
                420                 425                 430
Leu Tyr His Leu His Gly Gly Asp Ser His Ser Val Leu Tyr Thr Leu
            435                 440                 445
His His Leu Thr Asn Leu Pro Ala Leu Arg Glu Glu Asp Val Leu Lys
450                 455                 460
Leu Leu Gln Lys Val Pro Ala Lys Asp Pro Gln Gln Glu Pro Asp Ala
465                 470                 475                 480
Val Asp Ala Pro Val Pro Glu His Leu Ser Gln Cys Gln Asn Leu Thr
                485                 490                 495
Leu Tyr Gln Gly Phe Cys Ala Met Lys Tyr Ala Ile Tyr Ala Leu Cys
            500                 505                 510
Val Asn Ser His Gln His Ser Gln Cys Gln Asp Cys Lys Asp Ser Leu
            515                 520                 525
Ser Glu Asp Leu Ala Ser Ala Thr Glu Pro Ala Asn Asp Ser Leu Ser
530                 535                 540
Ser Pro Gly Ala Ala Asn Leu Phe Ser Thr Tyr Leu Ala Arg Cys Gln
545                 550                 555                 560
Gln Tyr Leu Cys Ser Ile Pro Asp Ser Leu Cys Leu Glu Leu Leu Glu
                565                 570                 575
Asn Ile Phe Ser Leu Leu Leu Ile Thr Ser Ala Asp Leu His Pro Glu
            580                 585                 590
Pro His Leu Pro Glu Asp Tyr Ala Glu Asp Asp Ile Glu Gly Lys
            595                 600                 605
Ser Pro Ser Gly Leu Arg Ser Pro Ser Glu Ser Pro Gln His Ile Ala
610                 615                 620
His Pro Glu Arg Lys Ser Glu Arg Gly Ser Leu Gly Val Pro Lys Thr
625                 630                 635                 640
Leu Ala Tyr Thr Met Pro Ser His Val Lys Ala Glu Pro Lys Asp Ser
                645                 650                 655
Tyr Pro Gly Pro His Arg His Ser Phe Leu Asp Leu Lys His Phe Thr
                660                 665                 670
Ser Gly Ile Ser Gly Phe Leu Ala Asp Glu Phe Ala Ile Gly Ala Phe
            675                 680                 685
Leu Arg Leu Leu Gln Glu Gln Leu Asp Glu Ile Ser Ser Arg Ser Pro
690                 695                 700
Pro Glu Lys Pro Lys Gln Glu Ser Gln Ser Cys Ser Gly Ser Arg Asp
705                 710                 715                 720
Gly Leu Gln Ser Arg Leu His Arg Leu Ser Lys Val Val Ser Glu Ala
                725                 730                 735
Gln Trp Arg His Lys Val Val Thr Ser Asn His Arg Ser Glu Glu Gln
                740                 745                 750
Pro Ser Arg Arg Tyr Gln Pro Ala Thr Arg His Pro Ser Leu Arg Arg
                755                 760                 765
Gly Arg Arg Thr Arg Arg Ser Gln Ala Asp Gly Arg Asp Arg Gly Ser
770                 775                 780
Asn Pro Ser Leu Glu Ser Thr Ser Ser Glu Leu Ser Thr Ser Thr Ser
```

```
            785                 790                 795                 800
        Glu Gly Ser Leu Ser Ala Met Ser Gly Arg Asn Glu Leu His Ser Arg
                        805                 810                 815

Leu His Pro His Pro Gln Ser Ser Leu Ile Pro Met Met Phe Ser Pro
                        820                 825                 830

Pro Glu Ser Leu Leu Ala Ser Cys Ile Leu Arg Gly Asn Phe Ala Glu
                        835                 840                 845

Ala His Gln Val Leu Phe Thr Phe Asn Leu Lys Ser Ser Pro Ser Ser
                    850                 855                 860

Gly Glu Leu Met Phe Met Glu Arg Tyr Gln Glu Val Ile Gln Glu Leu
        865                 870                 875                 880

Ala Gln Val Glu His Lys Ile Glu Asn Gln Asn Ser Asp Ala Gly Ser
                        885                 890                 895

Ser Thr Ile Arg Arg Thr Gly Ser Gly Arg Ser Thr Leu Gln Ala Ile
                        900                 905                 910

Gly Ser Ala Ala Ala Gly Met Val Phe Tyr Ser Ile Ser Asp Val
                        915                 920                 925

Thr Asp Lys Leu Leu Asn Thr Ser Gly Asp Pro Ile Pro Met Leu Gln
                    930                 935                 940

Glu Asp Phe Trp Ile Ser Thr Ala Leu Val Glu Pro Thr Ala Pro Leu
        945                 950                 955                 960

Arg Glu Val Leu Glu Asp Leu Ser Pro Pro Ala Met Ala Ala Phe Asp
                        965                 970                 975

Leu Ala Cys Ser Gln Cys Gln Leu Trp Lys Thr Cys Lys Gln Leu Leu
                        980                 985                 990

Glu Thr Ala Glu Arg Arg Leu Asn  Ser Ser Leu Glu Arg  Arg Gly Arg
                    995                 1000                1005

Arg Ile  Asp His Val Leu Leu  Asn Ala Asp Gly Ile  Arg Gly Phe
            1010                1015                1020

Pro Val  Val Leu Gln Gln Ile  Ser Lys Ser Leu Asn  Tyr Leu Leu
            1025                1030                1035

Met Ser  Ala Ser Gln Thr Lys  Ser Glu Ser Val Glu  Glu Lys Gly
            1040                1045                1050

Gly Gly  Pro Pro Arg Cys Ser  Ile Thr Glu Leu Leu  Gln Met Cys
            1055                1060                1065

Trp Pro  Ser Leu Ser Glu Asp  Cys Val Ala Ser His  Thr Thr Leu
            1070                1075                1080

Ser Gln  Gln Leu Asp Gln Val  Leu Gln Ser Leu Arg  Glu Ala Leu
            1085                1090                1095

Glu Leu  Pro Glu Pro Arg Thr  Pro Pro Leu Ser Ser  Leu Val Glu
            1100                1105                1110

Gln Ala  Ala Gln Lys Ala Pro  Glu Ala Glu Ala His  Pro Val Gln
            1115                1120                1125

Ile Gln  Thr Gln Leu Leu Gln  Lys Asn Leu Gly Lys  Gln Thr Pro
            1130                1135                1140

Ser Gly  Ser Arg Gln Met Asp  Tyr Leu Gly Thr Phe  Phe Ser Tyr
            1145                1150                1155

Cys Ser  Thr Leu Ala Ala Val  Leu Leu Gln Ser Leu  Ser Ser Glu
            1160                1165                1170

Pro Asp  His Val Glu Val Lys  Val Gly Asn Pro Phe  Val Leu Leu
            1175                1180                1185

Gln Gln  Ser Ser Ser Gln Leu  Val Ser His Leu Leu  Phe Glu Arg
            1190                1195                1200
```

-continued

```
Gln Val Pro Pro Glu Arg Leu Ala Ala Leu Leu Ala Gln Glu Asn
    1205                1210                1215

Leu Ser Leu Ser Val Pro Gln Val Ile Val Ser Cys Cys Cys Glu
    1220                1225                1230

Pro Leu Ala Leu Cys Ser Ser Arg Gln Ser Gln Gln Thr Ser Ser
    1235                1240                1245

Leu Leu Thr Arg Leu Gly Thr Leu Ala Gln Leu His Ala Ser His
    1250                1255                1260

Cys Leu Asp Asp Leu Pro Leu Ser Thr Pro Ser Ser Pro Arg Thr
    1265                1270                1275

Thr Glu Asn Pro Thr Leu Glu Arg Lys Pro Tyr Ser Ser Pro Arg
    1280                1285                1290

Asp Ser Ser Leu Pro Ala Leu Thr Ser Ser Ala Leu Ala Phe Leu
    1295                1300                1305

Lys Ser Arg Ser Lys Leu Leu Ala Thr Val Ala Cys Leu Gly Ala
    1310                1315                1320

Ser Pro Arg Leu Lys Val Ser Lys Pro Ser Leu Ser Trp Lys Glu
    1325                1330                1335

Leu Arg Gly Arg Arg Glu Val Pro Leu Ala Ala Glu Gln Val Ala
    1340                1345                1350

Arg Glu Cys Glu Arg Leu Leu Glu Gln Phe Pro Leu Phe Glu Ala
    1355                1360                1365

Phe Leu Leu Ala Ala Trp Glu Pro Leu Arg Gly Ser Leu Gln Gln
    1370                1375                1380

Gly Gln Ser Leu Ala Val Asn Leu Cys Gly Trp Ala Ser Leu Ser
    1385                1390                1395

Thr Val Leu Leu Gly Leu His Ser Pro Ile Ala Leu Asp Val Leu
    1400                1405                1410

Ser Glu Ala Phe Glu Glu Ser Leu Val Ala Arg Asp Trp Ser Arg
    1415                1420                1425

Ala Leu Gln Leu Thr Glu Val Tyr Gly Arg Asp Val Asp Asp Leu
    1430                1435                1440

Ser Ser Ile Lys Asp Ala Val Leu Ser Cys Ala Val Ala Cys Asp
    1445                1450                1455

Lys Glu Gly Trp Gln Tyr Leu Phe Pro Val Lys Asp Ala Ser Leu
    1460                1465                1470

Arg Ser Arg Leu Ala Leu Gln Phe Val Asp Arg Trp Pro Leu Glu
    1475                1480                1485

Ser Cys Leu Glu Ile Leu Ala Tyr Cys Ile Ser Asp Thr Ala Val
    1490                1495                1500

Gln Glu Gly Leu Lys Cys Glu Leu Gln Arg Lys Leu Ala Glu Leu
    1505                1510                1515

Gln Val Tyr Gln Lys Ile Leu Gly Leu Gln Ser Pro Pro Val Trp
    1520                1525                1530

Cys Asp Trp Gln Thr Leu Arg Ser Cys Cys Val Glu Asp Pro Ser
    1535                1540                1545

Thr Val Met Asn Met Ile Leu Glu Ala Gln Glu Tyr Glu Leu Cys
    1550                1555                1560

Glu Glu Trp Gly Cys Leu Tyr Pro Ile Pro Arg Glu His Leu Ile
    1565                1570                1575

Ser Leu His Gln Lys His Leu Leu His Leu Leu Glu Arg Arg Asp
    1580                1585                1590
```

```
His Asp Lys Ala Leu Gln Leu Leu Arg Arg Ile Pro Asp Pro Thr
    1595                1600                1605

Met Cys Leu Glu Val Thr Glu Gln Ser Leu Asp Gln His Thr Ser
    1610                1615                1620

Leu Ala Thr Ser His Phe Leu Ala Asn Tyr Leu Thr Thr His Phe
    1625                1630                1635

Tyr Gly Gln Leu Thr Ala Val Arg His Arg Glu Ile Gln Ala Leu
    1640                1645                1650

Tyr Val Gly Ser Lys Ile Leu Leu Thr Leu Pro Glu Gln His Arg
    1655                1660                1665

Ala Ser Tyr Ser His Leu Ser Ser Asn Pro Leu Phe Met Leu Glu
    1670                1675                1680

Gln Leu Leu Met Asn Met Lys Val Asp Trp Ala Thr Val Ala Val
    1685                1690                1695

Gln Thr Leu Gln Gln Leu Leu Val Gly Gln Glu Ile Gly Phe Thr
    1700                1705                1710

Met Asp Glu Val Asp Ser Leu Leu Ser Arg Tyr Ala Glu Lys Ala
    1715                1720                1725

Leu Asp Phe Pro Tyr Pro Gln Arg Glu Lys Arg Ser Asp Ser Val
    1730                1735                1740

Ile His Leu Gln Glu Ile Val His Gln Ala Ala Asp Pro Glu Thr
    1745                1750                1755

Leu Pro Arg Ser Pro Ser Ala Glu Phe Ser Pro Ala Ala Pro Pro
    1760                1765                1770

Gly Ile Ser Ser Ile His Ser Pro Ser Leu Arg Glu Arg Ser Phe
    1775                1780                1785

Pro Pro Thr Gln Pro Ser Gln Glu Phe Val Pro Ala Thr Pro
    1790                1795                1800

Pro Ala Arg His Gln Trp Val Pro Asp Glu Thr Glu Ser Ile Cys
    1805                1810                1815

Met Val Cys Cys Arg Glu His Phe Thr Met Phe Asn Arg Arg His
    1820                1825                1830

His Cys Arg Arg Cys Gly Arg Leu Val Cys Ser Ser Cys Ser Thr
    1835                1840                1845

Lys Lys Met Val Val Glu Gly Cys Arg Glu Asn Pro Ala Arg Val
    1850                1855                1860

Cys Asp Gln Cys Tyr Ser Tyr Cys Asn Lys Asp Val Pro Glu Glu
    1865                1870                1875

Pro Ser Glu Lys Pro Glu Ala Leu Asp Ser Ser Lys Asn Glu Ser
    1880                1885                1890

Pro Pro Tyr Ser Phe Val Val Arg Val Pro Lys Ala Asp Glu Val
    1895                1900                1905

Glu Trp Ile Leu Asp Leu Lys Glu Glu Glu Asn Glu Leu Val Arg
    1910                1915                1920

Ser Glu Phe Tyr Tyr Glu Gln Ala Pro Ser Ala Ser Leu Cys Ile
    1925                1930                1935

Ala Ile Leu Asn Leu His Arg Asp Ser Ile Ala Cys Gly His Gln
    1940                1945                1950

Leu Ile Glu His Cys Cys Arg Leu Ser Lys Gly Leu Thr Asn Pro
    1955                1960                1965

Glu Val Asp Ala Gly Leu Leu Thr Asp Ile Met Lys Gln Leu Leu
    1970                1975                1980

Phe Ser Ala Lys Met Met Phe Val Lys Ala Gly Gln Ser Gln Asp
```

```
                1985                1990                1995
Leu Ala Leu Cys Asp Thr Tyr Ile Ser Lys Val Asp Val Leu Asn
        2000            2005            2010

Ile Leu Val Ala Ala Ala Tyr Arg His Val Pro Ser Leu Asp Gln
        2015            2020            2025

Ile Leu Gln Pro Ala Ala Val Thr Arg Leu Arg Asn Gln Leu Leu
        2030            2035            2040

Glu Ala Glu Tyr Tyr Gln Leu Gly Val Glu Val Ser Thr Lys Thr
        2045            2050            2055

Gly Leu Asp Thr Thr Gly Ala Trp His Ala Trp Gly Met Ala Cys
        2060            2065            2070

Leu Lys Ala Gly Asn Leu Thr Ala Ala Arg Glu Lys Phe Ser Arg
        2075            2080            2085

Cys Leu Lys Pro Pro Phe Asp Leu Asn Gln Leu Asn His Gly Ser
        2090            2095            2100

Arg Leu Val Gln Asp Val Val Glu Tyr Leu Glu Ser Thr Val Arg
        2105            2110            2115

Pro Phe Val Ser Leu Gln Asp Asp Asp Tyr Phe Ala Thr Leu Arg
        2120            2125            2130

Glu Leu Glu Ala Thr Leu Arg Thr Gln Ser Leu Ser Leu Ala Val
        2135            2140            2145

Ile Pro Glu Gly Lys Ile Met Asn Asn Thr Tyr Tyr Gln Glu Cys
        2150            2155            2160

Leu Phe Tyr Leu His Asn Tyr Ser Thr Asn Leu Ala Ile Ile Ser
        2165            2170            2175

Phe Tyr Val Arg His Ser Cys Leu Arg Glu Ala Leu Leu His Leu
        2180            2185            2190

Leu Asn Lys Glu Ser Pro Pro Glu Val Phe Ile Glu Gly Ile Phe
        2195            2200            2205

Gln Pro Ser Tyr Lys Ser Gly Lys Leu His Thr Leu Glu Asn Leu
        2210            2215            2220

Leu Glu Ser Ile Asp Pro Thr Leu Glu Ser Trp Gly Lys Tyr Leu
        2225            2230            2235

Ile Ala Ala Cys Gln His Leu Gln Lys Lys Asn Tyr Tyr His Ile
        2240            2245            2250

Leu Tyr Glu Leu Gln Gln Phe Met Lys Asp Gln Val Arg Ala Ala
        2255            2260            2265

Met Thr Cys Ile Arg Phe Phe Ser His Lys Ala Lys Ser Tyr Thr
        2270            2275            2280

Glu Leu Gly Glu Lys Leu Ser Trp Leu Leu Lys Ala Lys Asp His
        2285            2290            2295

Leu Lys Ile Tyr Leu Gln Glu Thr Ser Arg Ser Ser Gly Arg Lys
        2300            2305            2310

Lys Thr Thr Phe Phe Arg Lys Lys Met Thr Ala Ala Asp Val Ser
        2315            2320            2325

Arg His Met Asn Thr Leu Gln Leu Gln Met Glu Val Thr Arg Phe
        2330            2335            2340

Leu His Arg Cys Glu Ser Ala Gly Thr Ser Gln Ile Thr Thr Leu
        2345            2350            2355

Pro Leu Pro Thr Leu Phe Gly Asn Asn His Met Lys Met Asp Val
        2360            2365            2370

Ala Cys Lys Val Met Leu Gly Gly Lys Asn Val Glu Asp Gly Phe
        2375            2380            2385
```

-continued

Gly Ile Ala Phe Arg Val Leu Gln Asp Phe Gln Leu Asp Ala Ala
            2390                2395                2400

Met Thr Tyr Cys Arg Ala Ala Arg Gln Leu Val Glu Lys Glu Lys
        2405                2410                2415

Tyr Ser Glu Ile Gln Gln Leu Leu Lys Cys Val Ser Glu Ser Gly
    2420                2425                2430

Met Ala Ala Lys Ser Asp Gly Asp Thr Ile Leu Leu Asn Cys Leu
    2435                2440                2445

Glu Ala Phe Lys Arg Ile Pro Pro Gln Glu Leu Glu Gly Leu Ile
    2450                2455                2460

Gln Ala Ile His Asn Asp Asp Asn Lys Val Arg Ala Tyr Leu Ile
    2465                2470                2475

Cys Cys Lys Leu Arg Ser Ala Tyr Leu Ile Ala Val Lys Gln Glu
    2480                2485                2490

His Ser Arg Ala Thr Ala Leu Val Gln Gln Val Gln Gln Ala Ala
    2495                2500                2505

Lys Ser Ser Gly Asp Ala Val Val Gln Asp Ile Cys Ala Gln Trp
    2510                2515                2520

Leu Leu Thr Ser His Pro Arg Gly Ala His Gly Pro Gly Ser Arg
    2525                2530                2535

Lys

<210> SEQ ID NO 116
<211> LENGTH: 2110
<212> TYPE: PRT
<213> ORGANISM: Homo sapiens

<400> SEQUENCE: 116

Met Asn His Pro Phe Gly Lys Glu Glu Ala Ala Ser Gln Lys Gln Leu
1               5                   10                  15

Phe Gly Phe Phe Cys Glu Cys Leu Arg Arg Gly Glu Trp Glu Leu Ala
            20                  25                  30

Gln Ala Cys Val Pro Gln Leu Gln Glu Gly Gln Gly Asp Ile Pro Lys
        35                  40                  45

Arg Val Glu Asp Ile Leu Gln Ala Leu Val Val Cys Pro Asn Leu Leu
    50                  55                  60

Arg Cys Gly Gln Asp Ile Asn Pro Gln Arg Val Ala Trp Val Trp Leu
65                  70                  75                  80

Leu Val Leu Glu Lys Trp Leu Ala Arg Glu Lys Lys Leu Leu Pro Val
                85                  90                  95

Val Phe Arg Arg Lys Leu Glu Phe Leu Leu Leu Ser Glu Asp Leu Gln
            100                 105                 110

Gly Asp Ile Pro Glu Asn Ile Leu Glu Glu Leu Tyr Glu Thr Leu Thr
        115                 120                 125

Gln Gly Ala Val Gly His Val Pro Asp Gly Asn Pro Arg Arg Glu Ser
    130                 135                 140

Trp Thr Pro Arg Leu Ser Ser Glu Ala Val Ser Val Leu Trp Asp Leu
145                 150                 155                 160

Leu Arg Gln Ser Pro Gln Pro Ala Gln Ala Leu Leu Glu Leu Leu
                165                 170                 175

Glu Glu Asp Asp Gly Thr Gly Leu Cys His Trp Pro Leu Gln Asn Ala
            180                 185                 190

Leu Val Asp Leu Ile Arg Lys Ala Leu Arg Ala Leu Gln Gly Pro Asp
        195                 200                 205

```
Ser Val Pro Pro Gly Val Val Asp Ala Ile Tyr Gly Ala Leu Arg Thr
    210                 215                 220

Leu Arg Cys Pro Ala Glu Pro Leu Gly Val Glu Leu His Leu Leu Cys
225                 230                 235                 240

Glu Glu Leu Leu Glu Ala Cys Arg Thr Glu Gly Ser Pro Leu Arg Glu
                245                 250                 255

Glu Arg Leu Leu Ser Cys Leu Leu His Lys Ala Ser Arg Gly Leu Leu
            260                 265                 270

Ser Leu Tyr Gly His Thr Tyr Ala Glu Lys Val Thr Glu Lys Pro Pro
        275                 280                 285

Arg Ala Thr Ala Ser Gly Lys Val Ser Pro Asp His Leu Asp Pro Glu
    290                 295                 300

Arg Ala Met Leu Ala Leu Phe Ser Asn Pro Asn Pro Ala Glu Ala Trp
305                 310                 315                 320

Lys Val Ala Tyr Phe Tyr Cys Leu Ser Asn Asn Lys His Phe Leu Glu
                325                 330                 335

Gln Ile Leu Val Thr Ala Leu Thr Leu Leu Lys Glu Glu Asp Phe Pro
            340                 345                 350

Asn Leu Gly Cys Leu Leu Asp Arg Glu Phe Arg Pro Leu Ser Cys Leu
        355                 360                 365

Leu Val Leu Leu Gly Trp Thr His Cys Gln Ser Leu Glu Ser Ala Lys
    370                 375                 380

Arg Leu Leu Gln Thr Leu His Arg Thr Gln Gly Pro Gly Cys Asp Glu
385                 390                 395                 400

Leu Leu Arg Asp Ala Cys Asp Gly Leu Trp Ala His Leu Glu Val Leu
                405                 410                 415

Glu Trp Cys Ile Gln Gln Ser Ser Asn Pro Ile Pro Lys Arg Asp Leu
            420                 425                 430

Leu Tyr His Leu His Gly Gly Asp Ser His Ser Val Leu Tyr Thr Leu
        435                 440                 445

His His Leu Thr Asn Leu Pro Ala Leu Arg Glu Glu Asp Val Leu Lys
    450                 455                 460

Leu Leu Gln Lys Val Pro Ala Lys Asp Pro Gln Gln Glu Pro Asp Ala
465                 470                 475                 480

Val Asp Ala Pro Val Pro Glu His Leu Ser Gln Cys Gln Asn Leu Thr
                485                 490                 495

Leu Tyr Gln Gly Phe Cys Ala Met Lys Tyr Ala Ile Tyr Ala Leu Cys
            500                 505                 510

Val Asn Ser His Gln His Ser Gln Cys Gln Asp Cys Lys Asp Ser Leu
        515                 520                 525

Ser Glu Asp Leu Ala Ser Ala Thr Glu Pro Ala Asn Asp Ser Leu Ser
    530                 535                 540

Ser Pro Gly Ala Ala Asn Leu Phe Ser Thr Tyr Leu Ala Arg Cys Gln
545                 550                 555                 560

Gln Tyr Leu Cys Ser Ile Pro Asp Ser Leu Cys Leu Glu Leu Leu Glu
                565                 570                 575

Asn Ile Phe Ser Leu Leu Leu Ile Thr Ser Ala Asp Leu His Pro Glu
            580                 585                 590

Pro His Leu Pro Glu Asp Tyr Ala Glu Asp Asp Ile Glu Gly Lys
        595                 600                 605

Ser Pro Ser Gly Leu Arg Ser Pro Ser Glu Ser Pro Gln His Ile Ala
    610                 615                 620
```

```
His Pro Glu Arg Lys Ser Glu Arg Gly Ser Leu Gly Val Pro Lys Thr
625                 630                 635                 640

Leu Ala Tyr Thr Met Pro Ser His Val Lys Ala Glu Pro Lys Asp Ser
            645                 650                 655

Tyr Pro Gly Pro His Arg His Ser Phe Leu Asp Leu Lys His Phe Thr
        660                 665                 670

Ser Gly Ile Ser Gly Phe Leu Ala Asp Glu Phe Ala Ile Gly Ala Phe
        675                 680                 685

Leu Arg Leu Leu Gln Glu Gln Leu Asp Glu Ile Ser Ser Arg Ser Pro
690                 695                 700

Pro Glu Lys Pro Lys Gln Glu Ser Gln Ser Cys Ser Gly Ser Arg Asp
705                 710                 715                 720

Gly Leu Gln Ser Arg Leu His Arg Leu Ser Lys Val Val Ser Glu Ala
            725                 730                 735

Gln Trp Arg His Lys Val Val Thr Ser Asn His Arg Ser Glu Glu Gln
                740                 745                 750

Pro Ser Arg Arg Tyr Gln Pro Ala Thr Arg His Pro Ser Leu Arg Arg
        755                 760                 765

Gly Arg Arg Thr Arg Arg Ser Gln Ala Asp Gly Arg Asp Arg Gly Ser
770                 775                 780

Asn Pro Ser Leu Glu Ser Thr Ser Ser Glu Leu Ser Thr Ser Thr Ser
785                 790                 795                 800

Glu Gly Ser Leu Ser Ala Met Ser Gly Arg Asn Glu Leu His Ser Arg
            805                 810                 815

Leu His Pro His Pro Gln Ser Ser Leu Ile Pro Met Met Phe Ser Pro
        820                 825                 830

Pro Glu Ser Leu Leu Ala Ser Cys Ile Leu Arg Gly Asn Phe Ala Glu
        835                 840                 845

Ala His Gln Val Leu Phe Thr Phe Asn Leu Lys Ser Ser Pro Ser Ser
850                 855                 860

Gly Glu Leu Met Phe Met Glu Arg Tyr Gln Val Ile Gln Glu Leu
865                 870                 875                 880

Ala Gln Val Glu His Lys Ile Glu Asn Gln Asn Ser Asp Ala Gly Ser
            885                 890                 895

Ser Thr Ile Arg Arg Thr Gly Ser Gly Arg Ser Thr Leu Gln Ala Ile
        900                 905                 910

Gly Ser Ala Ala Ala Ala Gly Met Val Phe Tyr Ser Ile Ser Asp Val
        915                 920                 925

Thr Asp Lys Leu Leu Asn Thr Ser Gly Asp Pro Ile Pro Met Leu Gln
930                 935                 940

Glu Asp Phe Trp Ile Ser Thr Ala Leu Val Glu Pro Thr Ala Pro Leu
945                 950                 955                 960

Arg Glu Val Leu Glu Asp Leu Ser Pro Pro Ala Met Ala Ala Phe Asp
            965                 970                 975

Leu Ala Cys Ser Gln Cys Gln Leu Trp Lys Thr Cys Lys Gln Leu Leu
            980                 985                 990

Glu Thr Ala Glu Arg Arg Leu Asn  Ser Ser Leu Glu Arg  Arg Gly Arg
        995                 1000                1005

Arg Ile Asp His Val Leu Leu  Asn Ala Asp Gly Ile  Arg Gly Phe
        1010                1015                1020

Pro Val  Val Leu Gln Gln Ile  Ser Lys Ser Leu Asn  Tyr Leu Leu
    1025                1030                1035

Met Ser  Ala Ser Gln Thr Lys  Ser Glu Ser Val Glu  Glu Lys Gly
```

-continued

```
                1040                1045                1050
Gly Gly Pro Pro Arg Cys Ser Ile Thr Glu Leu Leu Gln Met Cys
                1055                1060                1065
Trp Pro Ser Leu Ser Glu Asp Cys Val Ala Ser His Thr Thr Leu
                1070                1075                1080
Ser Gln Gln Leu Asp Gln Val Leu Gln Ser Leu Arg Glu Ala Leu
                1085                1090                1095
Glu Leu Pro Glu Pro Arg Thr Pro Pro Leu Ser Leu Val Glu
                1100                1105                1110
Gln Ala Ala Gln Lys Ala Pro Glu Ala Glu Ala His Pro Val Gln
                1115                1120                1125
Ile Gln Thr Gln Leu Leu Gln Lys Asn Leu Gly Lys Gln Thr Pro
                1130                1135                1140
Ser Gly Ser Arg Gln Met Asp Tyr Leu Gly Thr Phe Phe Ser Tyr
                1145                1150                1155
Cys Ser Thr Leu Ala Ala Val Leu Leu Gln Ser Leu Ser Ser Glu
                1160                1165                1170
Pro Asp His Val Glu Val Lys Val Gly Asn Pro Phe Val Leu Leu
                1175                1180                1185
Gln Gln Ser Ser Ser Gln Leu Val Ser His Leu Leu Phe Glu Arg
                1190                1195                1200
Gln Val Pro Pro Glu Arg Leu Ala Ala Leu Leu Ala Gln Glu Asn
                1205                1210                1215
Leu Ser Leu Ser Val Pro Gln Val Ile Val Ser Cys Cys Cys Glu
                1220                1225                1230
Pro Leu Ala Leu Cys Ser Ser Arg Gln Ser Gln Gln Thr Ser Ser
                1235                1240                1245
Leu Leu Thr Arg Leu Gly Thr Leu Ala Gln Leu His Ala Ser His
                1250                1255                1260
Cys Leu Asp Asp Leu Pro Leu Ser Thr Pro Ser Ser Pro Arg Thr
                1265                1270                1275
Thr Glu Asn Pro Thr Leu Glu Arg Lys Pro Tyr Ser Ser Pro Arg
                1280                1285                1290
Asp Ser Ser Leu Pro Ala Leu Thr Ser Ser Ala Leu Ala Phe Leu
                1295                1300                1305
Lys Ser Arg Ser Lys Leu Leu Ala Thr Val Ala Cys Leu Gly Ala
                1310                1315                1320
Ser Pro Arg Leu Lys Val Ser Lys Pro Ser Leu Ser Trp Lys Glu
                1325                1330                1335
Leu Arg Gly Arg Arg Glu Val Pro Leu Ala Ala Glu Gln Val Ala
                1340                1345                1350
Arg Glu Cys Glu Arg Leu Leu Glu Gln Phe Pro Leu Phe Glu Ala
                1355                1360                1365
Phe Leu Leu Ala Ala Trp Glu Pro Leu Arg Gly Ser Leu Gln Gln
                1370                1375                1380
Gly Gln Ser Leu Ala Val Asn Leu Cys Gly Trp Ala Ser Leu Ser
                1385                1390                1395
Thr Val Leu Leu Gly Leu His Ser Pro Ile Ala Leu Asp Val Leu
                1400                1405                1410
Ser Glu Ala Phe Glu Glu Ser Leu Val Ala Arg Asp Trp Ser Arg
                1415                1420                1425
Ala Leu Gln Leu Thr Glu Val Tyr Gly Arg Asp Val Asp Asp Leu
                1430                1435                1440
```

-continued

```
Ser Ser Ile Lys Asp Ala Val Leu Ser Cys Ala Val Ala Cys Asp
1445                1450                1455

Lys Glu Gly Trp Gln Tyr Leu Phe Pro Val Lys Asp Ala Ser Leu
1460                1465                1470

Arg Ser Arg Leu Ala Leu Gln Phe Val Asp Arg Trp Pro Leu Glu
1475                1480                1485

Ser Cys Leu Glu Ile Leu Ala Tyr Cys Ile Ser Asp Thr Ala Val
1490                1495                1500

Gln Glu Gly Leu Lys Cys Glu Leu Gln Arg Lys Leu Ala Glu Leu
1505                1510                1515

Gln Val Tyr Gln Lys Ile Leu Gly Leu Gln Ser Pro Pro Val Trp
1520                1525                1530

Cys Asp Trp Gln Thr Leu Arg Ser Cys Val Glu Asp Pro Ser
1535                1540                1545

Thr Val Met Asn Met Ile Leu Glu Ala Gln Glu Tyr Glu Leu Cys
1550                1555                1560

Glu Glu Trp Gly Cys Leu Tyr Pro Ile Pro Arg Glu His Leu Ile
1565                1570                1575

Ser Leu His Gln Lys His Leu Leu His Leu Leu Glu Arg Arg Asp
1580                1585                1590

His Asp Lys Ala Leu Gln Leu Leu Arg Arg Ile Pro Asp Pro Thr
1595                1600                1605

Met Cys Leu Glu Val Thr Glu Gln Ser Leu Asp Gln His Thr Ser
1610                1615                1620

Leu Ala Thr Ser His Phe Leu Ala Asn Tyr Leu Thr Thr His Phe
1625                1630                1635

Tyr Gly Gln Leu Thr Ala Val Arg His Arg Glu Ile Gln Ala Leu
1640                1645                1650

Tyr Val Gly Ser Lys Ile Leu Leu Thr Leu Pro Glu Gln His Arg
1655                1660                1665

Ala Ser Tyr Ser His Leu Ser Ser Asn Pro Leu Phe Met Leu Glu
1670                1675                1680

Gln Leu Leu Met Asn Met Lys Val Asp Trp Ala Thr Val Ala Val
1685                1690                1695

Gln Thr Leu Gln Gln Leu Leu Val Gly Gln Glu Ile Gly Phe Thr
1700                1705                1710

Met Asp Glu Val Asp Ser Leu Leu Ser Arg Tyr Ala Glu Lys Ala
1715                1720                1725

Leu Asp Phe Pro Tyr Pro Gln Arg Glu Lys Arg Ser Asp Ser Val
1730                1735                1740

Ile His Leu Gln Glu Ile Val His Gln Ala Ala Asp Pro Glu Thr
1745                1750                1755

Leu Pro Arg Ser Pro Ser Ala Glu Phe Ser Pro Ala Ala Pro Pro
1760                1765                1770

Gly Ile Ser Ser Ile His Ser Pro Ser Leu Arg Glu Arg Ser Phe
1775                1780                1785

Pro Pro Thr Gln Pro Ser Gln Glu Phe Val Pro Pro Ala Thr Pro
1790                1795                1800

Pro Ala Arg His Gln Trp Val Pro Asp Glu Thr Glu Ser Ile Cys
1805                1810                1815

Met Val Cys Cys Arg Glu His Phe Thr Met Phe Asn Arg Arg His
1820                1825                1830
```

His Cys Arg Arg Cys Gly Arg Leu Val Cys Ser Ser Cys Ser Thr
1835                1840                1845

Lys Lys Met Val Val Glu Gly Cys Arg Glu Asn Pro Ala Arg Val
    1850                1855                1860

Cys Asp Gln Cys Tyr Ser Tyr Cys Asn Lys Asp Val Pro Glu Glu
1865                1870                1875

Pro Ser Glu Lys Pro Glu Ala Leu Asp Ser Ser Lys Asn Glu Ser
    1880                1885                1890

Pro Pro Tyr Ser Phe Val Val Arg Val Pro Lys Ala Asp Glu Val
1895                1900                1905

Glu Trp Ile Leu Asp Leu Lys Glu Glu Glu Asn Glu Leu Val Arg
    1910                1915                1920

Ser Glu Phe Tyr Tyr Glu Gln Ala Pro Ser Ala Ser Leu Cys Ile
1925                1930                1935

Ala Ile Leu Asn Leu His Arg Asp Ser Ile Ala Cys Gly His Gln
    1940                1945                1950

Leu Ile Glu His Cys Cys Arg Leu Ser Lys Gly Leu Thr Asn Pro
1955                1960                1965

Glu Val Asp Ala Gly Leu Leu Thr Asp Ile Met Lys Gln Leu Leu
    1970                1975                1980

Phe Ser Ala Lys Met Met Phe Val Lys Ala Gly Gln Ser Gln Asp
1985                1990                1995

Leu Ala Leu Cys Asp Ser Tyr Ile Ser Lys Val Asp Val Leu Asn
    2000                2005                2010

Ile Leu Val Ala Ala Ala Tyr Arg His Val Pro Ser Leu Asp Gln
2015                2020                2025

Ile Leu Gln Pro Ala Ala Val Thr Arg Leu Arg Asn Gln Leu Leu
    2030                2035                2040

Glu Ala Glu Tyr Tyr Gln Leu Gly Val Glu Val Ser Thr Lys Thr
2045                2050                2055

Gly Leu Asp Thr Thr Gly Ala Trp His Ala Trp Gly Met Ala Cys
    2060                2065                2070

Leu Lys Ala Gly Asn Leu Thr Ala Ala Arg Glu Lys Phe Ser Arg
2075                2080                2085

Cys Leu Lys Pro Pro Phe Asp Leu Asn Gln Leu Glu Ser Trp Leu
    2090                2095                2100

Lys Ala Gly Ala Gly Cys Gly
2105                2110

<210> SEQ ID NO 117
<211> LENGTH: 2237
<212> TYPE: PRT
<213> ORGANISM: Homo sapiens

<400> SEQUENCE: 117

Met Asn His Pro Phe Gly Lys Glu Glu Ala Ala Ser Gln Lys Gln Leu
1               5                   10                  15

Phe Gly Phe Phe Cys Glu Cys Leu Arg Arg Gly Glu Trp Glu Leu Ala
                20                  25                  30

Gln Ala Cys Val Pro Gln Leu Gln Glu Gly Gln Gly Asp Ile Pro Lys
            35                  40                  45

Arg Val Glu Asp Ile Leu Gln Ala Leu Val Cys Pro Asn Leu Leu
    50                  55                  60

Arg Cys Gly Gln Asp Ile Asn Pro Gln Arg Val Ala Trp Val Trp Leu
65                  70                  75                  80

```
Leu Val Leu Glu Lys Trp Leu Ala Arg Glu Lys Lys Leu Leu Pro Val
             85                  90                  95

Val Phe Arg Arg Lys Leu Glu Phe Leu Leu Ser Glu Asp Leu Gln
            100                 105                 110

Gly Asp Ile Pro Glu Asn Ile Leu Glu Leu Tyr Glu Thr Leu Thr
            115                 120                 125

Gln Gly Ala Val Gly His Val Pro Asp Gly Asn Pro Arg Arg Glu Ser
130                 135                 140

Trp Thr Pro Arg Leu Ser Ser Glu Ala Val Ser Val Leu Trp Asp Leu
145                 150                 155                 160

Leu Arg Gln Ser Pro Gln Pro Ala Gln Ala Leu Leu Glu Leu Leu
            165                 170                 175

Glu Glu Asp Asp Gly Thr Gly Leu Cys His Trp Pro Leu Gln Asn Ala
            180                 185                 190

Leu Val Asp Leu Ile Arg Lys Ala Leu Arg Ala Leu Gln Gly Pro Asp
            195                 200                 205

Ser Val Pro Pro Gly Val Val Asp Ala Ile Tyr Gly Ala Leu Arg Thr
            210                 215                 220

Leu Arg Cys Pro Ala Glu Pro Leu Gly Val Glu Leu His Leu Leu Cys
225                 230                 235                 240

Glu Glu Leu Leu Glu Ala Cys Arg Thr Glu Gly Ser Pro Leu Arg Glu
            245                 250                 255

Glu Arg Leu Leu Ser Cys Leu Leu His Lys Ala Ser Arg Gly Leu Leu
            260                 265                 270

Ser Leu Tyr Gly His Thr Tyr Ala Glu Lys Val Thr Glu Lys Pro Pro
            275                 280                 285

Arg Ala Thr Ala Ser Gly Lys Val Ser Pro Asp His Leu Asp Pro Glu
290                 295                 300

Arg Ala Met Leu Ala Leu Phe Ser Asn Pro Asn Pro Ala Glu Ala Trp
305                 310                 315                 320

Lys Val Ala Tyr Phe Tyr Cys Leu Ser Asn Asn Lys His Phe Leu Glu
            325                 330                 335

Gln Ile Leu Val Thr Ala Leu Thr Leu Leu Lys Glu Glu Asp Phe Pro
            340                 345                 350

Asn Leu Gly Cys Leu Leu Asp Arg Glu Phe Arg Pro Leu Ser Cys Leu
            355                 360                 365

Leu Val Leu Leu Gly Trp Thr His Cys Gln Ser Leu Glu Ser Ala Lys
            370                 375                 380

Arg Leu Leu Gln Thr Leu His Arg Thr Gln Gly Pro Gly Cys Asp Glu
385                 390                 395                 400

Leu Leu Arg Asp Ala Cys Asp Gly Leu Trp Ala His Leu Glu Val Leu
            405                 410                 415

Glu Trp Cys Ile Gln Gln Ser Ser Asn Pro Ile Pro Lys Arg Asp Leu
            420                 425                 430

Leu Tyr His Leu His Gly Gly Asp Ser His Ser Val Leu Tyr Thr Leu
            435                 440                 445

His His Leu Thr Asn Leu Pro Ala Leu Arg Glu Glu Asp Val Leu Lys
450                 455                 460

Leu Leu Gln Lys Val Pro Ala Lys Asp Pro Gln Gln Glu Pro Asp Ala
465                 470                 475                 480

Val Asp Ala Pro Val Pro Glu His Leu Ser Gln Cys Gln Asn Leu Thr
            485                 490                 495
```

-continued

```
Leu Tyr Gln Gly Phe Cys Ala Met Lys Tyr Ala Ile Tyr Ala Leu Cys
                500                 505                 510

Val Asn Ser His Gln His Ser Gln Cys Gln Asp Cys Lys Asp Ser Leu
            515                 520                 525

Ser Glu Asp Leu Ala Ser Ala Thr Glu Pro Ala Asn Asp Ser Leu Ser
        530                 535                 540

Ser Pro Gly Ala Ala Asn Leu Phe Ser Thr Tyr Leu Ala Arg Cys Gln
545                 550                 555                 560

Gln Tyr Leu Cys Ser Ile Pro Asp Ser Leu Cys Leu Glu Leu Leu Glu
                565                 570                 575

Asn Ile Phe Ser Leu Leu Leu Ile Thr Ser Ala Asp Leu His Pro Glu
            580                 585                 590

Pro His Leu Pro Glu Asp Tyr Ala Glu Asp Asp Ile Glu Gly Lys
        595                 600                 605

Ser Pro Ser Gly Leu Arg Ser Pro Ser Glu Ser Pro Gln His Ile Ala
    610                 615                 620

His Pro Glu Arg Lys Ser Glu Arg Gly Ser Leu Gly Val Pro Lys Thr
625                 630                 635                 640

Leu Ala Tyr Thr Met Pro Ser His Val Lys Ala Glu Pro Lys Asp Ser
                645                 650                 655

Tyr Pro Gly Pro His Arg His Ser Phe Leu Asp Leu Lys His Phe Thr
            660                 665                 670

Ser Gly Ile Ser Gly Phe Leu Ala Asp Glu Phe Ala Ile Gly Ala Phe
        675                 680                 685

Leu Arg Leu Leu Gln Glu Gln Leu Asp Glu Ile Ser Ser Arg Ser Pro
690                 695                 700

Pro Glu Lys Pro Lys Gln Glu Ser Gln Ser Cys Ser Gly Ser Arg Asp
705                 710                 715                 720

Gly Leu Gln Ser Arg Leu His Arg Leu Ser Lys Val Val Ser Glu Ala
                725                 730                 735

Gln Trp Arg His Lys Val Val Thr Ser Asn His Arg Ser Glu Glu Gln
            740                 745                 750

Pro Ser Arg Arg Tyr Gln Pro Ala Thr Arg His Pro Ser Leu Arg Arg
        755                 760                 765

Gly Arg Arg Thr Arg Arg Ser Gln Ala Asp Gly Arg Asp Arg Gly Ser
770                 775                 780

Asn Pro Ser Leu Glu Ser Thr Ser Ser Glu Leu Ser Thr Ser Thr Ser
785                 790                 795                 800

Glu Gly Ser Leu Ser Ala Met Ser Gly Arg Asn Glu Leu His Ser Arg
                805                 810                 815

Leu His Pro His Pro Gln Ser Ser Leu Ile Pro Met Met Phe Ser Pro
            820                 825                 830

Pro Glu Ser Leu Leu Ala Ser Cys Ile Leu Arg Gly Asn Phe Ala Glu
        835                 840                 845

Ala His Gln Val Leu Phe Thr Phe Asn Leu Lys Ser Ser Pro Ser Ser
850                 855                 860

Gly Glu Leu Met Phe Met Glu Arg Tyr Gln Glu Val Ile Gln Glu Leu
865                 870                 875                 880

Ala Gln Val Glu His Lys Ile Glu Asn Gln Asn Ser Asp Ala Gly Ser
                885                 890                 895

Ser Thr Ile Arg Arg Thr Gly Ser Gly Arg Ser Thr Leu Gln Ala Ile
            900                 905                 910

Gly Ser Ala Ala Ala Ala Gly Met Val Phe Tyr Ser Ile Ser Asp Val
```

-continued

```
            915                 920                 925
Thr Asp Lys Leu Leu Asn Thr Ser Gly Asp Pro Ile Pro Met Leu Gln
        930                 935                 940

Glu Asp Phe Trp Ile Ser Thr Ala Leu Val Glu Pro Thr Ala Pro Leu
945                 950                 955                 960

Arg Glu Val Leu Glu Asp Leu Ser Pro Pro Ala Met Ala Ala Phe Asp
                965                 970                 975

Leu Ala Cys Ser Gln Cys Gln Leu Trp Lys Thr Cys Lys Gln Leu Leu
                980                 985                 990

Glu Thr Ala Glu Arg Arg Leu Asn  Ser Ser Leu Glu Arg  Arg Gly Arg
            995                 1000                1005

Arg Ile Asp His Val Leu  Leu Asn Ala Asp Gly Ile  Arg Gly Phe
        1010                1015                1020

Pro Val  Val Leu Gln Gln Ile  Ser Lys Ser Leu Asn  Tyr Leu Leu
        1025                1030                1035

Met Ser  Ala Ser Gln Thr Lys  Ser Glu Ser Val Glu  Glu Lys Gly
        1040                1045                1050

Gly Gly  Pro Pro Arg Cys Ser   Ile Thr Glu Leu Leu   Gln Met Cys
        1055                1060                1065

Trp Pro  Ser Leu Ser Glu Asp   Cys Val Ala Ser His   Thr Thr Leu
        1070                1075                1080

Ser Gln  Gln Leu Asp Gln Val  Leu Gln Ser Leu Arg   Glu Ala Leu
        1085                1090                1095

Glu Leu  Pro Glu Pro Arg Thr   Pro Pro Leu Ser Ser   Leu Val Glu
        1100                1105                1110

Gln Ala  Ala Gln Lys Ala Pro   Glu Ala Glu Ala His   Pro Val Gln
        1115                1120                1125

Ile Gln   Thr Gln Leu Leu Gln  Lys Asn Leu Gly Lys   Gln Thr Pro
        1130                1135                1140

Ser Gly   Ser Arg Gln Met Asp   Tyr Leu Gly Thr Phe   Phe Ser Tyr
        1145                1150                1155

Cys Ser   Thr Leu Ala Ala Val   Leu Leu Gln Ser Leu   Ser Ser Glu
        1160                1165                1170

Pro Asp   His Val Glu Val Lys   Val Gly Asn Pro Phe   Val Leu Leu
        1175                1180                1185

Gln Gln   Ser Ser Ser Gln Leu   Val Ser His Leu Leu   Phe Glu Arg
        1190                1195                1200

Gln Val   Pro Pro Glu Arg Leu   Ala Ala Leu Leu Ala   Gln Glu Asn
        1205                1210                1215

Leu Ser   Leu Ser Val Pro Gln   Val Ile Val Ser Cys   Cys Cys Glu
        1220                1225                1230

Pro Leu   Ala Leu Cys Ser Ser   Arg Gln Ser Gln Gln   Thr Ser Ser
        1235                1240                1245

Leu Leu   Thr Arg Leu Gly Thr   Leu Ala Gln Leu His   Ala Ser His
        1250                1255                1260

Cys Leu   Asp Asp Leu Pro Leu   Ser Thr Pro Ser Ser   Pro Arg Thr
        1265                1270                1275

Thr Glu   Asn Pro Thr Leu Glu   Arg Lys Pro Tyr Ser   Ser Pro Arg
        1280                1285                1290

Asp Ser   Ser Leu Pro Ala Leu   Thr Ser Ser Ala Leu   Ala Phe Leu
        1295                1300                1305

Lys Ser   Arg Ser Lys Leu Leu   Ala Thr Val Ala Cys   Leu Gly Ala
        1310                1315                1320
```

```
Ser Pro Arg Leu Lys Val Ser Lys Pro Ser Leu Ser Trp Lys Glu
    1325                1330                1335

Leu Arg Gly Arg Arg Glu Val Pro Leu Ala Ala Glu Gln Val Ala
    1340                1345                1350

Arg Glu Cys Glu Arg Leu Leu Glu Gln Phe Pro Leu Phe Glu Ala
    1355                1360                1365

Phe Leu Leu Ala Ala Trp Glu Pro Leu Arg Gly Ser Leu Gln Gln
    1370                1375                1380

Gly Gln Ser Leu Ala Val Asn Leu Cys Gly Trp Ala Ser Leu Ser
    1385                1390                1395

Thr Val Leu Leu Gly Leu His Ser Pro Ile Ala Leu Asp Val Leu
    1400                1405                1410

Ser Glu Ala Phe Glu Glu Ser Leu Val Ala Arg Asp Trp Ser Arg
    1415                1420                1425

Ala Leu Gln Leu Thr Glu Val Tyr Gly Arg Asp Val Asp Asp Leu
    1430                1435                1440

Ser Ser Ile Lys Asp Ala Val Leu Ser Cys Ala Val Ala Cys Asp
    1445                1450                1455

Lys Glu Gly Trp Gln Tyr Leu Phe Pro Val Lys Asp Ala Ser Leu
    1460                1465                1470

Arg Ser Arg Leu Ala Leu Gln Phe Val Asp Arg Trp Pro Leu Glu
    1475                1480                1485

Ser Cys Leu Glu Ile Leu Ala Tyr Cys Ile Ser Asp Thr Ala Val
    1490                1495                1500

Gln Glu Gly Leu Lys Cys Glu Leu Gln Arg Lys Leu Ala Glu Leu
    1505                1510                1515

Gln Val Tyr Gln Lys Ile Leu Gly Leu Gln Ser Pro Pro Val Trp
    1520                1525                1530

Cys Asp Trp Gln Thr Leu Arg Ser Cys Cys Val Glu Asp Pro Ser
    1535                1540                1545

Thr Val Met Asn Met Ile Leu Glu Ala Gln Glu Tyr Glu Leu Cys
    1550                1555                1560

Glu Glu Trp Gly Cys Leu Tyr Pro Ile Pro Arg Glu His Leu Ile
    1565                1570                1575

Ser Leu His Gln Lys His Leu Leu His Leu Leu Glu Arg Arg Asp
    1580                1585                1590

His Asp Lys Ala Leu Gln Leu Leu Arg Arg Ile Pro Asp Pro Thr
    1595                1600                1605

Met Cys Leu Glu Val Thr Glu Gln Ser Leu Asp Gln His Thr Ser
    1610                1615                1620

Leu Ala Thr Ser His Phe Leu Ala Asn Tyr Leu Thr Thr His Phe
    1625                1630                1635

Tyr Gly Gln Leu Thr Ala Val Arg His Arg Glu Ile Gln Ala Leu
    1640                1645                1650

Tyr Val Gly Ser Lys Ile Leu Leu Thr Leu Pro Glu Gln His Arg
    1655                1660                1665

Ala Ser Tyr Ser His Leu Ser Ser Asn Pro Leu Phe Met Leu Glu
    1670                1675                1680

Gln Leu Leu Met Asn Met Lys Val Asp Trp Ala Thr Val Ala Val
    1685                1690                1695

Gln Thr Leu Gln Gln Leu Leu Val Gly Gln Glu Ile Gly Phe Thr
    1700                1705                1710
```

```
Met Asp Glu Val Asp Ser Leu Leu Ser Arg Tyr Ala Glu Lys Ala
1715                1720                1725

Leu Asp Phe Pro Tyr Pro Gln Arg Glu Lys Arg Ser Asp Ser Val
1730                1735                1740

Ile His Leu Gln Glu Ile Val His Gln Ala Ala Asp Pro Glu Thr
1745                1750                1755

Leu Pro Arg Ser Pro Ser Ala Glu Phe Ser Pro Ala Ala Pro Pro
1760                1765                1770

Gly Ile Ser Ser Ile His Ser Pro Ser Leu Arg Glu Arg Ser Phe
1775                1780                1785

Pro Pro Thr Gln Pro Ser Gln Glu Phe Val Pro Ala Thr Pro
1790                1795                1800

Pro Ala Arg His Gln Trp Val Pro Asp Glu Thr Glu Ser Ile Cys
1805                1810                1815

Met Val Cys Cys Arg Glu His Phe Thr Met Phe Asn Arg Arg His
1820                1825                1830

His Cys Arg Arg Cys Gly Arg Leu Val Cys Ser Ser Cys Ser Thr
1835                1840                1845

Lys Lys Met Val Val Glu Gly Cys Arg Glu Asn Pro Ala Arg Val
1850                1855                1860

Cys Asp Gln Cys Tyr Ser Tyr Cys Asn Lys Asp Val Pro Glu Glu
1865                1870                1875

Pro Ser Glu Lys Pro Glu Ala Leu Asp Ser Ser Lys Asn Glu Ser
1880                1885                1890

Pro Pro Tyr Ser Phe Val Val Arg Val Pro Lys Ala Asp Glu Val
1895                1900                1905

Glu Trp Ile Leu Asp Leu Lys Glu Glu Glu Asn Glu Leu Val Arg
1910                1915                1920

Ser Glu Phe Tyr Tyr Glu Gln Ala Pro Ser Ala Ser Leu Cys Ile
1925                1930                1935

Ala Ile Leu Asn Leu His Arg Asp Ser Ile Ala Cys Gly His Gln
1940                1945                1950

Leu Ile Glu His Cys Cys Arg Leu Ser Lys Gly Leu Thr Asn Pro
1955                1960                1965

Glu Val Asp Ala Gly Leu Leu Thr Asp Ile Met Lys Gln Leu Leu
1970                1975                1980

Phe Ser Ala Lys Met Met Phe Val Lys Ala Gly Gln Ser Gln Asp
1985                1990                1995

Leu Ala Leu Cys Asp Ser Tyr Ile Ser Lys Val Asp Val Leu Asn
2000                2005                2010

Ile Leu Val Ala Ala Ala Tyr Arg His Val Pro Ser Leu Asp Gln
2015                2020                2025

Ile Leu Gln Pro Ala Ala Val Thr Arg Leu Arg Asn Gln Leu Leu
2030                2035                2040

Glu Ala Glu Tyr Tyr Gln Leu Gly Val Glu Val Ser Thr Lys Thr
2045                2050                2055

Gly Leu Asp Thr Thr Gly Ala Trp His Ala Trp Gly Met Ala Cys
2060                2065                2070

Leu Lys Ala Gly Asn Leu Thr Ala Ala Arg Glu Lys Phe Ser Arg
2075                2080                2085

Cys Leu Lys Pro Pro Phe Leu Asn Gln Leu Asn His Gly Ser
2090                2095                2100

Arg Leu Val Gln Asp Val Val Glu Tyr Leu Glu Ser Thr Val Arg
```

```
                2105                2110                2115
Pro Phe Val Ser Leu Gln Asp Asp Tyr Phe Ala Thr Leu Arg
        2120                2125                2130
Glu Leu Glu Ala Thr Leu Arg Thr Gln Ser Leu Ser Leu Ala Val
    2135                2140                2145
Ile Pro Glu Gly Lys Ile Met Asn Asn Thr Tyr Tyr Gln Glu Cys
    2150                2155                2160
Leu Phe Tyr Leu His Asn Tyr Ser Thr Asn Leu Ala Ile Ile Ser
    2165                2170                2175
Phe Tyr Val Arg His Ser Cys Leu Arg Glu Ala Leu Leu His Leu
    2180                2185                2190
Leu Asn Lys Glu Ser Pro Pro Glu Val Phe Ile Glu Gly Ile Phe
    2195                2200                2205
Gln Pro Ser Tyr Lys Ser Gly Lys Leu His Thr Leu Glu Asn Leu
    2210                2215                2220
Leu Glu Ser Ile Asp Pro Thr Leu Glu Ser Cys Ser Ser Leu
    2225                2230                2235
```

<210> SEQ ID NO 118
<211> LENGTH: 728
<212> TYPE: PRT
<213> ORGANISM: Homo sapiens
<220> FEATURE:
<221> NAME/KEY: misc_feature
<222> LOCATION: (728)..(728)
<223> OTHER INFORMATION: Xaa can be any naturally occurring amino acid

<400> SEQUENCE: 118

```
Met Asn His Pro Phe Gly Lys Glu Glu Ala Ser Gln Lys Gln Leu
1               5                   10                  15
Phe Gly Phe Phe Cys Glu Cys Leu Arg Arg Gly Glu Trp Glu Leu Ala
                20                  25                  30
Gln Ala Cys Val Pro Gln Leu Gln Glu Gly Gln Gly Asp Ile Pro Lys
            35                  40                  45
Arg Val Glu Asp Ile Leu Gln Ala Leu Val Val Cys Pro Asn Leu Leu
        50                  55                  60
Arg Cys Gly Gln Asp Ile Asn Pro Gln Arg Val Ala Trp Val Trp Leu
65                  70                  75                  80
Leu Val Leu Glu Lys Trp Leu Ala Arg Glu Lys Lys Leu Leu Pro Val
                85                  90                  95
Val Phe Arg Arg Lys Leu Glu Phe Leu Leu Leu Ser Glu Asp Leu Gln
                100                 105                 110
Gly Asp Ile Pro Glu Asn Ile Leu Glu Glu Leu Tyr Glu Thr Leu Thr
            115                 120                 125
Gln Gly Ala Val Gly His Val Pro Asp Gly Asn Pro Arg Arg Glu Ser
        130                 135                 140
Trp Thr Pro Arg Leu Ser Ser Glu Ala Val Ser Val Leu Trp Asp Leu
145                 150                 155                 160
Leu Arg Gln Ser Pro Gln Pro Ala Gln Ala Leu Leu Glu Leu Leu Leu
                165                 170                 175
Glu Glu Asp Asp Gly Thr Gly Leu Cys His Trp Pro Leu Gln Asn Ala
                180                 185                 190
Leu Val Asp Leu Ile Arg Lys Ala Leu Arg Ala Leu Gln Gly Pro Asp
            195                 200                 205
Ser Val Pro Pro Gly Val Val Asp Ala Ile Tyr Gly Ala Leu Arg Thr
        210                 215                 220
```

```
Leu Arg Cys Pro Ala Glu Pro Leu Gly Val Glu Leu His Leu Leu Cys
225                 230                 235                 240

Glu Glu Leu Leu Glu Ala Cys Arg Thr Glu Gly Ser Pro Leu Arg Glu
            245                 250                 255

Glu Arg Leu Leu Ser Cys Leu Leu His Lys Ala Ser Arg Gly Leu Leu
        260                 265                 270

Ser Leu Tyr Gly His Thr Tyr Ala Glu Lys Val Thr Glu Lys Pro Pro
    275                 280                 285

Arg Ala Thr Ala Ser Gly Lys Val Ser Pro Asp His Leu Asp Pro Glu
    290                 295                 300

Arg Ala Met Leu Ala Leu Phe Ser Asn Pro Asn Pro Ala Glu Ala Trp
305                 310                 315                 320

Lys Val Ala Tyr Phe Tyr Cys Leu Ser Asn Asn Lys His Phe Leu Glu
                325                 330                 335

Gln Ile Leu Val Thr Ala Leu Thr Leu Leu Lys Glu Glu Asp Phe Pro
            340                 345                 350

Asn Leu Gly Cys Leu Leu Asp Arg Glu Phe Arg Pro Leu Ser Cys Leu
        355                 360                 365

Leu Val Leu Leu Gly Trp Thr His Cys Gln Ser Leu Glu Ser Ala Lys
    370                 375                 380

Arg Leu Leu Gln Thr Leu His Arg Thr Gln Gly Pro Gly Cys Asp Glu
385                 390                 395                 400

Leu Leu Arg Asp Ala Cys Asp Gly Leu Trp Ala His Leu Glu Val Leu
                405                 410                 415

Glu Trp Cys Ile Gln Gln Ser Ser Asn Pro Ile Pro Lys Arg Asp Leu
            420                 425                 430

Leu Tyr His Leu His Gly Gly Asp Ser His Ser Val Leu Tyr Thr Leu
        435                 440                 445

His His Leu Thr Asn Leu Pro Ala Leu Arg Glu Glu Asp Val Leu Lys
    450                 455                 460

Leu Leu Gln Lys Val Pro Ala Lys Asp Pro Gln Gln Glu Pro Asp Ala
465                 470                 475                 480

Val Asp Ala Pro Val Pro Glu His Leu Ser Gln Cys Gln Asn Leu Thr
                485                 490                 495

Leu Tyr Gln Gly Phe Cys Ala Met Lys Tyr Ala Ile Tyr Ala Leu Cys
            500                 505                 510

Val Asn Ser His Gln His Ser Gln Cys Gln Asp Cys Lys Asp Ser Leu
        515                 520                 525

Ser Glu Asp Leu Ala Ser Ala Thr Glu Pro Ala Asn Asp Ser Leu Ser
    530                 535                 540

Ser Pro Gly Ala Ala Asn Leu Phe Ser Thr Tyr Leu Ala Arg Cys Gln
545                 550                 555                 560

Gln Tyr Leu Cys Ser Ile Pro Asp Ser Leu Cys Leu Glu Leu Leu Glu
                565                 570                 575

Asn Ile Phe Ser Leu Leu Ile Thr Ser Ala Asp Leu His Pro Glu
            580                 585                 590

Pro His Leu Pro Glu Asp Tyr Ala Glu Asp Asp Ile Glu Gly Lys
        595                 600                 605

Ser Pro Ser Gly Leu Arg Ser Pro Glu Ser Pro Gln His Ile Ala
    610                 615                 620

His Pro Glu Arg Lys Ser Glu Arg Gly Ser Leu Gly Val Pro Lys Thr
625                 630                 635                 640
```

```
Leu Ala Tyr Thr Met Pro Ser His Val Lys Ala Glu Pro Lys Asp Ser
                645                 650                 655

Tyr Pro Gly Pro His Arg His Ser Phe Leu Asp Leu Lys His Phe Thr
            660                 665                 670

Ser Gly Ile Ser Gly Phe Leu Ala Asp Glu Phe Ala Ile Gly Ala Phe
        675                 680                 685

Leu Arg Leu Leu Gln Glu Gln Leu Asp Glu Ile Ser Ser Arg Ser Pro
    690                 695                 700

Pro Glu Lys Pro Lys Gln Glu Ser Gln Ser Cys Ser Gly Ser Arg Asp
705                 710                 715                 720

Gly Leu Gln Ser Arg Leu His Xaa
                725

<210> SEQ ID NO 119
<211> LENGTH: 793
<212> TYPE: PRT
<213> ORGANISM: Homo sapiens
<220> FEATURE:
<221> NAME/KEY: misc_feature
<222> LOCATION: (793)..(793)
<223> OTHER INFORMATION: Xaa can be any naturally occurring amino acid

<400> SEQUENCE: 119

Met Asn His Pro Phe Gly Lys Glu Glu Ala Ser Gln Lys Gln Leu
1               5                   10                  15

Phe Gly Phe Phe Cys Glu Cys Leu Arg Arg Gly Glu Trp Glu Leu Ala
            20                  25                  30

Gln Ala Cys Val Pro Gln Leu Gln Glu Gly Gln Gly Asp Ile Pro Lys
        35                  40                  45

Arg Val Glu Asp Ile Leu Gln Ala Leu Val Val Cys Pro Asn Leu Leu
    50                  55                  60

Arg Cys Gly Gln Asp Ile Asn Pro Gln Arg Val Ala Val Trp Leu
65                  70                  75                  80

Leu Val Leu Glu Lys Trp Leu Ala Arg Glu Lys Lys Leu Leu Pro Val
                85                  90                  95

Val Phe Arg Arg Lys Leu Glu Phe Leu Leu Leu Ser Glu Asp Leu Gln
            100                 105                 110

Gly Asp Ile Pro Glu Asn Ile Leu Glu Glu Leu Tyr Glu Thr Leu Thr
        115                 120                 125

Gln Gly Ala Val Gly His Val Pro Asp Gly Asn Pro Arg Arg Glu Ser
    130                 135                 140

Trp Thr Pro Arg Leu Ser Ser Glu Ala Val Ser Val Leu Trp Asp Leu
145                 150                 155                 160

Leu Arg Gln Ser Pro Gln Pro Ala Gln Ala Leu Leu Glu Leu Leu
                165                 170                 175

Glu Glu Asp Asp Gly Thr Gly Leu Cys His Trp Pro Leu Gln Asn Ala
            180                 185                 190

Leu Val Asp Leu Ile Arg Lys Ala Leu Arg Ala Leu Gln Gly Pro Asp
        195                 200                 205

Ser Val Pro Pro Gly Val Val Asp Ala Ile Tyr Gly Ala Leu Arg Thr
    210                 215                 220

Leu Arg Cys Pro Ala Glu Pro Leu Gly Val Glu Leu His Leu Leu Cys
225                 230                 235                 240

Glu Glu Leu Leu Glu Ala Cys Arg Thr Glu Gly Ser Pro Leu Arg Glu
                245                 250                 255

Glu Arg Leu Leu Ser Cys Leu Leu His Lys Ala Ser Arg Gly Leu Leu
```

```
                260                 265                 270
Ser Leu Tyr Gly His Thr Tyr Ala Glu Lys Val Thr Glu Lys Pro Pro
            275                 280                 285

Arg Ala Thr Ala Ser Gly Lys Val Ser Pro Asp His Leu Asp Pro Glu
            290                 295                 300

Arg Ala Met Leu Ala Leu Phe Ser Asn Pro Asn Pro Ala Glu Ala Trp
305                 310                 315                 320

Lys Val Ala Tyr Phe Tyr Cys Leu Ser Asn Asn Lys His Phe Leu Glu
                325                 330                 335

Gln Ile Leu Val Thr Ala Leu Thr Leu Leu Lys Glu Glu Asp Phe Pro
            340                 345                 350

Asn Leu Gly Cys Leu Leu Asp Arg Glu Phe Arg Pro Leu Ser Cys Leu
            355                 360                 365

Leu Val Leu Leu Gly Trp Thr His Cys Gln Ser Leu Glu Ser Ala Lys
            370                 375                 380

Arg Leu Leu Gln Thr Leu His Arg Thr Gln Gly Pro Gly Cys Asp Glu
385                 390                 395                 400

Leu Leu Arg Asp Ala Cys Asp Gly Leu Trp Ala His Leu Glu Val Leu
                405                 410                 415

Glu Trp Cys Ile Gln Gln Ser Ser Asn Pro Ile Pro Lys Arg Asp Leu
            420                 425                 430

Leu Tyr His Leu His Gly Gly Asp Ser His Ser Val Leu Tyr Thr Leu
            435                 440                 445

His His Leu Thr Asn Leu Pro Ala Leu Arg Glu Glu Asp Val Leu Lys
450                 455                 460

Leu Leu Gln Lys Val Pro Ala Lys Asp Pro Gln Gln Glu Pro Asp Ala
465                 470                 475                 480

Val Asp Ala Pro Val Pro Glu His Leu Ser Gln Cys Gln Asn Leu Thr
                485                 490                 495

Leu Tyr Gln Gly Phe Cys Ala Met Lys Tyr Ala Ile Tyr Ala Leu Cys
            500                 505                 510

Val Asn Ser His Gln His Ser Gln Cys Gln Asp Cys Lys Asp Ser Leu
            515                 520                 525

Ser Glu Asp Leu Ala Ser Ala Thr Glu Pro Ala Asn Asp Ser Leu Ser
            530                 535                 540

Ser Pro Gly Ala Ala Asn Leu Phe Ser Thr Tyr Leu Ala Arg Cys Gln
545                 550                 555                 560

Gln Tyr Leu Cys Ser Ile Pro Asp Ser Leu Cys Leu Glu Leu Leu Glu
                565                 570                 575

Asn Ile Phe Ser Leu Leu Ile Thr Ser Ala Asp Leu His Pro Glu
            580                 585                 590

Pro His Leu Pro Glu Asp Tyr Ala Glu Asp Asp Ile Glu Gly Lys
            595                 600                 605

Ser Pro Ser Gly Leu Arg Ser Pro Ser Glu Ser Pro Gln His Ile Ala
            610                 615                 620

His Pro Glu Arg Lys Ser Glu Arg Gly Ser Leu Gly Val Pro Lys Thr
625                 630                 635                 640

Leu Ala Tyr Thr Met Pro Ser His Val Lys Ala Glu Pro Lys Asp Ser
                645                 650                 655

Tyr Pro Gly Pro His Arg His Ser Phe Leu Asp Leu Lys His Phe Thr
            660                 665                 670

Ser Gly Ile Ser Gly Phe Leu Ala Asp Glu Phe Ala Ile Gly Ala Phe
            675                 680                 685
```

```
Leu Arg Leu Leu Gln Glu Gln Leu Asp Glu Ile Ser Ser Arg Ser Pro
        690                 695                 700

Pro Glu Lys Pro Lys Gln Glu Ser Gln Ser Cys Ser Gly Ser Arg Asp
705                 710                 715                 720

Gly Leu Gln Ser Arg Leu His Arg Leu Ser Lys Val Val Ser Glu Ala
                725                 730                 735

Gln Trp Arg His Lys Val Val Thr Ser Asn His Arg Ser Glu Glu Gln
            740                 745                 750

Pro Ser Arg Arg Tyr Gln Pro Ala Thr Arg His Pro Ser Leu Arg Arg
        755                 760                 765

Gly Arg Arg Thr Arg Arg Ser Gln Ala Arg Trp Pro Arg Gln Arg Phe
    770                 775                 780

Lys Pro Ile Pro Gly Lys Tyr Lys Xaa
785                 790
```

<210> SEQ ID NO 120
<211> LENGTH: 21
<212> TYPE: DNA
<213> ORGANISM: Artificial
<220> FEATURE:
<223> OTHER INFORMATION: primer

<400> SEQUENCE: 120
tcagaacact ggggtatgct c                                         21

<210> SEQ ID NO 121
<211> LENGTH: 21
<212> TYPE: DNA
<213> ORGANISM: Artificial
<220> FEATURE:
<223> OTHER INFORMATION: primer

<400> SEQUENCE: 121
gcatggaaaa tttctgaaag g                                         21

<210> SEQ ID NO 122
<211> LENGTH: 20
<212> TYPE: DNA
<213> ORGANISM: Artificial
<220> FEATURE:
<223> OTHER INFORMATION: primer

<400> SEQUENCE: 122
acatcccgca gctctggaag                                           20

<210> SEQ ID NO 123
<211> LENGTH: 20
<212> TYPE: DNA
<213> ORGANISM: Artificial
<220> FEATURE:
<223> OTHER INFORMATION: primer

<400> SEQUENCE: 123
gcaacatatc aggtaggccc                                           20

<210> SEQ ID NO 124
<211> LENGTH: 20
<212> TYPE: DNA
<213> ORGANISM: Artificial
<220> FEATURE:
<223> OTHER INFORMATION: primer

<400> SEQUENCE: 124

```
tgtaccagag gagccttcag                                              20
```

<210> SEQ ID NO 125
<211> LENGTH: 20
<212> TYPE: DNA
<213> ORGANISM: Artificial
<220> FEATURE:
<223> OTHER INFORMATION: primer

<400> SEQUENCE: 125

```
ctcaacgccc agttggtagt                                              20
```

<210> SEQ ID NO 126
<211> LENGTH: 16
<212> TYPE: PRT
<213> ORGANISM: Artificial
<220> FEATURE:
<223> OTHER INFORMATION: peptide

<400> SEQUENCE: 126

```
Leu Arg Arg Gly Glu Trp Glu Leu Ala Gln Ala Cys Val Pro Gln Leu
1               5                  10                  15
```

<210> SEQ ID NO 127
<211> LENGTH: 18
<212> TYPE: PRT
<213> ORGANISM: Artificial
<220> FEATURE:
<223> OTHER INFORMATION: peptide

<400> SEQUENCE: 127

```
Pro Glu Arg Leu Ala Ala Leu Leu Ala Gln Glu Asn Leu Ser Leu Ser
1               5                  10                  15

Val Pro
```

<210> SEQ ID NO 128
<211> LENGTH: 19
<212> TYPE: PRT
<213> ORGANISM: Artificial
<220> FEATURE:
<223> OTHER INFORMATION: peptide

<400> SEQUENCE: 128

```
Pro Ala Ala Val Thr Arg Leu Arg Asn Gln Leu Leu Glu Ala Glu Tyr
1               5                  10                  15

Tyr Gln Leu
```

<210> SEQ ID NO 129
<211> LENGTH: 15
<212> TYPE: PRT
<213> ORGANISM: Artificial
<220> FEATURE:
<223> OTHER INFORMATION: peptide

<400> SEQUENCE: 129

```
Ala Ala Lys Ser Ser Gly Asp Ala Val Val Gln Asp Ile Cys Ala
1               5                  10                  15
```

<210> SEQ ID NO 130
<211> LENGTH: 1957
<212> TYPE: PRT
<213> ORGANISM: Homo sapiens
<220> FEATURE:
<221> NAME/KEY: misc_feature
<222> LOCATION: (1957)..(1957)

<223> OTHER INFORMATION: Xaa can be any naturally occurring amino acid

<400> SEQUENCE: 130

```
Met Asn His Pro Phe Gly Lys Glu Glu Ala Ala Ser Gln Lys Gln Leu
1               5                   10                  15

Phe Gly Phe Phe Cys Glu Cys Leu Arg Arg Gly Glu Trp Glu Leu Ala
                20                  25                  30

Gln Ala Cys Val Pro Gln Leu Gln Glu Gly Gln Gly Asp Ile Pro Lys
            35                  40                  45

Arg Val Glu Asp Ile Leu Gln Ala Leu Val Val Cys Pro Asn Leu Leu
        50                  55                  60

Arg Cys Gly Gln Asp Ile Asn Pro Gln Arg Val Ala Trp Val Trp Leu
65                  70                  75                  80

Leu Val Leu Glu Lys Trp Leu Ala Arg Glu Lys Lys Leu Leu Pro Val
                85                  90                  95

Val Phe Arg Arg Lys Leu Glu Phe Leu Leu Leu Ser Glu Asp Leu Gln
                100                 105                 110

Gly Asp Ile Pro Glu Asn Ile Leu Glu Glu Leu Tyr Glu Thr Leu Thr
            115                 120                 125

Gln Gly Ala Val Gly His Val Pro Asp Gly Asn Pro Arg Arg Glu Ser
130                 135                 140

Trp Thr Pro Arg Leu Ser Ser Glu Ala Val Ser Val Leu Trp Asp Leu
145                 150                 155                 160

Leu Arg Gln Ser Pro Gln Pro Ala Gln Ala Leu Leu Glu Leu Leu Leu
                165                 170                 175

Glu Glu Asp Asp Gly Thr Gly Leu Cys His Trp Pro Leu Gln Asn Ala
                180                 185                 190

Leu Val Asp Leu Ile Arg Lys Ala Leu Arg Ala Leu Gln Gly Pro Asp
            195                 200                 205

Ser Val Pro Pro Gly Val Val Asp Ala Ile Tyr Gly Ala Leu Arg Thr
210                 215                 220

Leu Arg Cys Pro Ala Glu Pro Leu Gly Val Glu Leu His Leu Leu Cys
225                 230                 235                 240

Glu Glu Leu Leu Glu Ala Cys Arg Thr Glu Gly Ser Pro Leu Arg Glu
                245                 250                 255

Glu Arg Leu Leu Ser Cys Leu Leu His Lys Ala Ser Arg Gly Leu Leu
                260                 265                 270

Ser Leu Tyr Gly His Thr Tyr Ala Glu Lys Val Thr Glu Lys Pro Pro
            275                 280                 285

Arg Ala Thr Ala Ser Gly Lys Val Ser Pro Asp His Leu Asp Pro Glu
290                 295                 300

Arg Ala Met Leu Ala Leu Phe Ser Asn Pro Asn Pro Ala Glu Ala Trp
305                 310                 315                 320

Lys Val Ala Tyr Phe Tyr Cys Leu Ser Asn Asn Lys His Phe Leu Glu
                325                 330                 335

Gln Ile Leu Val Thr Ala Leu Thr Leu Leu Lys Glu Glu Asp Phe Pro
            340                 345                 350

Asn Leu Gly Cys Leu Leu Asp Arg Glu Phe Arg Pro Leu Ser Cys Leu
            355                 360                 365

Leu Val Leu Leu Gly Trp Thr His Cys Gln Ser Leu Glu Ser Ala Lys
            370                 375                 380

Arg Leu Leu Gln Thr Leu His Arg Thr Gln Gly Pro Gly Cys Asp Glu
385                 390                 395                 400
```

-continued

```
Leu Leu Arg Asp Ala Cys Asp Gly Leu Trp Ala His Leu Glu Val Leu
                405                 410                 415
Glu Trp Cys Ile Gln Gln Ser Ser Asn Pro Ile Pro Lys Arg Asp Leu
            420                 425                 430
Leu Tyr His Leu His Gly Gly Asp Ser His Ser Val Leu Tyr Thr Leu
        435                 440                 445
His His Leu Thr Asn Leu Pro Ala Leu Arg Glu Glu Asp Val Leu Lys
    450                 455                 460
Leu Leu Gln Lys Val Pro Ala Lys Asp Pro Gln Glu Pro Asp Ala
465                 470                 475                 480
Val Asp Ala Pro Val Pro Glu His Leu Ser Gln Cys Gln Asn Leu Thr
                485                 490                 495
Leu Tyr Gln Gly Phe Cys Ala Met Lys Tyr Ala Ile Tyr Ala Leu Cys
            500                 505                 510
Val Asn Ser His Gln His Ser Gln Cys Gln Asp Cys Lys Asp Ser Leu
        515                 520                 525
Ser Glu Asp Leu Ala Ser Ala Thr Glu Pro Ala Asn Asp Ser Leu Ser
    530                 535                 540
Ser Pro Gly Ala Ala Asn Leu Phe Ser Thr Tyr Leu Ala Arg Cys Gln
545                 550                 555                 560
Gln Tyr Leu Cys Ser Ile Pro Asp Ser Leu Cys Leu Glu Leu Leu Glu
                565                 570                 575
Asn Ile Phe Ser Leu Leu Ile Thr Ser Ala Asp Leu His Pro Glu
            580                 585                 590
Pro His Leu Pro Glu Asp Tyr Ala Glu Asp Asp Ile Glu Gly Lys
        595                 600                 605
Ser Pro Ser Gly Leu Arg Ser Pro Ser Glu Ser Pro Gln His Ile Ala
    610                 615                 620
His Pro Glu Arg Lys Ser Glu Arg Gly Ser Leu Gly Val Pro Lys Thr
625                 630                 635                 640
Leu Ala Tyr Thr Met Pro Ser His Val Lys Ala Glu Pro Lys Asp Ser
                645                 650                 655
Tyr Pro Gly Pro His Arg His Ser Phe Leu Asp Leu Lys His Phe Thr
            660                 665                 670
Ser Gly Ile Ser Gly Phe Leu Ala Asp Glu Phe Ala Ile Gly Ala Phe
        675                 680                 685
Leu Arg Leu Leu Gln Glu Gln Leu Asp Glu Ile Ser Ser Arg Ser Pro
    690                 695                 700
Pro Glu Lys Pro Lys Gln Glu Ser Gln Ser Cys Ser Gly Ser Arg Asp
705                 710                 715                 720
Gly Leu Gln Ser Arg Leu His Arg Leu Ser Lys Val Val Ser Glu Ala
                725                 730                 735
Gln Trp Arg His Lys Val Val Thr Ser Asn His Arg Ser Glu Glu Gln
            740                 745                 750
Pro Ser Arg Arg Tyr Gln Pro Ala Thr Arg His Pro Ser Leu Arg Arg
        755                 760                 765
Gly Arg Arg Thr Arg Arg Ser Gln Ala Asp Gly Arg Asp Arg Gly Ser
    770                 775                 780
Asn Pro Ser Leu Glu Ser Thr Ser Ser Glu Leu Ser Thr Ser Thr Ser
785                 790                 795                 800
Glu Gly Ser Leu Ser Ala Met Ser Gly Arg Asn Glu Leu His Ser Arg
                805                 810                 815
Leu His Pro His Pro Gln Ser Ser Leu Ile Pro Met Met Phe Ser Pro
```

```
                820             825             830
Pro Glu Ser Leu Leu Ala Ser Cys Ile Leu Arg Gly Asn Phe Ala Glu
            835             840             845
Ala His Gln Val Leu Phe Thr Phe Asn Leu Lys Ser Ser Pro Ser Ser
        850             855             860
Gly Glu Leu Met Phe Met Glu Arg Tyr Gln Glu Val Ile Gln Glu Leu
865             870             875             880
Ala Gln Val Glu His Lys Ile Glu Asn Gln Asn Ser Asp Ala Gly Ser
            885             890             895
Ser Thr Ile Arg Arg Thr Gly Ser Gly Arg Ser Thr Leu Gln Ala Ile
        900             905             910
Gly Ser Ala Ala Ala Gly Met Val Phe Tyr Ser Ile Ser Asp Val
        915             920             925
Thr Asp Lys Leu Leu Asn Thr Ser Gly Asp Pro Ile Pro Met Leu Gln
        930             935             940
Glu Asp Phe Trp Ile Ser Thr Ala Leu Val Glu Pro Thr Ala Pro Leu
945             950             955             960
Arg Glu Val Leu Glu Asp Leu Ser Pro Pro Ala Met Ala Ala Phe Asp
            965             970             975
Leu Ala Cys Ser Gln Cys Gln Leu Trp Lys Thr Cys Lys Gln Leu Leu
            980             985             990
Glu Thr Ala Glu Arg Arg Leu Asn Ser Ser Leu Glu Arg Arg Gly Arg
        995             1000            1005
Arg Ile Asp His Val Leu Leu Asn Ala Asp Gly Ile Arg Gly Phe
    1010            1015            1020
Pro Val Val Leu Gln Gln Ile Ser Lys Ser Leu Asn Tyr Leu Leu
    1025            1030            1035
Met Ser Ala Ser Gln Thr Lys Ser Glu Ser Val Glu Glu Lys Gly
    1040            1045            1050
Gly Gly Pro Pro Arg Cys Ser Ile Thr Glu Leu Leu Gln Met Cys
    1055            1060            1065
Trp Pro Ser Leu Ser Glu Asp Cys Val Ala Ser His Thr Thr Leu
    1070            1075            1080
Ser Gln Gln Leu Asp Gln Val Leu Gln Ser Leu Arg Glu Ala Leu
    1085            1090            1095
Glu Leu Pro Glu Pro Arg Thr Pro Pro Leu Ser Ser Leu Val Glu
    1100            1105            1110
Gln Ala Ala Gln Lys Ala Pro Glu Ala Glu Ala His Pro Val Gln
    1115            1120            1125
Ile Gln Thr Gln Leu Leu Gln Lys Asn Leu Gly Lys Gln Thr Pro
    1130            1135            1140
Ser Gly Ser Arg Gln Met Asp Tyr Leu Gly Thr Phe Phe Ser Tyr
    1145            1150            1155
Cys Ser Thr Leu Ala Ala Val Leu Leu Gln Ser Leu Ser Ser Glu
    1160            1165            1170
Pro Asp His Val Glu Val Lys Val Gly Asn Pro Phe Val Leu Leu
    1175            1180            1185
Gln Gln Ser Ser Ser Gln Leu Val Ser His Leu Leu Phe Glu Arg
    1190            1195            1200
Gln Val Pro Pro Glu Arg Leu Ala Ala Leu Leu Ala Gln Glu Asn
    1205            1210            1215
Leu Ser Leu Ser Val Pro Gln Val Ile Val Ser Cys Cys Cys Glu
    1220            1225            1230
```

```
Pro Leu Ala Leu Cys Ser Ser Arg Gln Ser Gln Gln Thr Ser Ser
    1235                1240                1245

Leu Leu Thr Arg Leu Gly Thr Leu Ala Gln Leu His Ala Ser His
    1250                1255                1260

Cys Leu Asp Asp Leu Pro Leu Ser Thr Pro Ser Ser Pro Arg Thr
    1265                1270                1275

Thr Glu Asn Pro Thr Leu Glu Arg Lys Pro Tyr Ser Ser Pro Arg
    1280                1285                1290

Asp Ser Ser Leu Pro Ala Leu Thr Ser Ser Ala Leu Ala Phe Leu
    1295                1300                1305

Lys Ser Arg Ser Lys Leu Leu Ala Thr Val Ala Cys Leu Gly Ala
    1310                1315                1320

Ser Pro Arg Leu Lys Val Ser Lys Pro Ser Leu Ser Trp Lys Glu
    1325                1330                1335

Leu Arg Gly Arg Arg Glu Val Pro Leu Ala Ala Glu Gln Val Ala
    1340                1345                1350

Arg Glu Cys Glu Arg Leu Leu Glu Gln Phe Pro Leu Phe Glu Ala
    1355                1360                1365

Phe Leu Leu Ala Ala Trp Glu Pro Leu Arg Gly Ser Leu Gln Gln
    1370                1375                1380

Gly Gln Ser Leu Ala Val Asn Leu Cys Gly Trp Ala Ser Leu Ser
    1385                1390                1395

Thr Val Leu Leu Gly Leu His Ser Pro Ile Ala Leu Asp Val Leu
    1400                1405                1410

Ser Glu Ala Phe Glu Glu Ser Leu Val Ala Arg Asp Trp Ser Arg
    1415                1420                1425

Ala Leu Gln Leu Thr Glu Val Tyr Gly Arg Asp Val Asp Asp Leu
    1430                1435                1440

Ser Ser Ile Lys Asp Ala Val Leu Ser Cys Ala Val Ala Cys Asp
    1445                1450                1455

Lys Glu Gly Trp Gln Tyr Leu Phe Pro Val Lys Asp Ala Ser Leu
    1460                1465                1470

Arg Ser Arg Leu Ala Leu Gln Phe Val Asp Arg Trp Pro Leu Glu
    1475                1480                1485

Ser Cys Leu Glu Ile Leu Ala Tyr Cys Ile Ser Asp Thr Ala Val
    1490                1495                1500

Gln Glu Gly Leu Lys Cys Glu Leu Gln Arg Lys Leu Ala Glu Leu
    1505                1510                1515

Gln Val Tyr Gln Lys Ile Leu Gly Leu Gln Ser Pro Pro Val Trp
    1520                1525                1530

Cys Asp Trp Gln Thr Leu Arg Ser Cys Cys Val Glu Asp Pro Ser
    1535                1540                1545

Thr Val Met Asn Met Ile Leu Glu Ala Gln Glu Tyr Glu Leu Cys
    1550                1555                1560

Glu Glu Trp Gly Cys Leu Tyr Pro Ile Pro Arg Glu His Leu Ile
    1565                1570                1575

Ser Leu His Gln Lys His Leu Leu His Leu Leu Glu Arg Arg Asp
    1580                1585                1590

His Asp Lys Ala Leu Gln Leu Leu Arg Arg Ile Pro Asp Pro Thr
    1595                1600                1605

Met Cys Leu Glu Val Thr Glu Gln Ser Leu Asp Gln His Thr Ser
    1610                1615                1620
```

```
Leu Ala Thr Ser His Phe Leu Ala Asn Tyr Leu Thr Thr His Phe
1625                1630                1635

Tyr Gly Gln Leu Thr Ala Val Arg His Arg Glu Ile Gln Ala Leu
1640                1645                1650

Tyr Val Gly Ser Lys Ile Leu Leu Thr Leu Pro Glu Gln His Arg
1655                1660                1665

Ala Ser Tyr Ser His Leu Ser Ser Asn Pro Leu Phe Met Leu Glu
1670                1675                1680

Gln Leu Leu Met Asn Met Lys Val Asp Trp Ala Thr Val Ala Val
1685                1690                1695

Gln Thr Leu Gln Gln Leu Leu Val Gly Gln Glu Ile Gly Phe Thr
1700                1705                1710

Met Asp Glu Val Asp Ser Leu Leu Ser Arg Tyr Ala Glu Lys Ala
1715                1720                1725

Leu Asp Phe Pro Tyr Pro Gln Arg Glu Lys Arg Ser Asp Ser Val
1730                1735                1740

Ile His Leu Gln Glu Ile Val His Gln Ala Ala Asp Pro Glu Thr
1745                1750                1755

Leu Pro Arg Ser Pro Ser Ala Glu Phe Ser Pro Ala Ala Pro Pro
1760                1765                1770

Gly Ile Ser Ser Ile His Ser Pro Ser Leu Arg Glu Arg Ser Phe
1775                1780                1785

Pro Pro Thr Gln Pro Ser Gln Glu Phe Val Pro Pro Ala Thr Pro
1790                1795                1800

Pro Ala Arg His Gln Trp Val Pro Asp Glu Thr Glu Ser Ile Cys
1805                1810                1815

Met Val Cys Cys Arg Glu His Phe Thr Met Phe Asn Arg Arg His
1820                1825                1830

His Cys Arg Arg Cys Gly Arg Leu Val Cys Ser Ser Cys Ser Thr
1835                1840                1845

Lys Lys Met Val Val Glu Gly Cys Arg Glu Asn Pro Ala Arg Val
1850                1855                1860

Cys Asp Gln Cys Tyr Ser Tyr Cys Asn Lys Asp Val Pro Glu Glu
1865                1870                1875

Pro Ser Glu Lys Pro Glu Ala Leu Asp Ser Ser Lys Asn Glu Ser
1880                1885                1890

Pro Pro Tyr Ser Phe Val Val Arg Val Pro Lys Ala Asp Glu Val
1895                1900                1905

Glu Trp Ile Leu Asp Leu Lys Glu Glu Asn Glu Leu Val Arg
1910                1915                1920

Ser Glu Phe Tyr Tyr Glu Gln Pro Gly Pro Gln Arg Leu Leu Val
1925                1930                1935

His Cys His Pro Glu Ser Ala Pro Gly Gln His Cys Leu Trp Ser
1940                1945                1950

Pro Ala Asp Xaa
1955
```

<210> SEQ ID NO 131
<211> LENGTH: 2337
<212> TYPE: PRT
<213> ORGANISM: Homo sapiens
<220> FEATURE:
<221> NAME/KEY: misc_feature
<222> LOCATION: (2337)..(2337)
<223> OTHER INFORMATION: Xaa can be any naturally occurring amino acid

<400> SEQUENCE: 131

```
Met Asn His Pro Phe Gly Lys Glu Glu Ala Ala Ser Gln Lys Gln Leu
1               5                   10                  15

Phe Gly Phe Phe Cys Glu Cys Leu Arg Arg Gly Glu Trp Glu Leu Ala
            20                  25                  30

Gln Ala Cys Val Pro Gln Leu Gln Glu Gly Gln Gly Asp Ile Pro Lys
        35                  40                  45

Arg Val Glu Asp Ile Leu Gln Ala Leu Val Cys Pro Asn Leu Leu
    50                  55                  60

Arg Cys Gly Gln Asp Ile Asn Pro Gln Arg Val Ala Trp Val Trp Leu
65                  70                  75                  80

Leu Val Leu Glu Lys Trp Leu Ala Arg Glu Lys Lys Leu Leu Pro Val
                85                  90                  95

Val Phe Arg Arg Lys Leu Glu Phe Leu Leu Ser Glu Asp Leu Gln
            100                 105                 110

Gly Asp Ile Pro Glu Asn Ile Leu Glu Glu Leu Tyr Glu Thr Leu Thr
        115                 120                 125

Gln Gly Ala Val Gly His Val Pro Asp Gly Asn Pro Arg Arg Glu Ser
130                 135                 140

Trp Thr Pro Arg Leu Ser Ser Glu Ala Val Ser Val Leu Trp Asp Leu
145                 150                 155                 160

Leu Arg Gln Ser Pro Gln Pro Ala Gln Ala Leu Leu Glu Leu Leu
                165                 170                 175

Glu Glu Asp Asp Gly Thr Gly Leu Cys His Trp Pro Leu Gln Asn Ala
            180                 185                 190

Leu Val Asp Leu Ile Arg Lys Ala Leu Arg Ala Leu Gln Gly Pro Asp
        195                 200                 205

Ser Val Pro Pro Gly Val Val Asp Ala Ile Tyr Gly Ala Leu Arg Thr
210                 215                 220

Leu Arg Cys Pro Ala Glu Pro Leu Gly Val Glu Leu His Leu Leu Cys
225                 230                 235                 240

Glu Glu Leu Leu Glu Ala Cys Arg Thr Glu Gly Ser Pro Leu Arg Glu
                245                 250                 255

Glu Arg Leu Leu Ser Cys Leu Leu His Lys Ala Ser Arg Gly Leu Leu
            260                 265                 270

Ser Leu Tyr Gly His Thr Tyr Ala Glu Lys Val Thr Glu Lys Pro Pro
        275                 280                 285

Arg Ala Thr Ala Ser Gly Lys Val Ser Pro Asp His Leu Asp Pro Glu
290                 295                 300

Arg Ala Met Leu Ala Leu Phe Ser Asn Pro Asn Pro Ala Glu Ala Trp
305                 310                 315                 320

Lys Val Ala Tyr Phe Tyr Cys Leu Ser Asn Asn Lys His Phe Leu Glu
                325                 330                 335

Gln Ile Leu Val Thr Ala Leu Thr Leu Leu Lys Glu Glu Asp Phe Pro
            340                 345                 350

Asn Leu Gly Cys Leu Leu Asp Arg Glu Phe Arg Pro Leu Ser Cys Leu
        355                 360                 365

Leu Val Leu Leu Gly Trp Thr His Cys Gln Ser Leu Glu Ser Ala Lys
370                 375                 380

Arg Leu Leu Gln Thr Leu His Arg Thr Gln Gly Pro Gly Cys Asp Glu
385                 390                 395                 400

Leu Leu Arg Asp Ala Cys Asp Gly Leu Trp Ala His Leu Glu Val Leu
                405                 410                 415
```

-continued

```
Glu Trp Cys Ile Gln Gln Ser Ser Asn Pro Ile Pro Lys Arg Asp Leu
            420                 425                 430

Leu Tyr His Leu His Gly Gly Asp Ser His Ser Val Leu Tyr Thr Leu
            435                 440                 445

His His Leu Thr Asn Leu Pro Ala Leu Arg Glu Glu Asp Val Leu Lys
450                 455                 460

Leu Leu Gln Lys Val Pro Ala Lys Asp Pro Gln Gln Glu Pro Asp Ala
465                 470                 475                 480

Val Asp Ala Pro Val Pro Glu His Leu Ser Gln Cys Gln Asn Leu Thr
                485                 490                 495

Leu Tyr Gln Gly Phe Cys Ala Met Lys Tyr Ala Ile Tyr Ala Leu Cys
            500                 505                 510

Val Asn Ser His Gln His Ser Gln Cys Gln Asp Cys Lys Asp Ser Leu
            515                 520                 525

Ser Glu Asp Leu Ala Ser Ala Thr Glu Pro Ala Asn Asp Ser Leu Ser
            530                 535                 540

Ser Pro Gly Ala Ala Asn Leu Phe Ser Thr Tyr Leu Ala Arg Cys Gln
545                 550                 555                 560

Gln Tyr Leu Cys Ser Ile Pro Asp Ser Leu Cys Leu Glu Leu Leu Glu
                565                 570                 575

Asn Ile Phe Ser Leu Leu Leu Ile Thr Ser Ala Asp Leu His Pro Glu
            580                 585                 590

Pro His Leu Pro Glu Asp Tyr Ala Glu Asp Asp Ile Glu Gly Lys
            595                 600                 605

Ser Pro Ser Gly Leu Arg Ser Pro Glu Ser Pro Gln His Ile Ala
            610                 615                 620

His Pro Glu Arg Lys Ser Glu Arg Gly Ser Leu Gly Val Pro Lys Thr
625                 630                 635                 640

Leu Ala Tyr Thr Met Pro Ser His Val Lys Ala Glu Pro Lys Asp Ser
                645                 650                 655

Tyr Pro Gly Pro His Arg His Ser Phe Leu Asp Leu Lys His Phe Thr
            660                 665                 670

Ser Gly Ile Ser Gly Phe Leu Ala Asp Glu Phe Ala Ile Gly Ala Phe
            675                 680                 685

Leu Arg Leu Leu Gln Glu Gln Leu Asp Glu Ile Ser Ser Arg Ser Pro
            690                 695                 700

Pro Glu Lys Pro Lys Gln Glu Ser Gln Ser Cys Ser Gly Ser Arg Asp
705                 710                 715                 720

Gly Leu Gln Ser Arg Leu His Arg Leu Ser Lys Val Val Ser Glu Ala
                725                 730                 735

Gln Trp Arg His Lys Val Val Thr Ser Asn His Arg Ser Glu Glu Gln
            740                 745                 750

Pro Ser Arg Arg Tyr Gln Pro Ala Thr Arg His Pro Ser Leu Arg Arg
            755                 760                 765

Gly Arg Arg Thr Arg Arg Ser Gln Ala Asp Gly Arg Asp Arg Gly Ser
            770                 775                 780

Asn Pro Ser Leu Glu Ser Thr Ser Ser Glu Leu Ser Thr Ser Thr Ser
785                 790                 795                 800

Glu Gly Ser Leu Ser Ala Met Ser Gly Arg Asn Glu Leu His Ser Arg
                805                 810                 815

Leu His Pro His Pro Gln Ser Ser Leu Ile Pro Met Met Phe Ser Pro
            820                 825                 830
```

```
Pro Glu Ser Leu Leu Ala Ser Cys Ile Leu Arg Gly Asn Phe Ala Glu
            835                 840                 845

Ala His Gln Val Leu Phe Thr Phe Asn Leu Lys Ser Ser Pro Ser Ser
850                 855                 860

Gly Glu Leu Met Phe Met Glu Arg Tyr Gln Glu Val Ile Gln Glu Leu
865                 870                 875                 880

Ala Gln Val Glu His Lys Ile Glu Asn Gln Asn Ser Asp Ala Gly Ser
            885                 890                 895

Ser Thr Ile Arg Arg Thr Gly Ser Gly Arg Ser Thr Leu Gln Ala Ile
            900                 905                 910

Gly Ser Ala Ala Ala Gly Met Val Phe Tyr Ser Ile Ser Asp Val
            915                 920                 925

Thr Asp Lys Leu Leu Asn Thr Ser Gly Asp Pro Ile Pro Met Leu Gln
            930                 935                 940

Glu Asp Phe Trp Ile Ser Thr Ala Leu Val Glu Pro Thr Ala Pro Leu
945                 950                 955                 960

Arg Glu Val Leu Glu Asp Leu Ser Pro Pro Ala Met Ala Ala Phe Asp
                965                 970                 975

Leu Ala Cys Ser Gln Cys Gln Leu Trp Lys Thr Cys Lys Gln Leu Leu
            980                 985                 990

Glu Thr Ala Glu Arg Arg Leu Asn  Ser Ser Leu Glu Arg  Arg Gly Arg
            995                 1000                1005

Arg Ile Asp His Val Leu Leu  Asn Ala Asp Gly Ile  Arg Gly Phe
            1010                1015                1020

Pro Val Val Leu Gln Gln Ile  Ser Lys Ser Leu Asn  Tyr Leu Leu
            1025                1030                1035

Met Ser  Ala Ser Gln Thr Lys  Ser Glu Ser Val Glu  Glu Lys Gly
            1040                1045                1050

Gly Gly  Pro Pro Arg Cys Ser  Ile Thr Glu Leu Leu  Gln Met Cys
            1055                1060                1065

Trp Pro  Ser Leu Ser Glu Asp  Cys Val Ala Ser His  Thr Thr Leu
            1070                1075                1080

Ser Gln  Gln Leu Asp Gln Val  Leu Gln Ser Leu Arg  Glu Ala Leu
            1085                1090                1095

Glu Leu Pro Glu Pro Arg Thr  Pro Pro Leu Ser Ser  Leu Val Glu
            1100                1105                1110

Gln Ala  Ala Gln Lys Ala Pro  Glu Ala Glu Ala His  Pro Val Gln
            1115                1120                1125

Ile Gln  Thr Gln Leu Leu Gln  Lys Asn Leu Gly Lys  Gln Thr Pro
            1130                1135                1140

Ser Gly  Ser Arg Gln Met Asp  Tyr Leu Gly Thr Phe  Phe Ser Tyr
            1145                1150                1155

Cys Ser  Thr Leu Ala Ala Val  Leu Leu Gln Ser Leu  Ser Ser Glu
            1160                1165                1170

Pro Asp  His Val Glu Val Lys  Val Gly Asn Pro Phe  Val Leu Leu
            1175                1180                1185

Gln Gln  Ser Ser Ser Gln Leu  Val Ser His Leu Leu  Phe Glu Arg
            1190                1195                1200

Gln Val  Pro Pro Glu Arg Leu  Ala Ala Leu Leu Ala  Gln Glu Asn
            1205                1210                1215

Leu Ser  Leu Ser Val Pro Gln  Val Ile Val Ser Cys  Cys Cys Glu
            1220                1225                1230

Pro Leu  Ala Leu Cys Ser Ser  Arg Gln Ser Gln Gln  Thr Ser Ser
```

-continued

```
            1235                1240                1245
Leu Leu Thr Arg Leu Gly Thr Leu Ala Gln Leu His Ala Ser His
    1250                1255                1260
Cys Leu Asp Asp Leu Pro Leu Ser Thr Pro Ser Ser Pro Arg Thr
    1265                1270                1275
Thr Glu Asn Pro Thr Leu Glu Arg Lys Pro Tyr Ser Ser Pro Arg
    1280                1285                1290
Asp Ser Ser Leu Pro Ala Leu Thr Ser Ser Ala Leu Ala Phe Leu
    1295                1300                1305
Lys Ser Arg Ser Lys Leu Leu Ala Thr Val Ala Cys Leu Gly Ala
    1310                1315                1320
Ser Pro Arg Leu Lys Val Ser Lys Pro Ser Leu Ser Trp Lys Glu
    1325                1330                1335
Leu Arg Gly Arg Arg Glu Val Pro Leu Ala Ala Glu Gln Val Ala
    1340                1345                1350
Arg Glu Cys Glu Arg Leu Leu Glu Gln Phe Pro Leu Phe Glu Ala
    1355                1360                1365
Phe Leu Leu Ala Ala Trp Glu Pro Leu Arg Gly Ser Leu Gln Gln
    1370                1375                1380
Gly Gln Ser Leu Ala Val Asn Leu Cys Gly Trp Ala Ser Leu Ser
    1385                1390                1395
Thr Val Leu Leu Gly Leu His Ser Pro Ile Ala Leu Asp Val Leu
    1400                1405                1410
Ser Glu Ala Phe Glu Glu Ser Leu Val Ala Arg Asp Trp Ser Arg
    1415                1420                1425
Ala Leu Gln Leu Thr Glu Val Tyr Gly Arg Asp Val Asp Asp Leu
    1430                1435                1440
Ser Ser Ile Lys Asp Ala Val Leu Ser Cys Ala Val Ala Cys Asp
    1445                1450                1455
Lys Glu Gly Trp Gln Tyr Leu Phe Pro Val Lys Asp Ala Ser Leu
    1460                1465                1470
Arg Ser Arg Leu Ala Leu Gln Phe Val Asp Arg Trp Pro Leu Glu
    1475                1480                1485
Ser Cys Leu Glu Ile Leu Ala Tyr Cys Ile Ser Asp Thr Ala Val
    1490                1495                1500
Gln Glu Gly Leu Lys Cys Glu Leu Gln Arg Lys Leu Ala Glu Leu
    1505                1510                1515
Gln Val Tyr Gln Lys Ile Leu Gly Leu Gln Ser Pro Pro Val Trp
    1520                1525                1530
Cys Asp Trp Gln Thr Leu Arg Ser Cys Cys Val Glu Asp Pro Ser
    1535                1540                1545
Thr Val Met Asn Met Ile Leu Glu Ala Gln Glu Tyr Glu Leu Cys
    1550                1555                1560
Glu Glu Trp Gly Cys Leu Tyr Pro Ile Pro Arg Glu His Leu Ile
    1565                1570                1575
Ser Leu His Gln Lys His Leu Leu His Leu Leu Glu Arg Arg Asp
    1580                1585                1590
His Asp Lys Ala Leu Gln Leu Leu Arg Arg Ile Pro Asp Pro Thr
    1595                1600                1605
Met Cys Leu Glu Val Thr Glu Gln Ser Leu Asp Gln His Thr Ser
    1610                1615                1620
Leu Ala Thr Ser His Phe Leu Ala Asn Tyr Leu Thr Thr His Phe
    1625                1630                1635
```

```
Tyr Gly Gln Leu Thr Ala Val Arg His Arg Glu Ile Gln Ala Leu
1640                1645                1650

Tyr Val Gly Ser Lys Ile Leu Leu Thr Leu Pro Glu Gln His Arg
1655                1660                1665

Ala Ser Tyr Ser His Leu Ser Ser Asn Pro Leu Phe Met Leu Glu
1670                1675                1680

Gln Leu Leu Met Asn Met Lys Val Asp Trp Ala Thr Val Ala Val
1685                1690                1695

Gln Thr Leu Gln Gln Leu Leu Val Gly Gln Glu Ile Gly Phe Thr
1700                1705                1710

Met Asp Glu Val Asp Ser Leu Leu Ser Arg Tyr Ala Glu Lys Ala
1715                1720                1725

Leu Asp Phe Pro Tyr Pro Gln Arg Glu Lys Arg Ser Asp Ser Val
1730                1735                1740

Ile His Leu Gln Glu Ile Val His Gln Ala Ala Asp Pro Glu Thr
1745                1750                1755

Leu Pro Arg Ser Pro Ser Ala Glu Phe Ser Pro Ala Ala Pro Pro
1760                1765                1770

Gly Ile Ser Ser Ile His Ser Pro Ser Leu Arg Glu Arg Ser Phe
1775                1780                1785

Pro Pro Thr Gln Pro Ser Gln Glu Phe Val Pro Ala Thr Pro
1790                1795                1800

Pro Ala Arg His Gln Trp Val Pro Asp Glu Thr Glu Ser Ile Cys
1805                1810                1815

Met Val Cys Cys Arg Glu His Phe Thr Met Phe Asn Arg Arg His
1820                1825                1830

His Cys Arg Arg Cys Gly Arg Leu Val Cys Ser Ser Cys Ser Thr
1835                1840                1845

Lys Lys Met Val Val Glu Gly Cys Arg Glu Asn Pro Ala Arg Val
1850                1855                1860

Cys Asp Gln Cys Tyr Ser Tyr Cys Asn Lys Asp Val Pro Glu Glu
1865                1870                1875

Pro Ser Glu Lys Pro Glu Ala Leu Asp Ser Ser Lys Asn Glu Ser
1880                1885                1890

Pro Pro Tyr Ser Phe Val Val Arg Val Pro Lys Ala Asp Glu Val
1895                1900                1905

Glu Trp Ile Leu Asp Leu Lys Glu Glu Glu Asn Glu Leu Val Arg
1910                1915                1920

Ser Glu Phe Tyr Tyr Glu Gln Ala Pro Ser Ala Ser Leu Cys Ile
1925                1930                1935

Ala Ile Leu Asn Leu His Arg Asp Ser Ile Ala Cys Gly His Gln
1940                1945                1950

Leu Ile Glu His Cys Cys Arg Leu Ser Lys Gly Leu Thr Asn Pro
1955                1960                1965

Glu Val Asp Ala Gly Leu Leu Thr Asp Ile Met Lys Gln Leu Leu
1970                1975                1980

Phe Ser Ala Lys Met Met Phe Val Lys Ala Gly Gln Ser Gln Asp
1985                1990                1995

Leu Ala Leu Cys Asp Ser Tyr Ile Ser Lys Val Asp Val Leu Asn
2000                2005                2010

Ile Leu Val Ala Ala Ala Tyr Arg His Val Pro Ser Leu Asp Gln
2015                2020                2025
```

-continued

```
Ile Leu Gln Pro Ala Ala Val Thr Arg Leu Arg Asn Gln Leu Leu
    2030            2035            2040

Glu Ala Glu Tyr Tyr Gln Leu Gly Val Glu Val Ser Thr Lys Thr
    2045            2050            2055

Gly Leu Asp Thr Thr Gly Ala Trp His Ala Trp Gly Met Ala Cys
    2060            2065            2070

Leu Lys Ala Gly Asn Leu Thr Ala Ala Arg Glu Lys Phe Ser Arg
    2075            2080            2085

Cys Leu Lys Pro Pro Phe Asp Leu Asn Gln Leu Asn His Gly Ser
    2090            2095            2100

Arg Leu Val Gln Asp Val Val Glu Tyr Leu Glu Ser Thr Val Arg
    2105            2110            2115

Pro Phe Val Ser Leu Gln Asp Asp Asp Tyr Phe Ala Thr Leu Arg
    2120            2125            2130

Glu Leu Glu Ala Thr Leu Arg Thr Gln Ser Leu Ser Leu Ala Val
    2135            2140            2145

Ile Pro Glu Gly Lys Ile Met Asn Asn Thr Tyr Tyr Gln Glu Cys
    2150            2155            2160

Leu Phe Tyr Leu His Asn Tyr Ser Thr Asn Leu Ala Ile Ile Ser
    2165            2170            2175

Phe Tyr Val Arg His Ser Cys Leu Arg Glu Ala Leu Leu His Leu
    2180            2185            2190

Leu Asn Lys Glu Ser Pro Pro Glu Val Phe Ile Glu Gly Ile Phe
    2195            2200            2205

Gln Pro Ser Tyr Lys Ser Gly Lys Leu His Thr Leu Glu Asn Leu
    2210            2215            2220

Leu Glu Ser Ile Asp Pro Thr Leu Glu Ser Trp Gly Lys Tyr Leu
    2225            2230            2235

Ile Ala Ala Cys Gln His Leu Gln Lys Lys Asn Tyr Tyr His Ile
    2240            2245            2250

Leu Tyr Glu Leu Gln Gln Phe Met Lys Asp Gln Val Arg Ala Ala
    2255            2260            2265

Met Thr Cys Ile Arg Phe Phe Ser His Lys Ala Lys Ser Tyr Thr
    2270            2275            2280

Glu Leu Gly Glu Lys Leu Ser Trp Leu Leu Lys Ala Lys Asp His
    2285            2290            2295

Leu Lys Ile Tyr Leu Gln Glu Thr Ser Arg Ser Ser Gly Arg Lys
    2300            2305            2310

Lys Thr Thr Phe Phe Arg Lys Lys Met Thr Ala Ala Asp Val Ser
    2315            2320            2325

Arg Ser Cys Trp Glu Gly Lys Met Xaa
    2330            2335
```

DIAGNOSIS OF HEREDITARY SPASTIC PARAPLEGIAS (HSP) BY IDENTIFICATION OF A MUTATION IN THE ZFYVE26 GENE OR PROTEIN

CROSS-REFERENCE TO RELATED APPLICATIONS

This application is a Continuation Application of U.S. application Ser. No. 12/934,841 filed Sep. 27, 2010.

FIELD OF THE INVENTION

The invention relates to the identification of mutations in the ZFYVE26 gene or protein, associated with a hereditary spastic paraplegias (HSP), and to diagnostic applications that benefit from this identification.

BACKGROUND OF THE INVENTION

Hereditary spastic paraplegias (HSP) are genetically heterogeneous Mendelian disorders characterized by weakness, spasticity and loss of vibratory sense in the lower limbs (Harding et al. 1983; Tallaksen et al. 2001; Fink et al, 2006; Depienne et al, 2007; Stevanin et al, 2008). They reveal themselves clinically through difficulties in walking possibly evolving into total paralysis of both legs. The physiopathology of this set of diseases is, to date, relatively undocumented; however, anatomopathological data make it possible to conclude that the attack in pure forms of the disease is limited to the pyramidal tracts responsible for voluntary motricity in the spinal cord. The incidence of HSPs, which remains difficult to estimate because of rare epidemiological studies and the considerable clinical variability, varies from 0.9:100000 in Denmark, 3 to 9.6:100000 in certain regions of Spain (Polo et al., 1991) 5:100000 in South-Tunisia (Boukrhis et al, 2009) or 14:100000 in Norway (Skre, 1974) (approximately 3:100000 in France). Various clinical and genetic forms of HSP exist. The so-called "pure" HSPs, which correspond to isolated spasticity of the lower limbs, are clinically distinguished from the "complex" HSPs, for which the spasticity of the legs is associated with other clinical signs of neurological or non-neurological type.

Although forms of HSP have been recognized for over a century, new phenotypes are regularly described, demonstrating wide clinical heterogeneity. Genetically, autosomal dominant (AD), autosomal recessive (AR) and X-linked inheritance are observed and almost 34 genetic loci have been identified, but only 17 genes have been cloned (Depienne et al, 2007; Stevanin et al, 2008a). According to the putative roles of these genes, mitochondrial function, protein folding, abnormal development, cholesterol/neurosteroid metabolism and axonal transport have been implicated in the dying back of pyramidal tract axons in these disorders (Stevanin et al, 2008a).

The most common forms of AD-HSP, accounting for about 40-50% of cases (Depienne et al, 2007; Stevanin et al, 2008a), are caused by mutations in the SPG4 and SPG3A genes that encode for spartin and atlastin, respectively (Hazan et al. 1990, Zhao et al. 2001 and international patent application WO 01/18198). In AR-HSP, which is less common and more varied in clinical presentation, greater genetic heterogeneity is expected but SPG11 (patent application No 06 291 433.8) was found to be frequently mutated, accounting for ~21% of all ARHSP, but up to 59% of ARHSP with thin corpus callosum and mental impairment (Stevanin et al, 2007 and 2008b). The five other AR-HSP genes cloned so far (details are available on the "Online Mendelien Inheritance in Man" database at http://www.ncbi.nlm.nih.gov/entrez/query.fcgi?db=OMIM), encoding for CYP7B1 (SPG5, MIM#270800, Tsaousidou et al. 2008), paraplegin (SPG7, MIM#607259, Casari et al. 1998), spartin (SPG20; MIM#275900, Patel et al. 2002) and maspardin (SPG21, MIM 248900, Simpson et al. 2003) as well as the gene responsible for the related spastic ataxia of Charlevoix Saguenay (ARSACS, MIM#270550, Engert et al. 2000) probably represent less than 10% of all cases (Depienne et al, 2007; Stevanin et al, 2008a).

In a clinical point of view, a very common form of AR-HSP associates spastic paraplegia, mental or cognitive deficit and thin corpus callosum (Martinez et al 1999, Shibasaki et al. 2000, Casali et al. 2004, Winner et al. 2004 and 2005, Lossos et al. 2006, Stevanin et al. 2006, Franca et al, 2007, Boukhris et al 2008a). The majority of the families appear to be linked to the SPG11 gene (Stevanin et al, 2007, Stevanin et al, 2008b). In the patent application No 06 291 433.8 related to this SPG11 gene, the inventors claimed to have identified a gene responsible for a frequent form of Autosomal Recessive Hereditary Spastic Paraplegia (AR-HSP). They have indeed demonstrated that the disease is caused by mutations in the KIAA1840 gene (also known as FLJ21439), affecting the spatacsin protein expression, which was further confirmed independently by other groups (for review, see Stevanin et al, 2008a). The typical clinical features of this disease consist of early-onset spastic paraplegia (usually <20 years), urinary bladder dysfunction, deep sensory deficits in the legs and cognitive impairment that progress insidiously to severe functional disability over a period of 10-20 years (Winner et al, 2005; Franca et al, 2007, Boukhris et al 2008a). Some patients also develop arm involvement, dysarthria, contractures and muscle atrophy. Auxiliary studies frequently identify a thin corpus callosum (TCC) with white matter lesions and variable cerebral cortical atrophy on magnetic resonance imaging (MRI), variable cortical and thalamic glucose hypometabolism on positron emission tomography and predominantly axonal motor or sensorimotor peripheral neuropathy on nerve conduction studies (Winner et al. 2004).

Other loci have been found associated with this phenotype however: SPG15 (Hughes et al 2000), SPG21 (Simpson et al, 2003), HSP with epilespy (Al-Yahyaee, 2006) and occasionally SPG7 (Coutinho et al, 1999) or SPG4 (Orlacchio et al, 2004). More particularly, SPG15 was thought to be a rare form of spastic paraplegia associated with pigmentary maculopathy, also known as the Kjellin syndrome (MIM 270700, www.ncbi.nlm.nih.gov/omim/), when it was mapped in two Irish families to a region of 16 Mb on chromosome 14q (Hughes et al, 2000). Recently, the inventors identified 7 families linked to SPG15 locus (Elleuch et al, 2007; Boukhris et al, 2008a and 2008b); Muglia et al, submitted), reduced its size to 5.3 Mb between markers D14S981 and rs8688 (Elleuch et al, 2007) then between markers VNTR25TG (identified in the human genome sequence by the inventors, primers in the table 4) and D14S1029 (FIG. 1) and estimated its frequency to 15% of ARHSP (Elleuch et al, 2007). In addition, the inventors showed that the clinical features varied among patients and families, but cognitive impairment with distal amyotrophy were frequently associated. Peripheral neuropathy, thin corpus callosum, maculopathy and cerebellar ataxia were also observed in some but not all patients (Elleuch et al, 2007, Boukhris et al, 2008a and 2008b). Therefore, SPG15 is expected to account for a significant proportion of the very common sub-form of ARHSP associating mental or cognitive deficits and thin corpus callosum, as SPG11, but could also account for other forms of ARHSP since all features of this clinical entity can be absent in certain families.

SUMMARY OF THE INVENTION

The inventors have now identified a new gene responsible for a complicated Autosomal Recessive Hereditary Spastic Paraplegia (AR-HSP). They have indeed demonstrated that the disease is caused by mutations in the ZFYVE26 gene (also known as KIAA0321), which are located at various positions along the gene (FIG. 2) and segregate with the HSP (FIG. 3 to 10) by affecting the spastizin protein expression, structure or stability. Eighteen mutations were identified by the inventors in 16 unrelated families, including those previously published by the inventors as linked and that were used to restrict the candidate interval (Elleuch et al, 2007, Boukhris et al, 2008a and 2008b, FIG. 1).

The invention therefore provides the identification of a frequent gene responsible of AR-HSPs and opens thereby new opportunities to improve diagnosis and genetic counselling of said disease. Moreover, the invention also provides a mean to improve the medical care management of patient affected with said disease. In addition, since most patients with spastic paraplegia have isolated forms, it is conceivable that this new gene could account for a small proportion of these patients as well. Indeed, in Europe, due to the small size of the families, recessively inherited diseases are often found in apparently isolated cases.

A first aspect of the invention thus relates to an ex vivo method of diagnosing or predicting a hereditary spastic paraplegias (HSP), in a subject, which method comprises detecting a mutation in the ZFYVE26 gene or protein (spastizin), wherein said mutation is indicative of a hereditary spastic paraplegias (HSP).

A second aspect of the invention relates to an isolated nucleic acid specifically hybridizable to a region of ZFYVE26 gene that contains a mutation selected from the group consisting of:
the substitutions: c.307G>T, c.427G>T, c.1240G>T, c.1477C>T, c.2182C>T, c.4312C>T, c.5422C>T, c.5791–6G>A/r.5791_5792ins5791–4_5791-1, c.5485–1G>A (predicted to alter splicing), c.7128+2T>A/r.6987_7128del, c.6011G>C (predicated to alter splicing),
the deletions: c.2049delT, c.4068_4069delTG, c.5036delT, c.6702_6771del,
the insertions: c.2331_2332insA, c.6296_6297insT,
the complex rearrangement: g.67316025_67319414del/ g.67316025_67316026insTCTA/ g.67319319_67319414i nv. Such an isolated nucleic acid can be used as a primer or probe.

More preferentially the invention relates to an isolated nucleic acid, which comprises a ZFYVE26 gene or cDNA or mRNA sequence that contains one or several mutations) selected from the group consisting of
the substitutions: c.307G>T, c.427G>T, c.1240G>T, c.1477C>T, c.2182C>T, c.4312C>T, c.5422C>T, c.5791–6G>A/r.5791_5792ins5791–4_5791-1, c.5485–1G>A (predicted to alter splicing), c.7128+2T>A/r.6987_7128del, c.6011G>C (predicated to alter splicing),
the deletions: c.2049delT, c.4068_4069delTG, c.5036delT, c.6702_6771del,
the insertions: c.2331_2332insA, c.6296_6297insT,
the complex rearrangement: g.67316025_67319414del/ g.67316025_67316026insTCTA/ g.67319319_67319414i nv.

Another aspect of the invention relates to an isolated polypeptide which comprises the amino acid sequence of the spastizin or ZFYVE26 protein containing one or several mutation(s) selected from the group consisting of p.E103X, p.E143X, p.E414X, p.Q493X, p.F683LfsX685, p.R728X, p.D778RfsX793, p.R1209fsX1220, p.C1356fsX1356, p.R1438X, p.L1679RfsX1687, p.Q1808X, p.A1931PfxX1957X, p.S2004T, p.L2099LfsX2111, p.W2234CfsX2238, p.R2329RfsX2337 and those resulting from aberrant splicing identified by the inventors but for which the consequence on the protein, although clearly deleterious in silico since affecting splicing consensus sequences, could not be verified because of the absence of patient's cells for their analysis up to now (c.5485–1G>A, c.6011G>C). In addition, it should be noted that the consequence of the 6011G>C mutation might result in a missense substitution (p.S2004T) and/or of aberrant splicing (since affecting the last codon of an exon and predicted in silico to strongly alter splicing) or both.

Another aspect of the invention relates to an isolated monoclonal or polyclonal antibody that specifically recognizes a ZFYVE26 protein containing a mutation selected from the group consisting of p.E103X, p.E143X, p.E414X, p.Q493X, p.F683LfsX685, p.R728X, p.D778RfsX793, p.R1209fsX1220, p.C1356fsX1356, p.R1438X, p.L1679RfsX1687, p.Q1808X, p.A1931PfxX1957X, p.S2004T, p.L2099LfsX2111, p.W2234CfsX2238, p.R2329RfsX2337 and those resulting from aberrant splicing identified by the inventors but for which the consequence on the protein, although clearly deleterious in silico since affecting splicing consensus sequences, could not be verified because of the absence of patient's cells for their analysis up to now (c.5485–1G>A, c.6011G>C).

Another aspect of the present invention relates to the use of a monoclonal or polyclonal antibody recognizing the wild type protein to identify truncated forms of the protein spastizin.

DETAILED DESCRIPTION OF THE INVENTION

Definitions

A "coding sequence" or a sequence "encoding" an expression product, such as a RNA, polypeptide, protein, or enzyme, is a nucleotide sequence that, when expressed, results in the production of that RNA, polypeptide, protein, or enzyme, i.e., the nucleotide sequence encodes an amino acid sequence for that polypeptide, protein or enzyme. A coding sequence for a protein may include a start codon (usually ATG) and a stop codon.

The term "gene" means a DNA sequence that codes for or corresponds to a particular sequence of amino acids which comprise all or part of one or more proteins or enzymes, and may or may not include regulatory DNA sequences, such as promoter sequences, which determine for example the conditions under which the gene is expressed. Some genes, which are not structural genes, may be transcribed from DNA to RNA, but are not translated into an amino acid sequence. Other genes may function as regulators of structural genes or as regulators of DNA transcription. In particular, the term gene may be intended for the genomic sequence encoding a protein, i.e. a sequence comprising regulator, promoter, intron and exon sequences.

As used herein, the term "oligonucleotide" refers to a nucleic acid, generally of at least 10, preferably at least 15, and more preferably at least 20 nucleotides, preferably no more than 100 nucleotides, still preferably no more than 70 nucleotides, and which is hybridizable to a ZFYVE26 genomic DNA, cDNA, or mRNA. Oligonucleotides can be labelled according to any technique known in the art, such as with radiolabels, fluorescent labels, enzymatic labels, sequence tags, etc. A labelled oligonucleotide may be used as a probe to detect the presence of a mutated ZFYVE26 nucleic acid. Alternatively, oligonucleotides (one or both of which may be labelled) can be used for amplifying a ZFYVE26 nucleic acid, for instance by PCR (Saiki et al., 1988), to detect the presence of a mutation. Generally, oligonucleotides are prepared synthetically, preferably on a nucleic acid synthesizer. Accordingly, oligonucleotides can be prepared with non-naturally occurring phosphoester analog bonds, such as thioester bonds, etc.

A nucleic acid molecule is "hybridizable" or "hybridizes" to another nucleic acid molecule, such as a cDNA, genomic DNA, or RNA, when a single stranded form of the nucleic acid molecule can anneal to the other nucleic acid molecule under the appropriate conditions of temperature and solution ionic strength (Sambrook et al., 1989).

The conditions of temperature and ionic strength determine the "stringency" of the hybridization. For preliminary screening for homologous nucleic acids, low stringency hybridization conditions, corresponding to a Tm (melting temperature) of 55° C., can be used, e.g., 5×SSC, 0.1% SDS, 0.25% milk, and no formamide; or 30% formamide, 5×SSC, 0.5% SDS). Moderate stringency hybridization conditions correspond to a higher Tm, e.g., 40% formamide, with 5× or 6×SCC. High stringency hybridization conditions correspond to the highest Tm, e.g., 50% formamide, 5× or 6×SCC. SCC is a 0.15 M NaCl, 0.015 M Na-citrate. Hybridization requires that the two nucleic acids contain complementary sequences, although depending on the stringency of the hybridization, mismatches between bases are possible. The appropriate stringency for hybridizing nucleic acids depends on the length of the nucleic acids and the degree of complementation, variables well known in the art. The greater the degree of similarity or homology between two nucleotide sequences, the greater the value of Tm for hybrids of nucleic acids having those sequences. The relative stability (corresponding to higher Tm) of nucleic acid hybridizations decreases in the following order: RNA:RNA, DNA:RNA, DNA:DNA. For hybrids of greater than 100 nucleotides in length, equations for calculating Tm have been derived (see Sambrook et al., 1989, 9.50-9.51). For hybridization with shorter nucleic acids, i.e., oligonucleotides, the position of mismatches becomes more important, and the length of the oligonucleotide determines its specificity (see Sambrook et al., 1989 I1.7-11.8). A minimum length for a hybridizable nucleic acid is at least about 10 nucleotides, preferably at least about 15 nucleotides, and more preferably the length is at least about 20 nucleotides.

In a specific embodiment, the term "standard hybridization conditions" refers to a Tm of 55° C., and utilizes conditions as set forth above. In a preferred embodiment, the Tm is 60° C. In a more preferred embodiment, the Tm is 65° C. In a specific embodiment, "high stringency" refers to hybridization and/or washing conditions at 68° C. in 0.2× SSC, at 42° C. in 50% formamide, 4×SSC, or under conditions that afford levels of hybridization equivalent to those observed under either of these two conditions.

As used herein, an "amplification primer" is an oligonucleotide for amplification of a target sequence by extension of the oligonucleotide after hybridization to the target sequence or by ligation of multiple oligonucleotides, which are adjacent when hybridized to the target sequence. At least a portion of the amplification primer hybridizes to the target. This portion is referred to as the target binding sequence and it determines the target-specificity of the primer. In addition to the target binding sequence, certain amplification methods require specialized non-target binding sequences in the amplification primer. These specialized sequences are necessary for the amplification reaction to proceed and typically serve to append the specialized sequence to the target. For example, the amplification primers used in Strand Displacement Amplification (SDA) include a restriction endonuclease recognition site 5' to the target binding sequence (U.S. Pat. No. 5,455,166 and U.S. Pat. No. 5,270,184). Nucleic Acid Based Amplification (NASBA), self-sustaining sequence replication (3SR) and transcription based amplification primers require an RNA polymerase promoter linked to the target binding sequence of the primer. Linking such specialized sequences to a target binding sequence for use in a selected amplification reaction is routine in the art. In contrast, amplification methods such as PCR, which do not require specialized sequences at the ends of the target, generally employ amplification primers consisting of only target binding sequence.

As used herein, the terms "primer" and "probe" refer to the function of the oligonucleotide. A primer is typically extended by polymerase or ligation following hybridization to the target but a probe typically is not. A hybridized oligonucleotide may function as a probe if it is used to capture or detect a target sequence, and the same oligonucleotide may function as a primer when it is employed as a target binding sequence in an amplification primer. It will therefore be appreciated that any of the target binding sequences disclosed herein for amplification, detection or quantisation of ZFYVE26 may be used either as hybridization probes or as target binding sequences in primers for detection or amplification, optionally linked to a specialized sequence required by the selected amplification reaction or to facilitate detection.

As used herein, the terms "ZFYVE26 gene" (or its synonyms: SPG15, KIAA0321) denotes the ZFYVE26 gene of any species, especially human, but also other mammals or vertebrates to which the methods of the invention can apply. The human ZFYVE26 gene encodes a large protein of 2539 amino-acids (aa) of unknown function that the inventors have named Spastizin (SPASTIcity due to the ZFYVE26 proteIN) (SEQ ID NO: 2). Homo sapiens ZFYVE26 gene consists of 42 exons (Table 1) covering a genomic region of 70,064 bp (deposited in Genbank under accession number NC_000014, see Table 1) localized on chromosome 14q24.1 (FIG. 2), and its Coding Sequence (CDS) of 7,620 bp (exons 2-42) is deposited in Genebank under accession number NM_015346 (SEQ ID NO: 1) and in Ensembl (ENSG00000072121). Its expression in human tissues is ubiquitous (FIG. 11) and its brain expression pattern in rats (FIG. 12) closely resembles the one of SPG11, another gene responsible for a similar disease (Stevanin et al, 2007).

The ZFYVE26 protein, belongs to the FYVE-finger family, which includes more than 30 different members in mammals, including ZFYVE27 (Gillooly et al. 2001, Seet et al, 2001; Mannan et al, 2006). The FYVE domain is a highly conserved zinc-finger binding domain characterized by the presence of eight conserved cysteine residues, the third of which is flanked by characteristic basic amino acids: $CX_2CX_{9-39}RRHHCRXCX_4CX_{2-6}CX_{4-48}CX_2C$ (where X represents non-conserved amino acid residues) and is suggested to bind the FYVE-finger proteins to endosomes. The majority of FYVE-finger proteins is involved in interactions with different forms of phosphoinositides and serve as regulators of endocytic membrane trafficking (Gillooly et al, 2001). All mutations identified by the inventors in the SPG15 families (FIG. 3 to 10) appear to truncate this domain either because clearly located before it (FIG. 2), or because as non-sense mutations the mRNA of ZFYVE26 will be probably subjected to non-sense mediated mRNA decay, a well known mechanism of mRNA regulation and degradation in mammals (Frischmeyer et al. 1999, Amrani et al. 2006). In one case (c.6011G>C), the mutation is predicted to affect splicing and to produce amissense variation at the protein level (p.S2004T) (no mRNA of the corresponding patient was available to confirm the consequence on splicing). All mutations are thus expected to result in alteration of endosomal trafficking. Indeed, by overexpression in vitro in COS-7 cells, the inventors have shown that the epitope-tagged wild-type spastizin colocalized with endosomal markers, but not with markers of the Golgi, lysosomes, mitochondria or endoplasmic reticulum (FIG. 6).

TABLE 1

Partial genomic sequence from chromosome 14 reference assembly NC000014 with full exon composition and exon-intron boundaries of the human ZFYVE26 gene (according to the Ensembl database: ENSG00000072121)

| Exon | Reference of exon/intron | Position in the genomic sequence of chromosome in 14 base pairs | | Length in base pairs | Sequence |
|---|---|---|---|---|---|
| | 5' upstream sequence | | | | . . . tgtcaccaccccaccaccgctgttcggag tgggttctgtcacctgactc |
| 1 | ENSE00001355414 | 67,353,004 | 67,353,055 | 52 | GGCTCAAACATGGCTGCGCTGAGAGCTCTATTGCTT TGGGCGCCGGGAGCAG |
| | Intron 1-2 | 67,352,517 | 67,353,003 | 487 | gtgagtgtaagacaccccctgagagg . . . ctca ctggcgttgtgttgtttctag |
| 2 | ENSE00001338166 | 67,352,240 | 67,352,516 | 277 | GAGGTACTCCGCGAATGAGAACATTGAGAATGTGTT CGGCATAACTCATTTCTTTGTATCTCCCTGCACTCT GTGCTGGGAAAATGAATCATCCATTTGGAAAAGAGG AAGCTGCTTCGCAGAAGCAGCTTTTTGGATTTTTCT GCGAATGCCTGCGGAGGGGAGAATGGGAGCTGGCAC AGGCATGTGTACCTCAGCTACAGGAGGGACAAGGGG ATATCCCAAAGAGGGTAGAAGACATACTTCAGGCAT TGGTGGTGTGTCCAAATCTGCTGAG |
| | Intron 2-3 | 67,350,535 | 67,352,239 | 1,705 | gtaagggatctcttttcctaccaga . . . aagt ctttcttttacctttttcag |
| 3 | ENSE00001338165 | 67,350,456 | 67,350,534 | 79 | ATGTGGGCAGGACATCAACCCTCAAAGAGTAGCCTG GGTGTGGCTTCTTGTACTGGAGAAATGGTTGGCCCG GGAAAAG |
| | Intron 3-4 | 67,345,760 | 67,350,455 | 4,696 | gtaagtaggtttatattaaattttc . . . tgct tcattcttttgattcttctag |
| 4 | ENSE00001338164 | 67,345,670 | 67,345,759 | 90 | AAGTTACTCCCAGTTGTTTTCCGGAGAAAGCTTGAG TTTCTTTTATTGTCAGAAGACCTCCAAGGTGACATT CCAGAGAACATCCTCGAG |
| | Intron 4-5 | 67,344,391 | 67,345,669 | 1,279 | gtgagagagagccctggtaccatct . . . atcc ttttcttcatcctctatttag |
| 5 | ENSE00001338163 | 67,343,868 | 67,344,390 | 523 | GAGCTGTATGAGACCTTAACACAGGGTGCAGTAGGC CACGTGCCTGACGGAAATCCAAGGAGGGAGAGCTGG ACTCCTCGTCTCAGCTCCGAAGCTGTCTCTGTGCTC TGGGATCTCCTGAGGCAGTCTCCCCAGCCAGCACAG GCCCTGCTGGAGCTCCTGCTTGAGGAGGATGACGGT ACTGGCCTCTGTCACTGGCCTCTGCAGAATGCACTG GTGGACCTCATTCGAAAGGCATTGCGGGCTTTGCAG GGCCCTGATTCGGTGCCCCCTGGGGTAGTCGATGCC ATCTATGGAGCCCTGCGGACTCTGCGTTGCCCCGCA GAACCACTTGGGGTTGAGTTGCATCTCCTGTGTGAG GAACTACTAGAGGCCTGCAGGACCGAGGGGAGTCCC CTGCGGGAGGAGCGGCTGCTCAGCTGCCTGCTGCAC AAGGCCAGCCGGGGCTGCTGTCCCTGTATGGCCAT ACCTATGCAGAGAAGGTCACAGAAAAGCCACCGAGG GCTACAGCCTCGGGAAAAG |
| | Intron 5-6 | 67,343,146 | 67,343,867 | 722 | gtgtgttccctttgctgctgctcct . . . gata accgtcttgtttgatgttcag |

TABLE 1-continued

Partial genomic sequence from chromosome 14 reference assembly NC000014 with
full exon composition and exon-intron boundaries of the human ZFYVE26 gene
(according to the Ensembl database: ENSG00000072121)

| Exon | Reference of exon/intron | Position in the genomic sequence of chromosome in 14 base pairs | | Length in base pairs | Sequence |
|---|---|---|---|---|---|
| 6 | ENSE00001338160 | 67,343,015 | 67,343,145 | 131 | TCTCACCGGATCATCTAGATCCTGAGCGGGCAATGC TAGCCCTGTTCTCCAATCCCAACCCAGCCGAGGCTT GGAAAGTGGCCTATTTCTACTGCCTGAGCAACAACA AACACTTCCTCGAGCAGATTCTG |
| | Intron 6-7 | 67,342,089 | 67,343,014 | 926 | gtaagtcaagcttaattgttcatca . . . tata acagctttctttgacttacag |
| 7 | ENSE00001338158 | 67,341,924 | 67,342,088 | 165 | GTAACAGCACTAACATTGTTGAAAGAAGAAGACTTC CCAAATCTTGGCTGCCTACTTGATAGAGAATTCAGG CCCCTCAGTTGCCTGCTTGTACTCCTGGGCTGGACA CACTGCCAGAGCCTAGAGTCAGCCAAGAGGCTGCTC CAGACCCTGCACAGGACCCAG |
| | Intron 7-8 | 67,341,776 | 67,341,923 | 148 | gtaactctcactcagcatcccaggc . . . tctt tcttctcccatatcaacatag |
| 8 | ENSE00001338155 | 67,341,687 | 67,341,775 | 89 | GGCCCAGGCTGTGATGAGCTCCTCAGGGATGCCTGT GATGGGTTGTGGGCTCACCTGGAGGTCCTGGAGTGG TGCATACAGCAGAGCAG |
| | Intron 8-9 | 67,340,735 | 67,341,686 | 952 | gtatggccctgtgcagtcagcgcct . . . ccat cctcccaacttttccattcag |
| 9 | ENSE00001338153 | 67,340,571 | 67,340,734 | 164 | CAACCCCATACCAAAGAGAGATCTGTTGTATCATTT ACACGGTGGAGACAGCCACTCAGTGCTCTACACTCT CCATCACCTTACAAACCTTCCAGCCCTCAGGGAGGA AGATGTTCTCAAGCTCTTACAGAAAGTGCCAGCCAA GGACCCCCAGCAAGAGCCTG |
| | Intron 9-10 | 67,338,753 | 67,340,570 | 1,818 | gtgagttgggatggaatgacctggc . . . cagc ctgtttctctttgtaattcag |
| 10 | ENSE00001338151 | 67,338,549 | 67,338,752 | 204 | ATGCAGTTGATGCTCCAGTCCCTGAGCACCTGAGCC AGTGTCAGAACCTGACACTCTACCAGGGCTTCTGTG CCATGAAGTATGCCATCTATGCCCTCTGTGTAAACT CACACCAGCACTCCCAGTGCCAGGACTGCAAAGACA GCCTCTCTGAGGACCTGGCCTCAGCTACAGAGCCAG CGAATGACTCTCTCTCCTCCCCAG |
| | Intron 10-11 | 67,335,093 | 67,338,548 | 3,456 | gtacagcacttccctccatccgtga . . . tctt ctcttgtacatgtttttgtag |
| 11 | ENSE00001338147 | 67,334,484 | 67,335,092 | 609 | GTGCTGCAAATCTCTTCTCAACTTACCTGGCCAGGT GTCAACAGTATCTGTGCAGTATTCCTGACTCTCTGT GCCTGGAGCTTCTGGAAAACATCTTCTCATTGCTTC TCATCACCTCTGCTGATCTTCACCCAGAGCCTCACT TGCCTGAGGACTATGCTGAGGATGATGACATTGAGG GGAAGAGCCCCTCAGGTTTGAGGTCCCCATCAGAGA GCCCTCAGCACATAGCACCATCCTGAAAGGAAGTCA GAACGGGGTTCCCTGGGAGTCCCAAAGACCCTTGCT TATACAATGCCAAGCCATGTGAAGGCAGAGCCAAAA GACAGTTACCCAGGGCCTCATAGGCACAGCTTTTTG GACTTAAAACACTTTACTAGTGGTATCAGTGGATTT CTGGCTGATGAATTTGCAATAGGGGCCTTCCTCAGG CTTCTCCAAGAGCAACTGGATGAGATCAGTAGCCGC AGCCCTCCTGAGAAGCAAAGCAAGAAAGTCAGAGC TGCTCAGGAAGCAGAGATGGACTGCAGAGCCGCCTG CATCGACTTTCCAAGGTTGTCTCTGAGGCCCAGTGG AGACACAAGGTGGTGACAAGCAACCATCGTTCAG |
| | Intron 11-12 | 67,334,226 | 67,334,483 | 258 | gtgagagaagggtggaactggtggg . . . tgtc ccattgggtttgctctttcag |
| 12 | ENSE00001338145 | 67,334,142 | 67,334,225 | 84 | AGGAGCAACCTTCCCGAAGATACCAGCCTGCCACAC GTCACCCCAGTCTCCGCCGGGGTCGTCGGACAAGAA GGAGCCAGGCAG |
| | Intron 12-13 | 67,330,710 | 67,334,141 | 3,432 | gtaatctgaagagctcattcccatg . . . tctc tcttcttcccaatacctgtag |

TABLE 1-continued

Partial genomic sequence from chromosome 14 reference assembly NC000014 with
full exon composition and exon-intron boundaries of the human ZFYVE26 gene
(according to the Ensembl database: ENSG00000072121)

| Exon | Reference of exon/intron | Position in the genomic sequence of chromosome 14 base pairs | Length in base pairs | | Sequence |
|---|---|---|---|---|---|
| 13 | ENSE00001338143 | 67,330,641 | 67,330,709 | 69 | ATGGCCGAGACAGAGGTTCAAACCCATCCTGGAAA GTACAAGTAGTGAGCTGAGCACAAGTACGTCAG |
| | Intron 13-14 | 67,330,230 | 67,330,640 | 411 | gtatgcagatttccaccagttgcca . . . ccca cacattcttgtgtcccaacag |
| 14 | ENSE00001338141 | 67,330,078 | 67,330,229 | 152 | AGGGAAGTCTGAGTGCCATGTCTGGCCGGAATGAGC TGCACAGTAGATTGCACCCCCATCCTCAAAGTTCAC TCATCCCCATGATGTTCTCCCCACCTGAGTCACTGC TGGCATCCTGCATCCTTCGCGGGAACTTCGCAGAAG CCCATCAG |
| | Intron 14-15 | 67,327,244 | 67,330,077 | 2,834 | gtgaggggaggccatacctttcag . . . ccac acactccctctcctatgacag |
| 15 | ENSE00001338140 | 67,327,042 | 67,327,243 | 202 | GTGCTGTTCACGTTCAACCTGAAGTCCTCACCCAGT TCAGGGGAACTGATGTTCATGGAGCGCTACCAGGAA GTGATCCAAGAACTGGCCCAAGTAGAGCACAAGATT GAAAACCAGAACTCAGATGCGGGTAGCAGCACCATT CGGAGAACTGGCAGTGGCCGCTCAACTCTACAGGCC ATTGGCAGCGCTGCAGCAGCAG |
| | Intron 15-16 | 67,326,069 | 67,327,041 | 973 | gtcaggcttccctgctaacaccata . . . tttt attcctctgctgggcggccag |
| 16 | ENSE00001338139 | 67,325,805 | 67,325,805 | 264 | GAATGGTGTTTTACTCTATCTCTGACGTGACTGACA AGCTGCTCAACACCTCTGGAGACCCCATCCCCATGC TCCAGGAGGACTTTTGGATAAGCACGGCTCTAGTGG AGCCCACTGCTCCCCTGAGAGAGGTTCTGGAAGACC TCAGTCCCCCTGCCATGGCTGCATTTGACCTAGCTT GCTCTCAGTGCCAGCTCTGGAAAACCTGCAAGCAGC TTTTGGAGACAGCCGAACGGCGTTTGAATAGTAGCC TTGAAAGGCGGG |
| | Intron 16-17 | 67,322,704 | 67,325,804 | 3,101 | gtgagtgtgctgtgttagctgtatc . . . tccc tcttccttcatctatttccag |
| 17 | ENSE00000807790 | 67,322,584 | 67,322,703 | 120 | GTCGACGGATAGACCACGTACTCCTAAATGCTGATG GCATTCGAGGTTTTCCAGTTGTTCTTCAGCAAATCA GTAAGAGTCTCAATTATCTGCTTATGTCAGCCAGTC AAACCAAATCAG |
| | Intron 17-18 | 67,322,493 | 67,322,583 | 91 | gtgagttgcttttttctcttttctt . . . tttc tttctcatttgctttccatag |
| 18 | ENSE00000658697 | 67,322,328 | 67,322,492 | 165 | AGAGTGTGGAAGAAAAGGGAGGAGGCCCTCCACGGT GCAGCATCACTGAACTGCTTCAGATGTGCTGGCCCA GCCTAAGCGAGGACTGTGTTGCCAGCCACACCACCC TCTCCCAGCAGCTAGATCAGGTCCTTCAGTCACTGA GAGAGGCACTAGAGCTGCCAG |
| | Intron 18-19 | 67,321,748 | 67,322,327 | 580 | gtataaggctgtctgcttgggaaca . . . cttt ctcctgccatcctcctctcag |
| 19 | ENSE00000658696 | 67,321,529 | 67,321,747 | 219 | AGCCCAGGACTCCTCCACTGTCTTCCCTGGTGGAGC AGGCAGCCCAGAAAGCTCCAGAGGCAGAGGCCCACC CTGTGCAGATCCAGACTCAGCTCCTCCAGAAGAACC TGGGCAAACAGACCCCATCAGGCAGCAGGCAGATGG ACTACTTGGGCACCTTCTTCAGTTACTGCAGCACCC TTGCTGCAGTTCTCCTTCAAAGTTTGAGCTCTGAGC CTG |
| | Intron 19-20 | 67,320,907 | 67,321,528 | 622 | gtaggtagcaagaaagaggcaatag . . . aaga tcatgttctttaccttgcag |
| 20 | ENSE00000658695 | 67,320,804 | 67,320,906 | 103 | ATCATGTGGAGGTCAAGGTAGGAAATCCCTTTGTTC TGCTGCAACAGAGCTCTTCCCAACTGGTGTCACATC TCCTGTTTGAGAGACAAGTTCCCCCAGAGAG |
| | Intron 20-21 | 67,319,996 | 67,320,803 | 808 | gtaggagccacctccatgcaagtca . . . atgc tttctgcttctctccttccag |

TABLE 1-continued

Partial genomic sequence from chromosome 14 reference assembly NC000014 with
full exon composition and exon-intron boundaries of the human ZFYVE26 gene
(according to the Ensembl database: ENSG00000072121)

| Exon | Reference of exon/intron | Position in the genomic sequence of chromosome in 14 base pairs | Length in base pairs | | Sequence |
|---|---|---|---|---|---|
| 21 | ENSE00000658694 | 67,319,250 | 67,319,995 | 746 | ACTGGCAGCCCTTCTGGCCCAAGAGAATCTCAGCCT AAGTGTGCCACAGGTCATCGTCAGCTGCTGCTGTGA GCCCCTTGCTCTTTGCTCATCCCGGCAAAGCCAGCA GACCTCCTCCCTCCTGACTCGTCTGGGTACTCTGGC CCAGCTACACGCCTCTCACGCCTGGATGACCTCCCA CTTTCTACACCGAGCTCCCCGAGGACAACTGAGAAC CCTACATTGGAAAGAAAGCCCTACTCCTCCCCAAGG GACTCATCACTCCCAGCCCTCACCTCCTCTGCCTTG GCCTTTCTTAAGTCACGCTCAAAGCTCCTAGCTACG GTGGCCTGCCTGGGGCTTCCCCGAGGTTAAAGGTC AGCAAACCCAGCTTGTCATGGAAGGAACTTCGTGGC CGCAGGGAGGTGCCTCTGGCTGCAGAGCAGGTAGCC CGGGAGTGTGAGCGCCTTCTGGAACAATTCCCTCTG TTTGAGGCCTTCCTCCTGGCTGCCTGGGAGCCCCTG CGAGGGTCTTTGCAGCAGGGGCAGAGTCTGGCAGTG AATCTCTGTGGTTGGGCCAGTCTTTCTACCGTTCTC CTGGGCCTACATTCTCCCATTGCCCTAGATGTACTG AGTGAGGCTTTTGAGGAATCTTGGTGGCCAGAGAT TGGTCCCGGGCCCTTCAGCTCACTGAAGTGTACGGG CGAGATGTGGACGATTTGAGCAGCATAAAGGATGCA GTCCTGAGCTGTGCTGTGGCATGTG |
| | Intron 21-22 | 67,318,000 | 67,319,249 | 1,250 | gtgagcagaatgctatgcctcccctt . . . tctg agcatcttttttgtcttatag |
| 22 | ENSE00000658693 | 67,317,803 | 67,317,999 | 197 | ACAAAGAAGGTTGGCAATACCTGTTTCCCGTGAAGG ATGCATCTCTGAGAAGTCGGCTGGCCCTACAGTTTG TGGACAGGTGGCCCCTGGAGTCATGCCTGGAGATTC TGGCCTACTGCATTTCAGACACGGCTGTCCAAGAAG GACTAAAGTGTGAGCTACAGAGGAAGCTGGCGGAGC TGCAGGTGTATCAGAAG |
| | Intron 22-23 | 67,316,816 | 67,317,802 | 987 | gtatgggccctcgcatcaagagaaa . . . gacg gatttcttgtcttttccttag |
| 23 | ENSE00000658692 | 67,316,711 | 67,316,815 | 105 | ATTCTGGGTTTGCAGTCTCCCCCAGTGTGGTGTGAC TGGCAGACCTTGAGGAGCTGTTGTGTTGAGGACCCA TCAACTGTCATGAACATGATTCTAGAAGCACAG |
| | Intron 23-24 | 67,314,719 | 67,316,710 | 1,992 | gtaccgttttcctgggtggtgttcc . . . tgaa ggcatgtgtgtttccttccag |
| 24 | ENSE00000658691 | 67,314,596 | 67,314,718 | 123 | GAGTATGAACTGTGTGAAGAGTGGGGCTGCCTGTAC CCCATTCCAAGAGAACATTTAATCAGCCTTCATCAA AAGCATCTTCTCCACCTTCTAGAAAGAAGAGATCAT GACAAGGCTCTGCAA |
| | Intron 24-25 | 67,314,206 | 67,314,595 | 390 | gtaagcccccagttctttccatttt . . . ttcc tcctctaccctttgacaatag |
| 25 | ENSE00000658690 | 67,314,029 | 67,314,205 | 177 | CTCCTGCGAAGAATCCCTGACCCCACCATGTGCCTT GAAGTGACAGAGCAATCCCTCGACCAGCACACTAGC TTGGCCACTTCTCACTTCTTGGCCAACTACCTCACC ACCCACTTCTATGGACAACTGACTGCTGTCCGACAC CGTGAAATCCAGGCGCTGTATGTGGGATCCAAG |
| | Intron 25-26 | 67,312,577 | 67,314,028 | 1,452 | gtaaggatacaccgtgaaatccagg . . . ctct atggatctaccccacaaacag |
| 26 | ENSE00000658689 | 67,312,330 | 67,312,576 | 247 | ATTCTGCTGACCCTGCCTGAGCAGCACCGGGCCAGC TATTCCCACTTGTCCTCTAACCCCCTGTTCATGCTG GAGCAGCTGCTTATGAACATGAAGGTGGATTGGGCC ACTGTGGCTGTGCAGACTCTCCAGCAGCTGCTGGTT GGACAGGAGATTGGCTTCACTATGGACGAGGTGGAC TCACTGCTTTCCAGATACGCAGAGAAAGCCCTGGAC TTTCCATACCCTCAGAGGGAGAAACGATCAG |
| | Intron 26-27 | 67,311,585 | 67,312,329 | 745 | gtaactgctagcatcctagaagggg . . . ttgt cagcattttccctctctacag |

TABLE 1-continued

Partial genomic sequence from chromosome 14 reference assembly NC000014 with
full exon composition and exon-intron boundaries of the human ZFYVE26 gene
(according to the Ensembl database: ENSG00000072121)

| Exon | Reference of exon/intron | Position in the genomic sequence of chromosome in 14 base pairs | Length in base pairs | | Sequence |
|---|---|---|---|---|---|
| 27 | ENSE00000658688 | 67,311,486 | 67,311,584 | 99 | ATTCTGTGATTCACCTCCAAGAAATTGTCCACCAGG CTGCAGATCCCGAGACCCTCCCTAGATCACCATCAG CAGAGTTCTCTCCTGCTGCTCCTCCTG |
| | Intron 27-28 | 67,308,681 | 67,311,485 | 2,805 | gtaagaactggctctgatgattcac . . . tctg acctctggctctgcctcccag |
| 28 | ENSE00000658687 | 67,308,517 | 67,308,517 | 164 | GTATCTCCAGTATACATTCCCCTAGTCTAAGGGAAA GGAGTTTCCCACCAACCCAGCCCTCACAGGAATTTG TGCCCCAGCGACACCCCTGCCAGGCACCAGTGGG TACCGGATGAGACTGAGAGTATCTGCATGGTCTGCT GCAGGGAGCACTTCACCATG |
| | Intron 28-29 | 67,306,201 | 67,308,516 | 2,316 | gtaagcagcatcggtctccactgtc . . . ttct cctcctgatggcattcctcag |
| 29 | ENSE00000658686 | 67,306,064 | 67,306,200 | 137 | TTTAACAGGCGTCATCATTGTCGCCGCTGTGGCCGG CTAGTGTGCAGCTCCTGCTCCACTAAGAAAATGGTG GTTGAAGGCTGCAGAGAGAACCCTGCTCGTGTGTGT GATCAGTGCTATAGTTACTGCAACAAAGA |
| | Intron 29-30 | 67,305,019 | 67,306,063 | 1,045 | gtgagtgtcctacagcagggctgtt . . . ataa ttttctttctctgttttcag |
| 30 | ENSE00000658685 | 67,304,987 | 67,305,018 | 32 | GTACCAGAGGAGCCTTCAGAAAAACCAGAAG |
| | Intron 30-31 | 67,304,311 | 67,304,986 | 676 | gtaaggccaaatcccgttctctgtg . . . acat gaatggcatttctcttctcag |
| 31 | ENSE00000658684 | 67,304,174 | 67,304,310 | 137 | CTCTAGACAGCTCCAAGAATGAAAGCCCTCCATACT CGTTTGTGGTGAGAGTCCCCAAAGCAGATGAGGTGG AATGGATTTTGGATCTCAAAGAGGAGGAAAATGAGC TGGTGCGGAGTGAATTTTACTATGAGCAG |
| | Intron 31-32 | 67,302,918 | 67,304,173 | 1,256 | gtaatagcaataaaatgcaatggtc . . . ttct cccttcttccaccccggccag |
| 32 | ENSE00000807789 | 67,302,697 | 67,302,917 | 221 | GCCCCCAGCGCCTCCTTGTGCATTGCCATCCTGAAT CTGCACCGGGACAGCATTGCCTGTGGTCACCAGCTG ATTGAGCACTGCTGCAGGCTCTCCAAGGGCCTCACC AACCCAGAGGTGGATGCCGGGCTGCTCACGGACATC ATGAAGCAGCTGCTGTTCAGCGCCAAGATGATGTTC GTCAAAGCCGGCCAGAGCCAAGACTTGGCTCTTTGT GACAG |
| | Intron 32-33 | 67,299,290 | 67,302,696 | 3,407 | gtagagggcagtgggtctctattct . . . ggcc ttgccctttttcctccttgtag |
| 33 | ENSE00000658682 | 67,299,142 | 67,299,289 | 148 | CTACATCAGCAAGGTAGATGTGCTGAATATTTTAGT TGCTGCTGCCTATCGCCACGTGCCATCTTTGGATCA GATCTTGCAGCCAGCTGCAGTAACCAGGCTAAGGAA CCAGCTTTTGGAAGCCGAGTACTACCAACTGGGCGT TGAG |
| | Intron 33-34 | 67,298,883 | 67,299,141 | 259 | gtgagacaaagacaaagacaaagct . . . ctaa aaggggcaatttttctcccag |
| 34 | ENSE00000658681 | 67,298,673 | 67,298,882 | 210 | GTCTCCACAAAGACTGGGCTTGATACCACCGGGGCG TGGCATGCTTGGGGCATGGCCTGCCTCAAAGCCGGG AACCCTCACTGCTGCACGGGAGAAGTTCAGTCGCTGT CTGAAGCCCCCATTTGACCTCAATCAGCTGAATCAT GGCTCAAGGCTGGTGCAGGATGTGGTTGAGTACCTA GAGTCCACAGTGAGGCCCTTTGTATCCTTG |
| | Intron 34-35 | 67,298,055 | 67,298,672 | 618 | gtaagagcaaggcaggaagagtgcc . . . tctc tctcgctccctgtgctgtcag |
| 35 | ENSE00000658680 | 67,297,836 | 67,298,054 | 219 | CAAGATGACGATTACTTTGCCACCCTGAGGGAACTG GAAGCTACCCTTCGGACGCAGAGCCTTTCTCTGGCA GTGATTCCTGAAGGGAAAATCATGAACAACACCTAC TACCAGGAATGCCTCTTCTACCTGCACAACTATAGC |

TABLE 1-continued

Partial genomic sequence from chromosome 14 reference assembly NC000014 with
full exon composition and exon-intron boundaries of the human ZFYVE26 gene
(according to the Ensembl database: ENSG00000072121)

| Exon | Reference of exon/intron | Position in the genomic sequence of chromosome in 14 base pairs | Length in base pairs | Sequence |
|---|---|---|---|---|
| | | | | ACCAACCTGGCCATCATCAGCTTCTACGTGAGGCAC AGCTGCCTGCGGGAAGCTCTTCTGCACCTTCTCAAC AAG |
| | Intron 35-36 | 67,292,616 | 67,297,835 | 5,220 gtgggacatggacacagctcaaaaa . . . gact tctcgccctgccctgctccag |
| 36 | ENSE00000658679 | 67,292,418 | 67,292,615 | 198 GAGAGTCCTCCAGAAGTTTTTATAGAAGGCATTTTC CAACCAAGCTATAAAAGTGGGAAGCTACACACTTTG GAGAACTTGCTAGAATCCATTGATCCAACCTTGGAG AGCTGGGGAAAGTACTTGATTGCTGCCTGCCAACAT TTACAGAAGAAGAACTACTACCACATTCTGTATGAG CTGCAGCAGTTTATGAAG |
| | Intron 36-37 | 67,291,721 | 67,292,417 | 697 gtaatggcagccccttcctgccttc . . . ctga acatttattttcctcttcag |
| 37 | ENSE00000658678 | 67,291,521 | 67,291,720 | 200 GACCAAGTTCGGGCCGCCATGACCTGTATTCGGTTC TTCAGTCACAAAGCAAAGTCATATACAGAACTGGGA GAGAAGCTCTCATGGCTACTTAAGGCCAAGGACCAC CTGAAGATCTACCTCCAAGAAACATCCCGCAGCTCT GGAAGGAAGAAAACCACATTCTTCAGAAAGAAGATG ACTGCAGCTGATGTGTCAAG |
| | Intron 37-38 | 67,290,683 | 67,291,520 | 838 gtagctggaggttcagggactatt . . . gact gtgcatattctgtcaccacag |
| 38 | ENSE00000658677 | 67,290,541 | 67,290,682 | 142 GCACATGAACACACTTCAGCTGCAGATGGAAGTGAC CAGGTTCTTGCATCGGTGCGAAAGTGCTGGGACCTC TCAAATCACCACTTTGCCTCTGCCAACCCTGTTTGG AAATAACCACATGAAAATGGATGTTGCCTGCAAG |
| | Intron 38-39 | 67,290,237 | 67,290,540 | 304 gtacatgcagcgtttcagacctctg . . . aagc atgattcccttcctttcag |
| 39 | ENSE00000658676 | 67,290,177 | 67,290,236 | 60 GTCATGCTGGGAGGGAAAAATGTAGAAGATGGTTTT GGAATTGCTTTCCGTGTTCTGCAT |
| | Intron 39-40 | 67,288,997 | 67,290,176 | 1,180 gtatgacttggatcattcaaatcat . . . ccca tcatgttgtgttctgttctag |
| 40 | ENSE00000658675 | 67,288,814 | 67,288,996 | 183 GACTTCCAGCTGGATGCTGCCATGACCTACTGCAGA GCTGCCCGCCAGTTGGTGGAGAAAGAGAAGTACAGT GAGATCCAGCAACTGCTCAAATGTGTCAGTGAGTCA GGCATGGCAGCCAAAAGTGACGGGGACACCATCCTC CTCAACTGCCTGGAAGCGTTCAAGAGAATTCCGCCC CAG |
| | Intron 40-41 | 67,287,567 | 67,288,813 | 1,247 gtacactccctcccgtacctcttgg . . . acag tgctgtttctgttctgcacag |
| 41 | ENSE00000807788 | 67,287,522 | 67,287,566 | 45 GAGCTGGAGGGCCTGATCCAGGCAATACACAATGAT GACAACAAG |
| | Intron 41-42 | 67,285,110 | 67,287,521 | 2,412 gtgagcggaattgtctccaaacgct . . . gctg tctcttataactgactgccag |
| 42 | ENSE00001395974 | 67,282,992 | 67,285,109 | 2,118 GTTCGGGCCTACCTGATATGTTGCAAACTGCGTTCT GCCTACTTGATTGCTGTGAAGCAAGAACACTCACGG GCCACAGCCCTTGTCCAGCAGGTGCAGCAGGCCGCC AAGAGCAGCGGGGATGCAGTAGTGCAAGACATCTGT GCCCAGTGGCTTCTGACAAGCCACCCCCGGGGTGCC CATGGCCCAGGCTCCAGGAAGTGACCTTGGGCAGTG GGGCCAGGAACACGTGGCCTGAGAGCTGGGCAACAG CAGTGATGGCGATGCCCTCCACCTCTTTCCTCCAGT GGAGTGGGACTTCTCTGGCTCTGCCCTAGGTTGGAA AGAGTTGGATTGGACCCTACTTGCCTTCCCGGGCAA GGATAGGACCTTTCACGCAAGTGCCATGTTTCTCTA AAATTGTGAATCTATGTGTGTTTGTCTGGAGATGG CCAGTTCTTTCTACCTCAGAGTGAGTGAGTGAGTAT GTGTGCACACACGTGTGCATGTTCCTGTGCGCTGAT |

TABLE 1-continued

Partial genomic sequence from chromosome 14 reference assembly NC000014 with
full exon composition and exon-intron boundaries of the human ZFYVE26 gene
(according to the Ensembl database: ENSG00000072121)

| Exon | Reference of exon/intron | Position in the genomic sequence of chromosome in 14 base pairs | Length in base pairs | Sequence |
|---|---|---|---|---|
| | | | | GTTTACGCCCAAGCATTTCTGAACAAATGAAACTCT<br>TCTCCATTTAAAAGAGGCACTTTACTTTAGACTTGC<br>CACTCTGAAAACCTTCCCTGCGTTTTGGTTCTTGAC<br>CCGGGTTGTCCTGTTTGTATAGTCCCCCCTCTGTGG<br>ACGTGCTTTAGTAGCTCCTCTTACCTAGAGGGCTTT<br>TACAGAGAATTAGAGCAACACCAAAAGGATTGCCTC<br>TTTTCCTTCCTTCCCATTCCAAAATTCAGAGATGGC<br>TTTGGGGCAAGTGCTACCTGTGGAATAAACCTGTTT<br>TCCAGGTGTCTCTTCTCCCAAGCACAAGAAGTCCTG<br>GAGTCTTTGGAAGGTAGTCTGAATAGAAGGGTTTTC<br>AGGTGCAGGCATCTGAAAGCTGTGGGTATGTGTATA<br>AATGATCAGGTCTGTGAGGCTAACACGGGCAAGAGG<br>GAAAGAAAGGCTAACCATCCAAACAGGGATACAGGG<br>GAGGCGGTGGGGGGTGGTGGGGGGAGCGGGTGCTCA<br>CAAGCACAGAGCTGCCTGTTGTGAATGTCCCTGCTG<br>CAAAGTTGGTGGGTGAGAGAATGGGACTTCCTCTTT<br>GAGAGTCTGGGGAGAGAAAAGGTGGCCAGGATCCTA<br>GGACTGAATGACTCGATTTTACCTATTTGAGCTGCA<br>GTCCTGTTTGCGCTCCTTGAATTGGTTAGGAAGCTG<br>CTTCCTTTTCCCTCCTGCTTCCCTTCAGTCTCTTCA<br>GGACCACAGGATGGATATGCAGACATGTGGGGTCAT<br>TGGGAAGGGAGTGCGCTTCTTTTCTCTGTCTTAGAA<br>AAGGGAGTCAAGGGTTGGCTTTGGAATTGGGCCTCT<br>GGACAGAGTCAGAATGAGGGAATAATGAATAGGTCA<br>CATCTGGTTGGTGGAAAACTAGGTGAAGTGCTTCTT<br>TAATATGCACTGTCTTGTCTTCCCACGCAAGATGTG<br>ACAATGTTTGAGAAAAGGTGTGTCATACTCAGTGAC<br>TTCAATTTGCAAATGTGGGGCCTAAAGAAAGCTCTG<br>CAGCTCTGAACCTCTCACTGGCCAGAGCTCAGCCTA<br>TTGGTCCCATCCATGATGCTGAGACAAACAGAAACT<br>GGAAGCTGAAGTCAGTGTCTCTGGTGCTCAGAAACC<br>CTGTGGATTTCCCTCTGAACCAAGATTTTTAGTAGT<br>AAAATAAACAACTCATGGACATCTGTCAGATGAGAA<br>GTTTTGGTCCTGTTAGAGAGGAGAAAGACTGTAATG<br>AAACTACTAGACCCATTTGGGCTAAAGTTTGGCTTT<br>TCCTTCCTTGAGTCATAGAACGTATCCATCTCCCAG<br>GAAATGTCCTTCTCTGGCGTCTGCTTGCCCTTCTGA<br>GTCTGCCTTTTTTGCACTGAACATAAGCACTTTATA<br>CTAATGGGTCACAAATCTTGCAGCCCTTAATTTGGG<br>ATAAGACCAGATTTTCCTGACATTTTCCTCTAACTC<br>ATTGAACTATCAAATTATAGGCAACCACTGACTAGA<br>CTGATATGAGATGAGGCTAAAAGCCTTTGAACACCA<br>CGCTGTAGTCTCCAACAGAAAAACACCACCAAAACA<br>GATACCCATGTTGAGGGGTTGAATGTTTTACTACAA<br>ACAAGCCACAATAAAGTGTCTATCAACATG |
| | 3' downstream sequence | | | tttcttggcttcataacttcttggtgctgtcttgct<br>cctacccttttgcat |

As used herein, the term "Spastizin" denotes the "SPAS-TIcity due to the ZFYVE26 proteIN", which is encoded by the ZFYVE26 gene. The amino-acid sequence of the human form is shown in SEQ ID NO:2.

The terms "mutant" and "mutation" mean any detectable change in genetic material, e.g. DNA, RNA, cDNA, or any process, mechanism, or result of such a change. This includes gene mutations, in which the structure (e.g. DNA sequence) of a gene is altered, any gene or DNA arising from any mutation process, and any expression product (e.g. protein or enzyme) expressed by a modified gene or DNA sequence. Generally a mutation is identified in a subject by comparing the sequence of a nucleic acid or polypeptide expressed by said subject with the corresponding nucleic acid or polypeptide expressed in a control population. A mutation in the genetic material may also be "silent", i.e. the mutation does not result in an alteration of the amino acid sequence of the expression product.

In the context of the instant application, mutations identified in ZFYVE26 gene are designated pursuant to the nomenclature of Den Dunnen et al. 2001 approved by the Human Genome Variation Society (http://www.genomic.u-nimelb.edu.au/mdi/mutnomen/). According to the invention, the position +1 in ZFYVE26 gene is the A of the start codon ATG of the cDNA sequence (see FIG. 2 and Table 1) which corresponds to the position +136 in SEQ ID NO: 1.

As defined by Dunnen and Antonarakis at the nucleic acid level, substitutions are designated by "c.position(nt)>(nt)", e.g. "c.1240G>T denotes that at nucleotide 1240 of the reference sequence G is changed to a T. The mutation at the protein level is denoted p.E414X: which means that a glutamic acid (E or Glu) at position 414 encoded by GAG is replaced by a STOP (TAG). Deletions are designated by "del" after the deleted interval (following the deleted nucleotides). For instance c.2049delT denotes a T deletion at nucleotide 2049. The consequence of this deletion, p.F683LfsX3, is a frameshift ("fs") leading to the replacement of aminoacid phenylalanine (F or Phe) at position 683 by a Leucine (L or Leu) and appearance of a premature STOP codon ("X") 2 codons after (F683 considered at position 1), at codon 685. An alternative nomenclature is to indicate the position of the stop codon in the resulting protein after the X; p.Phe683LeufsX685 indicates that the stop codon resulting from the mutation is at codon 685. Insertions are designated by "ins," followed by the inserted nucleotides. For example, c. 6296_6297insT denotes that a T was inserted between nucleotides 6296 and 6297. This leads to a frameshift maintaining the Leucine at position 2099 but leading to a premature STOP codon at position 2111: p.L2099LfsX2111. Inversions are designated by "inv", after positions of the inverted nucleotides. For example g.67319319-67319414inv denotes that nucleotides from positions 67319319 to 67319414 have been inverted. This inversion occurred at the genomic level and is not purely affecting the coding sequence as indicated by "g."

Figure 2:
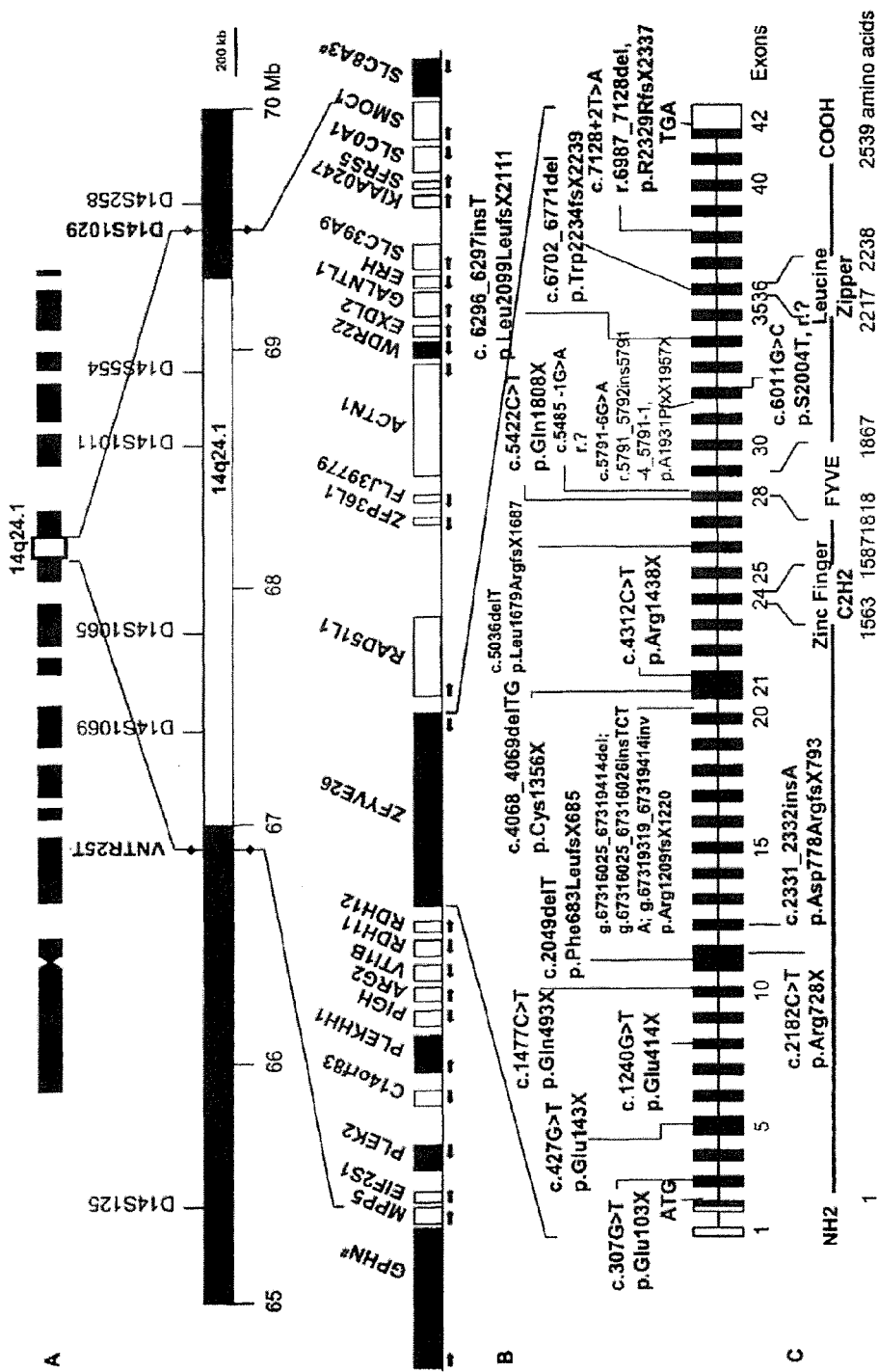
Figure 7:
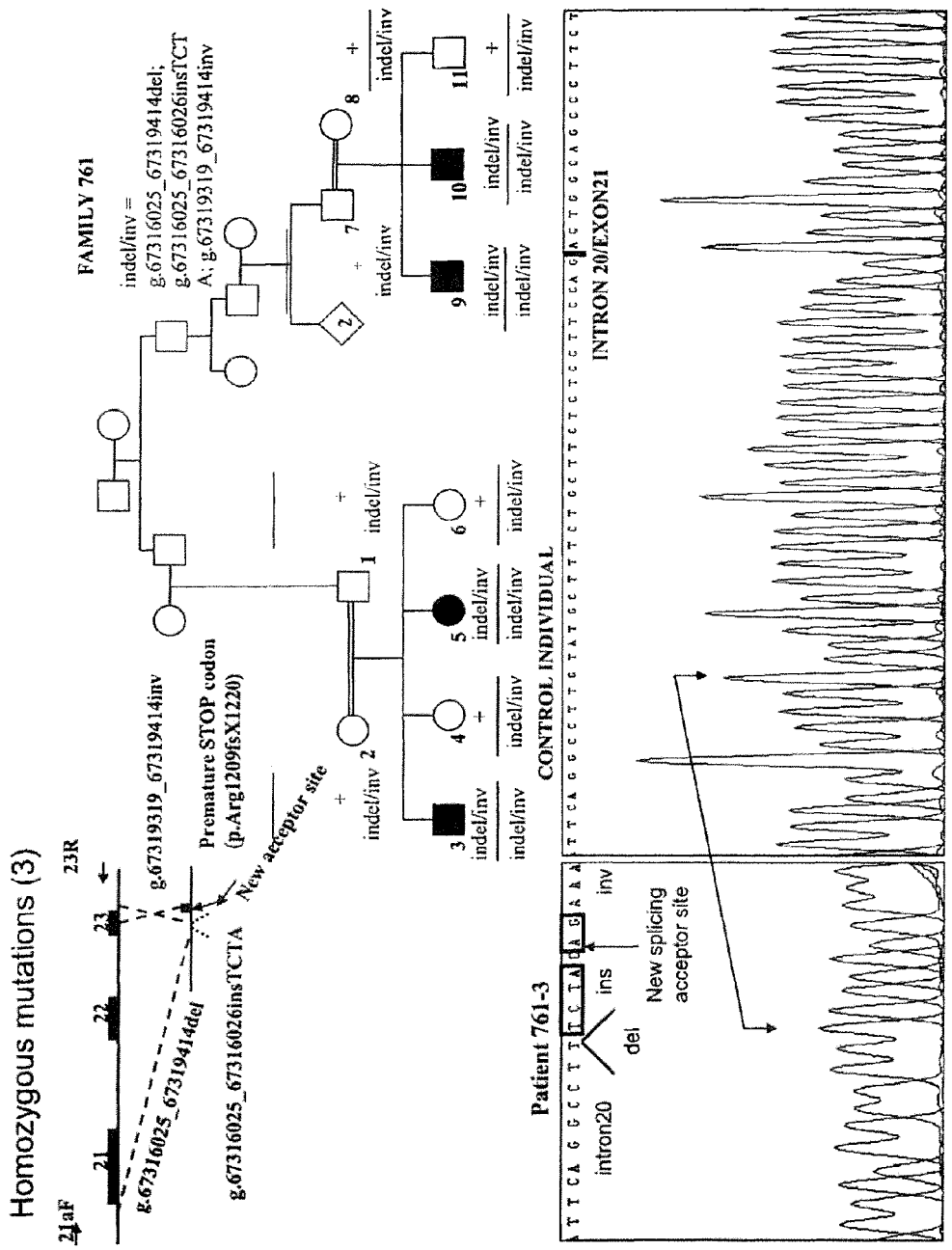
Figure 8:
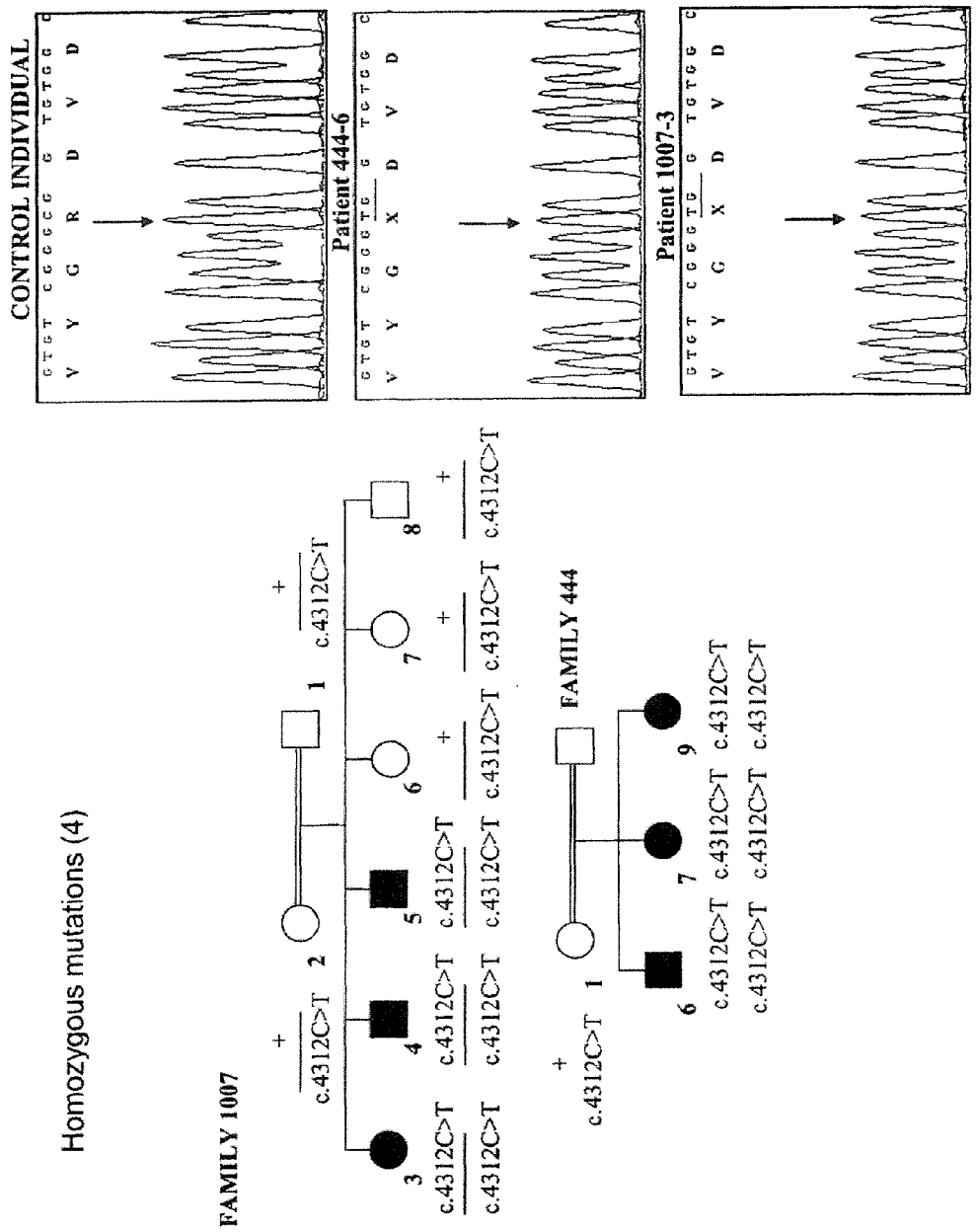

Sometimes, complex rearrangements are observed and their exact mechanism of origin is unknown: for example, the mutation g.67316025_67319414del/ g.67316025_67316026insTCTA/g.67319319_67319414inv likely combines at least three events which are a large deletion, a small insertion and the inversion of a small motif (FIG. 7-2). In such large genomic events, nucleotide numbering uses genomic positions according to the human genome sequence available at Ensembl, NCBI, Genbank or UCSC databases online.

Another class of mutations affects the correct splicing of a gene either directly by altering the splicing consensus sequences at intron-exon junctions or indirectly by alteration of exonic sequences responsible for the binding of enhancers of splicing elements (ESE: http://rulai.cshl.edu/cgi-bin/tools/ESE3/esefinder.cgi?process=home). More frequently and easily, splicing mutations are found at exon-intron junctions. For example the c.6011G>C mutation in ZFYVE26 is located at the end of exon 32 in the splicing consensus sequence and its splice site score (see legend of table 2), which represent the probability of a given site to be cognized by the splicing machinery, decreases from +4.5 to +0.7. In that case, because mRNA of patients was not available, the effect of the mutation, although likely, could not be verified and is therefore indicated "r.?" (r for RNA level) by convention. However, since the mutation is present in the exon, it can also alter the protein if synthesized and this fact is indicated too: p.S2004T so that the full description of the mutation is: c.6011G>C, r.?, p.S2004T. In another example, the mutation c.5791–6G>A is found in intron 31, again in a splicing consensus sequence. While there is no direct effect of the mutation in the coding sequence, in silico predictions indicate that there is creation of a novel splicing site with a better splice score of +4.2 versus +3.7. This was validated on mRNA of patients after PCR using flanking primers followed by direct sequencing of the PCR product allowing to precise the exact mutational effect which is a misplaced splicing leading to incorporation of 4 intronic bases to the mRNA (r.5791_5792ins5791–4_5791–1) and subsequent protein modification with frameshift and premature stop codon (p.A1931PfsX1957X).

Thus, the ZFYVE26 mutations according to the invention are as follows:
c.307G>T which denotes that at nucleotide 307 (which corresponds to the position 442 in SEQ ID NO:1) of the ZFYVE26 sequence (coding sequence) G is changed to a T,
c.427G>T which denotes that at nucleotide 427 (which corresponds to the position 562 in SEQ ID NO:1) of the ZFYVE26 sequence (coding sequence) G is changed to a T,
c.1240G>T which denotes that at nucleotide 1240 (which corresponds to the position 1375 in SEQ ID NO:1) of the ZFYVE26 sequence (coding sequence) G is changed to a T,
c.1477C>T which denotes that at nucleotide 1477 (which corresponds to the position 1612 in SEQ ID NO:1) of the ZFYVE26 sequence (coding sequence) C is changed to a T,
c.2182C>T which denotes that at nucleotide 2182 (which corresponds to the position 2317 in SEQ ID NO:1) of the ZFYVE26 sequence (coding sequence) C is changed to a T,
c.4312C>T which denotes that at nucleotide 4312 (which corresponds to the position 4447 in SEQ ID NO:1) of the ZFYVE26 sequence (coding sequence) C is changed to a T,
c.5422C>T which denotes that at nucleotide 5422 (which corresponds to the position 5557 in SEQ ID NO:1) of the ZFYVE26 sequence (coding sequence) C is changed to a T,
c.5791–6G>A/r.5791_5792ins5791–4_5791–1, which denotes that at the intronic nucleotide –6 before the exonic nucleotide 5791, the G is changed to A and which causes an insertion between nucleotide 5791 and 5792 of 4 intronic bases positioned at –4 to –1 relative to position 5791 (see table 1 for the position of the nucleotides).
c.5485–1G>A which denotes that at intronic nucleotide –1 before the exonic nucleotide 5485 the G is changed to A (see table 1 for the position of the nucleotides).
c.7128+2T>A/r.6987_7128del which denotes that at intronic nucleotide +2 after the exonic nucleotide 7128, the T is changed to A and which causes a deletion of the nucleotide between 6987 and 7128 in the RNA (see table 1 for the position of the nucleotides).
c.6011G>C which denotes that at nucleotide 6011 (which corresponds to the position 6146 in SEQ ID NO:1) of the ZFYVE26 sequence (coding sequence) G is changed to a C,
c.2049delT which denotes that at nucleotide 2049 (which corresponds to the position 2184 in SEQ ID NO:1) of the ZFYVE26 sequence (coding sequence) T is deleted,
c.4068_4069delTG which denotes that at nucleotide 4068 and 4069 (which corresponds to the position 4203 and 4204 in SEQ ID NO:1) of the ZFYVE26 sequence (coding sequence) T and G are deleted,
c.5036delT which denotes that at nucleotide 5036 (which corresponds to the position 5171 in SEQ ID NO:1) of the ZFYVE26 sequence (coding sequence) T is deleted,
c.6702_6771del which denotes that between nucleotide 6702 and 6771 (which corresponds to the position 6837 and 6906 in SEQ ID NO:1) the nucleotides are deleted,
c.2331_2332insA which denotes that between nucleotide 2331 and 2332 (which corresponds to the position 2466 and 2467 in SEQ ID NO:1) the nucleotide A is inserted,
c.6296_6297insT which denotes that between nucleotide 6296 and 6297 (which corresponds to the position 6431 and 6432 in SEQ ID NO:1) the nucleotide T is inserted,
g.67316025_67319414del/
g.67316025_67316026insTCTA/
g.67319319_67319414inv which denotes that there is a large genomic deletion between nucleotide 67316025 and 67319414 associated with a TCTA insertion between nucleotide 67316025 and 67316026 and inversion of the genomic sequence between nucleotide 67319319 and 67319414 (positions are here indicated relative to the chromosome 14 assembly NC000014 at Genbank) (see FIG. 7-2).

The term "hereditary spastic paraplegias (HSP)" denotes genetically heterogeneous Mendelian disorders characterized by weakness, spasticity and loss of vibratory sense in the lower limbs (Fink 2006, Depienne et al. 2007, Stevanin et al. 2008). The term "Autosomal Recessive Hereditary Spastic Paraplegia" or "AR-HSP" denotes spastic paraplegia that is transmitted as an autosomal recessive trait. In non-consanguineous populations, this mode of inheritance can account for "apparently" sporadic cases. Patients with HSP or AR-HSP can have a pure phenotype, or, more often, a complex phenotype that associates various neurological signs (cerebellar ataxia, mental retardation, peripheral neuropathy, etc). The term "AR-HSP-TCC" denotes an AR-HSP with Thin Corpus Callosum (TCC) usually associated with, mental or cognitive deficit and peripheral neuropathy (Winner et al. 2005, Franca et al. 2007; Boukhris et al. 2008a). Families without proved TCC can also be mutated in this gene either because of slow progression of the disease in the patient or because magnetic resonance imaging (MRI) couldn't be performed due to patient refusal or impossibility (patients leaving far from cities in North-Africa). Alternatively, clinical heterogeneity has already been proved in families mutated in the same gene (Depienne et al. 2007, Stevanin et al. 2008b) and the clinical presentation of the patients linked and mutated in SPG15 can perfectly fit with this AR-HSP-TCC phenotype but sometimes not (Elleuch et al. 2007, Boukhris et al. 2008a and 2008b). The full spectrum of the phenotypes linked to SPG15 remains to be determined and other HSP phenotypes could be caused by mutations in this gene.

As used herein, the term "subject" denotes a mammal, such as a rodent, a feline, a canine, and a primate. Preferably a subject according to the invention is a human.

Mutations in the ZFYVE26 Gene and Spastizin Protein

The inventors identified various mutations in the ZFYVE26 gene. Eighteen different mutations on human ZFYVE26 gene were indeed identified in 16 families. They were either nonsense mutations (n=7), deletions (n=4), insertions (n=2), splice site mutations (n=4) and genomic rearrangements (n=1) and resulted in an abnormally truncated protein in all cases. The mutations identified by the inventors are presented on the following Table 2.

TABLE 2

Mutations identified in the ZFYVE26 gene and protein.
Splice score predictions were calculated online at the BDGP Splice Site Prediction web site
(http://www.fruitfly.org/seq_tools/splice.html) and at the Cold Spring Harbor Laboratory web site
(http://rulai.cshl.edu/new_alt_exon_db2/HTML/score.html). For mutations predicted to affect the splicing, cells
were only available in two cases and were not available yet to confirm in silico predictions of two of the splicing
mutations but they were considered very likely as mutations given their locations in the splice consensus sites.

| Position | Nucleotide variation | Protein (alternative nomenclature) or RNA consequence | SEQ ID NO: | Mutated family at the homozygous state | Mutated family at the heterozygous state |
|---|---|---|---|---|---|
| Exon 4 | c.307G > T | p.E103X (p.Glu103X) | 105 | None | FSP 656 (France) |
| Exon 5 | c.427G > T | p.E143X (p.Glu143X) | 106 | None | FSP 656 (France) |
| Exon 8 | c. 1240G > T | p.E414X (p.Glu414X) | 107 | None | 708 (France) |
| Exon 10 | c.1477C > T | p.Q493X (p.Gln493X) | 108 | TUN16 (Tunisia) TUN17 (Tunisia) | None |
| Exon 11 | c.2049delT | p.F683LfsX685 (p.Phe683LeufsX3) | 109 | TUN30 (Tunisia) | None |
| Exon 11 | c.2182C > T | p.R728X | 118 | None | FSP917 (Belgium) |
| Exon 12 | c.2331_2332insA | p.D778RfsX793 (p.D778RfsX16) | 119 | None | FSP917 (Belgium) |
| Intron 20 to intron 23 | g.67316025_67319414 del; g.67316025_67316026 insTCTA; g.67319319_67319414 inv | p.R1209fsX1220 (p.Arg1209fsX12) | 110 | 761 (Italy) | None |
| Exon 21 | c.4068_4069delTG | p.C1356fsX1356 (p.Cys1356X) | 111 | None | 130 (France) |
| Exon 21 | c.4312 C > T | p.R1438X (p.Arg1438X) | 112 | 1007 (Ireland) 444 (Morocco) | None |
| Exon 26 | c.5036delT | p.L1679RfsX1687 (p.Leu1679ArgfsX9) | 113 | 203 (Syria) | None |
| Exon 28 | c.5422C > T | p.Q1808X (p.Gln1808X) | 114 | 739 (Turkey) | None |
| Intron 28 | c.5485 – 1G > A | r.? (Aberrant splicing: splice score decreases from +3.1 to −7.8) | | 353 (Algeria) | None |
| Intron 31 | c.5791 – 6G > A | r.5791_5792ins5791-4_5791-1, pA1931PfxX1957X (Aberrant splicing, abolition of the wild-type splicing site and appearance of another splicing site with a better splice score +4.2 versus +3.7). Validated on mRNA | 130 (protein) | None | 130 (France) |

TABLE 2-continued

Mutations identified in the ZFYVE26 gene and protein.
Splice score predictions were calculated online at the BDGP Splice Site Prediction web site
(http://www.fruitfly.org/seq_tools/splice.html) and at the Cold Spring Harbor Laboratory web site
(http://rulai.cshl.edu/new_alt_exon_db2/HTML/score.html). For mutations predicted to affect the splicing, cells
were only available in two cases and were not available yet to confirm in silico predictions of two of the splicing
mutations but they were considered very likely as mutations given their locations in the splice consensus sites.

| Position | Nucleotide variation | Mutations Protein (alternative nomenclature) or RNA consequence | SEQ ID NO: | Mutated family at the homozygous state | Mutated family at the heterozygous state |
|---|---|---|---|---|---|
| Exon 32 | c.6011G > C | p.S2004T, r.? (Aberrant splicing: splice score decreases from +4.5 to +0.7) | 115 | TUN 8 (Tunisia) | None |
| Exon 34 | c. 6296_6297insT | p.L2099LfsX2111 (p.Leu2099LeufsX13) | 116 | 352 (Portugal) | None |
| Exon 36 | c.6702_6771del | p.W2234CfsX2238 (p.Trp2234CysfsX5) | 117 | 671 (Israel Arab) | None |
| Intron 38 | c.7128 + 2T > A | r.6987_7128del, p.R2329RfsX2337 (Aberrant splicing: splice score decreases from +5.9 to −4.8). Validated on mRNA. | 131 (protein) | None | 708 (France) |

Each mutation are herein numbered according to human ZFYVE26 CDS using the A of first coding ATG in exon 2 (see table 1) for nucleotide +1 (position +136 in the SEQ ID NO: 1), and amino acid sequence.

Accordingly, the invention relates to an isolated nucleic acid specifically hybridizable to a region of ZFYVE26 gene coding sequence that contains a mutation selected from the group consisting of:

the substitutions: c.307G>T, c.427G>T, c.1240G>T, c.1477C>T, c.2182C>T, c.4312C>T, c.5422C>T, c.5791−6G>A/r.5791_5792ins5791−4_5791−1 (proved splice site effect), c.5485−1G>A (predicted to affect splicing), c.7128+2T>A/r.6987_7128del (proved splice site effect), c.6011G>C (predicted to affect splicing), the deletions: c.2049delT, c.4068_4069delTG, c.5036delT, c.6702_6771 del, the insertions: c.2331_2332insA, c.6296_6297insT, the complex rearrangement: g.67316025_67319414del/ g.67316025_67316026insTCTA/ g.67319319_67319414inv.

Said nucleic acid may be an oligonucleotide. Preferably, said nucleic acid or oligonucleotide is complementary to a region of the ZFYVE26 gene that contains at least one of the identified mutations. Such nucleic acid may advantageously be used as a primer or probe.

The invention also relates to an isolated nucleic acid, which comprises or consists in a ZFYVE26 gene coding sequence that contains one or several mutation(s) selected from the group consisting of:

the substitutions: c.307G>T, c.427G>T, c.1240G>T, c.1477C>T, c.2182C>T, c.4312C>T, c.5422C>T, c.5791−6G>A, c.5485−1G>A, c.7128+2T>A, c.6011G>C, the deletions: c.2049delT, c.4068_4069delTG, c.5036delT, c.6702_6771del, the insertions: c.2331_2332insA, c.6296_6297insT, the complex rearrangement: g.67316025_67319414del/ g.67316025_67316026insTCTA/ g.67319319_67319414inv or a sequence complementary thereto.

In another embodiment, the invention relates to an isolated polypeptide which comprises the polypeptide sequence of ZFYVE26 containing one or several mutation(s) selected from the group consisting of p.E103X, p.E143X, p.E414X, p.Q493X, p.F683LfsX685, p.R728X, p.D778RfsX793, p.R1209fsX1220, p.C1356fsX1356, p.R1438X, p.L1679RfsX1687, p.Q1808X, p.A1931PfxX1957X, p.S2004T, p.L2099LfsX2111, p.W2234CfsX2238, p.R2329RfsX2337 and those resulting from aberrant splicing identified by the inventors but for which the consequence on the protein, although clearly deleterious in silico since affecting splicing consensus sequences, could not be verified because of the absence of patient's cells for their analysis up to now (c.5485−1G>A, c.6011G>C). In the latter case, c.6011G>C is affecting the last codon of an exon, then probably affecting the splicing but also replacing the corresponding amino-acid as: p.S2004T.

Diagnostic Methods of the Invention

The inventors have further shown that ZFYVE26 mutations are associated with a hereditary spastic paraplegia (HSP), which is characterized by weakness, spasticity and often loss of vibration sense in the lower limbs. More particularly, the inventors have shown that ZFYVE26 mutations as above described in a subset of 22 affected patients correlated with early-onset spastic paraplegia (range: 5 to 19 years) associated with additional neurological symptoms that varied among patients and families: cognitive deterioration or mental retardation (73%, 16/22), axonal neuropathy (67%, 8/12), mild cerebellar signs (36%, 8/22) and, less frequently, a central hearing deficit, decreased visual acuity or retinal degeneration. A thin corpus callosum and white matter hyperintensities were found on brain MRI in 64% (7/11) and 36% (4/11) of the patients, respectively, independently of disease duration (see Table 5 in EXAMPLE).

Therefore the invention provides an ex vivo method of diagnosing or predicting a hereditary spastic paraplegias (HSP) in a subject, which method comprises detecting a mutation in the ZFYVE26 gene or protein (spastizin), as compared to a control population, wherein the presence of a mutation is indicative of a hereditary spastic paraplegia (HSP).

Nucleic Acids Assays:

According to a first embodiment the mutations may be detected by analysing a ZFYVE26 nucleic acid molecule. In the context of the invention, ZFYVE26 nucleic acid molecules include mRNA, genomic DNA and cDNA derived from mRNA. DNA or RNA can be single stranded or double stranded. These may be utilized for detection by amplification and/or hybridization with a probe, for instance.

Thus the invention provides an ex vivo method of diagnosing or predicting a hereditary spastic paraplegias (HSP), in a subject, which method may comprise the step consisting of detecting a ZFYVE26 mutation in a nucleic acid sample obtained from the subject, wherein the presence of a mutation is indicative of a hereditary spastic paraplegia (HSP).

The nucleic acid sample may be obtained from any cell source or tissue biopsy. Non-limiting examples of cell sources available include without limitation blood cells, buccal cells, epithelial cells, fibroblasts, or any cells present in a tissue obtained by biopsy or post-mortem. Cells may also be obtained from body fluids, such as blood, plasma, serum, lymph, etc. DNA may be extracted using any methods known in the art, such as described in Sambrook et al., 1989 or using new isolation method on purification column (Quiagen . . . ). RNA may also be isolated, for instance from tissue biopsy, using standard methods well known to the one skilled in the art such as guanidium thiocyanate-phenol-chloroform extraction (Chomocyznski et al., 1987).

A ZFYVE26 mutation according to the invention may be found and located in many exons or introns, including exon 4 and intron 38 (FIG. 2 and Table 2).

The ZFYVE26 mutations according to the invention are selected from the group consisting of:
the substitutions: c.307G>T, c.427G>T, c.1240G>T, c.1477C>T, c.2182C>T, c.4312C>T, c.5422C>T, c.5791−6G>A/r.5791_5792ins5791−4_5791−1 (proved splice site effect), c.5485−1G>A (predicted to affect splicing), c.7128+2T>A/r.6987_7128del (proved splice site effect), c.6011G>C (predicted to affect splicing),
the deletions: c.2049delT, c.4068_4069delTG, c.5036delT, c.6702_6771del,
the insertions: c.2331_2332insA, c.6296_6297insT,
the complex rearrangement: g.67316025_67319414del/g.67316025_67316026insTCTA/g.67319319_67319414inv.

ZFYVE26 mutations may be detected in a RNA or DNA sample, preferably after amplification. For instance, the isolated RNA may be subjected to coupled reverse transcription and amplification, such as reverse transcription and amplification by polymerase chain reaction (RT-PCR), using specific oligonucleotide primers that are specific for a mutated site or that enable amplification of a region containing the mutated site. According to a first alternative, conditions for primer annealing may be chosen to ensure specific reverse transcription (where appropriate) and amplification; so that the appearance of an amplification product be a diagnostic of the presence of a particular ZFYVE26 mutation. Otherwise, RNA may be reverse-transcribed and amplified, or DNA may be amplified, after which a mutated site may be detected in the amplified sequence by hybridization with a suitable probe or by direct sequencing, or any other appropriate method known in the art. For instance, a cDNA obtained from RNA may be cloned and sequenced to identify a mutation in ZFYVE26 sequence.

Actually numerous strategies for genotype analysis are available (Antonarakis et al., 1989; Cooper et al., 1991; Grompe, 1993). Briefly, the nucleic acid molecule may be tested for the presence or absence of a restriction site. When a base substitution mutation creates or abolishes the recognition site of a restriction enzyme, this allows a simple direct enzymatic test for the mutation. Further strategies include, but are not limited to, direct sequencing, restriction fragment length polymorphism (RFLP) analysis; hybridization with allele-specific oligonucleotides (ASO) that are short synthetic probes which hybridize only to a perfectly matched sequence under suitably stringent hybridization conditions; allele-specific PCR; PCR using mutagenic primers; ligase-PCR, HOT cleavage; denaturing gradient gel electrophoresis (DGGE), temperature denaturing gradient gel electrophoresis (TGGE), single-stranded conformational polymorphism (SSCP), high-resolution-melting (HRM) analysis, primer extension (Snapshot), and denaturing high performance liquid chromatography (DHPLC) (Kuklin et al., 1997). Direct sequencing may be accomplished by any method, including without limitation chemical sequencing, using the Maxam-Gilbert method; by enzymatic sequencing, using the Sanger method; mass spectrometry sequencing; sequencing using a chip-based technology; and real-time quantitative PCR. Preferably, DNA from a subject is first subjected to amplification by polymerase chain reaction (PCR) using specific amplification primers. However several other methods are available, allowing DNA to be studied independently of PCR, such as the rolling circle amplification (RCA), the Invader™ assay, or oligonucleotide ligation assay (OLA). OLA may be used for revealing base substitution mutations. According to this method, two oligonucleotides are constructed that hybridize to adjacent sequences in the target nucleic acid, with the join sited at the position of the mutation. DNA ligase will covalently join the two oligonucleotides only if they are perfectly hybridized (Nickerson et al., 1990).

The inventors designed a series of primers, manually or using Oligo6 (MBI, Cascade, Colo.), in order to amplify all coding exons of 6 genes from the candidate interval (primers and conditions available on request), including the mutated ZFYVE26 gene (see Table 4 in EXAMPLE). PCR-amplified fragments of genomic DNA were then sequenced using the fluorescent dideoxy-terminator method (BigDye v3, Applied Biosystem) on an automated ABI-3730 sequencer according to the manufacturer's recommendations. With the use of the software package SeqScape 2.5 (Applied Biosystems), sequences were aligned and compared to consensus sequences.

Protein Assays

According to a second embodiment said mutation may be detected in ZFYVE26 protein.

All of the identified mutations of the ZFYVE26 gene create some deletions of the C-terminal part of the spastizin protein either because of a premature STOP codon or because of abnormal splicing, both likely resulting in nonsense mediated mRNA decay. These deletions result in truncated proteins of sequences SEQ ID NO: 105 to SEQ ID NO:119 and SEQ ID NO: 130 and 131, respectively. It can not be excluded, however, that a shorten protein fragment may be synthesized due to the activation of new ATGs after the stop codon. Because mRNA couldn't be obtained yet from patients with two of the identified splicing mutations (n=4), the precise mutations at the protein level could not be established, although predicted in silico to strongly result in all cases on premature stop codons and likely on mRNA degradation.

Said mutation may be detected according to any appropriate method known in the art. In particular, a sample, such as a tissue biopsy, obtained from a subject may be contacted with antibodies specific of the mutated form of ZFYVE26 protein, i.e. antibodies that are capable of distinguishing between a mutated form of ZFYVE26 and the wild-type protein (or any other protein), to determine the presence or absence of a ZFYVE26 specified by the antibody. An antibody recognizing the wild type protein could also be used to check the presence of the protein or its abnormal location or size and could then be used as a diagnostic tool as well.

Antibodies that specifically recognize a mutated ZFYVE26 protein also make part of the invention. The antibodies are specific of mutated ZFYVE26 protein that is to say they do not cross-react with the wild-type ZFYVE26 protein. Such antibodies could detect an epitope modified by the mutation (ex: p.S2004T) and not the wild type protein. In addition, a truncated protein obtained because of premature stop codon could, if not degraded, adopt a different conformation that could be recognized by a specific antibody. In this latter case, whole protein injection in rabbits instead of peptides would probably be necessary to obtain a specific response.

A monoclonal or polyclonal antibody recognizing the wild-type ZFYVE26 protein may be used to detect the presence of the wild-type protein or one of its truncated forms. For instance, an antibody recognizing the N-terminal part of the wild-type ZFYVE26 protein may also recognize one or several truncated forms and can be used to reveal by immunoblotting, the different forms, wild-type and truncated, according to their molecular weights. An antibody recognizing the wild-type ZFYVE26 protein, but not recognizing the truncated forms, can be used for immunoblotting or in immunoassay as ELISA; in that case, an absence of signal reveals the presence of a truncated form in the sample or the absence of synthesis of a stable protein as compared with a positive control comprising the wild-type ZFYVE26 protein.

The antibodies of the present invention may be monoclonal or polyclonal antibodies, single chain or double chain, chimeric antibodies, humanized antibodies, or portions of an immunoglobulin molecule, including those portions known in the art as antigen binding fragments Fab, Fab', F(ab')$_2$ and F(v). They can also be immunoconjugated, e.g. with a toxin, or labelled antibodies.

Whereas polyclonal antibodies may be used, monoclonal antibodies are preferred for since they are more reproducible in the long run.

Procedures for raising "polyclonal antibodies" are also well known. Polyclonal antibodies can be obtained from serum of an animal immunized against spastizin, which may be produced by genetic engineering for example according to standard methods well-known by one skilled in the art. Typically, such antibodies can be raised by administering mutated ZFYVE26 protein or peptides of this protein subcutaneously to New Zealand white rabbits which have first been bled to obtain pre-immune serum. The antigens can be injected at a total volume of 100 µl per site at six different sites. Each injected material may contain adjuvants with or without pulverized acrylamide gel containing the protein or polypeptide after SDS-polyacrylamide gel electrophoresis. The rabbits are then bled two weeks after the first injection and periodically boosted with the same antigen three times every six weeks. A sample of serum is then collected 10 days after each boost. Polyclonal antibodies are then recovered from the serum by affinity chromatography using the corresponding antigen to capture the antibody. This and other procedures for raising polyclonal antibodies are disclosed by Harlow et al. (1988).

A "monoclonal antibody" in its various grammatical forms refers to a population of antibody molecules that contains only one species of antibody combining site capable of immunoreacting with a particular epitope. A monoclonal antibody thus typically displays a single binding affinity for any epitope with which it immunoreacts. A monoclonal antibody may therefore contain an antibody molecule having a plurality of antibody combining sites, each immunospecific for a different epitope, e.g. a bispecific monoclonal antibody. Although historically a monoclonal antibody was produced by immortalization of a clonally pure immunoglobulin secreting cell line, a monoclonally pure population of antibody molecules can also be prepared by the methods of the present invention.

Laboratory methods for preparing monoclonal antibodies are well known in the art (see, for example, Harlow et al., 1988). Monoclonal antibodies (mAbs) may be prepared by immunizing purified mutated ZFYVE26 protein into a mammal, e.g. a mouse, rat, human and the like mammals. The antibody-producing cells in the immunized mammal are isolated and fused with myeloma or heteromyeloma cells to produce hybrid cells (hybridoma). The hybridoma cells producing the monoclonal antibodies are utilized as a source of the desired monoclonal antibody. This standard method of hybridoma culture is described in Kohler and Milstein (1975).

While mAbs can be produced by hybridoma culture the invention is not to be so limited. Also contemplated is the use of mAbs produced by an expressing nucleic acid cloned from a hybridoma of this invention. That is, the nucleic acid expressing the molecules secreted by a hybridoma of this invention can be transferred into another cell line to produce a transformant. The transformant is genotypically distinct from the original hybridoma but is also capable of producing antibody molecules of this invention, including immunologically active fragments of whole antibody molecules, corresponding to those secreted by the hybridoma. See, for example, U.S. Pat. No. 4,642,334 to Reading; PCT Publication No.; European Patent Publications No. 0239400 to Winter et al. and No. 0125023 to Cabilly et al.

Antibody generation techniques not involving immunisation are also contemplated such as for example using phage display technology to examine naive libraries (from non-immunised animals); see Barbas et al. (1992), and Waterhouse et al. (1993).

Antibodies raised against mutated ZFYVE26 protein may be cross reactive with wild-type ZFYVE26 protein. Accordingly a selection of antibodies specific for mutated ZFYVE26 protein is required. This may be achieved by depleting the pool of antibodies from those that are reactive with the wild-type ZFYVE26 protein, for instance by submitting the raised antibodies to an affinity chromatography against wild-type ZFYVE26 protein.

Alternatively, binding agents other than antibodies may be used for the purpose of the invention. These may be for instance aptamers, which are a class of molecule that represents an alternative to antibodies in term of molecular recognition. Aptamers are oligonucleotide or oligopeptide sequences with the capacity to recognize virtually any class of target molecules with high affinity and specificity. Such ligands may be isolated through Systematic Evolution of Ligands by EXponential enrichment (SELEX) of a random sequence library. The random sequence library is obtainable by combinatorial chemical synthesis of DNA. In this library, each member is a linear oligomer, eventually chemically modified, of a unique sequence. Peptide aptamers consists of a conformationally constrained antibody variable region displayed by a platform protein, such as *E. coli* Thioredoxin A that are selected from combinatorial libraries by two hybrid methods (Colas et al., 1996).

Kits of the Invention

According to another aspect of the invention, the ZFYVE26 mutation is detected by contacting the DNA of the subject with a nucleic acid probe, which is optionally labelled.

Primers may also be useful to amplify, analyse (dHPLC, Southern . . . ) or sequence the portion of the ZFYVE26 gene containing the mutated positions of interest.

Such probes or primers are nucleic acids that are capable of specifically hybridizing with a portion of the ZFYVE26 gene sequence containing the mutated positions of interest. That means that they are sequences that hybridize with the portion mutated ZFYVE26 nucleic acid sequence to which they refer under conditions of high stringency.

The present invention further provides kits suitable for determining at least one of the mutations of the ZFYVE26 gene.

The kits may include the following components:

(i) a probe, usually made of DNA, and that may be pre-labelled. Alternatively, the probe may be unlabelled and the ingredients for labelling may be included in the kit in separate containers; and (ii) hybridization reagents: the kit may also contain other suitably packaged reagents and materials needed for the particular hybridization protocol, including solid-phase matrices, if applicable, and standards.

In another embodiment, the kits may include:

(i) sequence determination or amplification primers: sequencing primers may be pre-labelled or may contain an affinity purification or attachment moiety; and (2) sequence determination or amplification reagents: the kit may also contain other suitably packaged reagents and materials needed for the particular sequencing amplification protocol. In one preferred embodiment, the kit comprises a panel of sequencing or amplification primers, whose sequences correspond to sequences adjacent to at least one of the polymorphic positions, as well as a means for detecting the presence of each polymorphic sequence.

In a particular embodiment, it is provided a kit which comprises a pair of oligonucleotide primers specific for amplifying all or part of the ZFYVE26 gene comprising at least one of the mutated positions that are identified above (see Table 2).

More preferably, the kits of the invention comprise a pair of primers as shown in Table 3 either for detection by direct sequencing or by screening by other techniques such as dHPLC.

TABLE 3

Primers used for PCR and sequencing to detect the mutations.

| Position | Nucleotide variation | For/Rev primers | SEQ ID NO: |
|---|---|---|---|
| Exon 4 | c.307G > T | tgcttcatcttagagaaatagcagaa/atgggcaacatcttggagac | 3/4 |
| Exon 5 | c.427G > T | gaaagcatgaaggcacacaa/ggctgggcatactggaatta | 5/6 |
| Exon 8 | c.1240G > T | cttaggctgaatgcagagcc/ggtcaacattgccaactcaa | 7/8 |
| Exon 10 | c.1477C > T | aggaagtgcagggaactgaa/ccctgggtgaaataaaacca | 9/10 |
| Exon 11 | c.2049delT | taaatgagctaaagttgcgagaa/cctgaggaaggcccctatt | 11/12 |
|  | c.2182C > T | gaagtcagaacgggttcc/ggtgacgatatgccctgagt | 13/14 |
| Exon 12 | c.2331_2332insA | tcagaacactggggtatgctc/gcatggaaaatttctgaaagg | 120/121 |
| Intron 20 to intron 23 | g.67316025_67319414del; g.67316025_673160266insTCTA; g.67319319_673194144inv | caattaggaacttttatttacatttgc/ccgcctcggccagaatgtg | 15/16 |
| Exon 21 | c.4068_69delTG | caattaggaacttttatttacatttgc/actcccgggctacctgct | 15/17 |
|  |  | ctctgccttggccttttctta/gggcttctctctagagttaccg | 18/19 |
| Exon 21 | c.4312 C > T | caattaggaacttttatttacatttgc/actcccgggctacctgct | 15/17 |
|  |  | ctctgccttggccttttctta/gggcttctctctagagttaccg | 18/19 |
| Exon 26 | c.5036delT | cccctcatctggtgaaggta/tcctccaagaccaagatctctc | 20/21 |
| Exon 28 | c.5422C > T | tcaggaggcacacaatgttc/atggctgtttgagggtgtct | 22/23 |
| Intron 28 | c.5485 −1G > A | gcccatcagctgacagatatt/tggcatttcagtgtgaatgtt | 24/25 |
| Intron 31 | c.5791 −6G > A | gctttcttgtagaatctggttcc/ggaagaacacttgagatctgg | 26/27 |
| Exon 32 | c.6011G > C | gctttcttgtagaatctggttcc/ggaagaacacttgagatctgg | 26/27 |
| Exon 34 | c.6296_6297insT | ggcagatagtgggaatgagg/cttgatgctgagccaggact | 28/29 |

TABLE 3-continued

Primers used for PCR and sequencing to detect the mutations.

| Position | Nucleotide variation | For/Rev primers | SEQ ID NO: |
|---|---|---|---|
| Exon 36 | c.6702_6771del | aggagagaagtgaagcagtcg/gctctagggtcagccaaaca | 30/31 |
| Intron 38 | c.7128 + 2T > A | tggcacataggtgctcaataa/gaggcagccatcaaacaaac | 32/33 |

Note:
The large exons 11 and 21 are amplified using 2 sets of primers.

Therapeutic Methods of the Invention

The inventors have demonstrated that all mutations identified in the ZFYVE26 gene cause or highly likely cause truncation of the protein, suggesting that pathogenicity results from loss of function. Any method leading to the replacement or overexpression of endogenous or exogenous ZFYVE26 is expected to be beneficial. It can not be excluded however that inhibiting specifically certain mutant alleles will be beneficial too, or at least less deleterious: this may be the case if a truncating protein is still or de novo produced and has stronger toxic effects than the loss of the wild type protein.

These results identify mutated ZFYVE26 gene as target for the preventive or curative treatment of a hereditary spastic paraplegia.

Thus the invention further relates to a method of treatment of an HSP which comprises the step of administering a subject in need thereof with a ZFYVE26 nucleic acid, i.e. a nucleic acid sequence that encodes a wild-type ZFYVE26 protein, so that spastizin is expressed in vivo by the cells of the subject that have been transfected with said nucleic acid, or alternatively a construction of exogenous ZFYVE26 gene that will modify or replace or inhibit the endogenous mutated ZFYVE26 gene. Accordingly, said method leads to an overexpression of wild-type spastizin that compensates expression of defective mutated ZFYVE26 protein, or alternatively, to a modification of its abnormal splicing, or inhibition of its expression, or modification of it's structure so that it will loss part of its toxicity if such demonstrated.

The invention also relates to the use of a ZFYVE26 nucleic acid for the manufacture of a medicament intended for the treatment of an HSP.

In the context of the invention, the term "treating" or "treatment", as used herein, means reversing, alleviating, inhibiting the progress of, or preventing the disorder or condition to which such term applies, or one or more symptoms of such disorder or condition.

Preferably said ZFYVE26 nucleic acid is administered in a therapeutically effective amount. A "therapeutically effective amount" is intended for a minimal amount of active agent (e.g., ZFYVE26 nucleic acid) which is necessary to impart therapeutic benefit to a subject. For example, a "therapeutically effective amount" to a mammal is such an amount which induces, ameliorates or otherwise causes an improvement in the pathological symptoms, disease progression or physiological conditions associated with or resistance to succumbing to a disorder.

The administered polynucleotide comprises the nucleotide sequence SEQ ID NO:1, or any homologous or similar sequence as defined below:

a) a sequence showing at least 70%, preferably at least 75% or 80% or 85% or 90% or 95% or 99%, sequence similarity with SEQ ID NO:1;

b) a sequence hybridizing with SEQ ID NO:1, or its complementary sequence, under stringent conditions;

c) a sequence encoding a protein of sequence SEQ ID NO:2, or any sequence substantially similar with SEQ ID NO:2.

The term "sequence similarity" in all its grammatical forms refers to the degree of identity or correspondence between nucleic acid or amino acid sequences of proteins that may or may not share a common evolutionary origin. Preferably the degree of sequence identity is calculated compared with the totality of a reference sequence.

In a specific embodiment, two DNA sequences are "substantially homologous" or "substantially similar" when at least 70%, preferably at least 75% or 80% or 85% or 90% or 95% or 99%, of the nucleotides match over the defined length of the DNA sequences, as determined by sequence comparison algorithms, such as BLAST, FASTA, DNA Strider, etc. Sequences that are substantially homologous can be identified by comparing the sequences using standard software available in sequence data banks, or in a Southern hybridization experiment under, for example, stringent conditions as defined for that particular system.

Similarly, in a particular embodiment, two amino acid sequences are "substantially similar" when greater than 80%, preferably than 85% or 90% or 95% or 99%, of the amino acids are similar (functionally identical). "Functionally identical" polypeptides are those in which a given amino acid residue has been changed without altering the overall conformation and function of the polypeptide, including, but not limited to, replacement of an amino acid with one having similar properties (such as, for example, polarity, hydrogen bonding potential, acidic, basic, hydrophobic, aromatic, and the like). Amino acids with similar properties are well known in the art. For example, arginine, histidine and lysine are hydrophilic-basic amino acids and may be interchangeable. Similarly, isoleucine, a hydrophobic amino acid, may be replaced with leucine, methionine or valine. Such changes are expected to have little or no effect on the apparent molecular weight or isoelectric point of the protein or polypeptide. Preferably, the similar sequences are identified by alignment using, for example, the GCG (Genetics Computer Group, Program Manual for the GCG Package, Version 7, Madison, Wis.) pileup program, or any of the programs described above (BLAST, FASTA, etc.).

Preferably the ZFYVE26 nucleic acid sequence according to the invention is associated with elements that enable for regulation of its expression, such as a promoter sequence.

Such a nucleic acid may be in the form of a DNA vector. The terms "vector" means the vehicle by which a DNA or RNA sequence (e.g. a foreign gene) can be introduced into a host cell, so as to transform the host and promote expression (e.g. transcription and translation) of the introduced sequence. A common type of vector is a "plasmid", which generally is a self-contained molecule of double-stranded DNA, usually of bacterial origin, that can readily accept additional (foreign) DNA and which can readily introduced into a suitable host cell. A plasmid vector often contains coding DNA and promoter DNA and has one or more restriction sites suitable for inserting foreign DNA.

The ZFYVE26 nucleic acid may be introduced into a target cell by means of any procedure known for the delivery of nucleic acids to the nucleus of cells, ex vivo, on cells in culture or removed from an animal or a patient, or in vivo.

Ex vivo introduction may be performed by any standard method well known by one skilled in the art, e.g. transfection, electroporation, lipofection, microinjection, transduction, cell fusion, DEAE dextran, calcium phosphate precipitation, or use of a gene gun.

The above methods do not limit the scope of the invention and it is to be understood that the one skilled in the art may readily make use of any other known appropriate methods for delivering a nucleic acid to a cell in vivo or in vitro.

The invention also relates to the use of wild-type ZFYVE26 protein (Spastizin) for the manufacture of a medicament intended for the treatment of an HSP.

Thus the invention further relates to a method of treatment of an HSP which comprises the step of administering a subject in need thereof with a therapeutically effective amount of wild-type ZFYVE26 protein.

The ZFYVE26 protein may be introduced to a target cell by means of any procedure known for the delivery of proteins to cells, ex vivo, on cells in culture or removed from an animal or a patient, or in vivo.

Protein delivery is the process by which a protein crosses the cell plasma membrane. Traditionally, methods to introduce antibodies, peptides or other membrane-impermeable molecules into cells include micro-injection and electroporation.

A number of protein-transduction domains (PTDs) have also been developed that mediate protein delivery into cells. These PTDs or signal peptide sequences are naturally occurring polypeptides of 15 to 30 amino acids, which normally mediate protein secretion in the cells. They are composed of a positively charged amino terminus, a central hydrophobic core and a carboxyl-terminal cleavage site recognized by a signal peptidase. Examples of such membrane-transducing peptides include Trojan peptides, human immunodeficiency virus (HIV)-1 transcriptional activator (TAT) protein or its functional domain peptides, and other peptides containing protein-transduction domains (PTDs) derived from translocation proteins such as *Drosophilia* homeotic transcription factor Antennapedia (Antp) and herpes simplex virus DNA-binding protein, VP22, and the like. Some commercially available peptides, for example, penetratin 1, Pep-1 (Chariot reagent, Active Motif Inc., CA) and HIV GP41 fragment (519-541), can be used for protein delivery.

Recently, the use of lipid liposomes or the like that can complex with a protein of interest and promote the delivery of the protein into the cell has also been demonstrated. Products available commercially can be used, such as Bio-PORTER (Gene Therapy Systems), or ProVectin (Imgenex, San Diego, Calif.).

The above methods do not limit the scope of the invention and it is to be understood that the one skilled in the art may readily make use of any other known appropriate methods for delivering a protein to a cell in vivo or in vitro.

The invention will be further illustrated by the following figures and examples.

FIGURES

FIG. 1: Refinement of the SPG15 locus and pedigree structure of families 444 and 353 with haplotype reconstruction for informative markers on chromosome 14q23.3-q24.2. Black circles (women) and squares (men) indicate affected members. The code numbers of all sampled individuals are given below the symbols. VNTR: variable number of tandem repeat chosen from the Human Genome Working Draft at UCSC (http://genome.ucsc.edu/) and amplified using primers indicated in table 4. Chromosomal position of microsatellite markers are indicated in base pairs (bp) according to the human genome draft sequence (UCSC and Ensembl databases: http://genome.ucsc.edu/, http://www.ensembl.org). The homozygous haplotype in which the mutated gene is most likely located in affected patients is flanked by black boxes. Arrows indicate the position of key recombination events that were used to restrict the candidate interval. The SPG15 interval was refined to 2.64 Megabases (Mb) between loci VNTR25TG (primers in the table 4) and D14S1029 because of obligatory recombinations observed between loci VNTR25TG and D14S1069 (patient 444-6), and loci D14S588 and D14S1029 (Individual 353-11, who is still unaffected at age 18)

FIG. 2: Critical region of the SPG15 locus, structure of the ZFYVE26 gene and mutations identified in 16 SPG15 families.

(A) Physical and genetic map of human chromosome 14q23.3-q24.2 with markers defining the reduced SPG15 candidate interval in bold. Location and direction of transcription (arrow) of the known genes are schematically represented. The candidate genes analysed by the inventors are indicated by black boxes (# indicates genes analysed by the authors and reported in Elleuch et al, 2007). Distances on chromosome 14 are according to the Ensembl and UCSC Genome Browser databases (http://genome.ucsc.edu/, http://www.ensembl.org).

(B) Structure of the ZFYVE26 gene (GenBank NM_015346) and location of the 18 different disease-causing mutations. The gene, located on chromosome 14q24.1, is transcribed from telomere to centromere, and consists of 42 exons covering a genomic region of 70,063 bp. The full-length transcript is 9,688 bp long, with a coding sequence (exon 2-42) of 7,620 bp (mRNA NM_015346.2). The coding region is indicated in grey and UTRs (5' and 3') are in white. The mutations are numbered according to the nomenclature of the Human Genome Variation Society where +1 is the A of the start codon (ATG) of the cDNA sequence (http://www.hgvs.org/mutnomen/).

(C) Putative functional domains (boxes) present in spastizin (according to Predictprotein, http://www.predictprotein.org/).

Note: Numbering of nucleotides is respective to the A of the first coding ATG in exon 2 of ZFYVE26 gene sequence (position +136 in SEQ ID N01). In the case of the large genomic rearrangement, the genomic position of nucleotides in chromosome 14 is used according to the Ensembl (www.ensembl.org), NCBI (www.ncbi.nlm.nih.gov) databases (accession NO NC000014). Amino-acid positions are according to SEQ ID No 2.

FIGS. 3 to 10: Pedigrees showing segregation of disease-causing mutations in ZFYVE26 in 16 families, including those found linked to SPG15. Square symbols represent men, circles women. Subjects represented with filled symbols are affected. The numbers are an internal reference for each sampled individual. The genotypes are indicated below the analyzed individuals. +=Wild type allele. For the detection of the genomic rearrangement in family 761, primers 21aF and 23R (table 4) were used and generated a 238 bp-fragment in mutation carriers only.

Figure 11:
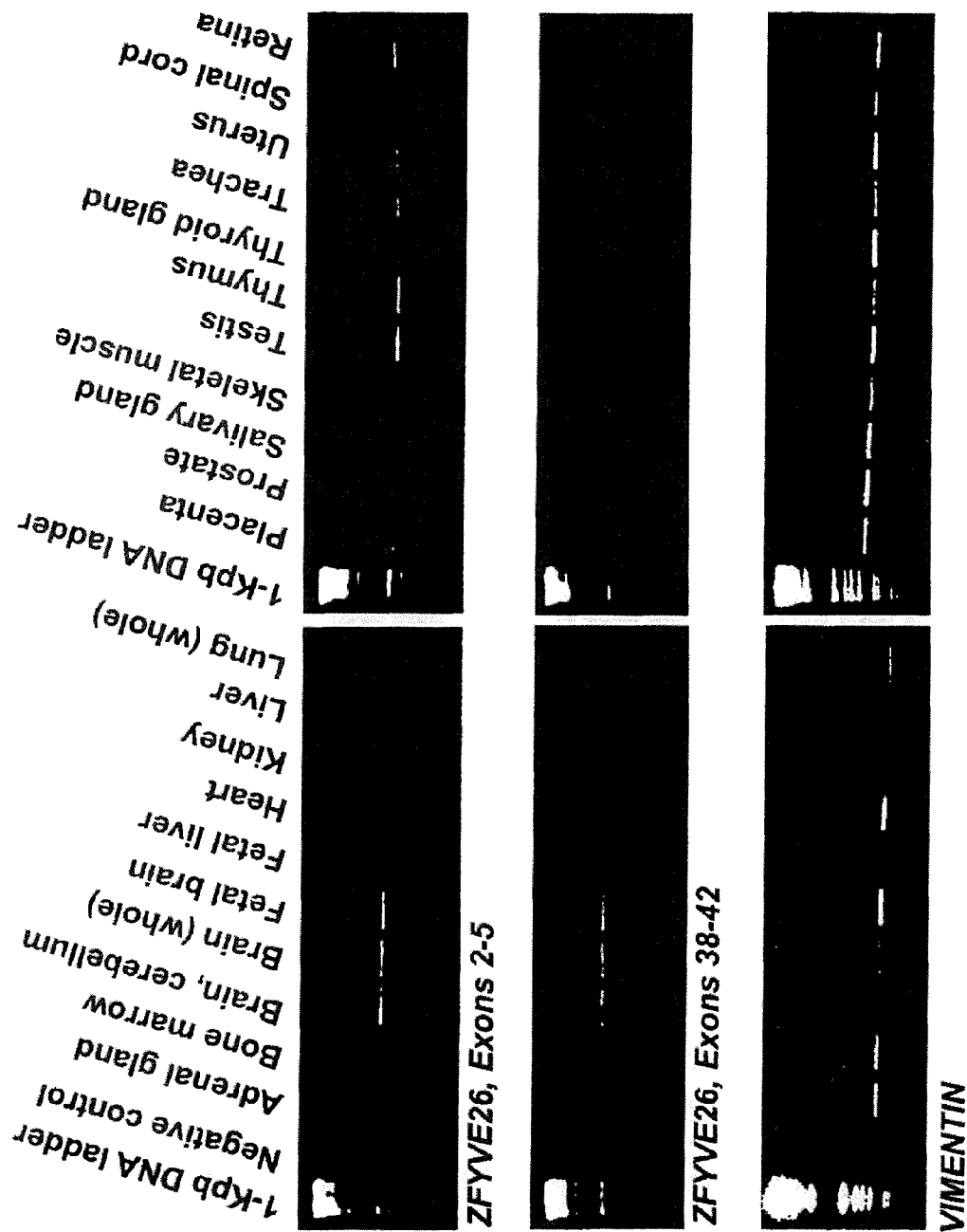

FIG. 11: Semiquantitative analysis of ZFYVE26 expression by RT-PCR in adult human tissues, in comparison with vimentin (NM_003380). Two probes that covered exons 2 to 5, and exons 38 to 42 gave similar results showing widespread expression of the gene in all tissues, but predominantly in adrenal gland, bone marrow, brain, fetal brain, lung, placenta, prostate, skeletal muscle, testis, thymus and retina.

Figure 12:
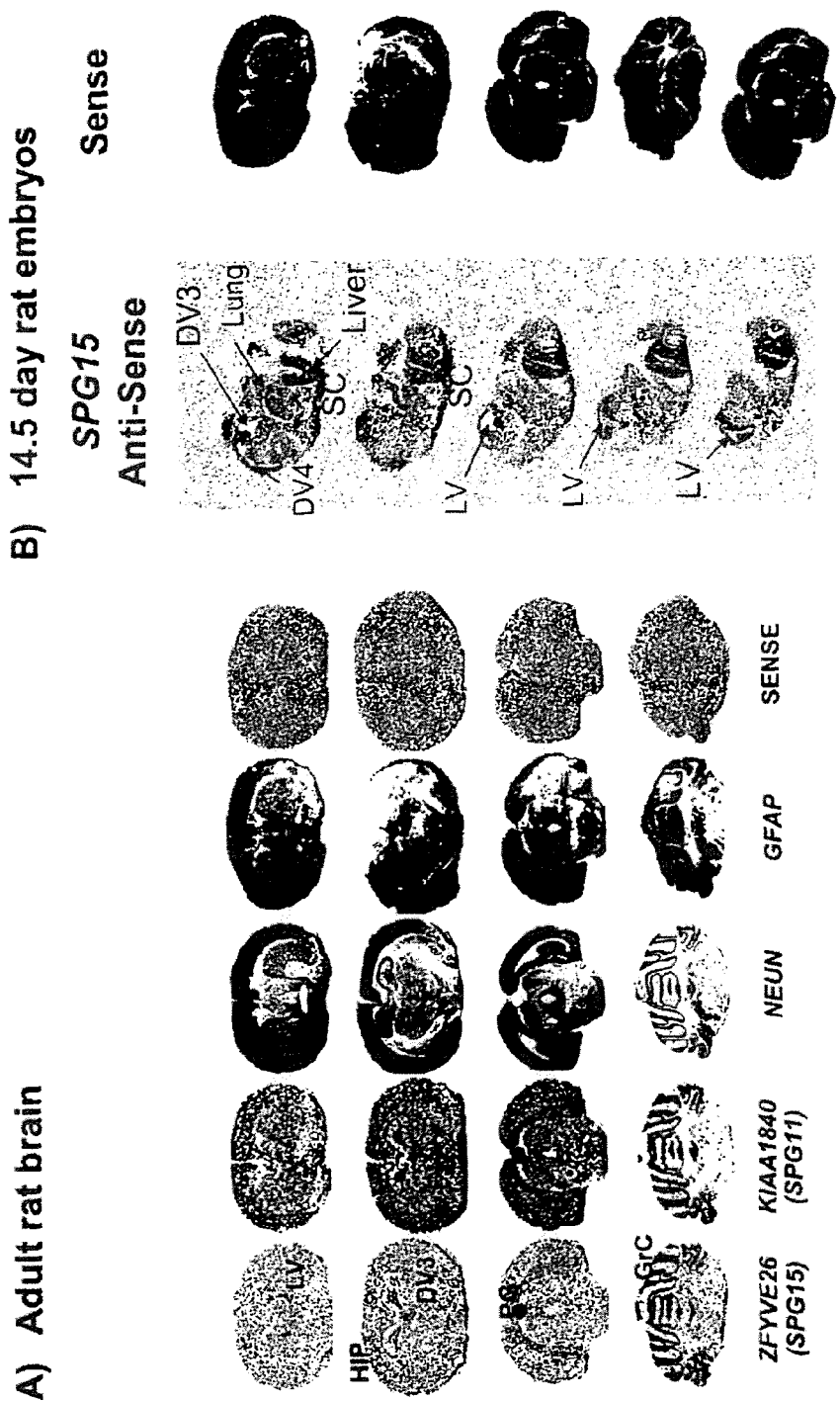

FIG. 12: Expression profile of ZFYVE26 in rats by in situ hybridization with a pool of three antisense probes or a pool of three sense probes. No specific staining was observed with the sense probes. The same results were obtained using the pool of three probes or each probe independently.
a) Comparison of ZFYVE26 (SPG15) and KIAA1840 (SPG11) mRNA expression in the adult rat brain (P68). Both ZFYVE26 and KIAA1840 expression resemble expression of the neuronal marker NeuN more than expression of the glial marker GFAP labelled on adjacent slices. ZFYVE26 expression, as KIAA1840, was low throughout the brain except in the following structures: HIP, hippocampus; PG, pineal gland; GrC, granular cell layer of the cerebellum; and the edges of the ventricles (DV3, third ventricle; LV, lateral ventricles).
b) In situ hybridization of ZFYVE26 in E14.5 rat embryos. Labelling concerns mainly the liver, lungs and the nervous system, particularly the spinal cord, the cortical, hippocampal, cerebellar and thalamic neuroepithelia, as well as the inferior and superior colliculi and the tegmental and basal telencephalic areas.

Figure 13:
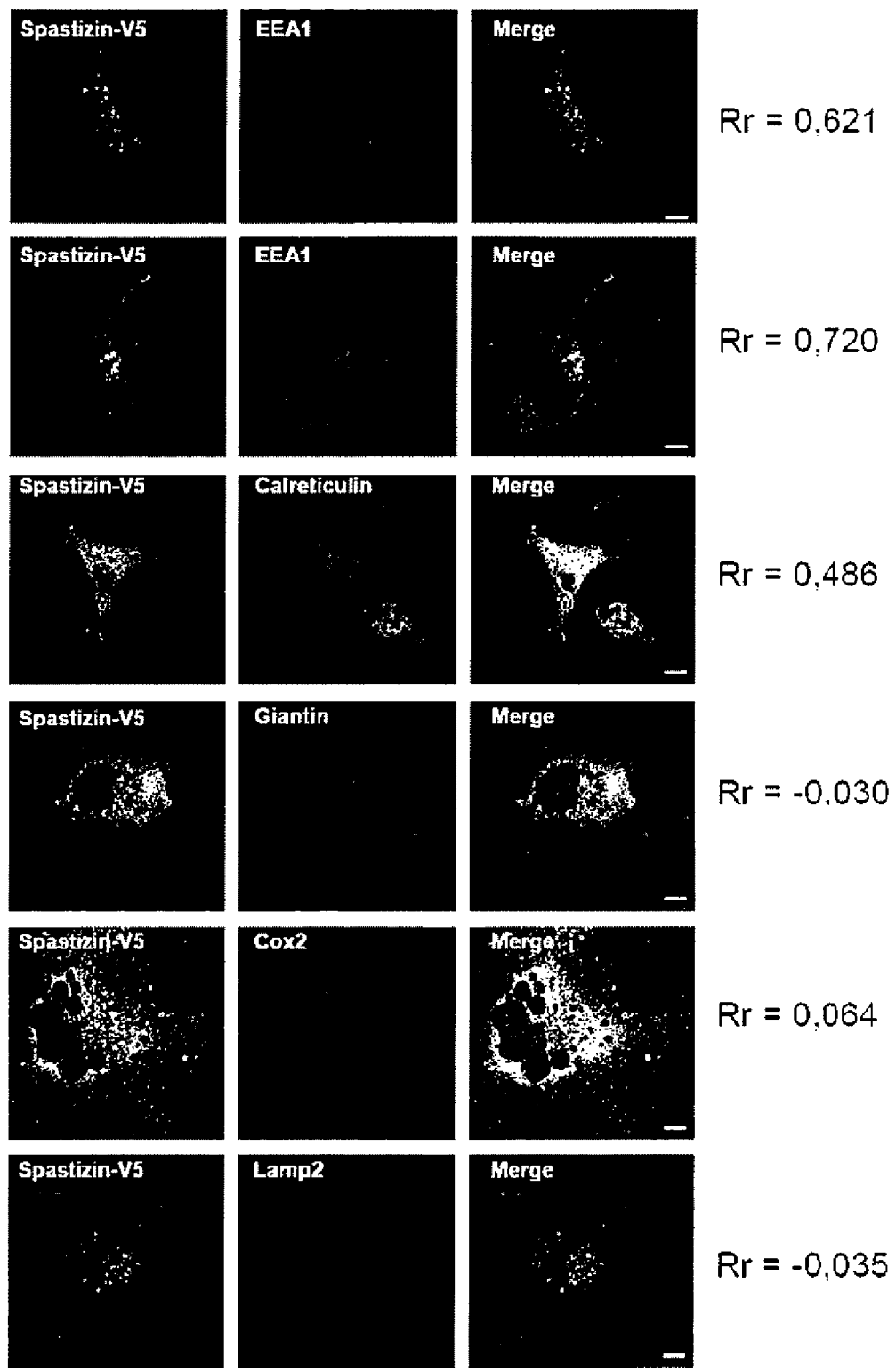

FIG. 13: Overexpression of ZFYVE26 in cell culture. Expression in COS-7 cells of a spastizin-HIS-V5 fusion protein labeled 48 hours after transfection with an antibody against the V5 tag (green) compared to specific markers (red). Images were obtained using a Leica SP1 confocal microscope (objective x63, scale bar=10 µm). The Pearson coefficient (Rr) was calculated to estimate the degree of colocalisation between spastizin-HISV5 and the organelle markers. The values range from −1.0 (not colocalized) and +1.0 (fully colocalized). Spastizin partially co-localized with the endosomal marker EEA1 and the endoplasmic reticulum marker calreticulin but did not show any significant colocalisation with Golgi (anti-Giantin), mitochondria (anti-Cox2) and lysosomes (anti-Lamp2). Expression of a V5-tagged fusion protein of the expected size was verified on western-blots of cell extracts with an anti-V5 antibody (data not shown).

Figures 1, 14:
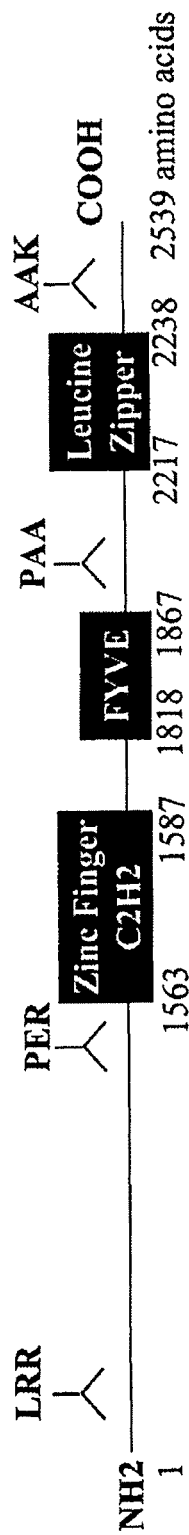
Figures 2, 14:
Figures 3, 14:
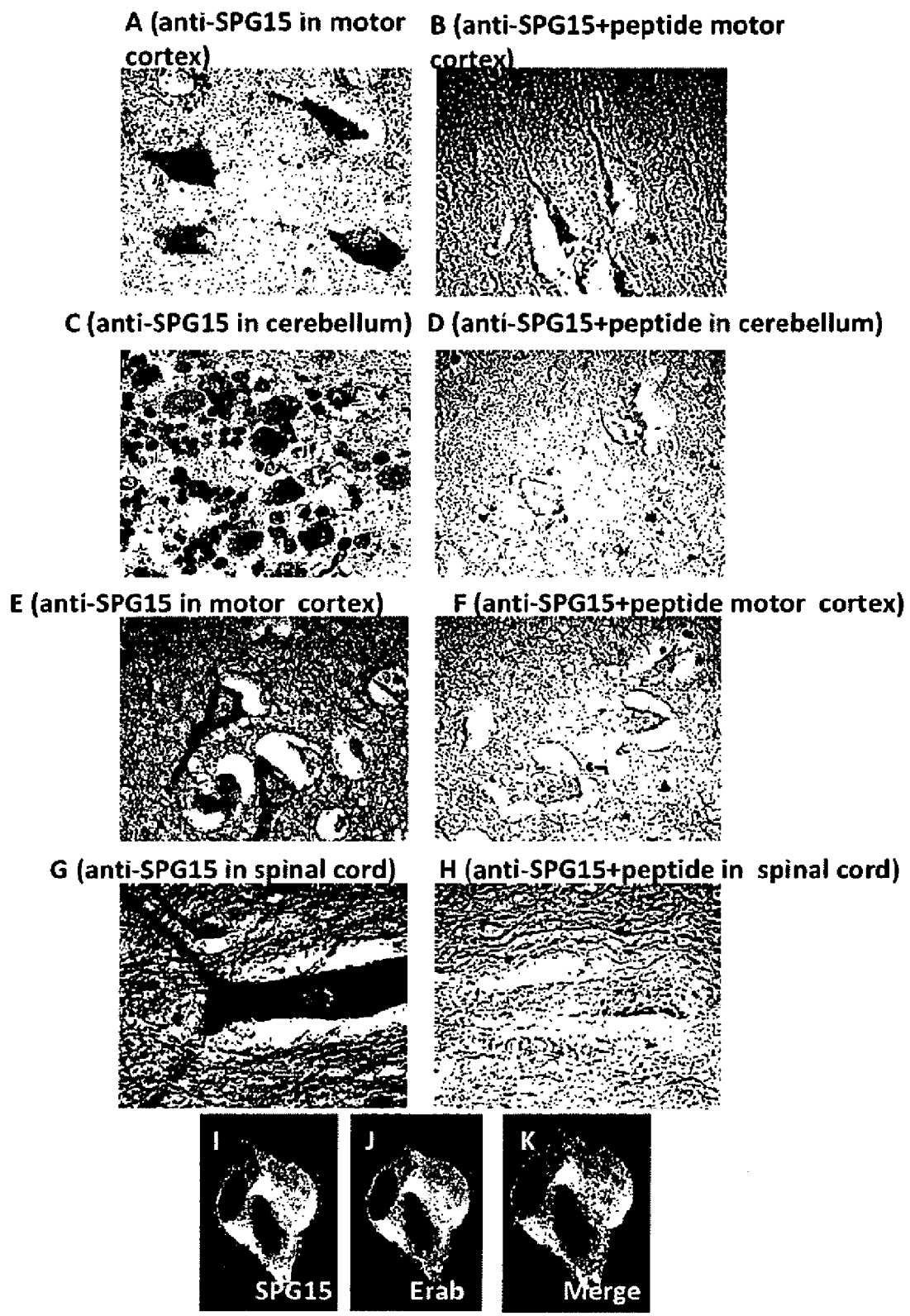

FIG. 14: Immuno-detection of the endogenous spastizin protein
14-1: Localisation of the 4 peptides (Table 6) used for immunization along the protein.
14-2: Western blot showing the detection of the protein by the PER antibody at its expected size (280 KDa) in COST protein extracts except after preadsorption with the peptide. Note the detection of an additional specific band at 100 KDa probably corresponding to a smaller iso form.
14-3: Immuno-detection in cells using the PER antibody.
(A-G): Immunohistochemical analysis of cells stained by anti-spastizin antibody.
(A-D): in rat brain.
(A) Large Betz cells of motor cortex stained by anti-spastizin antibody PER. Note spastizin in the cytoplasm & in the proximal dendrites of Betz cells; (B) spastizin staining blocked by PER antibody+peptide;
(C) Purkinje cells of cerebellum stained by anti-spastizin antibody PER. Note cytoplasmic as well as nuclear staining of Purkinje cells by spastizin;
(D) spastizin staining blocked by antibody+peptide;
(E-G) in human brain.
(E) Large Betz cells of motor cortex stained by anti-spastizin antibody PER. Note spastizin in the cytoplasm & in the proximal dendrites of Betz cells; (F) spastizin staining blocked by PER antibody+peptide;
(G) motor neurons of spinal cord stained by anti-spastizin antibody PER. Note cytoplasmic as well as dendritic staining by spastizin; (H) spastizin staining blocked by antibody+peptide;
(I-K) Confocal microscopic analysis of human neuronal cells (SH-SY5Y) stained by anti-spastizin antibodies PER. Note cytoplasmic staining of cells and partial co-localisation of SPG15 (in green) with mitochondria (Erab, in red), see merge pictures for co-localisation. In blue, nuclear counter-staining with Dapi.

EXAMPLE

Material & Methods

Patients and Controls:

We selected 8 previously described SPG15-linked AR-HSP families (Elleuch et al. 2007, Boukhris et al. 2008a and 2008b, Hughes et al. 2000), one large kindred partially reported (Casali et al. 2004) that we found significantly linked to SPG15 with a significant multipoint LOD score of +3.3 (FSP-761, Muglia et al. submitted), 3 families with linkage analysis compatible with segregation of SPG15 in patients and 3 index cases of families with a compatible phenotype. Affected patients and their relatives were recruited with their informed and written consent, as prescribed by the law on bioethics of the European Community and after approval by the local ethics committee (approval No. 03-12-07 granted to Drs. Brice and Dun by the "Comité Consultatif pour la Protection des Personnes et la Recherche Biomédicale", Paris-Necker). Genomic DNA from 300 unrelated healthy individuals (Caucasians n=200, North Africans n–100) were used as a control panel for molecular studies.

Linkage Analysis:

To further reduce the SPG15 interval, indirect genetic studies were undertaken in 2 of the families reported by Elleuch et al 2007. Primers flanking new polymorphic nucleotide repeats (table 4b) from the Working Draft of the Human Genome available at UCSC were designed in order to identify new critical recombination events in these 2 families that would allow the reduction of the SPG15 locus interval. Genotyping was performed by PCR with fluorescently-labeled primers, electrophoresis on an ABI-3730 sequencer and analysis with GeneMapper software 4.0 according to the manufacturer's recommendations (Applied Biosystems). Haplotypes were reconstructed manually by minimizing the number of recombination events. Genetic distances between markers were those of the Marshfield Centre for Medical Genetics (http://research.marshfield-clinic.org/genetics/home/index.asp) and map positions were verified on the draft of the Human Genome sequencing (UCSC and Ensembl centres).

Mutation Screening:

Four genes were screened for mutations in one affected member of each of the 15 families, using primers flanking the exon and intron-exon boundaries: ZFYVE26 (for zinc finger FYVE domain containing 26, Genbank accession number NM_015346; 42 exons); PLEK2 (encoding pleckstrin 2, NM_016445; 9 exons); PLEKHH (for pleckstrin homology domain containing, family H [with MyTH4 domain] member 1, NM_020715; 9 exons); and WDR22

(encoding WD repeat domain protein 22, NM_003861; 9 exons). PCR were performed in 10 μl final volume using 1 pmol of each primer, at final concentrations of 1.5 mM MgCl2, 0.24 mM dNTP, 50 ng of matrix genomic DNA in the Quiagen buffer supplemented with the Q solution (⅕ vol) and 0.4 unit of Tag polymerase (Quiagen). Primers used for the amplification of the ZFYVE26 gene are listed in the following Table 4. The PCR conditions are as follows:

95° C., 10 min
then 35 cycles of:
95° C., 30 s
60° C., 30 s,
72° C., 30 s
then
72° C., 10 min, and kept at 4° C.

TABLE 4

Primers used for the amplification of all exons of the ZFYVE26 gene.

| Exon | SEQ ID NO:Forward | sequence (5'-3') | Reverse sequence (5'-3') |
|---|---|---|---|
| 1 | 34/35 | cagccaggtagctgatttcc | aattcagcaggaacctccta |
| 2 | 36/37 | ataggaatccgcgtgaagag | gcagccaggcttacattcag |
| 3 | 38/39 | caccgcacttggctaatttt | ggcacaagactcatggtggt |
| 4 | 3/4 | tgcttcatcttagagaaatagcagaa | atgggcaacatcttggagac |
| 5 | 5/6 | gaaagcatgaaggcacacaa | ggctgggcatactggaatta |
| 6 | 40/41 | tgaagctcccaagggaagta | cgatgtaaaatgactgcaactg |
| 7 | 42/43 | ctcccaaagtgctgggatta | ctctgcattcagcctaagcc |
| 8 | 7/8 | cttaggctgaatgcagagcc | ggtcaacattgccaactcaa |
| 9 | 44/45 | ggcccttctaggacctttc | agacctcctcaccaccctct |
| 10 | 9/10 | aggaagtgcagggaactgaa | ccctgggtgaaataaaacca |
| 11a | 11/12 | taaatgagctaaagttgcgagaa | cctgaggaaggcccctatt |
| 11b | 13/14 | gaagtcagaacggggttcc | ggtgacgatatgccctgagt |
| 12 | 46/47 | tcagaacactggggtatgctc | gcatggaaaatttctgaaagg |
| 13 | 48/49 | acccaggtgaactctgttgc | gctaaaatctggccatctgc |
| 14 | 50/51 | gtttgcccttcatttgagga | cttgatgtggaccctgagt |
| 15 | 52/53 | tgaggctttggtggttttct | tggacgtatcaggtttgctg |
| 16 | 54/55 | gaaaaagccctccctcatct | ccatctgcctcctccaataa |
| 17 | 56/57 | tttgcattccctcttccttc | tgttgctgacctaatgttcca |
| 18 | 58/59 | tgtcagccagtcaaaccaaa | cctctgctccaaagtgcttc |
| 19 | 60/61 | ctggctgggaatcacttgtc | gccagagatgaataagagagga |
| 20 | 62/63 | gagagcaggagttggctgtc | agtgcagagtcacccactga |
| 21a | 15/17 | caattaggaacttttatttacattgc | actcccgggctacctgct |
| 21b | 18/19 | ctctgccttggcctttctta | gggcttctctctagagttaccg |
| 22 | 64/65 | tcttccttctgaaagtctcatgg | atgcaaagcaaaacccagac |
| 23 | 66/16 | tcctggataggttcactctgc | ccgcctcggcagaatgtg |
| 24 | 67/68 | tgaacagtaagcctgcttcaa | agctgagattgcatgggatt |
| 25 | 69/70 | gagaaagggttagtccaaaatga | ggcaaaagagccattgaaaa |
| 26 | 20/21 | cccctcatctggtgaaggta | tcctccaagaccaagatctctc |
| 27 | 71/72 | gtttgtttttcgaggcgttt | ttctgaaggatagaataaggcaaga |
| 28 | 22/23 | tcaggaggcacacaatgttc | atggctgtttgagggtgtct |
| 29 | 24/25 | gcccatcagctgacagatatt | tggcatttcagtgtgaatgtt |
| 30 | 73/74 | cgcataggaaggaagacaca | ggctgatacaaatgccaagaa |
| 31 | 75/76 | aagcaaacaaaaggaaccaagg | ccaagatgttcattattttctgc |

TABLE 4-continued

Primers used for the amplification of all exons of the ZFYVE26 gene.

| Exon | SEQ ID NO | Forward sequence (5'-3') | Reverse sequence (5'-3') |
|---|---|---|---|
| 32 | 26/27 | gctttcttgtagaatctggttcc | ggaagaacacttgagatctgg |
| 33 | 77/78 | gaatcgtttgaacccaggag | gtcatgtcccgattctacc |
| 34 | 30/31 | ggcagatagtgggaatgagg | cttgatgctgagccaggact |
| 35 | 79/80 | cacaacgtgcaggtttgttac | gttgtgcagagtcccctgtt |
| 36 | 32/33 | aggagagaagtgaagcagtcg | gctctagggtcagccaaaca |
| 37 | 81/82 | ccagtcagtgcacttcagga | caggattcaaggaatggacaa |
| 38 | 34/35 | tggcacataggtgctcaataa | gaggcagccatcaaacaaac |
| 39 | 83/84 | tggtgatcaggtccattttg | tcttgaatttgacccagttctgt |
| 40 | 85/86 | tgtggatgcttcctaaaggtc | ccattattgcagaggggttc |
| 41 | 87/88 | caggcagacattttcattctga | gtccatgttcacctgctcct |
| 42 | 89/90 | gcatatgtccagaatattgaaaga | tgcgtgaaaggtcctatcct |

These primers flanking newly described polymorphic markers were designed by the inventors on the human genome sequence draft in order to use them for the identification of critical recombination events in the SPG15 linked families. This was indeed successful since one of these markers revealed to be a flanking marker of the region (see FIG. 1) which allowed to focus the analysis of the candidate genes in the interval. Analysis of these markers was as described by Stevanin et al, 2006, a classical methodology for the analysis of microsatellite markers.

TABLE 4 bis: primers for the VNTR (VNTR = variable number of tandem repeat).

| VNTRs/ chromosomal position | SEQ ID NO | Forward sequence (5'-3') | Reverse sequence (5'-3') |
|---|---|---|---|
| VNTR20CA (66.57 Mb) | 91/92 | tctaatcaaagcgctaggc | tgttgactttgtaccctgc |
| VNTR25TG (66.91 Mb) | 93/94 | gcagcagcaaagcaaagatag | cctgtaatctcaaacattcc |
| VNTR17CA (66.66 Mb) | 95/96 | caaggacctaatgaattcct | ggaattttcattctctgggc |
| VNTR17AC (69.75 Mb) | 97/98 | gtgtgtagctgtcagtcaga | ttgaagacagctcccttatc |

PCR products of ZFYVE26 or other genes in the interval were sequenced using the Big Dye Terminator Cycle Sequencing Kit v3.1 (Applied Biosystems) on a ABI-3730 automated sequencer according to the manufacturer recommendations. Nucleotides were numbered relative to the A of the start codon (ATG) of the ZFYVE26 cDNA sequence (NM_015346).

Analysis at the mRNA Level:

Peripheral blood mononuclear cells from two affected patients of families FSP-130 and FSP-708, respectively, were isolated by Ficoll gradient using lymphocyte separation medium LSM 1077 (PAA Laboratories, Les Mureaux, France). Lymphoblastoid cell lines were established after infection with Epstein-Barr virus. Extraction of total RNA from ~$5.10^6$ lymphoblastoid cells was performed using the Rneasy Mini kit (Qiagen, Hilden, Germany), according to the manufacturer's instructions, after treatment with emetin (10 µg/ml) for 8 h in order to block nonsense-mediated mRNA decay (NMD). The quality of the RNA was verified and quantified using a BioAnalyzer2100 (Agilent Technologies). Reverse transcription (RT) of ~1 µg of total RNA was performed with the SuperScript kit (Invitrogen) to obtain double-strand cDNA. The SPG15 cDNA was amplified by PCR on a Thermocycler 3800 (Applied Biosystems) with 2.5 mmol $MgCl_2$, 1×Q solution, 1 U of Taq polymerase (Qiagen) in a final reaction volume of 25 µl using 10 pmol of each of the following exonic primers covering exons 37 to 42 for family FSP-708 (37f: ACATCCCGCAGCTCTGGAAG (SEQ ID NO° 122, 42ar: GCAACATATCAGGTAGGCCC (SEQ ID NO° 123)) and exons 30 to 33 for family FSP-130 (30f: TGTACCAGAGGAGCCTTCAG (SEQ ID NO° 124), 33r: CTCAACGCCCAGTTGGTAGT (SEQ ID NO° 125)). The PCR conditions for both sets used an annealing temperature of 60° C. PCR products were verified for their size and specificity on a 2% agarose gel, then sub-cloned in the pcDNA3.1/V5-His© TOPO® TA vector using TOP10 bacteria according to the manufacturer's recommendations (Invitrogen). Plasmid DNA extracted from bacterial clones with the Jetstar 2.0 kit (Genomed, Löhne, Germany) was amplified by PCR and clones having integrated the mutated allele were subsequently sequenced using universal and specific primers.

Quantification of ZFYVE26 mRNA in Human Tissues by RT-PCR ZFYVE26 mRNA:

expression was analysed semiquantitatively by RT-PCR in adult human tissues, normalized with respect to vimentin (VIM) expression. One microgram of commercially available RNA (Human Total RNA Master panel II, Clontech) were reverse-transcribed with the High Capacity cDNA Archive Kit (Applied Biosystems) primed with Oligo d(T) 16 (Applied Biosystems) in accordance with the supplier's recommendations. A 470 bp fragment from exon 2 to exon 5 was amplified with forward primer 5'-aggggatatc-ccaaagaggg-3' (SEQ ID NO: 99) and reverse primer 5'-cctttcgaatgaggtccacc-3' (SEQ ID NO: 100), and a 507 bp fragment including exons 38 to 42 was amplified with forward primer 5'-tcaccactttgcctctgcca-3' (SEQ ID NO: 101) and reverse primer 5'-gccactgggcacagatgtct-3' (SEQ ID NO: 102). A 274 bp fragment of VIM (Genbank accession number NM_003380) containing exons 1 to 4 was amplified with forward primer 5'-accagctaaccaacgacaaa-3' (SEQ ID NO: 103) and reverse primer 5'-tgctgttcctgaatctgagc-3' (SEQ ID NO: 104), as a reference.

Expression of Rat ZFYVE26 mRNA Detected by In Situ Hybridization:

Adult (P68, 200 g) Sprague-Dawley rats (Charles River) were killed by decapitation and their brains were rapidly extracted and frozen in isopentane at −50° C. Sections were cut every 600 µm on a cryostat (−20° C.) from the medulla to the striatum (+1.7 mm from the bregma, according to the rat brain coordinates of Paxinos and Watson, thaw-mounted on glass slides and stored at −80° C. Whole rat embryos (E14.5) were fixed in PFA 4% for 24 hours, rinsed in PBS, dehydrated in graded ethanols (70% to 100%), re-hydrated using the reverse procedure, cryoprotected in 15% sucrose for 24 hours, then frozen in isopentane at −35° C. Sixteen micron slices were cut every 250 µm and stored.

Rat ZFYVE26 mRNA expression was probed with three 34 bp antisense oligonucleotides recognizing exon 15 or the 5' or 3' portions of the large exon 21, designed with Helios ETC oligo design software (Helios Biosciences, Paris, France) from the mRNA sequence (XM 234335.3) of *Rattus norvegicus*. Each oligonucleotide or a mix of the three oligonucleotides gave identical results. A mix of three sense oligonucleotides was used as negative control. Briefly, the oligonucleotides were labeled with [$^{35}$S]-dATP using terminal transferase (Amersham Biosciences) to a specific activity of $5 \times 10^8$ dpm/µg. The day of the experiment, slices were fixed in 4% formaldehyde in PBS, washed with PBS, rinsed with water, dehydrated in 70% ethanol and air-dried. Sections were then covered with 140 µl of hybridization medium (Helios Biosciences, Paris, France) containing 3-5× $10^5$ dpm of the labeled oligonucleotide mix. Slices were incubated overnight at 42° C., washed and exposed to a BAS-SR Fujifilm Imaging Plate for 5-10 days. The plates were scanned with a Fujifilm BioImaging Analyzer BAS-5000 and analyzed with Multi Gauge Software (Fuji).

Immunohistochemistry in Rat Brain:

Brains were processed as for in situ hybridization. Sections were fixed in 4% paraformaldehyde/PBS, preincubated in PBS containing 6% goat serum and 0.1% triton, then incubated in the same buffer with antibodies against NeuN (Chemicon International, 1/250, mouse) or GFAP (Dako, 1/500, rabbit) or the specific anti-spastizin antibodies, followed by biotinylated horse anti-mouse or rabbit IgG and ABC reagents (Vector Laboratories, Burlingame, Calif.). Labeling was revealed by autoradiography. Specificity of the anti-spastizin antibodies was verified by preincubation of the antibody with a large amount (×200) of peptide used for immunization (see FIG. 14).

Expression of Epitope-Labeled or Endogenous Spastizin in Cultured Cells:

The ZFYVE26 cDNA from clone DKFZp781H1112Q (RPDZ) was PCR-amplified using Easy-A polymerase (Stratagene) and primers 5'-ggctcaaacatggctgcgct-3' and 5'-cttcttggagcctgggcca-3', and the PCR product was introduced in phase with the V5 and HIS tags in the pcDNA-3.1/V5-HIS-TOPO cloning vector, as recommended by the supplier (Invitrogen). The construction was verified by sequencing after ligation, transformation, plasmid extraction, using standard procedures, and correction of an initial nonsense mutation by directed-site mutagenesis (Quick-Change Site-Directed Mutagenesis Kit, Stratagene).

COS-7 cells, maintained in DMEM (Invitrogen) supplemented with 10% fetal bovine serum, penicillin (100 UI/ml) and streptomycin (100 µg/ml), were plated on cover slips coated with collagen and transfected 24 hrs later with 2 µg plasmid DNA per well, in 6-well plates with DMRIE-C, according to the manufacturer's instructions (Invitrogen). The cells were fixed for 15 minutes in 4% formaldehyde, 48 hours post-transfection, and immunocytochemistry was performed using classical procedures with the following primary antibodies: rabbit anti-giantin (1/2000, Abeam), rabbit anti-calreticulin (1/400, Stressgen), mouse anti-EAA1 (1/1000, BD Biosciences), rabbit anti-Cox2 (1/400, gift of Dr. A. Lombes), mouse anti-Lamp2 (1/200, Abeam), mouse anti-V5 (1/200, Invitrogen) mouse anti-erab (1/2,000, abeam) and rabbit anti-V5 (1 µg/ml, Sigma). Secondary antibodies were alexa-488 anti-mouse and anti-rabbit (1/1000, Molecular Probes) and Cy3 anti-mouse and anti-rabbit (1/1000, Sigma). Cells were counterstained with DAPI (1 µg/ml, Sigma) and mounted with Fluoromount-G (Southern Biotech). Images were acquired with a Leica SP1 confocal microscope and Leica software.

To detect the endogenous protein, COS-7 or SHSY5Y cell lines were cultured using a classical procedure as mentioned above. Protein extracts were processed for western-blot analysis after cell lysis, run on acrylamide gel, transfer into cellulose membrane and immunolabeling using a chemioluminescence kit (Pierce) as described (Latouche et al, 2006).

Results:

1. Refinement of the SPG15 Locus

The inventors recently refined the SPG15 locus in two large Arab families with AR-HSP and mental retardation but not maculopathy (Elleuch et al. 2007). To further restrict this interval, the authors analyzed additional polymorphic markers found in the Human Genome sequence draft (table 4b). Obligatory recombination events between loci VNTR25TG and D14S1069 (patient 444-6), and between loci D14S588 and D14S1029 (Individual 353-11, who is still unaffected at age 18 and assumed to be non-carrier of the disease gene), refined the centromeric and telomeric boundaries of this locus to a 2.64 Mb interval on chromosome 14q23.3-q24.2 (FIG. 1) containing 23 known genes and five putative new genes (FIG. 2).

2. Candidate Gene Analysis

Mutations causing other HSPs have been reported to affect cellular processes such as intracellular trafficking and mitochondrial function, but also myelination and development of corticospinal tract (Stevanin et al. 2008a). This information provided the inventors with criteria for selecting candidate genes located in the 2.64 Mb SPG15 interval (FIG. 2). The inventors first sequenced the exon and intron-exon boundaries of PLEK2, PLEKHH1 and WDR22. No disease causing alterations, but only already reported single nucleotide polymorphisms (reported at UCSC, available on request), were found in several affected patients of the families. Two other genes have been reported excluded by the authors previously (Elleuch et al. 2007).

The inventors then analysed the gene encoding ZFYVE26, which appeared to be a good candidate, since missense and nonsense mutations in two other genes of the same family were recently identified in patients with SPG33 (ZFYVE27 on chromosome 10q24.2; MIM#610244, Mannan et al. 2006) and Charcot-Marie-Tooth disease 411 (FGD4 on chromosome 12p11.21; MIM#611104, Delague et al. 2007, Stendel et al. 2007). Heighteen different truncating ZFYVE26 mutations were detected in the index patients of the 16 families (FIGS. 2 and 3, table 2). The 18 mutations segregated with the disease in all families (FIG. 3 to 10) and they were not detected in a panel of 600 chromosomes from unrelated controls (Caucasians, n=400; North Africans, n=200).

Seven were nonsense mutations including two that were recurrent: c.1477C>T in two consanguineous Tunisian families (F16 and F17) with similar flanking haplotypes suggesting a common ancestral event (Boukhris et al, 2008a and 2008b) and c.4312C>T in patients from two apparently unrelated consanguineous families from Morocco (F444) and Ireland (F1007), in which the mutation probably resulted from deamination of cytosine 4312 located in a CpG pair, a documented mechanism of mutation (Glass et al. 2007).

Four mutations were frameshift deletions including a large 70 base pair deletion (c.6702_6771del) in a large consanguineous family of Arab origin from Israel (F671).

Two mutations were frameshift insertions.

Four mutations affected the splicing sites. The c.5485-1G>A was homozygous in patients of the Algerian family 353, and was shown, in silica, to strongly alter the splice score from +3.1 to −7.8. The c.5791−6G>A, found heterozygous in the French family FSP130, creates a new acceptor splicing site in exon 32 with a better score leading to abnormal splicing 4 bases before its normal position, with the appearance of a premature stop codon after 27 additional codons which was confirmed by direct sequencing of mRNA extracts of patients (see FIG. 4). The c.6011G>C mutation (Portuguese family FSP352) corresponds to a missense variant (p.S2004T), but its location near the donor site of exon 32 is predicted to abolish the splicing at this position (score of +0.7 vs +4.5). The heterozygous c.7128+2T>A mutation in the French kindred FSP708 affects the donor site of exon 38 which is strongly abolished (score −4.8 vs +5.9) according to in silico predictions. This latter mutation was confirmed by direct sequencing of mRNA extracts of patients (see FIG. 3) leading to exon 38 skipping and a premature stop codon in exon 39.

Finally, one mutation was a complex indel-inversion rearrangement that deleted exons 21-23 in four patients from a consanguineous Italian family (F761) and leading to a premature stop codon (FIG. 7). For the detection of the genomic rearrangement in family 761, primers 21aF and 23R were used and generated a 238 bp-fragment in mutation carriers only instead of 3,532 bp in controls. This was due to deletion of a large sequence fragment containing exons 21, 22 and 23 and surrounding sequences, a small TCTA insertion and a 95 bp inversion).

3. Phenotype of SPG15 Mutation-Carriers and Phenotype-Genotype Correlations

Some of the clinical features of the 22 patients from 8 of the 16 SPG15 families are summarized in the Table 5.

TABLE 5

Clinical and paraclinical features of 22 SPG15 patients.

| Family/patient | Sex/Age at onset (years) | Disease duration (years) | Functional handicap (Scale) | LL/UL reflexes | Cognition Mental Retardation | Cognition Cognitive deterioration | Cerebellar Signs | Visual function | Others signs | ENMG | Brain MRI |
|---|---|---|---|---|---|---|---|---|---|---|---|
| 16/161 | M/12 | 20 | Severe(6/7) | Brisk/Brisk | +(Moderate) | No | No | Normal | Pes, cavus, pseudo bulbar dysarthria, severe UL and LL amyotrophy | Axonal PNP | Normal |
| 30/274 | F/11 | 17 | Severe (6/7) | Very brisk/Brisk | +(Moderate) | No | No | Normal | Pes cavus, scoliosis, pseudo bulbar dysarthria, moderate LL amyotrophy | Axonal PNP | Normal |
| 30/275 | F/8 | 19 | Severe (5/7) | Very brisk/Brisk | +(Moderate) | No | No | Normal | Severe LL amyotrophy | ND | ND |
| 30/279 | F/8 | 1 | Mild (2/7) | Very brisk/Normal | +(Mild) | No | No | Normal | None | ND | Normal |
| 761/3 | M/12 | 26 | Severe (6/7) | Very brisk/Very brisk | No | +(Severe) | + | Reduced visual acuity | Pseudo bulbar dysarthria; oral and hand dystonia-Sensorineural hearing deficit | Axonal PNP | TCC, WMA, marked cortical atrophy, mild cerebellar atrophy |
| 761/5 | F/12 | 22 | Severe (6/7) | Very brisk/Normal | No | +(Mild) | + | Normal | Pseudo bulbar dysarthria. Sensorineural hearing deficit | Axonal PNP | TCC, cortical and cerebellar atrophy |
| 761/9 | M/9 | 12 | Severe(5/7) | Very brisk/Brisk | No | +(Mild-Moderate) | No | Pigmentary retinopathy | Pseudo bulbar dysarthria and nystagmus Sensorineural hearing deficit | Axonal PNP | TCC and WMA |
| 761/10 | M/5 | 12 | Moderate (4/7) | Very brisk/Normal | + | No | No | Normal | Pseudo bulbar dysarthria | Normal | TCC |
| 17/168 | F/14 | 6 | Moderate (3/7) | Brisk/Normal | No | No | No | Normal | Pes cavus | ND | TCC, cortical and mild cerebellar atrophy |
| 1007/3 | F/13 | 20 | Severe (6/7) | Brisk/Brisk | + | + | + | Macular pigmentation | Epilepsy, distal amyotrophy, bladder dysfunction | Normal | Diffuse cerebral atrophy |
| 1007/4 | M/14 | 18 | Severe (6/7) | Brisk/Brisk | + | + | + | Macular pigmentation | Bladder dysfunction, pseudo bulbar dysarthria, distal amyotrophy | Normal | ND |
| 1007/5 | M/16 | 14 | Severe (6/7) | Brisk/Brisk | + | + | + | Normal | Focal dystonia, distal amyotrophy, bladder dysfunction | Normal | ND |
| 353/3 | F/12 | 20 | Severe (6/7) | Brisk/Brisk | No | + | + | Normal | Decreased vibration sense, distal amyotrophy, pes cavus, bladder dysfunction | Axonal PNP | ND |
| 353/4 | M/10 | 20 | Severe (6/7) | Brisk/Brisk | No | No | No | Normal | Decreased vibration sense, distal amyotrophy, pes cavus | ND | ND |
| 353/6 | F/10 | 15 | Moderate (4/7) | Brisk/Normal | No | No | No | Normal | Decreased vibration sense | ND | ND |
| 353/10 | M/10 | 6 | Moderate (3/7) | Brisk/Normal | No | No | + | Normal | Pes cavus, | Axonal PNP | ND |
| 444/7 | F/12 | 15 | Severe (7/7) | Brisk/Brisk | No | + | + | ND | Decreased vibration sense | ND | ND |
| 444/6 | M/12 | 15 | Severe (5/7) | Brisk/Brisk | No | No | + | ND | Decreased vibration sense | ND | ND |
| 444/9 | F/16 | 2 | Moderate (3/7) | Brisk/Brisk | No | No | No | ND | Pes cavus | ND | ND |
| 671/10 | F/<10 | >13 | Moderate (4/7) | Very brisk/Brisk | No | + | No | Normal | Decreased vibration sense, distal amyotrophy, bladder dysfunction | ND | ND |
| 671/4 | F/18 | 6 | Moderate (4/7) | Very brisk/Brisk | No | + | No | Normal | Raynaud phenomenon, high-arched palate, wide interdental spaces, distal amyotrophy, bladder dysfunction | Axonal PNP | TCC, WMA, mild cortical atrophy |
| 671/5 | F/19 | 4 | Moderate (3/7) | Brisk/Brisk | No | + | No | Normal | Hands extrapyramidal rigidity, mild hand tremor, decreased vibration sense, distal amyotrophy, | ND | TCC, WMA |

The overall phenotype associated with SPG15 mutations was early-onset spastic paraplegia (range: 5 to 19 years) associated with additional neurological symptoms that varied among patients and families: cognitive deterioration or mental retardation (73%, 16/22), axonal neuropathy (67%, 8/12), mild cerebellar signs (36%, 8/22) and, less frequently, a central hearing deficit, decreased visual acuity or retinal degeneration. A thin corpus callosum and white matter hyperintensities were found on brain MRI in 64% (7/11) and 36% (4/11) of the patients, respectively, independently of disease duration.

Most mutations resulted in the loss of the c-terminal putative leucine zipper domain and, of the FYVE domain as well. Since all mutations resulted in premature stop codons, the RNA is probably degraded by non-sense mediated mRNA decay, but this could not be confirmed because cells of SPG15 patients were not available.

4. Analysis of the Expression of the SPG15 Gene

In order to obtain insight into the function of the SPG15 gene, the inventors first analyzed expression of ZFYVE26 mRNA by RT-PCR on total RNA from various human tissues. It was widely expressed, but most strongly in the adrenal gland, bone marrow, adult brain, fetal brain, lung, placenta, prostate, skeletal muscle, testis, thymus and retina (FIG. 11). Intermediate levels were detected in other structures, including spinal cord.

When the expression of ZFYVE26 was investigated by in situ hybridization in adult rat brain (P68), mRNA levels were generally low, but strong signals were observed in the pineal gland, the edges of the lateral ventricles, the granular layer of the cerebellum and the hippocampus (FIG. 12). Interestingly, expression was wider and stronger in rat embryos (E14.5) than in adult brain, in particular in the spinal cord and the cortical, cerebellar, thalamic and hippocampal neuroepithelia.

The ZFYVE26 protein or "spastizin" (SPASTIcity due to the ZFYVE26 proteIN), belongs to the FYVE-finger family which includes the early endosome antigen 1 (EAA1, MIM#605070), involved in endocytic membrane trafficking (Gilloly et al 2001, Seet et al. 2001). Because there was initially no antibody against endogenous spastizin, the inventors explored its subcellular location by overexpression of a spastizin-HIS-V5 fusion protein in COS-7 cells. Epitope-tagged wild-type spastizin expressed in COS-7 cells, and immunolabeled with antibodies against the V5 tag, was partially colocalized in small dots or vesicles with immunolabeled endosomal marker EAA1 and calreticulin (CALR, MIM#109091), a marker of the endoplasmic reticulum, but not with giantin (GOLGB1, MIM#602500), lysosomal-associated membrane protein 2 (LAMP2, MIM#309060) or mitochondrially encoded cytochrome c oxidase II (MT-COS2 [COX2], MIM#516040), markers of the Golgi apparatus, lysosomes and mitochondria, respectively (FIG. 6).

In order to gain insight into the endogenous expression of spastizin, the inventors have then generated 4 polyclonal anti-spastizin antibodies using the Proteogenix facility (Table 6). Purified sera have been verified for their specificity on the endogenous proteins from various cell lines (COS-7, NSC34, SHSY5Y). One of them generated a specific signal at the expected size in western-blot (PER, FIG. 14), which was verified by competition tests with the peptides used for immunization.

TABLE 6

Peptide sequence used for immunization of rabbits.

| Name | Sequence | SEQ ID NO° |
|------|----------|------------|
| LRR | LRRGEWELAQACVPQL | 126 |
| PER | PERLAALLAQENLSLSVP | 127 |
| PAA | PAAVTRLRNQLLEAEYYQL | 128 |
| AAK | AAKSSGDAVVQDICA | 129 |

Thanks to the Brain Bank of INSERM/UPMC UMR679 (Dr E Hirsch) and the Neuropathology Department of the Pitié-Salpêtrière Hospital (Pr C Duyckaerts) for providing us paraffin embedded human brains, we have prepared sections from the human and the rat brain (adult female rat, P63). Immunohistochemical studies have been undertaken to determine the expression profile and subcellular localization of spastizin (SPG15) protein.

Expression studies with anti-spastizin revealed widespread pattern of expression of endogenous spastizin in the central nervous system of the adult rat. Spastizin is prominent in the cytoplasm of the cells though sometimes it is also observed in the nucleus of cells (FIG.—7C). Strongest expression of spastizin is found in the cerebral cortex, where the cells strongly express spastizin in their cytoplasm, including the Betz cells of layer V motor cortex (FIG.—7A). Spastizin is also expressed in the cells of cerebellum, hippocampus and the pons (FIG.—7C). This pattern of spastizin expression in brain cells was blocked by pre-incubation of the antibody with the peptide confirming specificity of spastizin staining (FIG.—7B, D).

In the adult human brain, Spastizin (SPG15) is also expressed strongly in neurons of cerebral cortex, spinal cord (FIG. 7E,G), and the pons and weakly in neurons of hippocampus and in the fibres of corpus callosum. Spastizin is pre-dominant in the cytoplasm of neurons sometimes also expressed in dendrite-like processes. Such immunoreactivity or pattern of expression was blocked by pre-incubation of the antibody with the peptide confirming that the staining observed are specific to spastizin (FIGS. 7F and H).

In SH-SY5Y (human neuroblastoma) and NSC34 (rodent motor-neuron), we observed cytoplasmic staining of cells. In both cell lines, spastizin seems to be distributed diffusely across the cytoplasm sometimes also staining punctuated vesicle-like structures (FIG. 7 I-K). This pattern of staining was specific as we did not observe it in cells treated only with secondary antibody. Its partial colocalization with Erab, a marker of mitochondria contrast with the results obtained in COS7 cells with the COX2 marker and might reveal cell type differences.

Discussion

The inventors, after identification of new families linked to the SPG15 locus (Elleuch et al. 2007, Boukhris et al. 2008a and 2008b) and its restriction to less than 6 Mbases (Elleuch et al. 2007), have then further refined the SPG5 locus to a 2.64 Mb interval on chromosome 14q23.3-q24.2 thanks to the analysis of newly described and designed markers in the interval (FIG. 1), which allowed them to identify ZFYVE26 as the causative gene.

Different pieces of evidence argue for the ZFYVE26 gene as responsible for SPG15: 1) the eighteen identified mutations segregated with a complex phenotype in 16 families, 2) 8 of these families were previously reported linked to SPG15, some of them significantly (Elleuch et al. 2007, Boukhris et al. 2008a and 2008b) and one was used to originally map the disease locus (Hughes et al. 2000), 3) the mutations were not found in a large series of control chromosomes (n=600), 4) among the genes of the restricted interval, 5 others were screened and no mutations were found, 5) the putative function of ZFYVE26 has already been implicated in other forms of HSP (Stevanin et al. 2008a) and its connection with endosomal trafficking has been highlighted by the inventors by overexpression studies (FIG. 6), 6) the expression profile in rat brain (FIG. 12) resembles SPG11, another HSP gene identified by the inventors (Stevanin et al, 2007).

The inventors have demonstrated the broad clinical variability of Kjellin syndrome, which is complete in only a minority of our mutated patients. The core features common to all mutated cases was a severe and early onset spastic paraplegia frequently associated with mental retardation and/or cognitive deterioration. Retinal degeneration, a major feature of this syndrome, as well as the MRI anomalies, may be absent in some patients, even after long disease durations, indicating that SPG15 might account for other forms HSP as well.

Spastizin, the product of the ZFYVE26 gene, is one of more than 30 different proteins with a FYVE domain in mammals (Gilloly et al. 2001, Seet et al. 2001). The FYVE domain is a zinc-finger binding domain, highly conserved from yeast to humans, characterized by the presence of eight conserved cysteine residues, the third of which is flanked by characteristic basic amino acids, $CX_2CX_{9-39}RRHHCRXCX_4CX_{2-6}CX_{4-48}CX_2C$ (X=non-conserved amino acid residues), suggested to bind the FYVE-finger proteins to endosomes. The majority of FYVE-finger proteins are involved in interactions with different forms of phosphoinositides (e.g. phosphatidylinositol 3-phosphate [PtdIns3P; PI3P]), which are found mainly in endosomes and serve as regulators of endocytic membrane trafficking. These phospholipids are components of membranes and have been implicated in the recruitment of proteins to membranes for signal transduction, membrane trafficking, cytoskeletal functions and apoptosis. FYVE fingers bind with much higher affinity to membrane-associated PI3P than to its soluble analogues, explaining why most FYVE finger proteins are associated with endosomal trafficking.

The colocalization of spastizin with markers of the endoplasmic reticulum and endosomes suggests that this protein plays a role in endosomal trafficking. Using a newly developed specific antibody against spastizin, the inventors confirmed that the endogenous protein labels vesicle-like structures (FIG. 14). This contributes to accumulating evidence that defects in trafficking are an important underlying cause of HSP.

Additionally, the temporal and regional distribution of ZFYVE26 mRNA observed by in situ hybridization in adult rat brain was very reminiscent of the expression of the SPG11 gene (Stevanin et al. 2007), the clinical features of which overlap those of SPG15, suggesting that the corresponding proteins may interact or function in a common pathway (FIG. 12). In addition, the stronger and wider expression of ZFYVE26 in embryos, including in spinal cord and cerebellar, hyppocampal, thalamic and cortical neuroepithelia, suggests a critical role of this gene during the development (FIG. 12).

It has been previously demonstrated that an intact FYVE domain and several conserved cysteine residues in this domain are necessary for the endosomal localization of the proteins of this family. Interestingly, all of the mutations identified in the SPG15 families in ZFYVE26 were truncating mutations. Non-sense mediated mRNA decay, a well documented cellular mechanism (Frischmeyer et al. 1999, Amrani et al. 2006), probably contributes to the loss of function of this protein in all cases.

It is interesting to note that a missense mutation in the FYVE domain protein encoded by ZFYVE27 was identified in an "uncomplicated" form of autosomal dominant HSP in a single German family with SPG33 (Mannan et al. 2006). The ZFYVE27 protein product was found to bind spastin (SPG4), another HSP-associated protein, but the missense mutation in ZFYVE27 induces an aberrant structure which interferes with its interaction with spastin, and thus with microtubules. Whether spastizin also binds spastin remains to be determined.

In conclusion, the identification of ZFYVE26 as the gene responsible for SPG15 has increased the knowledge of the genetic and clinical heterogeneity of HSPs, and will help orient the molecular analysis of patients in view of a diagnosis. The in situ hybridization and colocalisation studies are also a starting point for the understanding of the normal cellular mechanisms in which spastizin participates and for the elucidation of the mechanisms underlying axonal degeneration in the SPG15, which probably include endosomal trafficking and development anomalies. Elucidation of these mechanisms will be necessary for the development of effective therapeutic strategies.

REFERENCES

Throughout this application, various references describe the state of the art to which this invention pertains. The disclosures of these references are hereby incorporated by reference into the present disclosure.

Al-Yahyaee S, Al-Gazali L I, De Jonghe P, et al. A novel locus for hereditary spastic paraplegia with thin corpus callosum and epilepsy. Neurology. 2006; 66:1230-1234

Amrani, N., Sachs, M. S., and Jacobson, A. (2006). Early nonsense: mRNA decay solves a translation problem. Nat. Rev. (Mol. Cell. Biol.) 7, 415-425.

Antonarakis et al. (1989), N. Engl. J. Med. 320:153-163 Diagnosis of genetic disorders at the DNA level Barbas C F, Bain J D, Hoekstra D M, Lerner R A. (1992), Semisynthetic combinatorial antibody libraries: a chemical solution to the diversity problem. PNAS USA, 89, 4457-4461

Boukhris A, Stevanin G, Feki I, et al.: Hereditary spastic paraplegia with mental impairment and thin corpus callosum in Tunisia: SPG11, SPG15 and further genetic heterogeneity. Arch Neurol 2008a, 65:393-402.

Boukhris A, Feki I, Denis E, et al.: Spastic paraplegia 15: linkage and clinical description of three Tunisian families. Mov Disord 2008b, 23:429-433.

Boukhris A, Stevanin. G, Feki I, et al.: Tunisian hereditary spastic paraplegias: clinical variability supported by large genetic heterogeneity. Clin Genet 2009 (in press).

Callebaut, I. et al. Deciphering protein sequence information through hydrophobic cluster analysis (HCA): current status and perspectives. Cell Mol. Life Sci. 53, 621-645 (1997).

Casali, C. et al. Clinical and genetic studies in hereditary spastic paraplegia with thin corpus callosum. Neurology 62, 262-268 (2004).

Casari, G. et al. Spastic paraplegia and OXPHOS impairment caused by mutations in paraplegin, a nuclear-encoded mitochondrial metalloprotease. Cell 93, 973-983 (1998).

Chomocyznski et al., Anal. Biochem., 162:156, 1987

Cooper et al. (1991) Diagnosis of genetic disease using recombinant DNA, 3rd edition, Hum. Genet, 87:519-560

Coutinho P, Barros J, Zemmouri R, et al.: Clinical heterogeneity of autosomal recessive spastic paraplegias: analysis of 106 patients in 46 families. *Arch Neurol* 1999, 56:943-949

Delague, V., Jacquier, A., Hamadouche, T., Poitelon, Y., Baudot, C., Boccaccio, I., Chouery, E., Chaouch, M., Kassouri, N., Jabbour, R., et al. (2007). Mutations in FGD4 encoding the Rho GDP/GTP exchange factor FRABIN cause autosomal recessive Charcot-Marie-Tooth type 4H. Am. J. Hum. Genet. 81, 1-16.

Depienne C, Stevanin G, Brice A, Durr A: Hereditary spastic paraplegias: an update. *Curr Opin Neurol* 2007, 20:674-680.

Den Dunnen. J. T., Antonarakis S. E.: Hum Genet 109(1): 121-124, 2001.

Elleuch N, Bouslam N, Hanein S, et al.: Refinement of the SPG15 candidate interval and phenotypic heterogeneity in three large Arab families. *Neurogenetics* 2007, 8:307-315.

Engert, J. C. et al. ARSACS, a spastic ataxia common in northeastern Quebec, is caused by mutations in a new gene encoding an 11.5-kb ORF. Nat. Genet 24, 120-125 (2000).

Fink, J. K. Advances in the hereditary spastic paraplegias. Exp. Neurol 184 Suppl 1, S106-S110 (2003).

Fink, J. K. Hereditary spastic paraplegia. Curr. Neurol. Neurosci. Rep. 6, 65-76 (2006).

Franca M C Jr, D'Abreu A, Maurer-Morelli C V, et al.: Prospective neuroimaging study in hereditary spastic paraplegia with thin corpus callosum. *Mov Disord* 2007, 22:1556-1562

Frischmeyer, P. A., and Dietz, H. C. (1999). Nonsense-mediated mRNA decay in Health and disease. Hum. Mol. Genet. 8, 1893-1900.

Grompe M. The rapid detection of unknown mutations in nucleic acids (1993) Nat. Genet. 5 (2):111-7

Gudbjartsson, D. F., Jonasson, K., Frigge, M. L., & Kong, A. Allegro, a new computer program for multipoint linkage analysis. Nature Genet. 25, 12-13 (2000).

Gillooly, D. J., Simonsen, A., Stenmark, H. (2001). Cellular functions of phosphatidylinositol 3-phosphate and FYVE domain proteins. Biochem. J. 355, 249-258.

Glass, J. L., Thompson, R. F., Khulan, B., Figueroa, M. E., Olivier, E. N., Oakley, E. J., Van Zant, G., Bouhassira, E. E., Melnick, A., Golden, A., et al. (2007). CG dinucleotide clustering is a species-specific property of the genome. Nucleic. Acids. Res. 35, 6798-6807.

Harding, A. E. Classification of the hereditary ataxias and paraplegias. Lancet 1, 1151-1155 (1983).

Harlow E. et al., Antibodies: A Laboratory Manual, Cold Spring Harbor Laboratory, New York, (1988).

Hazan, J. et al. Spastin, a new AAA protein, is altered in the most frequent form of autosomal dominant spastic paraplegia. Nature Genet. 23, 296-303 (1999).

Hughes C A, Byrne P C, Webb S, et al. SPG15, a new locus for autosomal recessive complicated HSP on chromosome 14q. *Neurology.* 2000; 56:1230-1233

Kohler and Milstein (1975) Continuous cultures of fused cells secreting antibody of predefined specificity. Nature; 256, 495-7.

Kuklin et al. Detection of single-nucleotide polymorphisms with the WAVE DNA fragment analysis system Genet. Test (1997-98), 1(3):201-6

Lossos, A. et al. Hereditary spastic paraplegia with thin corpus callosum: reduction of the SPG11 interval and evidence for further heterogeneity. Arch Neurol 63(5): 756-60 (2006).

Mannan, A. U., Krawen, P., Sauter, S. M., Boehm, J., Chronowska, A, Paulus, W., Neesen, J., Engel, W. (2006). ZFYVE27 (SPG33), a novel spastin-binding protein, is mutated in hereditary spastic paraplegia. Am. J. Hum. Genet. 79, 351-357.

Martinez, M. F. et al. Genetic localization of a new locus for recessive familial spastic paraparesis to 15q13-15. Neurology 53, 50-56 (1999).

Moutsimilli, L. et al. Selective cortical VGLUT1 increase as a marker for antidepressant activity. Neuropharmacology 49, 890-900 (2005).

Olmez et al. Further Clinical and Genetic Characterization of SPG11: Hereditary Spastic Paraplegia with Thin Corpus Callosum. Neuropediatrics. 2006; 37:59-66.

Orlacchio A, Kawarai T, Totaro A, et al.: Hereditary spastic paraplegia: clinical genetic study of 15 families. *Arch Neurol* 2004, 61:849-855

Patel, H. et al. SPG20 is mutated in Troyer syndrome, an hereditary spastic paraplegia. Nature Genet. 31, 347-348 (2002).

Polo J M, Calleja J, Combarros O, Berciano J: Hereditary ataxias and paraplegias in Cantabria, Spain. An epidemiological and clinical study. *Brain* 1991, 114:855-866.

Saiki et al., Science 1988, 239:487

Sambrook, Fritsch & Maniatis, Molecular Cloning: A Laboratory Manual, Second Edition (1989) Cold Spring Harbor Laboratory Press, Cold Spring Harbor, N.Y.

Seet, L. F., and Hong, W. (2001). Endofin, an endosomal FYVE domain protein. J. Biol. Chem. 276, 42445-42454

Shibasaki, Y. et al. Linkage of autosomal recessive hereditary spastic paraplegia with mental impairment and thin corpus callosum to chromosome 15A13-15. Ann Neurol 48, 108-112 (2000).

Simpson, M. A. et al. Maspardin is mutated in mast syndrome, a complicated form of hereditary spastic paraplegia associated with dementia. Am. J. Hum. Genet. 73, 1147-1156 (2003).

Skre H. Hereditary spastic paraplegia in Western Norway. Clin Genet. 1974. 6:165-83

Stendel, C., Roos, A., Deconinck, T., Pereira, J., Castagner, F., Niemann, A., Kirschner, J., Korinthenberg, R., Ketelsen, U. P., Battaloglu, E., et al. (2007). Peripheral nerve demyelination caused by a mutant Rho GTPase guanine nucleotide exchange factor, frabin/FGD4. Am. J. Hum. Genet. 81, 158-164 (2007).

Stevanin, G. et al. Spastic paraplegia with thin corpus callosum: description of 20 new families, refinement of the SPG11 locus, candidate gene analysis and evidence of genetic heterogeneity. Neurogenetics, 7, 149-156 (2006).

Stevanin G, et al.: Mutations in SPG11, encoding spatacsin, are a major cause of spastic paraplegia with thin corpus callosum. Nat Genet, 39:366-372 (2007).

Stevanin G, Ruberg M, Brice A. Recent Advances in the Genetics of Spastic Paraplegias. Cur Neurol Neurosci Rep, 8: 198-210 (2008a).

Stevanin G, Azzedine H, Denora P, et al.: Mutations in SPG11 are frequent in autosomal recessive spastic paraplegia with thin corpus callosum, cognitive decline and lower motor neuron degeneration. Brain, 131:772-784 (2008b).

Tallaksen, C. M., Durr, A., & Brice, A. Recent advances in hereditary spastic paraplegia. Curr. Opin. Neurol. 14, 457-463 (2001).

Tsaousidou M K, et al.: Sequence alterations within CYP7B1 implicate defective cholesterol homeostasis in motor-neuron degeneration. *Am J Hum Genet* 2008, 82:510-515.

Waterhouse P, Griffiths A D, Johnson K S, Winter G. (1993) Combinatorial infection and in vivo recombination: a strategy for making large phage antibody repertoires. Nucleic Acids Research, 21, 2265-2266.

Winner, B. et al. Clinical progression and genetic analysis in hereditary spastic paraplegia with thin corpus callosum in spastic gait gene 11 (SPG11). Arch. Neurol. 61, 117-121 (2004).

Winner, B. et al. Thin corpus callosum and amyotrophy in spastic paraplegia-Case report and review of literature. Clin. Neurol. Neurosurg. (2005).

Woodcock, S., Mornon, J. P., & Henrissat, B. Detection of secondary structure elements in proteins by hydrophobic cluster analysis. Protein Eng 5, 629-635 (1992).

Zhao, X. et al. Mutations in a newly identified GTPase gene cause autosomal dominant hereditary spastic paraplegia. Nature Genet. 29, 326-331 (2001).

The invention claimed is:

1. A method of detecting a mutation in a ZFYVE26 nucleic acid comprising:
(a) contacting a ZFYVE26 nucleic acid in a sample with a detectably labeled oligonucleotide that specifically hybridizes to a region of the ZFYVE26 nucleic acid containing a mutation, wherein said mutation encodes a premature stop codon in a ZFYVE26 coding sequence, and wherein the mutation is not a frameshift mutation; and
(b) detecting hybridization of the oligonucleotide to the ZFYVE26 nucleic acid, wherein hybridization is indicative of the presence of the mutation in a ZFYVE26 nucleic acid.

2. The method according to claim 1, wherein said ZFYVE26 mutation is a C to T at position 1612 corresponding to SEQ ID NO:1.

3. The method of claim 1, wherein the ZFYVE26 nucleic acid comprises cDNA.

4. The method of claim 1, wherein the detectably labelled oligonucleotide comprises a moiety selected from a radiolabel, a fluorescent label, an enzymatic label and a sequence tag.

* * * * *